US009475851B2

(12) United States Patent
Prehaud et al.

(10) Patent No.: US 9,475,851 B2

(45) Date of Patent: Oct. 25, 2016

(54) HIGH MAST2-AFFINITY POLYPEPTIDES AND USES THEREOF

(71) Applicants: INSTITUT PASTEUR, Paris (FR); CENTRE NATIONAL DE LA RECHERCHE SCIENTIFIQUE, Paris (FR); UNVERSITE PIERRE ET MARIE CURIE (PARIS 6), Paris (FR)

(72) Inventors: Christophe Prehaud, Guyancourt (FR); Monique Lafon, Paris (FR); Nicolas Wolff, Paris (FR); Zakir Khan, Lucknow (IN); Elouan Terrien, Paris (FR); Sandrine Vitry, Courbevoie (FR)

(73) Assignees: INSTITUT PASTEUR, Paris (FR); CENTRE NATIONAL DE LA RECHERCHE SCIENTIFIQUE, Paris (FR); UNIVERSITE PIERRE ET MARIE CURIE, Paris (FR)

( * ) Notice: Subject to any disclaimer, the term of this patent is extended or adjusted under 35 U.S.C. 154(b) by 0 days.

(21) Appl. No.: 14/356,543

(22) PCT Filed: Nov. 7, 2012

(86) PCT No.: PCT/EP2012/072073

§ 371 (c)(1),
(2) Date: May 6, 2014

(87) PCT Pub. No.: WO2013/068430

PCT Pub. Date: May 16, 2013

(65) Prior Publication Data

US 2014/0315822 A1 Oct. 23, 2014

(30) Foreign Application Priority Data

Nov. 8, 2011 (EP) .................................... 11306454

(51) Int. Cl.

*C07K 14/435* (2006.01)
*C12Q 1/68* (2006.01)
*G01N 33/50* (2006.01)
*C07K 14/005* (2006.01)

(52) U.S. Cl.

CPC ........... *C07K 14/435* (2013.01); *C07K 14/005* (2013.01); *C12Q 1/6883* (2013.01); *G01N 33/5023* (2013.01); *G01N 33/5058* (2013.01); *C07K 2319/02* (2013.01); *C07K 2319/05* (2013.01); *C07K 2319/70* (2013.01); *C12N 2799/027* (2013.01); *C12Q 2600/158* (2013.01)

(58) Field of Classification Search

None

See application file for complete search history.

(56) References Cited

FOREIGN PATENT DOCUMENTS

| | | | |
|---|---|---|---|
| EP | 2239330 | A1 | 10/2010 |
| WO | 2006010834 | A1 | 2/2006 |
| WO | 2008138649 | A2 | 11/2008 |
| WO | 2010116258 | A1 | 10/2010 |

OTHER PUBLICATIONS

Babault et al., “Peptide Targeting the PDZ Domain of PTPN4 Are Efficiant Inducers of Glioblastoma Cell Death” Structure. vol. 19: 1518-1524, Oct. 12, 2011.

Boczek et al., “Gene expression pattern in PC12 cells with reduced PMCA2 or PMCA3 isoform: selective up-regulation of calmodulin and neuromodulin” Mol Cell Biochem. vol. 360: 89-102, 2012.

Database, Unit ProKB/Swiss-Prot. XP-002681547, Version 34, May 16, 2012.

European Search Report dated Aug. 9, 2012, issued in counterpart European Application No. EP 11 30 6454.

International Search Report dated Jun. 28, 2013, issued in counterpart International Application No. PCT/EP2012/072073.

Ibad et al, “Otx2 Promotes the Survival of Damaged Adult Retinal Ganglion Cells and Protects against Excitotoxic Loss of Visual Acuity In Vivo” The Journal of Neuroscience. XP-002699685. vol. 31 (14): 5495-5503, Apr. 6, 2011.

Lafon et al., Viral Neuroimmunology, XP-009161781. pp. 2-3, Aug. 2012.

Prehaud et al., “Attenuation of Rabies Virulence: Takeover by the Cytoplasmic Domain of Its Envelope Protein” Science Signaling. vol. 3 (105 ra5): 1-10, Jan. 19, 2010.

*Primary Examiner* — John Ulm

(74) *Attorney, Agent, or Firm* — McBee Moore Vanik and Woodward IP, LLC

(57) ABSTRACT

The invention relates to polypeptides containing a cytoplasmic domain ending with a MAST-2 binding domain, from 11 to 13 residues, the first two residues of which are S and W, and the last four residues of which are Q, T, R and L, the polypeptides presenting a high affinity for the PDZ domain of the human MAST2 protein. The invention also relates to polynucleotides, vectors, lentiviral particles, cells as well as compositions containing the same. The invention is also directed to the use of the polypeptides, polynucleotides, vectors, lentiviral particles, cells and compositions in the treatment and/or prevention of a disease, disorder or condition, which alters the Central Nervous System (CNS) and/or the Peripheral Nervous System (PNS). The invention also concerns molecular signatures of cellular genes to determine the neurosurvival and/or neuroprotection activity of a molecule.

21 Claims, 31 Drawing Sheets

A.

B.

A.

Neurovita1

Neurovita2

B.

A.

B.

A.

B.

Figure 20:
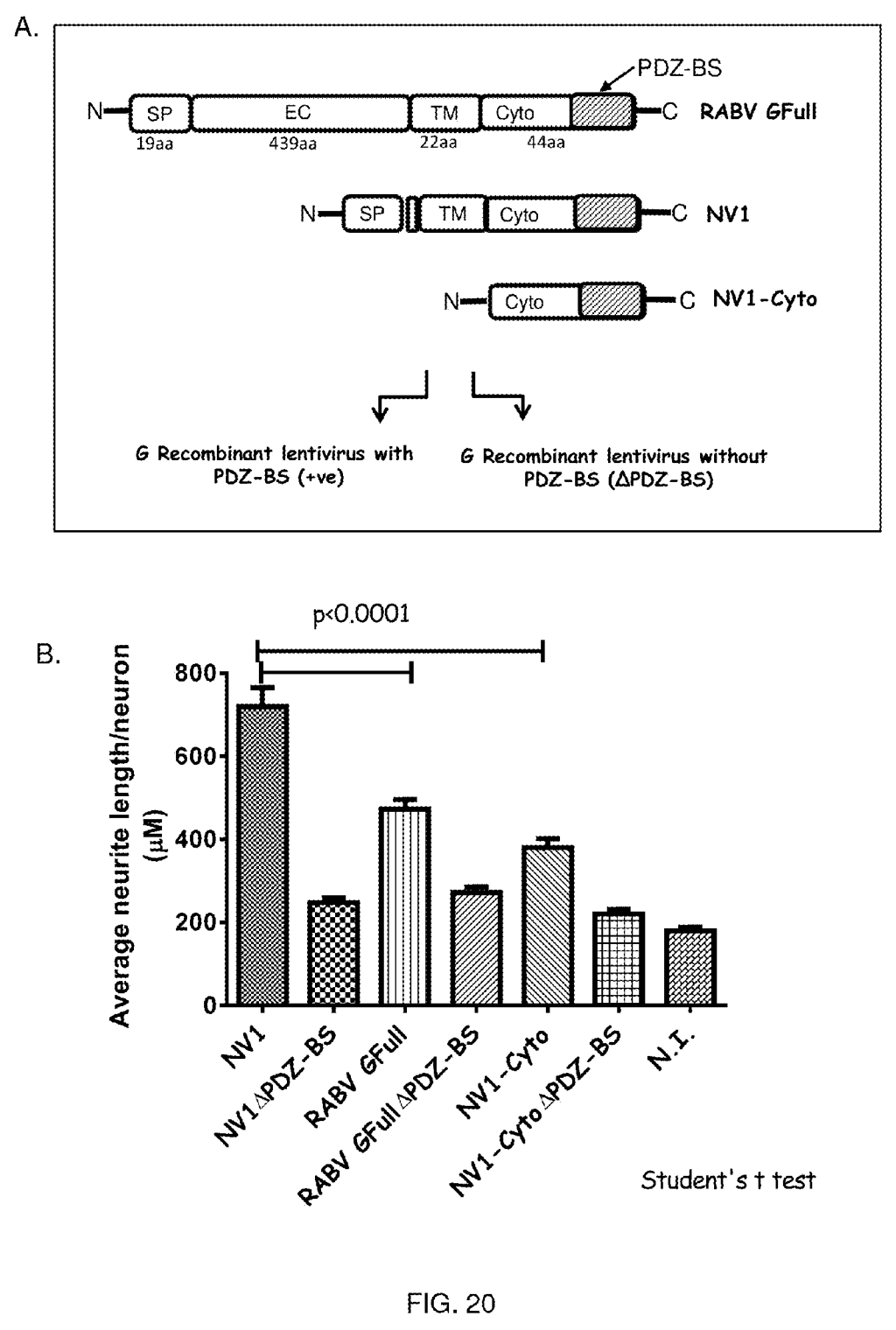

A.

N SP EC TM Cyto PDZ-BS C RABV GFull
19aa 439aa 22aa 44aa

N SP TM Cyto C NV1

N Cyto C NV1-Cyto

G Recombinant lentivirus with PDZ-BS (+ve)

G Recombinant lentivirus without PDZ-BS (ΔPDZ-BS)

B.

p<0.0001

Average neurite length/neuron (μM)

800
600
400
200
0

NV1
NV1ΔPDZ-BS
RABV GFull
RABV GFullΔPDZ-BS
NV1-Cyto
NV1-CytoΔPDZ-BS
N.I.

Student's t test

pLenti7.3 Neurovita — pCMV — Neurovita — pSV40 — emGFP

B.

C.

| | % of GFP expression |
| --- | --- |
| Neg | 0 |
| NV1Δ | 15,56 |
| NV1 | 48,98 |
| NV2 | 33,66 |
| NV3 | 59,7 |

D.

E.

C.

| | | | | | |
|---|---|---|---|---|---|
| Neg | | | | | |
| NV1Δ | 0,6076 | | | | |
| NV1 | 0,047 | 0,0010 | | | |
| NV2 | < 0,0001 | < 0,0001 | 0,0010 | | |
| NV3 | < 0,0001 | < 0,0001 | < 0,0001 | 0,0003 | |
| | Neg | NV1Δ | NV1 | NV2 | NV3 |

B.

| | Neg | NV1 |
|---|---|---|
| NV2 | 0.0178 | 0.0053 |

| | Neg | NV1 | NV2 |
|---|---|---|---|
| NV3 | < 0.0001 | < 0.0001 | 0.0007 |

B.

pLenti7.3 Neurovita — pCMV — NV3 or NV3 cyto — pSV40 — emGFP

C.

D.

| | Neg | NV3 | NV3 cyto |
|---|---|---|---|
| % of GFP expression | 0 | 60.41 | 36.71 |

A.

B.

C.

| | Neg | NV1 | NV2 | NV3 |
|---|---|---|---|---|
| NV3 cyto | < 0.0001 | 0.7784 | 0.0457 | < 0.0001 |

A.

B.

| | Neg | NV1 | NV2 | NV3 |
|---|---|---|---|---|
| NV3 cyto | < 0,0001 | 0,088 | 0,006 | < 0,0001 |

B.

D.

A.

C.

SEQUENCE LISTING

```
<160> NUMBER OF SEQ ID NOS: 288

<210> SEQ ID NO 1
<211> LENGTH: 13
<212> TYPE: PRT
<213> ORGANISM: Artificial Sequence
<220> FEATURE:
<223> OTHER INFORMATION: Neurovita1

<400> SEQUENCE: 1

Ser Trp Glu Ser His Lys Ser Gly Gly Gln Thr Arg Leu
1               5                   10


<210> SEQ ID NO 2
<211> LENGTH: 31
<212> TYPE: PRT
<213> ORGANISM: Artificial Sequence
<220> FEATURE:
<223> OTHER INFORMATION: Cytoplasmic domain

<400> SEQUENCE: 2

Arg Arg Val Asn Arg Ser Glu Pro Thr Gln His Asn Leu Arg Gly Thr
1               5                   10                  15

Gly Arg Glu Val Ser Val Thr Pro Gln Ser Gly Lys Ile Ile Ser
            20                  25                  30


<210> SEQ ID NO 3
<211> LENGTH: 19
<212> TYPE: PRT
<213> ORGANISM: Artificial Sequence
<220> FEATURE:
<223> OTHER INFORMATION: Signal peptide

<400> SEQUENCE: 3
```

```
Met Val Pro Gln Ala Leu Leu Phe Val Pro Leu Leu Val Phe Pro Leu
1               5                   10                  15

Cys Phe Gly


<210> SEQ ID NO 4
<211> LENGTH: 22
<212> TYPE: PRT
<213> ORGANISM: Artificial Sequence
<220> FEATURE:
<223> OTHER INFORMATION: Transmembrane domain

<400> SEQUENCE: 4

Tyr Val Leu Leu Ser Ala Gly Ala Leu Thr Ala Leu Met Leu Ile Ile
1               5                   10                  15

Phe Leu Met Thr Cys Cys
            20


<210> SEQ ID NO 5
<211> LENGTH: 31
<212> TYPE: PRT
<213> ORGANISM: Artificial Sequence
<220> FEATURE:
<223> OTHER INFORMATION: Cytoplasmic domain variant

<400> SEQUENCE: 5

Arg Arg Val Asn Arg Ser Glu Pro Thr Gln Leu Asn Leu Arg Gly Thr
1               5                   10                  15

Gly Arg Glu Val Ser Val Thr Pro Gln Ser Gly Lys Ile Ile Ser
            20                  25                  30


<210> SEQ ID NO 6
<211> LENGTH: 1798
<212> TYPE: PRT
<213> ORGANISM: Homo sapiens
<220> FEATURE:
<221> NAME/KEY: MISC_FEATURE
<222> LOCATION: (1)..(1798)
<223> OTHER INFORMATION: Microtubule-associated serine/threonine-protein
      kinase 2 (MAST2)

<400> SEQUENCE: 6

Met Lys Arg Ser Arg Cys Arg Asp Arg Pro Gln Pro Pro Pro Pro Asp
1               5                   10                  15

Arg Arg Glu Asp Gly Val Gln Arg Ala Ala Glu Leu Ser Gln Ser Leu
            20                  25                  30

Pro Pro Arg Arg Arg Ala Pro Pro Gly Arg Gln Arg Leu Glu Glu Arg
        35                  40                  45

Thr Gly Pro Ala Gly Pro Glu Gly Lys Glu Gln Asp Val Val Thr Gly
    50                  55                  60

Val Ser Pro Leu Leu Phe Arg Lys Leu Ser Asn Pro Asp Ile Phe Ser
65                  70                  75                  80

Ser Thr Gly Lys Val Lys Leu Gln Arg Gln Leu Ser Gln Asp Asp Cys
                85                  90                  95

Lys Leu Trp Arg Gly Asn Leu Ala Ser Ser Leu Ser Gly Lys Gln Leu
            100                 105                 110

Leu Pro Leu Ser Ser Ser Val His Ser Ser Val Gly Gln Val Thr Trp
        115                 120                 125

Gln Ser Ser Gly Glu Ala Ser Asn Leu Val Arg Met Arg Asn Gln Ser
    130                 135                 140

Leu Gly Gln Ser Ala Pro Ser Leu Thr Ala Gly Leu Lys Glu Leu Ser
```

```
145                 150                 155                 160

Leu Pro Arg Arg Gly Ser Phe Cys Arg Thr Ser Asn Arg Lys Ser Leu
                165                 170                 175

Ile Val Thr Ser Ser Thr Ser Pro Thr Leu Pro Arg Pro His Ser Pro
            180                 185                 190

Leu His Gly His Thr Gly Asn Ser Pro Leu Asp Ser Pro Arg Asn Phe
        195                 200                 205

Ser Pro Asn Ala Pro Ala His Phe Ser Phe Val Pro Ala Arg Arg Thr
    210                 215                 220

Asp Gly Arg Arg Trp Ser Leu Ala Ser Leu Pro Ser Ser Gly Tyr Gly
225                 230                 235                 240

Thr Asn Thr Pro Ser Ser Thr Val Ser Ser Ser Cys Ser Ser Gln Glu
                245                 250                 255

Lys Leu His Gln Leu Pro Phe Gln Pro Thr Ala Asp Glu Leu His Phe
            260                 265                 270

Leu Thr Lys His Phe Ser Thr Glu Ser Val Pro Asp Glu Glu Gly Arg
        275                 280                 285

Gln Ser Pro Ala Met Arg Pro Arg Ser Arg Ser Leu Ser Pro Gly Arg
    290                 295                 300

Ser Pro Val Ser Phe Asp Ser Glu Ile Ile Met Met Asn His Val Tyr
305                 310                 315                 320

Lys Glu Arg Phe Pro Lys Ala Thr Ala Gln Met Glu Glu Arg Leu Ala
                325                 330                 335

Glu Phe Ile Ser Ser Asn Thr Pro Asp Ser Val Leu Pro Leu Ala Asp
            340                 345                 350

Gly Ala Leu Ser Phe Ile His His Gln Val Ile Glu Met Ala Arg Asp
        355                 360                 365

Cys Leu Asp Lys Ser Arg Ser Gly Leu Ile Thr Ser Gln Tyr Phe Tyr
    370                 375                 380

Glu Leu Gln Asp Asn Leu Glu Lys Leu Leu Gln Asp Ala His Glu Arg
385                 390                 395                 400

Ser Glu Ser Ser Glu Val Ala Phe Val Met Gln Leu Val Lys Lys Leu
                405                 410                 415

Met Ile Ile Ile Ala Arg Pro Ala Arg Leu Leu Glu Cys Leu Glu Phe
            420                 425                 430

Asp Pro Glu Glu Phe Tyr His Leu Leu Glu Ala Ala Glu Gly His Ala
        435                 440                 445

Lys Glu Gly Gln Gly Ile Lys Cys Asp Ile Pro Arg Tyr Ile Val Ser
    450                 455                 460

Gln Leu Gly Leu Thr Arg Asp Pro Leu Glu Glu Met Ala Gln Leu Ser
465                 470                 475                 480

Ser Cys Asp Ser Pro Asp Thr Pro Glu Thr Asp Asp Ser Ile Glu Gly
                485                 490                 495

His Gly Ala Ser Leu Pro Ser Lys Lys Thr Pro Ser Glu Glu Asp Phe
            500                 505                 510

Glu Thr Ile Lys Leu Ile Ser Asn Gly Ala Tyr Gly Ala Val Phe Leu
        515                 520                 525

Val Arg His Lys Ser Thr Arg Gln Arg Phe Ala Met Lys Lys Ile Asn
    530                 535                 540

Lys Gln Asn Leu Ile Leu Arg Asn Gln Ile Gln Gln Ala Phe Val Glu
545                 550                 555                 560

Arg Asp Ile Leu Thr Phe Ala Glu Asn Pro Phe Val Val Ser Met Phe
                565                 570                 575
```

```
Cys Ser Phe Asp Thr Lys Arg His Leu Cys Met Val Met Glu Tyr Val
            580                 585                 590

Glu Gly Gly Asp Cys Ala Thr Leu Leu Lys Asn Ile Gly Ala Leu Pro
        595                 600                 605

Val Asp Met Val Arg Leu Tyr Phe Ala Glu Thr Val Leu Ala Leu Glu
    610                 615                 620

Tyr Leu His Asn Tyr Gly Ile Val His Arg Asp Leu Lys Pro Asp Asn
625                 630                 635                 640

Leu Leu Ile Thr Ser Met Gly His Ile Lys Leu Thr Asp Phe Gly Leu
                645                 650                 655

Ser Lys Ile Gly Leu Met Ser Leu Thr Thr Asn Leu Tyr Glu Gly His
            660                 665                 670

Ile Glu Lys Asp Ala Arg Glu Phe Leu Asp Lys Gln Val Cys Gly Thr
        675                 680                 685

Pro Glu Tyr Ile Ala Pro Glu Val Ile Leu Arg Gln Gly Tyr Gly Lys
    690                 695                 700

Pro Val Asp Trp Trp Ala Met Gly Ile Ile Leu Tyr Glu Phe Leu Val
705                 710                 715                 720

Gly Cys Val Pro Phe Phe Gly Asp Thr Pro Glu Glu Leu Phe Gly Gln
                725                 730                 735

Val Ile Ser Asp Glu Ile Val Trp Pro Glu Gly Asp Glu Ala Leu Pro
            740                 745                 750

Pro Asp Ala Gln Asp Leu Thr Ser Lys Leu Leu His Gln Asn Pro Leu
        755                 760                 765

Glu Arg Leu Gly Thr Gly Ser Ala Tyr Glu Val Lys Gln His Pro Phe
    770                 775                 780

Phe Thr Gly Leu Asp Trp Thr Gly Leu Leu Arg Gln Lys Ala Glu Phe
785                 790                 795                 800

Ile Pro Gln Leu Glu Ser Glu Asp Asp Thr Ser Tyr Phe Asp Thr Arg
                805                 810                 815

Ser Glu Arg Tyr His His Met Asp Ser Glu Asp Glu Glu Glu Val Ser
            820                 825                 830

Glu Asp Gly Cys Leu Glu Ile Arg Gln Phe Ser Ser Cys Ser Pro Arg
        835                 840                 845

Phe Asn Lys Val Tyr Ser Ser Met Glu Arg Leu Ser Leu Leu Glu Glu
    850                 855                 860

Arg Arg Thr Pro Pro Pro Thr Lys Arg Ser Leu Ser Glu Glu Lys Glu
865                 870                 875                 880

Asp His Ser Asp Gly Leu Ala Gly Leu Lys Gly Arg Asp Arg Ser Trp
                885                 890                 895

Val Ile Gly Ser Pro Glu Ile Leu Arg Lys Arg Leu Ser Val Ser Glu
            900                 905                 910

Ser Ser His Thr Glu Ser Asp Ser Ser Pro Pro Met Thr Val Arg Arg
        915                 920                 925

Arg Cys Ser Gly Leu Leu Asp Ala Pro Arg Phe Pro Glu Gly Pro Glu
    930                 935                 940

Glu Ala Ser Ser Thr Leu Arg Arg Gln Pro Gln Glu Gly Ile Trp Val
945                 950                 955                 960

Leu Thr Pro Pro Ser Gly Glu Gly Val Ser Gly Pro Val Thr Glu His
                965                 970                 975

Ser Gly Glu Gln Arg Pro Lys Leu Asp Glu Glu Ala Val Gly Arg Ser
            980                 985                 990
```

```
Ser Gly Ser Ser Pro Ala Met Glu  Thr Arg Gly Arg Gly  Thr Ser Gln
        995                 1000                1005

Leu Ala  Glu Gly Ala Thr Ala  Lys Ala Ile Ser Asp  Leu Ala Val
    1010                1015                1020

Arg Arg  Ala Arg His Arg Leu  Leu Ser Gly Asp Ser  Thr Glu Lys
    1025                1030                1035

Arg Thr  Ala Arg Pro Val Asn  Lys Val Ile Lys Ser  Ala Ser Ala
    1040                1045                1050

Thr Ala  Leu Ser Leu Leu Ile  Pro Ser Glu His His  Thr Cys Ser
    1055                1060                1065

Pro Leu  Ala Ser Pro Met Ser  Pro His Ser Gln Ser  Ser Asn Pro
    1070                1075                1080

Ser Ser  Arg Asp Ser Ser Pro  Ser Arg Asp Phe Leu  Pro Ala Leu
    1085                1090                1095

Gly Ser  Met Arg Pro Pro Ile  Ile Ile His Arg Ala  Gly Lys Lys
    1100                1105                1110

Tyr Gly  Phe Thr Leu Arg Ala  Ile Arg Val Tyr Met  Gly Asp Ser
    1115                1120                1125

Asp Val  Tyr Thr Val His His  Met Val Trp His Val  Glu Asp Gly
    1130                1135                1140

Gly Pro  Ala Ser Glu Ala Gly  Leu Arg Gln Gly Asp  Leu Ile Thr
    1145                1150                1155

His Val  Asn Gly Glu Pro Val  His Gly Leu Val His  Thr Glu Val
    1160                1165                1170

Val Glu  Leu Ile Leu Lys Ser  Gly Asn Lys Val Ala  Ile Ser Thr
    1175                1180                1185

Thr Pro  Leu Glu Asn Thr Ser  Ile Lys Val Gly Pro  Ala Arg Lys
    1190                1195                1200

Gly Ser  Tyr Lys Ala Lys Met  Ala Arg Arg Ser Lys  Arg Ser Arg
    1205                1210                1215

Gly Lys  Asp Gly Gln Glu Ser  Arg Lys Arg Ser Ser  Leu Phe Arg
    1220                1225                1230

Lys Ile  Thr Lys Gln Ala Ser  Leu Leu His Thr Ser  Arg Ser Leu
    1235                1240                1245

Ser Ser  Leu Asn Arg Ser Leu  Ser Ser Gly Glu Ser  Gly Pro Gly
    1250                1255                1260

Ser Pro  Thr His Ser His Ser  Leu Ser Pro Arg Ser  Pro Thr Gln
    1265                1270                1275

Gly Tyr  Arg Val Thr Pro Asp  Ala Val His Ser Val  Gly Gly Asn
    1280                1285                1290

Ser Ser  Gln Ser Ser Ser Pro  Ser Ser Ser Val Pro  Ser Ser Pro
    1295                1300                1305

Ala Gly  Ser Gly His Thr Arg  Pro Ser Ser Leu His  Gly Leu Ala
    1310                1315                1320

Pro Lys  Leu Gln Arg Gln Tyr  Arg Ser Pro Arg Arg  Lys Ser Ala
    1325                1330                1335

Gly Ser  Ile Pro Leu Ser Pro  Leu Ala His Thr Pro  Ser Pro Pro
    1340                1345                1350

Pro Pro  Thr Ala Ser Pro Gln  Arg Ser Pro Ser Pro  Leu Ser Gly
    1355                1360                1365

His Val  Ala Gln Ala Phe Pro  Thr Lys Leu His Leu  Ser Pro Pro
    1370                1375                1380

Leu Gly  Arg Gln Leu Ser Arg  Pro Lys Ser Ala Glu  Pro Pro Arg
```

```
    1385                1390                1395

Ser Pro  Leu Leu Lys Arg Val  Gln Ser Ala Glu Lys  Leu Ala Ala
    1400                1405                1410

Ala Leu  Ala Ala Ser Glu Lys  Lys Leu Ala Thr Ser  Arg Lys His
    1415                1420                1425

Ser Leu  Asp Leu Pro His Ser  Glu Leu Lys Lys Glu  Leu Pro Pro
    1430                1435                1440

Arg Glu  Val Ser Pro Leu Glu  Val Val Gly Ala Arg  Ser Val Leu
    1445                1450                1455

Ser Gly  Lys Gly Ala Leu Pro  Gly Lys Gly Val Leu  Gln Pro Ala
    1460                1465                1470

Pro Ser  Arg Ala Leu Gly Thr  Leu Arg Gln Asp Arg  Ala Glu Arg
    1475                1480                1485

Arg Glu  Ser Leu Gln Lys Gln  Glu Ala Ile Arg Glu  Val Asp Ser
    1490                1495                1500

Ser Glu  Asp Asp Thr Glu Glu  Gly Pro Glu Asn Ser  Gln Gly Ala
    1505                1510                1515

Gln Glu  Leu Ser Leu Ala Pro  His Pro Glu Val Ser  Gln Ser Val
    1520                1525                1530

Ala Pro  Lys Gly Ala Gly Glu  Ser Gly Glu Glu Asp  Pro Phe Pro
    1535                1540                1545

Ser Arg  Asp Pro Arg Ser Leu  Gly Pro Met Val Pro  Ser Leu Leu
    1550                1555                1560

Thr Gly  Ile Thr Leu Gly Pro  Pro Arg Met Glu Ser  Pro Ser Gly
    1565                1570                1575

Pro His  Arg Arg Leu Gly Ser  Pro Gln Ala Ile Glu  Glu Ala Ala
    1580                1585                1590

Ser Ser  Ser Ser Ala Gly Pro  Asn Leu Gly Gln Ser  Gly Ala Thr
    1595                1600                1605

Asp Pro  Ile Pro Pro Glu Gly  Cys Trp Lys Ala Gln  His Leu His
    1610                1615                1620

Thr Gln  Ala Leu Thr Ala Leu  Ser Pro Ser Thr Ser  Gly Leu Thr
    1625                1630                1635

Pro Thr  Ser Ser Cys Ser Pro  Pro Ser Ser Thr Ser  Gly Lys Leu
    1640                1645                1650

Ser Met  Trp Ser Trp Lys Ser  Leu Ile Glu Gly Pro  Asp Arg Ala
    1655                1660                1665

Ser Pro  Ser Arg Lys Ala Thr  Met Ala Gly Gly Leu  Ala Asn Leu
    1670                1675                1680

Gln Asp  Leu Glu Asn Thr Thr  Pro Ala Gln Pro Lys  Asn Leu Ser
    1685                1690                1695

Pro Arg  Glu Gln Gly Lys Thr  Gln Pro Pro Ser Ala  Pro Arg Leu
    1700                1705                1710

Ala His  Pro Ser Tyr Glu Asp  Pro Ser Gln Gly Trp  Leu Trp Glu
    1715                1720                1725

Ser Glu  Cys Ala Gln Ala Val  Lys Glu Asp Pro Ala  Leu Ser Ile
    1730                1735                1740

Thr Gln  Val Pro Asp Ala Ser  Gly Asp Arg Arg Gln  Asp Val Pro
    1745                1750                1755

Cys Arg  Gly Cys Pro Leu Thr  Gln Lys Ser Glu Pro  Ser Leu Arg
    1760                1765                1770

Arg Gly  Gln Glu Pro Gly Gly  His Gln Lys His Arg  Asp Leu Ala
    1775                1780                1785
```

```
Leu Val  Pro Asp Glu Leu Leu  Lys Gln Thr
    1790                 1795


<210> SEQ ID NO 7
<211> LENGTH: 93
<212> TYPE: PRT
<213> ORGANISM: Homo sapiens
<220> FEATURE:
<221> NAME/KEY: MISC_FEATURE
<222> LOCATION: (1)..(93)
<223> OTHER INFORMATION: PDZ domain of the human MAST2 protein

<400> SEQUENCE: 7

Met Arg Pro Pro Ile Ile Ile His Arg Ala Gly Lys Lys Tyr Gly Phe
1               5                   10                  15

Thr Leu Arg Ala Ile Arg Val Tyr Met Gly Asp Ser Asp Val Tyr Thr
            20                  25                  30

Val His His Met Val Trp His Val Glu Asp Gly Gly Pro Ala Ser Glu
        35                  40                  45

Ala Gly Leu Arg Gln Gly Asp Leu Ile Thr His Val Asn Gly Glu Pro
    50                  55                  60

Val His Gly Leu Val His Thr Glu Val Val Glu Leu Ile Leu Lys Ser
65                  70                  75                  80

Gly Asn Lys Val Ala Ile Ser Thr Thr Pro Leu Glu Asn
                85                  90


<210> SEQ ID NO 8
<211> LENGTH: 264
<212> TYPE: DNA
<213> ORGANISM: Artificial Sequence
<220> FEATURE:
<223> OTHER INFORMATION: Neurovita 1
<220> FEATURE:
<221> NAME/KEY: CDS
<222> LOCATION: (1)..(264)

<400> SEQUENCE: 8

atg gtt cct cag gct ctc ctg ttt gta ccc ctt ctg gtt ttt cca ttg       48
Met Val Pro Gln Ala Leu Leu Phe Val Pro Leu Leu Val Phe Pro Leu
1               5                   10                  15

tgt ttt ggg ggg aag tat gta tta ctg agt gca ggg gcc ctg act gcc       96
Cys Phe Gly Gly Lys Tyr Val Leu Leu Ser Ala Gly Ala Leu Thr Ala
            20                  25                  30

ttg atg ttg ata att ttc ctg atg aca tgt tgt aga aga gtc aat cga      144
Leu Met Leu Ile Ile Phe Leu Met Thr Cys Cys Arg Arg Val Asn Arg
        35                  40                  45

tca gaa cct acg caa cac aat ctc aga ggg aca ggg agg gag gtg tca      192
Ser Glu Pro Thr Gln His Asn Leu Arg Gly Thr Gly Arg Glu Val Ser
    50                  55                  60

gtc act ccc caa agc ggg aag atc ata tct tca tgg gaa tca cac aag      240
Val Thr Pro Gln Ser Gly Lys Ile Ile Ser Ser Trp Glu Ser His Lys
65                  70                  75                  80

agt ggg ggt cag acc aga ctg tga                                      264
Ser Gly Gly Gln Thr Arg Leu
                85


<210> SEQ ID NO 9
<211> LENGTH: 87
<212> TYPE: PRT
<213> ORGANISM: Artificial Sequence
<220> FEATURE:
<223> OTHER INFORMATION: Synthetic Construct
```

```
<400> SEQUENCE: 9

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Ser His Lys
65                  70                  75                  80

Ser Gly Gly Gln Thr Arg Leu
                85


<210> SEQ ID NO 10
<211> LENGTH: 252
<212> TYPE: DNA
<213> ORGANISM: Artificial Sequence
<220> FEATURE:
<223> OTHER INFORMATION: Neurovital delta MAST-2 binding domain
<220> FEATURE:
<221> NAME/KEY: CDS
<222> LOCATION: (1)..(252)

<400> SEQUENCE: 10

atg gtt cct cag gct ctc ctg ttt gta ccc ctt ctg gtt ttt cca ttg       48
Met Val Pro Gln Ala Leu Leu Phe Val Pro Leu Leu Val Phe Pro Leu
1               5                   10                  15

tgt ttt ggg ggg aag tat gta tta ctg agt gca ggg gcc ctg act gcc       96
Cys Phe Gly Gly Lys Tyr Val Leu Leu Ser Ala Gly Ala Leu Thr Ala
            20                  25                  30

ttg atg ttg ata att ttc ctg atg aca tgt tgt aga aga gtc aat cga      144
Leu Met Leu Ile Ile Phe Leu Met Thr Cys Cys Arg Arg Val Asn Arg
        35                  40                  45

tca gaa cct acg caa cac aat ctc aga ggg aca ggg agg gag gtg tca      192
Ser Glu Pro Thr Gln His Asn Leu Arg Gly Thr Gly Arg Glu Val Ser
    50                  55                  60

gtc act ccc caa agc ggg aag atc ata tct tca tgg gaa tca cac aag      240
Val Thr Pro Gln Ser Gly Lys Ile Ile Ser Ser Trp Glu Ser His Lys
65                  70                  75                  80

agt ggg ggt tga                                                      252
Ser Gly Gly


<210> SEQ ID NO 11
<211> LENGTH: 83
<212> TYPE: PRT
<213> ORGANISM: Artificial Sequence
<220> FEATURE:
<223> OTHER INFORMATION: Synthetic Construct

<400> SEQUENCE: 11

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Ser His Lys
```

```
65                  70                  75                  80

Ser Gly Gly


<210> SEQ ID NO 12
<211> LENGTH: 524
<212> TYPE: PRT
<213> ORGANISM: Rabies virus
<220> FEATURE:
<221> NAME/KEY: MISC_FEATURE
<222> LOCATION: (1)..(524)
<223> OTHER INFORMATION: G protein of CVS - NIV

<400> SEQUENCE: 12

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Pro Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335
```

```
Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Gln Thr Arg Leu
        515                 520


<210> SEQ ID NO 13
<211> LENGTH: 524
<212> TYPE: PRT
<213> ORGANISM: Rabies virus
<220> FEATURE:
<221> NAME/KEY: MISC_FEATURE
<222> LOCATION: (1)..(524)
<223> OTHER INFORMATION: G protein of ERA - NIV

<400> SEQUENCE: 13

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Ile
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
```

```
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Val Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln Leu Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520
```

```
<210> SEQ ID NO 14
<211> LENGTH: 522
<212> TYPE: PRT
<213> ORGANISM: Rabies virus
<220> FEATURE:
<221> NAME/KEY: MISC_FEATURE
<222> LOCATION: (1)..(522)
<223> OTHER INFORMATION: G protein  NCBI CAI43218

<400> SEQUENCE: 14
```

```
Met Val Pro Gln Ala Leu Leu Phe Val Pro Leu Leu Gly Phe Ser Leu
1               5                   10                  15

Cys Phe Gly Lys Phe Pro Ile Tyr Thr Ile Pro Asp Glu Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Arg Thr Pro Cys
        195                 200                 205

Asp Ile Phe Thr Asn Ser Arg Gly Lys Arg Ala Ser Lys Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Asp Gln Leu Val Asn Leu His Asp Phe Arg Ser Asp Glu Ile Glu His
        275                 280                 285

Leu Val Val Glu Glu Leu Val Lys Lys Arg Glu Glu Cys Leu Asp Ala
    290                 295                 300

Leu Glu Ser Ile Met Thr Thr Lys Ser Val Ser Phe Arg Arg Leu Ser
305                 310                 315                 320

His Leu Arg Lys Leu Val Pro Gly Gly Lys Ala Tyr Thr Ile Phe Asn
                325                 330                 335

Lys Thr Leu Met Glu Ala Asp Ala His Tyr Lys Ser Val Arg Thr Trp
            340                 345                 350

Asn Glu Ile Ile Pro Ser Lys Gly Cys Leu Lys Val Gly Gly Arg Cys
        355                 360                 365

His Pro His Val Asn Gly Val Phe Phe Asn Gly Ile Ile Leu Gly Pro
    370                 375                 380

Asp Gly His Val Leu Ile Pro Glu Met Gln Ser Ser Leu Leu Gln Gln
385                 390                 395                 400

His Met Glu Leu Leu Lys Ser Ser Val Ile Pro Leu Met His Pro Leu
                405                 410                 415
```

```
Ala Asp Pro Ser Thr Val Phe Lys Glu Gly Asp Glu Ala Glu Asp Phe
            420                 425                 430

Val Glu Val His Leu Pro Asp Val Tyr Lys Gln Ile Ser Gly Val Asp
        435                 440                 445

Leu Gly Leu Pro Asn Trp Gly Lys Tyr Val Leu Met Thr Ala Gly Ala
    450                 455                 460

Met Ile Gly Leu Val Leu Ile Phe Ser Leu Met Thr Trp Cys Arg Arg
465                 470                 475                 480

Ala Asn Arg Pro Glu Ser Lys Gln Arg Ser Phe Gly Gly Thr Gly Arg
                485                 490                 495

Asn Val Ser Val Thr Ser Gln Ser Gly Lys Val Ile Pro Ser Trp Glu
            500                 505                 510

Ser Tyr Lys Ser Gly Gly Gln Thr Arg Leu
        515                 520


<210> SEQ ID NO 15
<211> LENGTH: 87
<212> TYPE: PRT
<213> ORGANISM: Artificial Sequence
<220> FEATURE:
<223> OTHER INFORMATION: Polypeptide

<400> SEQUENCE: 15

Met Val Pro Gln Ala Leu Leu Phe Val Pro Leu Leu Gly Phe Ser Leu
1               5                   10                  15

Cys Phe Gly Gly Lys Tyr Val Leu Met Thr Ala Gly Ala Met Ile Gly
            20                  25                  30

Leu Val Leu Ile Phe Ser Leu Met Thr Trp Cys Arg Arg Ala Asn Arg
        35                  40                  45

Pro Glu Ser Lys Gln Arg Ser Phe Gly Gly Thr Gly Arg Asn Val Ser
    50                  55                  60

Val Thr Ser Gln Ser Gly Lys Val Ile Pro Ser Trp Glu Ser Tyr Lys
65                  70                  75                  80

Ser Gly Gly Gln Thr Arg Leu
                85


<210> SEQ ID NO 16
<211> LENGTH: 13
<212> TYPE: PRT
<213> ORGANISM: Rabies virus
<220> FEATURE:
<221> NAME/KEY: MISC_FEATURE
<222> LOCATION: (1)..(13)
<223> OTHER INFORMATION: MAST-2 binding domain

<400> SEQUENCE: 16

Ser Trp Glu Ser Tyr Lys Ser Gly Gly Gln Thr Arg Leu
1               5                   10


<210> SEQ ID NO 17
<211> LENGTH: 74
<212> TYPE: PRT
<213> ORGANISM: Artificial Sequence
<220> FEATURE:
<223> OTHER INFORMATION: Part of polypeptide

<400> SEQUENCE: 17

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30
```

```
Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser
65                  70
```

<210> SEQ ID NO 18
<211> LENGTH: 74
<212> TYPE: PRT
<213> ORGANISM: Artificial Sequence
<220> FEATURE:
<223> OTHER INFORMATION: Part of polypeptide

<400> SEQUENCE: 18

```
Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln Leu Asn Leu Arg Gly Thr Gly Arg Glu Val Ser
    50                  55                  60

Val Thr Pro Gln Ser Gly Lys Ile Ile Ser
65                  70
```

<210> SEQ ID NO 19
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(7)
<223> OTHER INFORMATION: Xaa can be any naturally occurring amino acid

<400> SEQUENCE: 19

```
Ser Trp Xaa Xaa Xaa Xaa Xaa Gln Thr Arg Leu
1               5                   10
```

<210> SEQ ID NO 20
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(7)
<223> OTHER INFORMATION: Xaa can be any naturally occurring amino acid

<400> SEQUENCE: 20

```
Ser Trp Glu Xaa Xaa Xaa Xaa Gln Thr Arg Leu
1               5                   10
```

<210> SEQ ID NO 21
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(7)

<223> OTHER INFORMATION: Xaa can be any naturally occurring amino acid

<400> SEQUENCE: 21

```
Ser Trp Ala Xaa Xaa Xaa Xaa Gln Thr Arg Leu
1               5                   10
```

<210> SEQ ID NO 22
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 22

```
Ser Trp Xaa Val Xaa Xaa Xaa Gln Thr Arg Leu
1               5                   10
```

<210> SEQ ID NO 23
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 23

```
Ser Trp Xaa Glu Xaa Xaa Xaa Gln Thr Arg Leu
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 24

```
Ser Trp Xaa Ser Xaa Xaa Xaa Gln Thr Arg Leu
1               5                   10
```

<210> SEQ ID NO 25
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature

```
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 25

Ser Trp Xaa Xaa His Xaa Xaa Gln Thr Arg Leu
1               5                   10


<210> SEQ ID NO 26
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 26

Ser Trp Xaa Xaa Ala Xaa Xaa Gln Thr Arg Leu
1               5                   10


<210> SEQ ID NO 27
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 27

Ser Trp Xaa Xaa Tyr Xaa Xaa Gln Thr Arg Leu
1               5                   10


<210> SEQ ID NO 28
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 28

Ser Trp Xaa Xaa Xaa Gly Xaa Gln Thr Arg Leu
1               5                   10


<210> SEQ ID NO 29
<211> LENGTH: 11
<212> TYPE: PRT
```

```
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 29

Ser Trp Xaa Xaa Xaa Thr Xaa Gln Thr Arg Leu
1               5                   10


<210> SEQ ID NO 30
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(6)
<223> OTHER INFORMATION: Xaa can be any naturally occurring amino acid

<400> SEQUENCE: 30

Ser Trp Xaa Xaa Xaa Xaa Gly Gln Thr Arg Leu
1               5                   10


<210> SEQ ID NO 31
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(6)
<223> OTHER INFORMATION: Xaa can be any naturally occurring amino acid

<400> SEQUENCE: 31

Ser Trp Xaa Xaa Xaa Xaa Gln Gln Thr Arg Leu
1               5                   10


<210> SEQ ID NO 32
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(7)
<223> OTHER INFORMATION: Xaa can be any naturally occurring amino acid

<400> SEQUENCE: 32

Ser Trp Glu Val Xaa Xaa Xaa Gln Thr Arg Leu
1               5                   10


<210> SEQ ID NO 33
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(7)
<223> OTHER INFORMATION: Xaa can be any naturally occurring amino acid
```

<400> SEQUENCE: 33

Ser Trp Glu Ser Xaa Xaa Xaa Gln Thr Arg Leu
1 5 10

<210> SEQ ID NO 34
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(7)
<223> OTHER INFORMATION: Xaa can be any naturally occurring amino acid

<400> SEQUENCE: 34

Ser Trp Glu Glu Xaa Xaa Xaa Gln Thr Arg Leu
1 5 10

<210> SEQ ID NO 35
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 35

Ser Trp Glu Xaa His Xaa Xaa Gln Thr Arg Leu
1 5 10

<210> SEQ ID NO 36
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 36

Ser Trp Glu Xaa Ala Xaa Xaa Gln Thr Arg Leu
1 5 10

<210> SEQ ID NO 37
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(7)

```
<223> OTHER INFORMATION: Xaa can be any naturally occurring amino acid

<400> SEQUENCE: 37

Ser Trp Glu Xaa Tyr Xaa Xaa Gln Thr Arg Leu
1               5                   10


<210> SEQ ID NO 38
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 38

Ser Trp Glu Xaa Xaa Gly Xaa Gln Thr Arg Leu
1               5                   10


<210> SEQ ID NO 39
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 39

Ser Trp Glu Xaa Xaa Thr Xaa Gln Thr Arg Leu
1               5                   10


<210> SEQ ID NO 40
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(6)
<223> OTHER INFORMATION: Xaa can be any naturally occurring amino acid

<400> SEQUENCE: 40

Ser Trp Glu Xaa Xaa Xaa Gly Gln Thr Arg Leu
1               5                   10


<210> SEQ ID NO 41
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(6)
<223> OTHER INFORMATION: Xaa can be any naturally occurring amino acid

<400> SEQUENCE: 41
```

```
Ser Trp Glu Xaa Xaa Xaa Gln Gln Thr Arg Leu
1               5                   10


<210> SEQ ID NO 42
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(7)
<223> OTHER INFORMATION: Xaa can be any naturally occurring amino acid

<400> SEQUENCE: 42

Ser Trp Glu Val His Xaa Xaa Gln Thr Arg Leu
1               5                   10


<210> SEQ ID NO 43
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(7)
<223> OTHER INFORMATION: Xaa can be any naturally occurring amino acid

<400> SEQUENCE: 43

Ser Trp Glu Val Ala Xaa Xaa Gln Thr Arg Leu
1               5                   10


<210> SEQ ID NO 44
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(7)
<223> OTHER INFORMATION: Xaa can be any naturally occurring amino acid

<400> SEQUENCE: 44

Ser Trp Glu Val Tyr Xaa Xaa Gln Thr Arg Leu
1               5                   10


<210> SEQ ID NO 45
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 45

Ser Trp Glu Val Xaa Gly Xaa Gln Thr Arg Leu
1               5                   10


<210> SEQ ID NO 46
<211> LENGTH: 11
```

<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(5)
<223> OTHER INFORMATION: Xaa can be any naturally occurring amino acid

<400> SEQUENCE: 46

Ser Trp Glu Val Xaa Thr Xaa Gln Thr Arg Leu
1 5 10

<210> SEQ ID NO 47
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(6)
<223> OTHER INFORMATION: Xaa can be any naturally occurring amino acid

<400> SEQUENCE: 47

Ser Trp Glu Val Xaa Xaa Gly Gln Thr Arg Leu
1 5 10

<210> SEQ ID NO 48
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(6)
<223> OTHER INFORMATION: Xaa can be any naturally occurring amino acid

<400> SEQUENCE: 48

Ser Trp Glu Val Xaa Xaa Gln Gln Thr Arg Leu
1 5 10

<210> SEQ ID NO 49
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)
<223> OTHER INFORMATION: Xaa can be any naturally occurring amino acid

<400> SEQUENCE: 49

Ser Trp Glu Val His Gly Xaa Gln Thr Arg Leu
1 5 10

<210> SEQ ID NO 50
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)

<223> OTHER INFORMATION: Xaa can be any naturally occurring amino acid

<400> SEQUENCE: 50

Ser Trp Glu Val His Thr Xaa Gln Thr Arg Leu
1 5 10

<210> SEQ ID NO 51
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)
<223> OTHER INFORMATION: Xaa can be any naturally occurring amino acid

<400> SEQUENCE: 51

Ser Trp Glu Val Ala Gly Xaa Gln Thr Arg Leu
1 5 10

<210> SEQ ID NO 52
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)
<223> OTHER INFORMATION: Xaa can be any naturally occurring amino acid

<400> SEQUENCE: 52

Ser Trp Glu Val Ala Thr Xaa Gln Thr Arg Leu
1 5 10

<210> SEQ ID NO 53
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)
<223> OTHER INFORMATION: Xaa can be any naturally occurring amino acid

<400> SEQUENCE: 53

Ser Trp Glu Val Tyr Gly Xaa Gln Thr Arg Leu
1 5 10

<210> SEQ ID NO 54
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Ser Trp Glu Val Tyr Thr Xaa Gln Thr Arg Leu
1 5 10

<210> SEQ ID NO 55
<211> LENGTH: 11
<212> TYPE: PRT

<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 55

Ser Trp Glu Val His Xaa Gly Gln Thr Arg Leu
1 5 10

<210> SEQ ID NO 56
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 56

Ser Trp Glu Val His Xaa Gln Gln Thr Arg Leu
1 5 10

<210> SEQ ID NO 57
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 57

Ser Trp Glu Val Ala Xaa Gly Gln Thr Arg Leu
1 5 10

<210> SEQ ID NO 58
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 58

Ser Trp Glu Val Ala Xaa Gln Gln Thr Arg Leu
1 5 10

<210> SEQ ID NO 59
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 59

Ser Trp Glu Val Tyr Xaa Gly Gln Thr Arg Leu

```
1               5                   10


<210> SEQ ID NO 60
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (6)..(6)
<223> OTHER INFORMATION: Xaa can be any naturally occurring amino acid

<400> SEQUENCE: 60

Ser Trp Glu Val Tyr Xaa Gln Gln Thr Arg Leu
1               5                   10


<210> SEQ ID NO 61
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is E or A
<220> FEATURE:
<221> NAME/KEY: misc_feature
<222> LOCATION: (4)..(4)
<223> OTHER INFORMATION: Xaa is S, E or V
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(6)
<223> OTHER INFORMATION: Xaa is G or T
<220> FEATURE:
<221> NAME/KEY: misc_feature
<222> LOCATION: (7)..(7)
<223> OTHER INFORMATION: Xaa is G or Q

<400> SEQUENCE: 61

Ser Trp Xaa Xaa Xaa Xaa Xaa Gln Thr Arg Leu
1               5                   10


<210> SEQ ID NO 62
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (4)..(4)
<223> OTHER INFORMATION: Xaa is S, E or V
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(6)
<223> OTHER INFORMATION: Xaa is G or T
<220> FEATURE:
<221> NAME/KEY: misc_feature
<222> LOCATION: (7)..(7)
<223> OTHER INFORMATION: Xaa is G or Q

<400> SEQUENCE: 62

Ser Trp Glu Xaa Xaa Xaa Xaa Gln Thr Arg Leu
```

1 5 10

<210> SEQ ID NO 63
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(6)
<223> OTHER INFORMATION: Xaa is G or T
<220> FEATURE:
<221> NAME/KEY: misc_feature
<222> LOCATION: (7)..(7)
<223> OTHER INFORMATION: Xaa is G or Q

<400> SEQUENCE: 63

Ser Trp Glu Val Xaa Xaa Xaa Gln Thr Arg Leu
1 5 10

<210> SEQ ID NO 64
<211> LENGTH: 11
<212> TYPE: PRT
<213> ORGANISM: Artificial Sequence
<220> FEATURE:
<223> OTHER INFORMATION: Neurovita2 MAST-2 binding domain

<400> SEQUENCE: 64

Ser Trp Glu Val His Gly Gly Gln Thr Arg Leu
1 5 10

<210> SEQ ID NO 65
<211> LENGTH: 11
<212> TYPE: PRT
<213> ORGANISM: Artificial Sequence
<220> FEATURE:
<223> OTHER INFORMATION: Neurovita3 (454) MAST-2 binding domain

<400> SEQUENCE: 65

Ser Trp Glu Val His Gly Gln Gln Thr Arg Leu
1 5 10

<210> SEQ ID NO 66
<211> LENGTH: 11
<212> TYPE: PRT
<213> ORGANISM: Artificial Sequence
<220> FEATURE:
<223> OTHER INFORMATION: 455 MAST-2 binding domain

<400> SEQUENCE: 66

Ser Trp Glu Val His Thr Gly Gln Thr Arg Leu
1 5 10

<210> SEQ ID NO 67
<211> LENGTH: 11
<212> TYPE: PRT
<213> ORGANISM: Artificial Sequence
<220> FEATURE:
<223> OTHER INFORMATION: 439 MAST-2 binding domain

<400> SEQUENCE: 67

Ser Trp Glu Val His Thr Gln Gln Thr Arg Leu
1 5 10

<210> SEQ ID NO 68
<211> LENGTH: 11
<212> TYPE: PRT
<213> ORGANISM: Artificial Sequence
<220> FEATURE:
<223> OTHER INFORMATION: 460 MAST-2 binding domain

<400> SEQUENCE: 68

Ser Trp Glu Val Ala Gly Gly Gln Thr Arg Leu
1 5 10

<210> SEQ ID NO 69
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 69

Ser Trp Glu Val Ala Gly Gln Gln Thr Arg Leu
1 5 10

<210> SEQ ID NO 70
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 70

Ser Trp Glu Val Ala Thr Gly Gln Thr Arg Leu
1 5 10

<210> SEQ ID NO 71
<211> LENGTH: 11
<212> TYPE: PRT
<213> ORGANISM: Artificial Sequence
<220> FEATURE:
<223> OTHER INFORMATION: 461 MAST-2 binding domain

<400> SEQUENCE: 71

Ser Trp Glu Val Ala Thr Gln Gln Thr Arg Leu
1 5 10

<210> SEQ ID NO 72
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 72

Ser Trp Glu Val Tyr Gly Gly Gln Thr Arg Leu
1 5 10

<210> SEQ ID NO 73
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 73

Ser Trp Glu Val Tyr Gly Gln Gln Thr Arg Leu
1 5 10

```
<210> SEQ ID NO 74
<211> LENGTH: 11
<212> TYPE: PRT
<213> ORGANISM: Artificial Sequence
<220> FEATURE:
<223> OTHER INFORMATION: 453 MAST-2 binding domain

<400> SEQUENCE: 74

Ser Trp Glu Val Tyr Thr Gly Gln Thr Arg Leu
1               5                   10


<210> SEQ ID NO 75
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 75

Ser Trp Glu Val Tyr Thr Gln Gln Thr Arg Leu
1               5                   10


<210> SEQ ID NO 76
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 76

Ser Trp Xaa Lys Ser Gly Gly Gln Thr Arg Leu
1               5                   10


<210> SEQ ID NO 77
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 77

Ser Trp Xaa Ser Ser Gly Gly Gln Thr Arg Leu
1               5                   10


<210> SEQ ID NO 78
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 78

Ser Trp Xaa Ser His Gly Gly Gln Thr Arg Leu
1               5                   10


<210> SEQ ID NO 79
<211> LENGTH: 11
```

<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 79

Ser Trp Xaa Ser His Lys Gly Gln Thr Arg Leu
1 5 10

<210> SEQ ID NO 80
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid preferably E or A

<400> SEQUENCE: 80

Ser Trp Xaa Ser His Lys Ser Gln Thr Arg Leu
1 5 10

<210> SEQ ID NO 81
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 81

Ser Trp Glu Lys Ser Gly Gly Gln Thr Arg Leu
1 5 10

<210> SEQ ID NO 82
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 82

Ser Trp Glu Ser Ser Gly Gly Gln Thr Arg Leu
1 5 10

<210> SEQ ID NO 83
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 83

Ser Trp Glu Ser His Gly Gly Gln Thr Arg Leu
1 5 10

<210> SEQ ID NO 84
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 84

```
Ser Trp Glu Ser His Lys Gly Gln Thr Arg Leu
1               5                   10


<210> SEQ ID NO 85
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 85

Ser Trp Glu Ser His Lys Ser Gln Thr Arg Leu
1               5                   10


<210> SEQ ID NO 86
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 86

Ser Trp Xaa His Ser Gly Gly Gln Thr Arg Leu
1               5                   10


<210> SEQ ID NO 87
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 87

Ser Trp Xaa His Lys Gly Gly Gln Thr Arg Leu
1               5                   10


<210> SEQ ID NO 88
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 88

Ser Trp Xaa His Lys Ser Gly Gln Thr Arg Leu
1               5                   10


<210> SEQ ID NO 89
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A
```

<400> SEQUENCE: 89

Ser Trp Xaa Ser Lys Gly Gly Gln Thr Arg Leu
1 5 10

<210> SEQ ID NO 90
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 90

Ser Trp Xaa Ser Lys Ser Gly Gln Thr Arg Leu
1 5 10

<210> SEQ ID NO 91
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 91

Ser Trp Xaa Ser His Ser Gly Gln Thr Arg Leu
1 5 10

<210> SEQ ID NO 92
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 92

Ser Trp Xaa Ser His Lys Gly Gln Thr Arg Leu
1 5 10

<210> SEQ ID NO 93
<211> LENGTH: 11
<212> TYPE: PRT
<213> ORGANISM: Artificial Sequence
<220> FEATURE:
<223> OTHER INFORMATION: 11 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 93

Ser Trp Xaa Ser Lys Gly Gly Gln Thr Arg Leu
1 5 10

<210> SEQ ID NO 94
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 94

Ser Trp Glu His Ser Gly Gly Gln Thr Arg Leu
1               5                   10

<210> SEQ ID NO 95
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 95

Ser Trp Glu His Lys Gly Gly Gln Thr Arg Leu
1               5                   10

<210> SEQ ID NO 96
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 96

Ser Trp Glu His Lys Ser Gly Gln Thr Arg Leu
1               5                   10

<210> SEQ ID NO 97
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 97

Ser Trp Glu Ser Lys Gly Gly Gln Thr Arg Leu
1               5                   10

<210> SEQ ID NO 98
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 98

Ser Trp Glu Ser Lys Ser Gly Gln Thr Arg Leu
1               5                   10

<210> SEQ ID NO 99
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 99

Ser Trp Glu Ser His Ser Gly Gln Thr Arg Leu
1               5                   10

<210> SEQ ID NO 100
<211> LENGTH: 11
<212> TYPE: PRT
<213> ORGANISM: Artificial Sequence
<220> FEATURE:

<223> OTHER INFORMATION: 11 residue MAST-2 binding domain

<400> SEQUENCE: 100

```
Ser Trp Glu Ser His Lys Gly Gln Thr Arg Leu
1               5                   10
```

<210> SEQ ID NO 101
<211> LENGTH: 11
<212> TYPE: PRT
<213> ORGANISM: Artificial Sequence
<220> FEATURE:
<223> OTHER INFORMATION: 11 residue MAST-2 binding domain

<400> SEQUENCE: 101

```
Ser Trp Glu Ser Lys Gly Gly Gln Thr Arg Leu
1               5                   10
```

<210> SEQ ID NO 102
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 102

```
Ser Trp Xaa His Lys Ser Gly Gly Gln Thr Arg Leu
1               5                   10
```

<210> SEQ ID NO 103
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 103

```
Ser Trp Xaa Ser Lys Ser Gly Gly Gln Thr Arg Leu
1               5                   10
```

<210> SEQ ID NO 104
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 104

```
Ser Trp Xaa Ser His Ser Gly Gly Gln Thr Arg Leu
1               5                   10
```

<210> SEQ ID NO 105
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:

<221> NAME/KEY: misc_feature
<222> LOCATION: (3)..(3)
<223> OTHER INFORMATION: Xaa is any amino acid, preferably E or A

<400> SEQUENCE: 105

Ser Trp Xaa Ser His Lys Gly Gly Gln Thr Arg Leu
1 5 10

<210> SEQ ID NO 106
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa is any amino acid, preferably E or A

<400> SEQUENCE: 106

Ser Trp Xaa Ser His Lys Ser Gly Gln Thr Arg Leu
1 5 10

<210> SEQ ID NO 107
<211> LENGTH: 12
<212> TYPE: PRT
<213> ORGANISM: Artificial Sequence
<220> FEATURE:
<223> OTHER INFORMATION: 12 residue MAST-2 binding domain

<400> SEQUENCE: 107

Ser Trp Glu His Lys Ser Gly Gly Gln Thr Arg Leu
1 5 10

<210> SEQ ID NO 108
<211> LENGTH: 12
<212> TYPE: PRT
<213> ORGANISM: Artificial Sequence
<220> FEATURE:
<223> OTHER INFORMATION: 12 residue MAST-2 binding domain

<400> SEQUENCE: 108

Ser Trp Glu Ser Lys Ser Gly Gly Gln Thr Arg Leu
1 5 10

<210> SEQ ID NO 109
<211> LENGTH: 12
<212> TYPE: PRT
<213> ORGANISM: Artificial Sequence
<220> FEATURE:
<223> OTHER INFORMATION: 12 residue MAST-2 binding domain

<400> SEQUENCE: 109

Ser Trp Glu Ser His Ser Gly Gly Gln Thr Arg Leu
1 5 10

<210> SEQ ID NO 110
<211> LENGTH: 12
<212> TYPE: PRT
<213> ORGANISM: Artificial Sequence
<220> FEATURE:
<223> OTHER INFORMATION: 12 residue MAST-2 binding domain

<400> SEQUENCE: 110

Ser Trp Glu Ser His Lys Gly Gly Gln Thr Arg Leu
1 5 10

<210> SEQ ID NO 111
<211> LENGTH: 12
<212> TYPE: PRT
<213> ORGANISM: Artificial Sequence
<220> FEATURE:
<223> OTHER INFORMATION: 12 residue MAST-2 binding domain

<400> SEQUENCE: 111

Ser Trp Glu Ser His Lys Ser Gly Gln Thr Arg Leu
1               5                   10

<210> SEQ ID NO 112
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(8)
<223> OTHER INFORMATION: Xaa can be any naturally occurring amino acid

<400> SEQUENCE: 112

Ser Trp Xaa Xaa Xaa Xaa Xaa Xaa Gln Thr Arg Leu
1               5                   10

<210> SEQ ID NO 113
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(8)
<223> OTHER INFORMATION: Xaa can be any naturally occurring amino acid

<400> SEQUENCE: 113

Ser Trp Glu Xaa Xaa Xaa Xaa Xaa Gln Thr Arg Leu
1               5                   10

<210> SEQ ID NO 114
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(8)
<223> OTHER INFORMATION: Xaa can be any naturally occurring amino acid

<400> SEQUENCE: 114

Ser Trp Ala Xaa Xaa Xaa Xaa Xaa Gln Thr Arg Leu
1               5                   10

<210> SEQ ID NO 115
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(8)
<223> OTHER INFORMATION: Xaa can be any naturally occurring amino acid

<400> SEQUENCE: 115

Ser Trp Val Xaa Xaa Xaa Xaa Xaa Gln Thr Arg Leu
1               5                   10

<210> SEQ ID NO 116
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(8)
<223> OTHER INFORMATION: Xaa can be any naturally occurring amino acid

<400> SEQUENCE: 116

Ser Trp Ser Xaa Xaa Xaa Xaa Xaa Gln Thr Arg Leu
1               5                   10

<210> SEQ ID NO 117
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 117

Ser Trp Xaa Ser Xaa Xaa Xaa Xaa Gln Thr Arg Leu
1               5                   10

<210> SEQ ID NO 118
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 118

Ser Trp Xaa Val Xaa Xaa Xaa Xaa Gln Thr Arg Leu
1               5                   10

<210> SEQ ID NO 119
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 119

Ser Trp Xaa His Xaa Xaa Xaa Xaa Gln Thr Arg Leu 1 5 10

<210> SEQ ID NO 120
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 120

Ser Trp Xaa Ala Xaa Xaa Xaa Xaa Gln Thr Arg Leu
1 5 10

<210> SEQ ID NO 121
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid

<400> SEQUENCE: 121

Ser Trp Xaa Tyr Xaa Xaa Xaa Xaa Gln Thr Arg Leu
1 5 10

<210> SEQ ID NO 122
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 122

Ser Trp Xaa Xaa His Xaa Xaa Xaa Gln Thr Arg Leu
1 5 10

<210> SEQ ID NO 123
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)

<223> OTHER INFORMATION: Xaa can be any naturally occurring amino acid

<400> SEQUENCE: 123

Ser Trp Xaa Xaa Ala Xaa Xaa Xaa Gln Thr Arg Leu
1 5 10

<210> SEQ ID NO 124
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 124

Ser Trp Xaa Xaa Tyr Xaa Xaa Xaa Gln Thr Arg Leu
1 5 10

<210> SEQ ID NO 125
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 125

Ser Trp Xaa Xaa Lys Xaa Xaa Xaa Gln Thr Arg Leu
1 5 10

<210> SEQ ID NO 126
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 126

Ser Trp Xaa Xaa Gln Xaa Xaa Xaa Gln Thr Arg Leu
1 5 10

<210> SEQ ID NO 127
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 127

Ser Trp Xaa Xaa Xaa Lys Xaa Xaa Gln Thr Arg Leu
1 5 10

<210> SEQ ID NO 128
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 128

Ser Trp Xaa Xaa Xaa Ala Xaa Xaa Gln Thr Arg Leu
1 5 10

<210> SEQ ID NO 129
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 129

Ser Trp Xaa Xaa Xaa Gln Xaa Xaa Gln Thr Arg Leu
1 5 10

<210> SEQ ID NO 130
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 130

Ser Trp Xaa Xaa Xaa Ser Xaa Xaa Gln Thr Arg Leu
1 5 10

<210> SEQ ID NO 131
<211> LENGTH: 12
<212> TYPE: PRT

<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 131

Ser Trp Xaa Xaa Xaa His Xaa Xaa Gln Thr Arg Leu
1               5                   10

<210> SEQ ID NO 132
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 132

Ser Trp Xaa Xaa Xaa Xaa Ser Xaa Gln Thr Arg Leu
1               5                   10

<210> SEQ ID NO 133
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 133

Ser Trp Xaa Xaa Xaa Xaa His Xaa Gln Thr Arg Leu
1               5                   10

<210> SEQ ID NO 134
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 134

Ser Trp Xaa Xaa Xaa Xaa Gly Xaa Gln Thr Arg Leu
1               5                   10

<210> SEQ ID NO 135
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 135

Ser Trp Xaa Xaa Xaa Xaa Thr Xaa Gln Thr Arg Leu
1               5                   10

<210> SEQ ID NO 136
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(7)
<223> OTHER INFORMATION: Xaa can be any naturally occurring amino acid

<400> SEQUENCE: 136

Ser Trp Xaa Xaa Xaa Xaa Xaa Gly Gln Thr Arg Leu
1               5                   10

<210> SEQ ID NO 137
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(7)
<223> OTHER INFORMATION: Xaa can be any naturally occurring amino acid

<400> SEQUENCE: 137

Ser Trp Xaa Xaa Xaa Xaa Xaa Thr Gln Thr Arg Leu
1               5                   10

<210> SEQ ID NO 138
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(7)
<223> OTHER INFORMATION: Xaa can be any naturally occurring amino acid

<400> SEQUENCE: 138

Ser Trp Xaa Xaa Xaa Xaa Xaa Gln Gln Thr Arg Leu
1               5                   10

<210> SEQ ID NO 139
<211> LENGTH: 12
<212> TYPE: PRT
<213> ORGANISM: Artificial Sequence
<220> FEATURE:

<223> OTHER INFORMATION: 12 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 139

Ser Trp Glu Xaa His Xaa Xaa Xaa Gln Thr Arg Leu
1               5                   10

<210> SEQ ID NO 140
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 140

Ser Trp Xaa Val His Xaa Xaa Xaa Gln Thr Arg Leu
1               5                   10

<210> SEQ ID NO 141
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (6)..(8)
<223> OTHER INFORMATION: Xaa can be any naturally occurring amino acid

<400> SEQUENCE: 141

Ser Trp Glu Val His Xaa Xaa Xaa Gln Thr Arg Leu
1               5                   10

<210> SEQ ID NO 142
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 142

Ser Trp Glu Xaa Ala Xaa Xaa Xaa Gln Thr Arg Leu
1               5                   10

<210> SEQ ID NO 143
<211> LENGTH: 12
<212> TYPE: PRT
<213> ORGANISM: Artificial Sequence

```
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 143

Ser Trp Xaa Val Ala Xaa Xaa Xaa Gln Thr Arg Leu
1               5                   10


<210> SEQ ID NO 144
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (6)..(8)
<223> OTHER INFORMATION: Xaa can be any naturally occurring amino acid

<400> SEQUENCE: 144

Ser Trp Glu Val Ala Xaa Xaa Xaa Gln Thr Arg Leu
1               5                   10


<210> SEQ ID NO 145
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 145

Ser Trp Glu Xaa Tyr Xaa Xaa Xaa Gln Thr Arg Leu
1               5                   10


<210> SEQ ID NO 146
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 146

Ser Trp Xaa Val Tyr Xaa Xaa Xaa Gln Thr Arg Leu
1               5                   10


<210> SEQ ID NO 147
<211> LENGTH: 12
<212> TYPE: PRT
```

<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (6)..(8)
<223> OTHER INFORMATION: Xaa can be any naturally occurring amino acid

<400> SEQUENCE: 147

Ser Trp Glu Val Tyr Xaa Xaa Xaa Gln Thr Arg Leu
1               5                   10

<210> SEQ ID NO 148
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 148

Ser Trp Glu Xaa Lys Xaa Xaa Xaa Gln Thr Arg Leu
1               5                   10

<210> SEQ ID NO 149
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 149

Ser Trp Xaa Val Lys Xaa Xaa Xaa Gln Thr Arg Leu
1               5                   10

<210> SEQ ID NO 150
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (6)..(8)
<223> OTHER INFORMATION: Xaa can be any naturally occurring amino acid

<400> SEQUENCE: 150

Ser Trp Glu Val Lys Xaa Xaa Xaa Gln Thr Arg Leu
1               5                   10

<210> SEQ ID NO 151
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 151

Ser Trp Glu Xaa Gln Xaa Xaa Xaa Gln Thr Arg Leu
1 5 10

<210> SEQ ID NO 152
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 152

Ser Trp Xaa Val Gln Xaa Xaa Xaa Gln Thr Arg Leu
1 5 10

<210> SEQ ID NO 153
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (6)..(8)
<223> OTHER INFORMATION: Xaa can be any naturally occurring amino acid

<400> SEQUENCE: 153

Ser Trp Glu Val Gln Xaa Xaa Xaa Gln Thr Arg Leu
1 5 10

<210> SEQ ID NO 154
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 154

Ser Trp Glu Xaa Xaa Lys Xaa Xaa Gln Thr Arg Leu
1 5 10

<210> SEQ ID NO 155
<211> LENGTH: 12
<212> TYPE: PRT
<213> ORGANISM: Artificial Sequence
<220> FEATURE:

<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 155

Ser Trp Xaa Val Xaa Lys Xaa Xaa Gln Thr Arg Leu
1               5                   10

<210> SEQ ID NO 156
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 156

Ser Trp Glu Val Xaa Lys Xaa Xaa Gln Thr Arg Leu
1               5                   10

<210> SEQ ID NO 157
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 157

Ser Trp Glu Xaa Xaa Ala Xaa Xaa Gln Thr Arg Leu
1               5                   10

<210> SEQ ID NO 158
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)

<223> OTHER INFORMATION: Xaa can be any naturally occurring amino acid

<400> SEQUENCE: 158

Ser Trp Xaa Val Xaa Ala Xaa Xaa Gln Thr Arg Leu
1 5 10

<210> SEQ ID NO 159
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 159

Ser Trp Glu Val Xaa Ala Xaa Xaa Gln Thr Arg Leu
1 5 10

<210> SEQ ID NO 160
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 160

Ser Trp Glu Xaa Xaa Gln Xaa Xaa Gln Thr Arg Leu
1 5 10

<210> SEQ ID NO 161
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 161

Ser Trp Xaa Val Xaa Gln Xaa Xaa Gln Thr Arg Leu
1 5 10

<210> SEQ ID NO 162
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 162

Ser Trp Glu Val Xaa Gln Xaa Xaa Gln Thr Arg Leu
1 5 10

<210> SEQ ID NO 163
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 163

Ser Trp Glu Xaa Xaa Ser Xaa Xaa Gln Thr Arg Leu
1 5 10

<210> SEQ ID NO 164
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 164

Ser Trp Xaa Val Xaa Ser Xaa Xaa Gln Thr Arg Leu
1 5 10

<210> SEQ ID NO 165
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 165

Ser Trp Glu Val Xaa Ser Xaa Xaa Gln Thr Arg Leu
1 5 10

<210> SEQ ID NO 166
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 166

Ser Trp Glu Xaa Xaa His Xaa Xaa Gln Thr Arg Leu
1 5 10

<210> SEQ ID NO 167
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 167

Ser Trp Xaa Val Xaa His Xaa Xaa Gln Thr Arg Leu
1 5 10

<210> SEQ ID NO 168
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 168

Ser Trp Glu Val Xaa His Xaa Xaa Gln Thr Arg Leu
1 5 10

<210> SEQ ID NO 169
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:

```
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 169

Ser Trp Glu Xaa Xaa Xaa Ser Xaa Gln Thr Arg Leu
1               5                   10


<210> SEQ ID NO 170
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 170

Ser Trp Xaa Val Xaa Xaa Ser Xaa Gln Thr Arg Leu
1               5                   10


<210> SEQ ID NO 171
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 171

Ser Trp Glu Val Xaa Xaa Ser Xaa Gln Thr Arg Leu
1               5                   10


<210> SEQ ID NO 172
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 172

Ser Trp Glu Xaa Xaa Xaa His Xaa Gln Thr Arg Leu
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 173

Ser Trp Xaa Val Xaa Xaa His Xaa Gln Thr Arg Leu
1 5 10

<210> SEQ ID NO 174
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 174

Ser Trp Glu Val Xaa Xaa His Xaa Gln Thr Arg Leu
1 5 10

<210> SEQ ID NO 175
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 175

Ser Trp Glu Xaa Xaa Xaa Gly Xaa Gln Thr Arg Leu
1 5 10

<210> SEQ ID NO 176
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid

```
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 176

Ser Trp Xaa Val Xaa Xaa Gly Xaa Gln Thr Arg Leu
1               5                   10


<210> SEQ ID NO 177
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 177

Ser Trp Glu Val Xaa Xaa Gly Xaa Gln Thr Arg Leu
1               5                   10


<210> SEQ ID NO 178
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 178

Ser Trp Glu Xaa Xaa Xaa Thr Xaa Gln Thr Arg Leu
1               5                   10


<210> SEQ ID NO 179
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 179

Ser Trp Xaa Val Xaa Xaa Thr Xaa Gln Thr Arg Leu
```

```
1               5                   10


<210> SEQ ID NO 180
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 180

Ser Trp Glu Val Xaa Xaa Thr Xaa Gln Thr Arg Leu
1               5                   10


<210> SEQ ID NO 181
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(7)
<223> OTHER INFORMATION: Xaa can be any naturally occurring amino acid

<400> SEQUENCE: 181

Ser Trp Glu Xaa Xaa Xaa Xaa Gly Gln Thr Arg Leu
1               5                   10


<210> SEQ ID NO 182
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 182

Ser Trp Xaa Val Xaa Xaa Xaa Gly Gln Thr Arg Leu
1               5                   10


<210> SEQ ID NO 183
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(7)
<223> OTHER INFORMATION: Xaa can be any naturally occurring amino acid

<400> SEQUENCE: 183

Ser Trp Glu Val Xaa Xaa Xaa Gly Gln Thr Arg Leu
1               5                   10
```

<210> SEQ ID NO 184
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(7)
<223> OTHER INFORMATION: Xaa can be any naturally occurring amino acid

<400> SEQUENCE: 184

Ser Trp Glu Xaa Xaa Xaa Xaa Thr Gln Thr Arg Leu
1 5 10

<210> SEQ ID NO 185
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 185

Ser Trp Xaa Val Xaa Xaa Xaa Thr Gln Thr Arg Leu
1 5 10

<210> SEQ ID NO 186
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(7)
<223> OTHER INFORMATION: Xaa can be any naturally occurring amino acid

<400> SEQUENCE: 186

Ser Trp Glu Val Xaa Xaa Xaa Thr Gln Thr Arg Leu
1 5 10

<210> SEQ ID NO 187
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (4)..(7)
<223> OTHER INFORMATION: Xaa can be any naturally occurring amino acid

<400> SEQUENCE: 187

Ser Trp Glu Xaa Xaa Xaa Xaa Gln Gln Thr Arg Leu
1 5 10

<210> SEQ ID NO 188
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:

```
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid

<400> SEQUENCE: 188

Ser Trp Xaa Val Xaa Xaa Xaa Gln Gln Thr Arg Leu
1               5                   10


<210> SEQ ID NO 189
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(7)
<223> OTHER INFORMATION: Xaa can be any naturally occurring amino acid

<400> SEQUENCE: 189

Ser Trp Glu Val Xaa Xaa Xaa Gln Gln Thr Arg Leu
1               5                   10


<210> SEQ ID NO 190
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (5)..(8)
<223> OTHER INFORMATION: Xaa can be any naturally occurring amino acid

<400> SEQUENCE: 190

Ser Trp Glu Val Xaa Xaa Xaa Xaa Gln Thr Arg Leu
1               5                   10


<210> SEQ ID NO 191
<211> LENGTH: 12
<212> TYPE: PRT
<213> ORGANISM: Artificial Sequence
<220> FEATURE:
<223> OTHER INFORMATION: 12 residue MAST-2 binding domain
<220> FEATURE:
<221> NAME/KEY: misc_feature
<222> LOCATION: (3)..(3)
<223> OTHER INFORMATION: Xaa is E, A, V or S
<220> FEATURE:
<221> NAME/KEY: misc_feature
<222> LOCATION: (4)..(4)
<223> OTHER INFORMATION: Xaa is S, V, H, A or Y
<220> FEATURE:
<221> NAME/KEY: misc_feature
<222> LOCATION: (5)..(5)
<223> OTHER INFORMATION: Xaa is H, A, Y, K or Q
<220> FEATURE:
<221> NAME/KEY: misc_feature
<222> LOCATION: (6)..(6)
<223> OTHER INFORMATION: Xaa is K, A, Q, S or H
<220> FEATURE:
<221> NAME/KEY: misc_feature
<222> LOCATION: (7)..(7)
<223> OTHER INFORMATION: Xaa is S, H, G or T
<220> FEATURE:
<221> NAME/KEY: misc_feature
<222> LOCATION: (8)..(8)
<223> OTHER INFORMATION: Xaa is G, T or Q
```

<400> SEQUENCE: 191

```
Ser Trp Xaa Xaa Xaa Xaa Xaa Xaa Gln Thr Arg Leu
1               5                   10
```

<210> SEQ ID NO 192
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(9)
<223> OTHER INFORMATION: Xaa can be any naturally occurring amino acid

<400> SEQUENCE: 192

```
Ser Trp Xaa Xaa Xaa Xaa Xaa Xaa Xaa Gln Thr Arg Leu
1               5                   10
```

<210> SEQ ID NO 193
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(3)
<223> OTHER INFORMATION: Xaa is E or A
<220> FEATURE:
<221> NAME/KEY: misc_feature
<222> LOCATION: (4)..(9)
<223> OTHER INFORMATION: Xaa can be any naturally occurring amino acid

<400> SEQUENCE: 193

```
Ser Trp Xaa Xaa Xaa Xaa Xaa Xaa Xaa Gln Thr Arg Leu
1               5                   10
```

<210> SEQ ID NO 194
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is selected from polar neutral residues, negatively charged residues or hydrophobic residues
<220> FEATURE:
<221> NAME/KEY: misc_feature
<222> LOCATION: (5)..(9)
<223> OTHER INFORMATION: Xaa can be any naturally occurring amino acid

<400> SEQUENCE: 194

```
Ser Trp Xaa Xaa Xaa Xaa Xaa Xaa Xaa Gln Thr Arg Leu
1               5                   10
```

<210> SEQ ID NO 195
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(3)

```
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa is S, V or E
<220> FEATURE:
<221> NAME/KEY: misc_feature
<222> LOCATION: (5)..(9)
<223> OTHER INFORMATION: Xaa can be any naturally occurring amino acid

<400> SEQUENCE: 195

Ser Trp Xaa Xaa Xaa Xaa Xaa Xaa Xaa Gln Thr Arg Leu
1               5                   10


<210> SEQ ID NO 196
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is selected from positively charged
      residues, non polar residues with small volume and polar aromatic
      residues
<220> FEATURE:
<221> NAME/KEY: misc_feature
<222> LOCATION: (6)..(9)
<223> OTHER INFORMATION: Xaa can be any naturally occurring amino acid

<400> SEQUENCE: 196

Ser Trp Xaa Xaa Xaa Xaa Xaa Xaa Xaa Gln Thr Arg Leu
1               5                   10


<210> SEQ ID NO 197
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(9)
<223> OTHER INFORMATION: Xaa can be any naturally occurring amino acid

<400> SEQUENCE: 197

Ser Trp Xaa Xaa Xaa Xaa Xaa Xaa Xaa Gln Thr Arg Leu
1               5                   10


<210> SEQ ID NO 198
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
```

<221> NAME/KEY: misc_feature
<222> LOCATION: (6)..(6)
<223> OTHER INFORMATION: Xaa is selected from non polar residues with small volume, polar neutral residues and positively charged residues
<220> FEATURE:
<221> NAME/KEY: misc_feature
<222> LOCATION: (7)..(9)
<223> OTHER INFORMATION: Xaa can be any naturally occurring amino acid

<400> SEQUENCE: 198

```
Ser Trp Xaa Xaa Xaa Xaa Xaa Xaa Xaa Gln Thr Arg Leu
1               5                   10
```

<210> SEQ ID NO 199
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is K, A or Q
<220> FEATURE:
<221> NAME/KEY: misc_feature
<222> LOCATION: (7)..(9)
<223> OTHER INFORMATION: Xaa can be any naturally occurring amino acid

<400> SEQUENCE: 199

```
Ser Trp Xaa Xaa Xaa Xaa Xaa Xaa Xaa Gln Thr Arg Leu
1               5                   10
```

<210> SEQ ID NO 200
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is selected from polar neutral residues and positively charged residues
<220> FEATURE:
<221> NAME/KEY: misc_feature
<222> LOCATION: (8)..(9)
<223> OTHER INFORMATION: Xaa can be any naturally occurring amino acid

<400> SEQUENCE: 200

```
Ser Trp Xaa Xaa Xaa Xaa Xaa Xaa Xaa Gln Thr Arg Leu
1               5                   10
```

<210> SEQ ID NO 201
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(6)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa is S or H
<220> FEATURE:
<221> NAME/KEY: misc_feature
<222> LOCATION: (8)..(9)
<223> OTHER INFORMATION: Xaa can be any naturally occurring amino acid

<400> SEQUENCE: 201

Ser Trp Xaa Xaa Xaa Xaa Xaa Xaa Xaa Gln Thr Arg Leu
1 5 10

<210> SEQ ID NO 202
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is selected from non polar residues with small volume, preferably flexible, and polar neutral residues
<220> FEATURE:
<221> NAME/KEY: misc_feature
<222> LOCATION: (9)..(9)
<223> OTHER INFORMATION: Xaa can be any naturally occurring amino acid

<400> SEQUENCE: 202

Ser Trp Xaa Xaa Xaa Xaa Xaa Xaa Xaa Gln Thr Arg Leu
1 5 10

<210> SEQ ID NO 203
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa is G or T
<220> FEATURE:
<221> NAME/KEY: misc_feature
<222> LOCATION: (9)..(9)
<223> OTHER INFORMATION: Xaa can be any naturally occurring amino acid

<400> SEQUENCE: 203

Ser Trp Xaa Xaa Xaa Xaa Xaa Xaa Xaa Gln Thr Arg Leu
1 5 10

<210> SEQ ID NO 204
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is selected from non polar residues with small volume, preferably flexible, and polar neutral residues

<400> SEQUENCE: 204

Ser Trp Xaa Xaa Xaa Xaa Xaa Xaa Xaa Gln Thr Arg Leu
1 5 10

<210> SEQ ID NO 205
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa is G or Q

<400> SEQUENCE: 205

Ser Trp Xaa Xaa Xaa Xaa Xaa Xaa Xaa Gln Thr Arg Leu
1 5 10

<210> SEQ ID NO 206
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(3)
<223> OTHER INFORMATION: Xaa is E or A
<220> FEATURE:
<221> NAME/KEY: misc_feature
<222> LOCATION: (4)..(4)
<223> OTHER INFORMATION: Xaa is S, V or E
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(6)
<223> OTHER INFORMATION: Xaa is K, A or Q
<220> FEATURE:
<221> NAME/KEY: misc_feature
<222> LOCATION: (7)..(7)
<223> OTHER INFORMATION: Xaa is S or H
<220> FEATURE:
<221> NAME/KEY: misc_feature
<222> LOCATION: (8)..(8)
<223> OTHER INFORMATION: Xaa is G or T
<220> FEATURE:
<221> NAME/KEY: misc_feature
<222> LOCATION: (9)..(9)
<223> OTHER INFORMATION: Xaa is G or Q

<400> SEQUENCE: 206

Ser Trp Xaa Xaa Xaa Xaa Xaa Xaa Xaa Gln Thr Arg Leu
1 5 10

<210> SEQ ID NO 207
<211> LENGTH: 13
<212> TYPE: PRT
<213> ORGANISM: Artificial Sequence
<220> FEATURE:
<223> OTHER INFORMATION: 13 residue MAST-2 binding domain
<220> FEATURE:
<221> NAME/KEY: misc_feature
<222> LOCATION: (3)..(3)
<223> OTHER INFORMATION: Xaa is E or A

```
<220> FEATURE:
<221> NAME/KEY: misc_feature
<222> LOCATION: (4)..(4)
<223> OTHER INFORMATION: Xaa is V or E
<220> FEATURE:
<221> NAME/KEY: misc_feature
<222> LOCATION: (5)..(5)
<223> OTHER INFORMATION: Xaa is H, A or Y
<220> FEATURE:
<221> NAME/KEY: misc_feature
<222> LOCATION: (6)..(6)
<223> OTHER INFORMATION: Xaa is K, A or Q
<220> FEATURE:
<221> NAME/KEY: misc_feature
<222> LOCATION: (7)..(7)
<223> OTHER INFORMATION: Xaa is S or H
<220> FEATURE:
<221> NAME/KEY: misc_feature
<222> LOCATION: (8)..(8)
<223> OTHER INFORMATION: Xaa is G or T
<220> FEATURE:
<221> NAME/KEY: misc_feature
<222> LOCATION: (9)..(9)
<223> OTHER INFORMATION: Xaa is G or Q

<400> SEQUENCE: 207

Ser Trp Xaa Xaa Xaa Xaa Xaa Xaa Xaa Gln Thr Arg Leu
1               5                   10


<210> SEQ ID NO 208
<211> LENGTH: 13
<212> TYPE: PRT
<213> ORGANISM: Artificial Sequence
<220> FEATURE:
<223> OTHER INFORMATION: 443 MAST-2 binding domain

<400> SEQUENCE: 208

Ser Trp Ala Glu Ala Gln His Thr Gln Gln Thr Arg Leu
1               5                   10


<210> SEQ ID NO 209
<211> LENGTH: 13
<212> TYPE: PRT
<213> ORGANISM: Artificial Sequence
<220> FEATURE:
<223> OTHER INFORMATION: 442 MAST-2 binding domain

<400> SEQUENCE: 209

Ser Trp Glu Val His Ala Ser Gly Gly Gln Thr Arg Leu
1               5                   10


<210> SEQ ID NO 210
<211> LENGTH: 85
<212> TYPE: PRT
<213> ORGANISM: Artificial Sequence
<220> FEATURE:
<223> OTHER INFORMATION: Neurovita2 (441) polypeptide

<400> SEQUENCE: 210

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val His Gly
```

```
65                  70                  75                  80

Gly Gln Thr Arg Leu
                85


<210> SEQ ID NO 211
<211> LENGTH: 85
<212> TYPE: PRT
<213> ORGANISM: Artificial Sequence
<220> FEATURE:
<223> OTHER INFORMATION: Neurovita3 (454) polypeptide

<400> SEQUENCE: 211

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val His Gly
65                  70                  75                  80

Gln Gln Thr Arg Leu
                85


<210> SEQ ID NO 212
<211> LENGTH: 85
<212> TYPE: PRT
<213> ORGANISM: Artificial Sequence
<220> FEATURE:
<223> OTHER INFORMATION: 461 polypeptide

<400> SEQUENCE: 212

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val Ala Thr
65                  70                  75                  80

Gln Gln Thr Arg Leu
                85


<210> SEQ ID NO 213
<211> LENGTH: 85
<212> TYPE: PRT
<213> ORGANISM: Artificial Sequence
<220> FEATURE:
<223> OTHER INFORMATION: 453 polypeptide

<400> SEQUENCE: 213

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45
```

```
Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val Tyr Thr
65                  70                  75                  80

Gly Gln Thr Arg Leu
                85
```

<210> SEQ ID NO 214
<211> LENGTH: 85
<212> TYPE: PRT
<213> ORGANISM: Artificial Sequence
<220> FEATURE:
<223> OTHER INFORMATION: 455 polypeptide

<400> SEQUENCE: 214

```
Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val His Thr
65                  70                  75                  80

Gly Gln Thr Arg Leu
                85
```

<210> SEQ ID NO 215
<211> LENGTH: 85
<212> TYPE: PRT
<213> ORGANISM: Artificial Sequence
<220> FEATURE:
<223> OTHER INFORMATION: 439 polypeptide

<400> SEQUENCE: 215

```
Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val His Thr
65                  70                  75                  80

Gln Gln Thr Arg Leu
                85
```

<210> SEQ ID NO 216
<211> LENGTH: 85
<212> TYPE: PRT
<213> ORGANISM: Artificial Sequence
<220> FEATURE:
<223> OTHER INFORMATION: 460 polypeptide

<400> SEQUENCE: 216

```
Met Val Pro Gln Ala Leu Leu Phe Val Pro Leu Leu Val Phe Pro Leu
1               5                   10                  15
```

```
Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val Ala Gly
65                  70                  75                  80

Gly Gln Thr Arg Leu
                85


<210> SEQ ID NO 217
<211> LENGTH: 87
<212> TYPE: PRT
<213> ORGANISM: Artificial Sequence
<220> FEATURE:
<223> OTHER INFORMATION: 443 polypeptide

<400> SEQUENCE: 217

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Ala Glu Ala Gln
65                  70                  75                  80

His Thr Gln Gln Thr Arg Leu
                85


<210> SEQ ID NO 218
<211> LENGTH: 87
<212> TYPE: PRT
<213> ORGANISM: Artificial Sequence
<220> FEATURE:
<223> OTHER INFORMATION: 442 polypeptide

<400> SEQUENCE: 218

Met Val Pro Gln Ala Leu Leu Phe Val Pro Leu Leu Val Phe Pro Leu
1               5                   10                  15

Cys Phe Gly Gly Lys Tyr Val Leu Leu Ser Ala Gly Ala Leu Thr Ala
            20                  25                  30

Leu Met Leu Ile Ile Phe Leu Met Thr Cys Cys Arg Arg Val Asn Arg
        35                  40                  45

Ser Glu Pro Thr Gln His Asn Leu Arg Gly Thr Gly Arg Glu Val Ser
    50                  55                  60

Val Thr Pro Gln Ser Gly Lys Ile Ile Ser Ser Trp Glu Val His Ala
65                  70                  75                  80

Ser Gly Gly Gln Thr Arg Leu
                85


<210> SEQ ID NO 219
<211> LENGTH: 258
<212> TYPE: DNA
<213> ORGANISM: Artificial Sequence
<220> FEATURE:
<223> OTHER INFORMATION: Neurovita2 (441) polynucleotide
```

<400> SEQUENCE: 219
atggttcctc aggctctcct gtttgtaccc cttctggttt ttccattgtg ttttgggggg 60
aagtatgtat tactgagtgc aggggccctg actgccttga tgttgataat tttcctgatg 120
acatgttgta gaagagtcaa tcgatcagaa cctacgcaac acaatctcag agggacaggg 180
agggaggtgt cagtcactcc ccaaagcggg aagatcatat cttcatggga agtacacggg 240
ggtcagacca gactgtga 258

<210> SEQ ID NO 220
<211> LENGTH: 258
<212> TYPE: DNA
<213> ORGANISM: Artificial Sequence
<220> FEATURE:
<223> OTHER INFORMATION: Neurovita3 (454) polynucleotide

<400> SEQUENCE: 220
atggttcctc aggctctcct gtttgtaccc cttctggttt ttccattgtg ttttgggggg 60
aagtatgtat tactgagtgc aggggccctg actgccttga tgttgataat tttcctgatg 120
acatgttgta gaagagtcaa tcgatcagaa cctacgcaac acaatctcag agggacaggg 180
agggaggtgt cagtcactcc ccaaagcggg aagatcatat cttcatggga agtacacggg 240
cagcagacca gactgtga 258

<210> SEQ ID NO 221
<211> LENGTH: 258
<212> TYPE: DNA
<213> ORGANISM: Artificial Sequence
<220> FEATURE:
<223> OTHER INFORMATION: Polynucleotide encoding the polypeptide of SEQ ID NO:212

<400> SEQUENCE: 221
atggttcctc aggctctcct gtttgtaccc cttctggttt ttccattgtg ttttgggggg 60
aagtatgtat tactgagtgc aggggccctg actgccttga tgttgataat tttcctgatg 120
acatgttgta gaagagtcaa tcgatcagaa cctacgcaac acaatctcag agggacaggg 180
agggaggtgt cagtcactcc ccaaagcggg aagatcatat cttcatggga agtagccacg 240
cagcagacca gactgtga 258

<210> SEQ ID NO 222
<211> LENGTH: 258
<212> TYPE: DNA
<213> ORGANISM: Artificial Sequence
<220> FEATURE:
<223> OTHER INFORMATION: Polynucleotide encoding the polypeptide of SEQ ID NO:213

<400> SEQUENCE: 222
atggttcctc aggctctcct gtttgtaccc cttctggttt ttccattgtg ttttgggggg 60
aagtatgtat tactgagtgc aggggccctg actgccttga tgttgataat tttcctgatg 120
acatgttgta gaagagtcaa tcgatcagaa cctacgcaac acaatctcag agggacaggg 180
agggaggtgt cagtcactcc ccaaagcggg aagatcatat cttcatggga agtatacacg 240
gggcagacca gactgtga 258

<210> SEQ ID NO 223
<211> LENGTH: 258
<212> TYPE: DNA
<213> ORGANISM: Artificial Sequence
<220> FEATURE:
<223> OTHER INFORMATION: Polynucleotide encoding the polypeptide of SEQ ID NO:214

<400> SEQUENCE: 223

```
atggttcctc aggctctcct gtttgtaccc cttctggttt ttccattgtg ttttgggggg     60

aagtatgtat tactgagtgc aggggccctg actgccttga tgttgataat tttcctgatg    120

acatgttgta gaagagtcaa tcgatcagaa cctacgcaac acaatctcag agggacaggg    180

agggaggtgt cagtcactcc ccaaagcggg aagatcatat cttcatggga agtacacacg    240

gggcagacca gactgtga                                                  258
```

<210> SEQ ID NO 224
<211> LENGTH: 258
<212> TYPE: DNA
<213> ORGANISM: Artificial Sequence
<220> FEATURE:
<223> OTHER INFORMATION: Polynucleotide encoding the polypeptide of SEQ ID NO:215

<400> SEQUENCE: 224

```
atggttcctc aggctctcct gtttgtaccc cttctggttt ttccattgtg ttttgggggg     60

aagtatgtat tactgagtgc aggggccctg actgccttga tgttgataat tttcctgatg    120

acatgttgta gaagagtcaa tcgatcagaa cctacgcaac acaatctcag agggacaggg    180

agggaggtgt cagtcactcc ccaaagcggg aagatcatat cttcatggga agtacacacg    240

cagcagacca gactgtga                                                  258
```

<210> SEQ ID NO 225
<211> LENGTH: 258
<212> TYPE: DNA
<213> ORGANISM: Artificial Sequence
<220> FEATURE:
<223> OTHER INFORMATION: Artificial/ polynucleotide encoding the polypeptide of SEQ ID NO:216

<400> SEQUENCE: 225

```
atggttcctc aggctctcct gtttgtaccc cttctggttt ttccattgtg ttttgggggg     60

aagtatgtat tactgagtgc aggggccctg actgccttga tgttgataat tttcctgatg    120

acatgttgta gaagagtcaa tcgatcagaa cctacgcaac acaatctcag agggacaggg    180

agggaggtgt cagtcactcc ccaaagcggg aagatcatat cttcatggga agtagccggg    240

gggcagacca gactgtga                                                  258
```

<210> SEQ ID NO 226
<211> LENGTH: 264
<212> TYPE: DNA
<213> ORGANISM: Artificial Sequence
<220> FEATURE:
<223> OTHER INFORMATION: Polynucleotide encoding the polypeptide of SEQ ID NO:217

<400> SEQUENCE: 226

```
atggttcctc aggctctcct gtttgtaccc cttctggttt ttccattgtg ttttgggggg     60

aagtatgtat tactgagtgc aggggccctg actgccttga tgttgataat tttcctgatg    120

acatgttgta gaagagtcaa tcgatcagaa cctacgcaac acaatctcag agggacaggg    180

agggaggtgt cagtcactcc ccaaagcggg aagatcatat cttcatgggc cgaagcccag    240

cacacgcagc agaccagact gtga                                           264
```

<210> SEQ ID NO 227
<211> LENGTH: 264
<212> TYPE: DNA
<213> ORGANISM: Artificial Sequence
<220> FEATURE:
<223> OTHER INFORMATION: Polynucleotide encoding the polypeptide of SEQ ID NO:218

<400> SEQUENCE: 227

```
atggttcctc aggctctcct gtttgtaccc cttctggttt ttccattgtg ttttgggggg     60

aagtatgtat tactgagtgc aggggccctg actgccttga tgttgataat tttcctgatg    120

acatgttgta gaagagtcaa tcgatcagaa cctacgcaac acaatctcag agggacaggg    180

agggaggtgt cagtcactcc ccaaagcggg aagatcatat cttcatggga agtacacgcc    240

tctggggggc agaccagact gtga                                            264
```

<210> SEQ ID NO 228
<211> LENGTH: 200
<212> TYPE: DNA
<213> ORGANISM: Artificial Sequence
<220> FEATURE:
<223> OTHER INFORMATION: CAEV FLAP

<400> SEQUENCE: 228

```
gttccagcca caatttgtcg ctgtagaatc agccatagca gcagccctag tcgccataaa     60

tataaaaaga aagggtgggc tggggacaag ccctatggat atttttatat ataataaaga    120

acagaaaaga ataaataata aatataataa aaattctcaa aaaattcaat tctgttatta    180

cagaataagg aaaagaggac                                                200
```

<210> SEQ ID NO 229
<211> LENGTH: 200
<212> TYPE: DNA
<213> ORGANISM: Artificial Sequence
<220> FEATURE:
<223> OTHER INFORMATION: EIAV FLAP

<400> SEQUENCE: 229

```
cttgtaacaa agggagggaa agtatgggag gacagacacc atgggaagta tttatcacta     60

atcaagcaca agtaatacat gagaaacttt tactacagca agcacaatcc tccaaaaaat    120

tttgttttta caaaatccct ggtgaacatg attggaaggg acctactagg gtgctgtgga    180

agggtgatgg tgcagtagta                                                200
```

<210> SEQ ID NO 230
<211> LENGTH: 200
<212> TYPE: DNA
<213> ORGANISM: Artificial Sequence
<220> FEATURE:
<223> OTHER INFORMATION: VISNA FLAP

<400> SEQUENCE: 230

```
ggaccctcat tactctaaat ataaaaagaa agggtgggct agggacaagc cctatggata     60

tatttatatt taataaggaa caacaaagaa tacagcaaca aagtaaatca aaacaagaaa    120

aaattcgatt ttgttattac agaacaagaa aaagagggca tccaggagag tggcaaggac    180

caacacaggt actttggggc                                                200
```

<210> SEQ ID NO 231
<211> LENGTH: 200
<212> TYPE: DNA

```
<213> ORGANISM: Artificial Sequence
<220> FEATURE:
<223> OTHER INFORMATION: SIV AGM FLAP

<400> SEQUENCE: 231

tactgatggc ttgcatactt cacaatttta aaagaaaggg aggaataggg ggacagactt     60

cagcagagag actaattaat ataataacaa cacaattaga aatacaacat ttacaaacca    120

aaattcaaaa aattttaaat tttagagtct actacagaga agggagagac cctgtgtgga    180

aaggaccggc acaattaatc                                                200


<210> SEQ ID NO 232
<211> LENGTH: 200
<212> TYPE: DNA
<213> ORGANISM: Artificial Sequence
<220> FEATURE:
<223> OTHER INFORMATION: HIV-2 RID FLAP

<400> SEQUENCE: 232

tgcatgaatt ttaaaagaag ggggggaata ggggatatga ctccatcaga aagattaatc     60

aatatgatca ccacagaaca agagatacaa ttcctccaag ccaaaaattc aaaattaaaa    120

gattttcggg tctatttcag agaaggcaga gatcagttgt ggaaaggacc tggggaacta    180

ctgtggaaag gagaaggagc                                                200


<210> SEQ ID NO 233
<211> LENGTH: 200
<212> TYPE: DNA
<213> ORGANISM: Artificial Sequence
<220> FEATURE:
<223> OTHER INFORMATION: HIV-1 LAI FLAP

<400> SEQUENCE: 233

cagtattcat ccacaatttt aaaagaaaag gggggattgg ggggtacagt gcaggggaaa     60

gaatagtaga cataatagca acagacatac aaactaaaga attacaaaaa caaattacaa    120

aaattcaaaa ttttcgggtt tattacaggg acagcagaga tccactttgg aaaggaccag    180

caaagctcct ctggaaaggt                                                200


<210> SEQ ID NO 234
<211> LENGTH: 119
<212> TYPE: DNA
<213> ORGANISM: Artificial Sequence
<220> FEATURE:
<223> OTHER INFORMATION: HIV-1 FLAP

<400> SEQUENCE: 234

ttttaaaaga aaagggggga ttggggggta cagtgcaggg gaaagaatag tagacataat     60

agcaacagac atacaaacta aagaattaca aaaacaaatt acaaaaattc aaaattttc     119


<210> SEQ ID NO 235
<211> LENGTH: 13
<212> TYPE: PRT
<213> ORGANISM: Rabies virus
<220> FEATURE:
<221> NAME/KEY: MISC_FEATURE
<222> LOCATION: (1)..(13)
<223> OTHER INFORMATION: MAST-2 binding domain of the G protein of an
      attenuated strain

<400> SEQUENCE: 235

Ser Trp Glu Ser His Lys Ser Gly Gly Glu Thr Arg Leu
1               5                   10
```

<210> SEQ ID NO 236
<211> LENGTH: 7385
<212> TYPE: DNA
<213> ORGANISM: Homo sapiens
<220> FEATURE:
<221> NAME/KEY: misc_feature
<222> LOCATION: (1)..(7385)
<223> OTHER INFORMATION: roundabout, axon guidance receptor, homolog 1
(ROBO1)

<400> SEQUENCE: 236

```
aattgagctg gagaggaggc agcgtgagag cagaaacttc agacgccgct gatccgggag     60
gagctggggt gagccgcggc ggccgtctct cccacccgca gcagcatcct ctctgccctt    120
ctctgccacc ccggggagag ccgggagctg cctctttaca gcttccacga gccaggggtg    180
caggcagctg cccccaggaa gtttgggctt ctgcgtagtt taggggtgcc tgcgagcgcc    240
ccagagggcg aggggccgag ggcgatgttg ggcgccgcgc ggggctgggg gcgcccagaa    300
gacgtgcgag tgtccgcggt cctgctgctg tctccagtac cctccgcatc ccccaagtga    360
tgggaacaag ggcccgccca ggcagccgct gtcgccgcac cgccccctcg ctcgctctct    420
gcgcgcggag tcacccagtc acactcccgg caccccgagc ccttcctccg gagctgctgc    480
ttctactttg gctgctatcg ccgccgccgc gggtggcccg ctgctgactg ggctcgccgg    540
gagacggaga agcacttttt ggccctccct cagcagctct cacaccccaa ctttgccgcc    600
gccgccgcgc ctgccctcgc agcggcgctc ggccgcacat tgtgggggcg cacgccggga    660
ggctccgcaa gaccgtggag gcaggaaacg gcactactgc gcttctgcct cggctctttg    720
ttgttcgctt tggatggttc ttgaaagtgt ctgagcctcc tcggaaatcc tggggccgga    780
gaagacaaac cttggaattc ttcctctgca aaagtctctg agatactgac aagcgtccgg    840
aaaggtcgac gagtaattgc cctgaaaact cttggctaat tgacccacgt tgcttatatt    900
aagcctttgt gtgtggtgtg tggcttcata catttgggga ccctatttcc actccctcct    960
cttggcatga gactgtatac aggatccacc cgaggacaat gattgcggag cccgctcact   1020
tttacctgtt tggattaata tgtctctgtt caggctcccg tcttcgtcag gaagattttc   1080
cacctcgcat tgttgaacac ccttcagacc tgattgtctc aaaaggagaa cctgcaactt   1140
tgaactgcaa agctgaaggc cgccccacac ccactattga atggtacaaa gggggagaga   1200
gagtggagac agacaaagat gaccctcgct cacaccgaat gttgctgccg agtggatctt   1260
tatttttctt acgtatagta catggacgga aaagtagacc tgatgaagga gtctatgtct   1320
gtgtagcaag gaattacctt ggagaggctg tgagccacaa tgcatcgctg gaagtagcca   1380
tacttcggga tgacttcaga caaaaccctt cggatgtcat ggttgcagta ggagagcctg   1440
cagtaatgga atgccaacct ccacgaggcc atcctgagcc caccatttca tggaagaaag   1500
atggctctcc actggatgat aaagatgaaa gaataactat acgaggagga aagctcatga   1560
tcacttacac ccgtaaaagt gacgctggca aatatgtttg tgttggtacc aatatggttg   1620
gggaacgtga gagtgaagta gccgagctga ctgtcttaga gagaccatca tttgtgaaga   1680
gacccagtaa cttggcagta actgtggatg acagtgcaga atttaaatgt gaggcccgag   1740
gtgaccctgt acctacagta cgatggagga aagatgatgg agagctgccc aaatccagat   1800
atgaaatccg agatgatcat accttgaaaa ttaggaaggt gacagctggt gacatgggtt   1860
catacacttg tgttgcagaa aatatggtgg gcaaagctga agcatctgct actctgactg   1920
ttcaagttgg gtctgaacct ccacattttg ttgtgaaacc ccgtgaccag gttgttgctt   1980
```

```
tgggacggac tgtaactttt cagtgtgaag caaccggaaa tcctcaacca gctattttct   2040
ggaggagaga agggagtcag aatctacttt tctcatatca accaccacag tcatccagcc   2100
gattttcagt ctcccagact ggcgacctca caattactaa tgtccagcga tctgatgttg   2160
gttattacat ctgccagact ttaaatgttg ctggaagcat catcacaaag gcatatttgg   2220
aagttacaga tgtgattgca gatcggcctc ccccagttat tcgacaaggt cctgtgaatc   2280
agactgtagc cgtggatggc actttcgtcc tcagctgtgt ggccacaggc agtccagtgc   2340
ccaccattct gtggagaaag gatggagtcc tcgtttcaac ccaagactct cgaatcaaac   2400
agttggagaa tggagtactg cagatccgat atgctaagct gggtgatact ggtcggtaca   2460
cctgcattgc atcaaccccc agtggtgaag caacatggag tgcttacatt gaagttcaag   2520
aatttggagt tccagttcag cctccaagac ctactgaccc aaatttaatc cctagtgccc   2580
catcaaaacc tgaagtgaca gatgtcagca gaaatacagt cacattatcg tggcaaccaa   2640
atttgaattc aggagcaact ccaacatctt atattataga agccttcagc catgcatctg   2700
gtagcagctg gcagaccgta gcagagaatg tgaaaacaga aacatctgcc attaaaggac   2760
tcaaacctaa tgcaatttac cttttccttg tgagggcagc taatgcatat ggaattagtg   2820
atccaagcca aatatcagat ccagtgaaaa cacaagatgt cctaccaaca agtcaggggg   2880
tggaccacaa gcaggtccag agagagctgg gaaatgctgt tctgcacctc cacaacccca   2940
ccgtcctttc ttcctcttcc atcgaagtgc actggacagt agatcaacag tctcagtata   3000
tacaaggata taaaattctc tatcggccat ctggagccaa ccacggagaa tcagactggt   3060
tagtttttga agtgaggacg ccagccaaaa acagtgtggt aatccctgat ctcagaaagg   3120
gagtcaacta tgaaattaag gctcgccctt tttttaatga atttcaagga gcagatagtg   3180
aaatcaagtt tgccaaaacc ctggaagaag cacccagtgc ccccaccccaa ggtgtaactg   3240
tatccaagaa tgatggaaac ggaactgcaa ttctagttag ttggcagcca cctccagaag   3300
acactcaaaa tggaatggtc caagagtata aggtttggtg tctgggcaat gaaactcgat   3360
accacatcaa caaaacagtg gatggttcca ccttttccgt ggtcattccc tttcttgttc   3420
ctggaatccg atacagtgtg gaagtggcag ccagcactgg ggctgggtct ggggtaaaga   3480
gtgagcctca gttcatccag ctggatgccc atggaaaccc tgtgtcacct gaggaccaag   3540
tcagcctcgc tcagcagatt tcagatgtgg tgaagcagcc ggccttcata gcaggtattg   3600
gagcagcctg ttggatcatc ctcatggtct tcagcatctg gctttatcga caccgcaaga   3660
agagaaacgg acttactagt acctacgcgg gtatcagaaa agtaacttac cagagaggag   3720
gcgaagctgt cagcagtgga gggaggcctg gacttctcaa catcagtgaa cctgccgcgc   3780
agccatggct ggcagacacg tggcctaata ctggcaacaa ccacaatgac tgctccatca   3840
gctgctgcac ggcaggcaat ggaaacagcg acagcaacct cactacctac agtcgcccag   3900
ggcagcctac tccttacgcc accactcagc tcatccagtc aaacctcagc aacaacatga   3960
acaatggcag cggggactct ggcgagaagc actggaaacc actgggacag cagaaacaag   4020
aagtggcacc agttcagtac aacatcgtgg agcaaaacaa gctgaacaaa gattatcgag   4080
caaatgacac agttcctcca actatcccat acaaccaatc atacgaccag aacacaggag   4140
gatcctacaa cagctcagac cggggcagta gtacatctgg gagtcagggg cacaagaaag   4200
gggcaagaac acccaaggta ccaaaacagg gtggcatgaa ctgggcagac ctgcttcctc   4260
ctcccccagc acatcctcct ccacacagca atagcgaaga gtacaacatt tctgtagatg   4320
```

-continued

```
aaagctatga ccaagaaatg ccatgtcccg tgccaccagc aaggatgtat ttgcaacaag   4380
atgaattaga agaggaggaa gatgaacgag gccccactcc ccctgttcgg ggagcagctt   4440
cttctccagc tgccgtgtcc tatagccatc agtccactgc cactctgact ccctccccac   4500
aggaagaact ccagcccatg ttacaggatt gtccagagga gactggccac atgcagcacc   4560
agcccgacag gagacggcag cctgtgagtc ctcctccacc accacggccg atctccccctc   4620
cacataccta tggctacatt tcaggacccc tggtctcaga tatggatacg gatgcgccag   4680
aagaggaaga agacgaagcc gacatggagg tagccaagat gcaaaccaga aggcttttgt   4740
tacgtgggct tgagcagaca cctgcctcca gtgttgggga cctggagagc tctgtcacgg   4800
ggtccatgat caacggctgg ggctcagcct cagaggagga caacatttcc agcggacgct   4860
ccagtgttag ttcttcggac ggctcctttt tcactgatgc tgactttgcc caggcagtcg   4920
cagcagcggc agagtatgct ggtctgaaag tagcacgacg gcaaatgcag gatgctgctg   4980
gccgtcgaca ttttcatgcg tctcagtgcc ctaggcccac aagtcccgtg tctacagaca   5040
gcaacatgag tgccgccgta atgcagaaaa ccagaccagc caagaaactg aaacaccagc   5100
caggacatct gcgcagagaa acctacacag atgatcttcc accacctcct gtgccgccac   5160
ctgctataaa gtcacctact gcccaatcca agacacagct ggaagtacga cctgtagtgg   5220
tgccaaaact cccttctatg gatgcaagaa cagacagatc atcagacaga aaaggaagca   5280
gttacaaggg gagagaagtg ttggatggaa gacaggttgt tgacatgcga acaaatccag   5340
gtgatcccag agaagcacag gaacagcaaa atgacgggaa aggacgtgga aacaaggcag   5400
caaaacgaga ccttccacca gcaaagactc atctcatcca agaggatatt ctaccttatt   5460
gtagacctac ttttccaaca tcaaataatc ccagagatcc cagttcctca agctcaatgt   5520
catcaagagg atcaggaagc agacaaagag aacaagcaaa tgtaggtcga agaaatattg   5580
cagaaatgca ggtacttgga ggatatgaaa gaggagaaga taataatgaa gaattagagg   5640
aaactgaaag ctgaagacaa ccaagaggct tatgagatct aatgtgaaaa tcatcactca   5700
agatgcctcc tgtcagatga cacatgacgc cagataaaat gttcagtgca atcagagtgt   5760
acaaattgtc gtttttattc ctcttattgg gatatcattt taaaaacttt attgggtttt   5820
tattgttgtt gtttgatccc taaccctaca aagagccttc ctattcccct cgctgttgga   5880
gcaaaccatt ataccttact tccagcaagc aaagtgcttt gacttcttgc ttcagtcatc   5940
agccagcaag agggaacaaa actgttcttt tgcattttgc cgctgagata tggcattgca   6000
ctgcttatat gccaagctaa tttatagcaa gatattgatc aaatatagaa agttgatatt   6060
caacctcaca agggctctca aagtataatc tttctatagc caactgctaa tgcaaattaa   6120
aacatatttc attttaacat gatttcaaaa tcagtttttc atactaccct ttgctggaag   6180
aaactaaaaa tatagcaaat gcagaaccac aaacaattcg aatggggtag aaacattgta   6240
aatatttact ctttgcaaac cctggtggta ttttattttg gcttcatttc aatcattgaa   6300
gtatattctt attggaaatg tacttttgga taagtagggc taagccagtt ggatctctgg   6360
ttgtctagtc attgtcataa gtaaacctag taaaaccttg ttctattttt caatcatcaa   6420
aaagtaatta taaatacgta ttacaaacaa gtggatgttt ttaatgacca attgagtaag   6480
aacatccctg tcttaactgg cctaaatttc ttctggtagt gtcagttcaa ctttcagaag   6540
tgccacttaa ggaagtttga tttttgtttt tgtaatgcac tgtttttaat ctctctctct   6600
ttttttttt tttttggtt ttaaaagcac aatcactaaa ctttatttgt aaaccattgt   6660
aactattaac ctttttgtc ttattgaaaa aaaaaatgtt gagaagcgtt tttaacctgt   6720
```

tttgttaatg ctctatgttt gtatttggaa tatttgaata atgacagatg gtgaagtaac 6780
atgcatactt tattgtgggc catgaaccaa atggttctta cttttcctgg acttaaagaa 6840
aaaaagaggt ttaagtttgt tgtggccaat gtcgaaacct acaagatttc cttaaaatct 6900
ctaatagagg cattacttgc tttcaattga caaatgatgc cctctgacta gtagatttct 6960
atgatccttt tttgtcattt tatgaatatc attgatttta taattggtgc tatttgaaga 7020
aaaaaatgta catttattca tagatagata agtatcaggt ctgaccccag tggaaaacaa 7080
agccaaacaa aactgaacca caaaaaaaaa ggctggtgtt caccaaaacc aaacttgttc 7140
atttagataa tttgaaaaag ttccatagaa aaggcgtgca gtactaaggg aacaatccat 7200
gtgattaatg ttttcattat gttcatgtaa gaagcccctt atttttagcc ataattttgc 7260
atactgaaaa tccaataatc agaaaagtaa ttttgtcaca ttatttatta aaaatgttct 7320
caaatacata aaaaaaaaaa aaaaaaaaaa aaaaaaaaaa aaaaaaaaaa aaaaaaaaaa 7380
aaaaa 7385

<210> SEQ ID NO 237
<211> LENGTH: 3817
<212> TYPE: DNA
<213> ORGANISM: Homo sapiens
<220> FEATURE:
<221> NAME/KEY: misc_feature
<222> LOCATION: (1)..(3817)
<223> OTHER INFORMATION: POU class 4 homeobox 1 (POU4F1)

<400> SEQUENCE: 237
gcggggctag agctgtcgga gaagcgggac cgcgaggccg gcgcgcggcg ctctgcgcgg 60
tcagagggag cgcctggcag cagcaggagc agcagcagca gcccgcggcg gggccgccgc 120
cagccgccgc gaccgccgcg gctgcagcct ccgaagggag gccgggtgag ccggcgtacg 180
cactttcccg cggactttcg gagtgtttgt ggatatacat gccaagccgc cacgatgatg 240
tccatgaaca gcaagcagcc tcactttgcc atgcatccca ccctccctga gcacaagtac 300
ccgtcgctgc actccagctc cgaggccatc cggcgggcct gcctgcccac gccgccgctg 360
cagagcaacc tcttcgccag cctggacgag acgctgctgg cgcgggccga ggcgctggcg 420
gccgtggaca tcgccgtgtc ccagggcaag agccatcctt tcaagccgga cgccacgtac 480
cacacgatga acagcgtgcc gtgcacgtcc acttccacgg tgcctctggc gcaccaccac 540
caccaccacc accaccacca ggcgctcgaa cccggcgatc tgctggacca catctcctcg 600
ccgtcgctcg cgctcatggc cggcgcgggc ggcgcgggcg cggcggccgg cggcggcggc 660
gcccacgacg gcccgggggg cggtggcggc ccgggcggcg gcggcggccc gggcggcggc 720
cccgggggag gcggcggtgg cggcccgggg ggcggcggcg gcggcccggg cggcgggctc 780
ctgggcggct ccgcgcaccc tcacccgcat atgcacagcc tgggccacct gtcgcacccc 840
gcggcggcgg ccgccatgaa catgccgtcc gggctgccgc accccgggct ggtggcggcg 900
gcggcgcacc acggcgcggc agcggcagcg gcggcggcgg cggccgggca ggtggcagcg 960
gcatcggcgg cggcggccgt ggtgggcgca gcgggcctgg cgtccatctg cgactcggac 1020
acggacccgc gcgagctcga ggcgttcgcg gagcgcttca agcagcggcg catcaagctg 1080
ggcgtgacgc aggccgacgt gggctcggcg ctggccaacc tcaagatccc gggcgtgggc 1140
tcactcagcc agagcaccat ctgcaggttc gagtcgctca cgctctcgca caacaacatg 1200
atcgcgctca agcccatcct gcaggcgtgg ctcgaggagg ccgagggcgc ccagcgcgag 1260

```
aaaatgaaca agcctgagct cttcaacggc ggcgagaaga agcgcaagcg gacttccatc   1320
gccgcgcccg agaagcgctc cctcgaggcc tacttcgccg tgcagccccg gccctcgtcc   1380
gagaagatcg ccgccatcgc cgagaaactg gacctcaaaa agaacgtggt gcgggtgtgg   1440
ttttgcaacc agagacagaa gcagaagcgg atgaaattct ctgccactta ctgagggggc   1500
tgggaggtgt cgggcgggac agaatgggga gctgaggagg catttttggg gggctttcct   1560
ctgcttgcct cccctcggat ttggagtgtc cgttatcctg cctgcatttg ggagtccct    1620
tctcgctctc tttcctccac ccattctctg attttcctgc ctttgctgtc ccctagcctt   1680
gaggactggg gtgctgggtg tggggattgg agtatagggt aggggagaag gggggggagca   1740
ttcgggggag tggggagtgg ggggaaggaa agcggagacc cgagcagggg ttttaaggag   1800
caggatggtt ctggggtttg ggtgggggga gacgcgggaa gggtaggaaa atggactgtt   1860
tctgaccaga gacacttacc taaatatcct ggggaccaag gaactatgta caaaaacaaa   1920
cctaccaacc accaaaaact agacaaataa agacaaacta aaacaaaaca gaacaaaagc   1980
aaaggaaaat gctttagaaa ttttaactcc ggggagccat aatctgcaac ttcattttcc   2040
cccatagaag agaaaaaaga gcaccaccat tattaccacc tccccaaccc tacacgcacg   2100
aactgagtcg aaaaacgaaa accaaacgag cgagaagttg aagttctggg tatcaaagct   2160
agttgttctg tctgcgtgtt taatttttcc ctctctcacc tccaccccat ccatatcctc   2220
tttatttcct ccgttccaat gagaggccta tggctgctct ccaatcccgg gaagtgagtg   2280
ggagcacagc tgaaaagaga gggtcagggg gaggctggct gcttgcttag gtggaatcca   2340
agttttcccg tggccctgcc tatactctgg tggcctggtc ctgttggggt gggggtcttt   2400
ggagagaagg gcatagtctt tgagctacta aaaagcagaa ttccggagct tcgagatatc   2460
ttattctagg aaaatgaaac aattttaaca acagtttttt ttcctcttat gtcgaagatc   2520
tagttttaga caatttcaaa ataagctttt cccactcata gaactttaac ttgccctttc   2580
agttttatct ttttttaga gagaggttta aactactgat ttttcctgtt gattcaaata    2640
gactaatggg gtgaaagtta ttaggagaga tactctctcc tgttttctcc actgaacgag   2700
actcatcttg ctcttctagg tcccgtttct tcctctcttg gaggacatga aattatagaa   2760
atgttgagaa gttcctgctt tcttttgcgg taggacttgg ctgtgagaaa atcacctaaa   2820
tcccagaaaa gaggaagaca gatttaaagt gcccccaccc ccatttgttt caaagaggtc   2880
tgcatgttgg gcgaaaacag aacaactgtg tttcctttta cttgttctta ttattcaaga   2940
gtcatttatt acaggggata aatgttgggt agcaagaact ttaatttgca ctaccagtct   3000
cccaaataga aaatcatgta tagtatttca tagtaataat caggtacctt acaagctgct   3060
ggtggatttt aaaaaattaa gatagttgaa ggtggttagg taaaatgcct gctttgtgta   3120
caagatactc tttggatctc tcgtagagat ggtttgttac catcctttaa tcataactaa   3180
aacattgaaa acagaacaaa tgagaaaaga aaaaaaacct gccgattaac aagactgaaa   3240
tcatgcatga tctgaaaggt gtggaaagaa acacaattag gtctcactct ggttaggcat   3300
tatttattta attatgttgt atatcattgt ttgcagggca aacattctat gcatttgaaa   3360
ctgagcacta aactgggcta gctttctggt agaccgtttt gtggctagtg cgatttcaca   3420
gtctactgcc tgtttccact gaaaacattt ttgtcatatt cttgtattca aagaaaaagg   3480
aaaaaagatt attgtaaata ttttatttaa tgcacacatt cacacagtgg taacagactg   3540
ccagtgttca tcctgaaatg tctcacggat tgatctacct gtccatgtat gtctgctgag   3600
ctttctcctt ggttatgttt tttctctttt acctttctcc tcccttactt ctatcagaac   3660
```

caattctatg cgccaaaata caacaggggg atgtgtccca gtacacttac aaataaaaca 3720
taactgaaag aagagcagtt ttatgatttg ggtgcgtttt tgtgtttata ctgggccagg 3780
tcctggtaga acctttcaac aaacaaccaa acaaaaa 3817

<210> SEQ ID NO 238
<211> LENGTH: 1558
<212> TYPE: DNA
<213> ORGANISM: Homo sapiens
<220> FEATURE:
<221> NAME/KEY: misc_feature
<222> LOCATION: (1)..(1558)
<223> OTHER INFORMATION: pleiotrophin (PTN)

<400> SEQUENCE: 238
gagtgcaaag cgctctccct ccctcgccca gccttcgtcc tcctggcccg ctcctctcat 60
ccctcccatt ctccatttcc cttccgttcc ctccctgtca gggcgtaatt gagtcaaagg 120
caggatcagg ttccccgcct tccagtccaa aaatcccgcc aagagagccc cagagcagag 180
gaaaatccaa agtggagaga ggggaagaaa gagaccagtg agtcatccgt ccagaaggcg 240
gggagagcag cagcggccca agcaggagct gcagcgagcc gggtacctgg actcagcggt 300
agcaacctcg cccccttgcaa caaaggcaga ctgagcgcca gagaggacgt ttccaactca 360
aaaatgcagg ctcaacagta ccagcagcag cgtcgaaaat ttgcagctgc cttcttggca 420
ttcattttca tactggcagc tgtggatact gctgaagcag ggaagaaaga gaaaccagaa 480
aaaaaagtga agaagtctga ctgtggagaa tggcagtgga gtgtgtgtgt gcccaccagt 540
ggagactgtg ggctgggcac acgggagggc actcggactg gagctgagtg caagcaaacc 600
atgaagaccc agagatgtaa gatcccctgc aactggaaga agcaatttgg cgcggagtgc 660
aaataccagt tccaggcctg ggggagaatgt gacctgaaca cagccctgaa gaccagaact 720
ggaagtctga agcgagccct gcacaatgcc gaatgccaga agactgtcac catctccaag 780
ccctgtggca aactgaccaa gcccaaacct caagcagaat ctaagaagaa gaaaaaggaa 840
ggcaagaaac aggagaagat gctggattaa aagatgtcac ctgtggaaca taaaaaggac 900
atcagcaaac aggatcagtt aactattgca tttatatgta ccgtaggctt tgtattcaaa 960
aattatctat agctaagtac acaataagca aaaacaaaaa gaaaagaaaa tttttgtagt 1020
agcgtttttt aaatgtatac tatagtacca gtaggggctt ataataaagg actgtaatct 1080
tatttaggaa gttgacttat agtacatgat aaatgataga caattgaggt aagtttttttg 1140 aaattatgtg acattttaca ttaaattttt tttacatttt ttgggcagca atttaaatgt 1200
tatgactatg taaactactt ctcttgttag gtaatttttt tcacctagat ttttttccca 1260
attgagaaaa atatatacta aacaaaatag caataaaaca taatcactct atttgaagaa 1320
aatatcttgt tttctgccaa tagatttttt aaaatgtagt cagcaaaatg ggggtgggga 1380
agcagagcat gtcctagttc aatgttgact tttttttttt ttaaagaaaa gcattaagac 1440
ataaaattct ttcactttgg cagaagcatt tgttttcttg atgaaattat ttttccatct 1500
gaggaaaaaa atactaggaa aataaatcaa ggtgatgctg aaaaaaaaaa aaaaaaaa 1558

<210> SEQ ID NO 239
<211> LENGTH: 4625
<212> TYPE: DNA
<213> ORGANISM: Homo sapiens
<220> FEATURE:
<221> NAME/KEY: misc_feature
<222> LOCATION: (1)..(4625)

<223> OTHER INFORMATION: par-6 partitioning defective 6 homolog beta (PARD6B)

<400> SEQUENCE: 239

```
gagggaggga gctgcttccc cgcctgccgc gccaccagtc cgaccctcgg tcccgccgtg     60
tgagcagctg gtggagtgga gctcagcgcg gacgccggag ctgcggccgc cccctctgca    120
ggtgcctgtg aggaggcgcc cgggccgcaa ccgctttccg agatccccag tcgcgcactc    180
gctccccgcg ctcctgaggg gccgcccggc cggaggaggc cgtcgcgggg ctcggcgttc    240
agcatgaacc gcagccaccg gcacggggcg ggcagcggct gcctgggcac tatggaggtg    300
aagagcaagt ttggagctga atttcgtcgg ttttcgctgg aaagatcaaa acctggaaaa    360
tttgaggagt tttatggatt actacaacat gttcataaga tccccaatgt tgacgttttg    420
gtaggctatg cagacatcca tggagactta ctacctataa ataatgatga taattatcac    480
aaagctgttt caacggccaa tccactgctt aggatattta tacaaaagaa ggaagaagca    540
gactacagtg cctttggtac agacacgcta ataaagaaga agaatgtttt aaccaacgta    600
ttgcgtcctg acaaccatag aaaaaagcca catatagtca ttagtatgcc ccaagacttt    660
agacctgtgt cttctattat agacgtggat attctcccag aaacgcatcg tagggtacgt    720
ctttacaaat acggcacgga gaaacccta ggattctaca tccgggatgg ctccagtgtc    780
agggtaacac cacatggctt agaaaaggtt ccagggatct ttatatccag gcttgtccca    840
ggaggtctgg ctcaaagtac aggactatta gctgttaatg atgaagtttt agaagttaat    900
ggcatagaag tttcagggaa gagccttgat caagtaacag acatgatgat tgcaaatagc    960
cgtaacctca tcataacagt gagaccggca aaccagagga ataatgttgt gaggaacagt   1020
cggacttctg gcagttccgg tcagtctact gataacagcc ttcttggcta cccacagcag   1080
attgaaccaa gctttgagcc agaggatgaa gacagcgaag aagatgacat tatcattgaa   1140
gacaatggag tgccacagca gattccaaaa gctgttccta atactgagag cctggagtca   1200
ttaacacaga tagagctaag ctttgagtct ggacagaatg gctttattcc ctctaatgaa   1260
gtgagcttag cagccatagc aagcagctca aacacggaat ttgaaacaca tgctccagat   1320
caaaaactct tagaagaaga tggaacaatc ataacattat gaaaccgtgg tttgaatgtt   1380
ttcagagtga ggatgccatg aggacttgta catttggcta gtttaaaagc atatatacct   1440
ctgaccagtg acgtggaata ggcatgagac gagtaacgtt gcaagcttac aatattatta   1500
aagtagtagt ttgataattg ttaatataaa ctttggtgga tcagaggtga atttaagtcc   1560
aaaacaaagg ggcctttgct gatgaagtta cgtgcttttg ctgttttgtc tgtggagaat   1620
cagatgttaa agcacattct tggaactatg tgagaagact agatcatttc tgttggaagt   1680
ggttgcatat ttaacctgct gtgcagagcc cagttaattt ttcctttaac tgtattttta   1740
aaattctaat gtgaagtctg attctctctt gtggtacatt ggggacctca gctcttaaag   1800
gtctcatgtt cccaatattt tattttgatt tttttttttt tttttttttt tttttttttt   1860
agtgactggg tctcactctg ttgcccacac tggaatgcag tggcatgatc acagctctct   1920
gcagcctcaa tcccctgggc tcaagcagtc ctcccacctc agcctcctga gtagctggga   1980
ccataggcac ataccaccac atctgtctac tttttgtatt ttttgtagag acagggtttc   2040
gccatgttgc ccaagttggt cttgaactcc tgggcttaag cagtcctgcc tcggcttccc   2100
aaaatgctag gattagagcc accatgccca gcctattttg atttttgttt ttttatgttc   2160
ctttctaata aattgtaaca aatgatgttc tcaagtacat ttccagtttc ttttcttttc   2220
```

```
tttctttttt tttttttttt tttttttgag atggagtctc gctctatcgc ccaggctgga   2280
gtgcagtggc gcgatcttgg ctcactgcaa gctctacctc ctgggttcac accattctcc   2340
tgcctcagcc tcccaagtag ctgggactac aggcgcctgc caccatgcct ggctaatttt   2400
tagtagagac ggggtttcgc agtgttagcc aggaaggtct caatctcctg acctcctgat   2460
ccgcccgcct cggcctccca aagtgctggg attacaggcg tgagccaccg cgcccagttg   2520
tgcatttctg gtttctaaga atcaaaccac ttggctgttt ttaggagtta cttcccatgt   2580
tataaagctg aggaagcttt tttttttttt ttttgagaca gagtctctgt cacccaggct   2640
ggagtgcagt ggtgcaatct cagctcccgg gttcaagcaa ttctcctgcc tcagccttct   2700
gagtagctaa gattacaggt gtgcgccaac acgtctggct tatttttttg tatttttagt   2760
agagatggag tttcaccatg ttggtcaggt gggtctcaaa ctcctgacct caagtgatcc   2820
gcccatctcc tcccaaagtg ctggattgca ggcatgagcg cctagccagg aagctatctt   2880
ttcttgagtt atgaaacttt gcaacagttg ttcaaattgg tgtttgtcct tcctatagct   2940
ttcatatttt caaattaatt ctgtatggct atataattta tgttttaaaa ggcaattctc   3000
ttgactttgg aaatatggaa gtctctcctt taacctattc ttgttcccat tcccagtctc   3060
atttgaaatc attcctttta ttgttagtgt gtgtattttt gttggtgtgc ttttaatgca   3120
tccaagtatg catcattttg gataaaaaat acatccaaat taagatgttt taacacatag   3180
gacaaacttg tgcacttttt atgccaaaaa aaaaaaaaat tgggttttcc ttcatgggat   3240
ttctagaaac actgcctaca ctttatgaaa actacatagt attcacctgt gacaggtaga   3300
gtttatcact attaatttta tgaggctatt tattactttc caatgcatcc acttagaaca   3360
agctaagagt aaggctgcta actttaattc cttgcctgat tttattgtac agtgtgcaca   3420
agcacaatgg tatgcttgta tatagaaact aaaaatacta tgaagtacat aagttcccta   3480
tggcttatgg agagttattt attaattaac tttatggtag ggctagtatg aatacctttt   3540
taacaattgt gtgctattac aacaatgaag attcaaatga ctccgctttg aaggatgttt   3600
tctctatatg gtaaaatata tatgaagaag tcttgattac gtgaagatca cttgactcag   3660
aatacttcaa tgtattttgt tcacattacc actaagcata ttatcagtaa actattaact   3720
gactgcacat tatgtaatac gttgtacttt ttgttgaatt caccgaagtt cttccattta   3780
tatgctattt ttaatggcat tccggcttta acattctgtg agtcttacaa atttgactct   3840
tgaatggcaa aataatgtta gtatgtagaa ggttaacttt catttataat ataagtggtg   3900
caggggttca acattttaag taaaaatatt tttacacact acctctctct tttttttttt   3960
aaagttttaa catcagaact tttgggggaa aaactacttc agggcttgac tttttgtaca   4020
aattttaact gtaaaataca gatttatctt gtacgcattc atggaaatgg aaatcaaagc   4080
tgctattgct ttttatttta attatcctgt taagggtatc tatcaatggt attttcaagt   4140
agatctctgt ttcttaaatt attggtgaaa taattgatta ctagatatat tgtaaaacca   4200
atagatcctg gttatacgat aaaatatcag ctcattggta ggctgaatca attatttcaa   4260
gtgcacctta ttaacaaaag tatcagtgga tccaacataa aattttatag tactaaatgt   4320
caagcctaac tgtgaatttt gttctgtatc ttaagtaaat ttatgataat gttctcgagc   4380
tatcaacaaa atatatgtac ttttgtgagc tatgaatttt ctaattaaat tttacatgct   4440
ataacatgat ttttacatga atgatacttt gtttataact atcaaatgtc agtattttac   4500
tacaatttta ttataaagtg tacattatca ctaaatgaac ttcgatttta aaaatcaaat   4560
tagctttagt tgtatattat tttttacaaa taaagataga cttgtataaa ggctaaaaaa   4620
```

aaaaa 4625

<210> SEQ ID NO 240
<211> LENGTH: 5614
<212> TYPE: DNA
<213> ORGANISM: Homo sapiens
<220> FEATURE:
<221> NAME/KEY: misc_feature
<222> LOCATION: (1)..(5614)
<223> OTHER INFORMATION: platelet-activating factor acetylhydrolase 1b, regulatory subunit 1 (PAFAH1B1)

<400> SEQUENCE: 240
agggcgttgg ggcagctcct gtgacagacg gagctggagc ggcggggcgg cggcggagtc 60
cggcggccgg gagagcgagt gagcgagcgg aggagcagcg acacgggagt ctagggagcg 120
agaaggagaa ggaggggagc gctcgggcgc gagcgagaga aaccgcgagc gccgagcttg 180
gactcgagcc ccggaacggc tgaggagccc gcccgctccc ctcccctccc cctccccggg 240
cccgggccca gcgcgccatc ctccccccctc cttccctccc tccctccttc ctccctcccc 300
tctccctccc cctccccccgc cggtggatgg gagtgaagga cggaagaggc cctgcggagg 360
cggcggtgca gcgctccggt ggaatgaatc ttacttgttg aatatcttct ggttactagt 420
tggattcatt tgtgaaagaa tcattttccc ctgtgtggaa gacacttagt ggcatattta 480
aattataagt ccacggatca aaaagctttt tgatttccca aaggagggac ataccactat 540
atcagataag cttgacatta cagccaagat ggtgctgtcc cagagacaac gagatgaact 600
aaatcgagct atagcagatt atcttcgttc aaatggctat gaagaggcat attcagtttt 660
taaaaaggaa gctgaattag atgtgaatga agaattagat aaaaagtatg ctggtctttt 720
ggaaaaaaaa tggacatctg ttattagatt acaaaagaag gttatggaat tagaatcaaa 780
gctaaatgaa gcaaaagaag aatttacgtc aggtggacct cttggtcaga aacgagaccc 840
aaaagaatgg attccccgtc cgccagaaaa atatgcattg agtggtcaca ggagtccagt 900
cactcgagtc attttccatc ctgtgttcag tgttatggtc tctgcttcag aggatgctac 960
aattaaggtg tgggattatg agactggaga ttttgaacga actcttaaag gacatacaga 1020
ctctgtacag gacatttcat tcgaccacag cggcaagctt ctggcttcct gttctgcaga 1080
tatgaccatt aaactatggg attttcaggg ctttgaatgc atcagaacca tgcacggcca 1140
tgaccacaat gtttcttcag tagccatcat gcccaatgga gatcatatag tgtctgcctc 1200
aagggataaa actataaaaa tgtgggaagt gcaaactggc tactgtgtga agacattcac 1260
aggacacaga gaatgggtac gtatggtacg gccaaatcaa gatggcactc tgatagccag 1320
ctgttccaat gaccagactg tgcgtgtatg ggtcgtagca acaaaggaat gcaaggctga 1380
gctccgagag catgagcatg tggtagaatg catttcctgg gctccagaaa gctcatattc 1440
ctccatctct gaagcaacag gatctgagac taaaaaaagt ggtaaacctg ggccattctt 1500
gctgtctgga tccagagaca agactattaa gatgtgggat gtcagtactg gcatgtgcct 1560
tatgaccctc gtgggtcatg ataactgggt acgtggagtt ctgttccatt ctgggggggaa 1620 gtttattttg agttgtgctg atgacaagac cctacgcgta tgggattaca agaacaagcg 1680
atgcatgaag accctcaatg cgcatgaaca ctttgttacc tccttggatt tccacaagac 1740
ggcaccctat gtcgtcactg gcagcgtaga tcaaacagta aaagtgtggg agtgccgttg 1800
attgtgtctc cttcggcccc tcctccctct tttcctctgg atgcactctg atgataccat 1860
ggttacccca ttgagctctg tttaaataaa tattgtcctt tcatgtaaat tattctggat 1920

```
gtagattgag cttattaaat gttacacaca aagtattcat gcatggtgaa tccaaattgt   1980
atactgtaaa tttacatacg ttgtctagaa gtaccatagg gtttaaaaac ctgggctggc   2040
attggtcaca ccaggcctaa gaaggcagaa gttgaatcaa ttgaactagg gcactaaact   2100
gaatagttga cagtgtcatt ttatgttgga ttattaattc ctgtttttct ttctgctatc   2160
tgttggtgcc tgacttgatg gcctcatttg ggaaaagtg gtggttatta gggcttttc   2220
tgaaatgtgt atctatgtaa catcacttaa gtgtgcttaa taaatcttct gtaaggattt   2280
tagatgataa ggctacaatt cagaatcttc tgaaccatct atgtaatgaa tggggattat   2340
acattggaat tttgtcatg acacatttgc caaatcagta ggatatattt gttttggcag   2400
cctatcacgc agaggctagt ggtatattta tgtaagaaaa tgactgtaaa tctcaagaaa   2460
aatctcagca gctaatagca actcatttat ttcattttgg tcttaatgct ttgtaaacag   2520
gtcaaaaaat actgtcatac tctaagcttc tattttccac actggacata cttctagttg   2580
tattctccat actattagac tgtgtagtga tgtgacttcc aagtagaatt taatctcccc   2640
attgagtgtg tcatggtaca aatcactatt cgtttttggt gttttttagg gatgtgcaat   2700
gtgcattaca taatgacaga aatactgaga aggttctgtg tgcccatttg aaaggagtgg   2760
gaggaataca gcagtttgtt tttcaacatg aatctgatat tgatttaaac tgtgtttcac   2820
ttacaagttt taaaaaaatg acagggttta atggagcgtg cataaaaatg tactgttttc   2880
accttttgtt tatatgtaaa tgtttgtaag tatatgggcc tatctgtaag tggataagtc   2940
tgtatgtgtg tatcatacac atcaacctcc atgtccttag tcctgggttt ttgaaaaagt   3000
gctaaaacgg acaagtagaa taaatgttgc tgtggaatgc catgctttag aacaaaccct   3060
ttttgatctt aatgcttctg aaaactaggt ctgactctgg ggattttttt ccagccgaag   3120
gaaaatcact tccgttatgt ccccctctaa tttagccgct cgacatttta cacaacccgg   3180
atatgttgta tattttgacc caaagttaca ggtaggttta agagaatttt tagccatgac   3240
ttttggagca ctattccatt gtcagttatt aataaagaat tccattgctt agctaaccaa   3300
caggtttttt ttgtttccaa gagagttatt tgaaaagtta acagaacaat gagataacag   3360
tgacagttta acaaagataa aattctgaac tgcgttttat tcatttgtgt actatgtgat   3420
tttttaaatg tccccttag tatttaatgg aaaattggtt cctgcaaaag acaaagggtg   3480
agagttagcg tcctgtagat acacacagag actaggccgt atattaacta gaagcagctt   3540
tatgtctagc ttgtgtcttt ttgtttgttt gcttgtttgt ttttagattc ctgagagatg   3600
tctctggaag ggaaagtttt gagaactaat ggctattttt gaggacaaaa attacatctt   3660
aagctaattc cttaaataca tacagtaggt gaattttcag gacaatattg cctcacaacc   3720
ctgcttacat tgaaaagtct ttttccctta gctcttctga ctggattttt ctacaaaaac   3780
tatggaaaat atctttgttc ttgtttgctg ctattttctg tcctattttg agaaatataa   3840
atacatagaa atggtgcatc ttaacatttg tttgtacatg tataaatgtc ttgtatttta   3900
attcattttt agcatgaatt gtttaagggt aagccacaac atctagaaat cactcataga   3960
tattgaacaa taaaggagaa tggtaccgat gcaggaggaa gcaagcgtgt cttcccctgc   4020
agcacacagc gacttgcgtt gacaaaggag gaggaaacga ttactctgta aacaaagtta   4080
tccttacttg ggagattgcc acagcctgct gctgagttga gttaccagac atcctccatg   4140
tgagaagcag cgaacattga atctcaggga tggcccacaa ctgggtccac atgtaatgag   4200
ccctgtttaa taacgaaggg gtgggggaga gcagtccgtc tacaacctgg aatcagattt   4260
```

```
gcaaaatttc ctgcactgct gtctgacact gtcctgttga tgccctttct gactgtgttc   4320

tctgttttct ctgtctgctg tctaaccctg tgccttgcct gggataagga caatgatgag   4380

gttactggtt tggattgtaa gtagaggact tttattaatt ggtttagagg ttcactgctg   4440

ctttgtcact ttctcaatca aattggccac ttaagaaata aagagctggt agaattgcat   4500

cctcagatga ttattgactg tgtgtgtgtg tgaaaacaga cattccagtg ccacccaaat   4560

atatatctgt aacgtgccca agaaatccta gctgcgctct tgagagtgca tgccatggag   4620

actggtttag acaccgcgtg gagcctagtt gcctgttgtc acggcatctt gcactttagg   4680

agactaagac cgtcctggtt cgtctgtgtg tggtgtgacc aatggtgtgc ccagagcact   4740

actctcaaaa tcactagtgt tagcaagtcg tcccgggctg gggagcgttc gccgtagtct   4800

ttggaagctt tggctttaga tttaccaagc cccgcctccc cgctgccagt gccctgctct   4860

cccgttcgcc tctttctgtt tctgtgtgaa ctttcccggt aatatcactc gttaaatagg   4920

ttttctttaa acttaattaa agaaaaacta tttaaaggta aaggatattt tgttgacatc   4980

ggtggctcga tcatccttaa gcaactgaag ttaaaattgt tgaaggaaaa ggcacttaaa   5040

ttggttactt tcatgtccag ctgtatataa gtccagtgtg ttcatctaga tgacgcaaag   5100

aatctcctgg tagagaagcg acatgtaaaa aactggtgga aaaaggtttt ggattttttt   5160

tccagtgggg tggggggagg gcaagctgga tttacaggtc acggctggac tgaatgggcc   5220

tttttatctt cccactgtat catggaagta gctgcttgct tgtactgtcc atccttcagg   5280

catccctaaa gctcactctg aagatgttag agacaaacac aaactcttcg agttaaagtt   5340

gatcctgaca ctgacatgaa ggcaagcctt gatttcgtat gaacgttgct gaagtggtaa   5400

ttgaggaaaa cagttcccca gattgttaag agttcactga agatattgac acaattttaa   5460

aaaatcagta aaggaatgta tataatattg ctctcgtgtt ttacagtaag atttgttgct   5520

ctcagactgt gtaaaacaaa atttattcat gttttctgca tattaaaaaa tcttattgta   5580

ccaactggta aactattaaa tgcctataaa acta                                5614
```

<210> SEQ ID NO 241
<211> LENGTH: 5379
<212> TYPE: DNA
<213> ORGANISM: Homo sapiens
<220> FEATURE:
<221> NAME/KEY: misc_feature
<222> LOCATION: (1)..(5379)
<223> OTHER INFORMATION: phosphoinositide-3-kinase, catalytic, gamma polypeptide (PIK3CG)

<400> SEQUENCE: 241

```
gcacttcctt ctcggctaga ttatctgaaa ctgttgtcgg ttcttgagat gatactacca     60

ccgaatgtct gtgtttcatt gtctagtcca acctgtattg tggatatcta caacgttccg    120

gcaatagttt tgcaggtgca tcacattttt gtttttgttt tgggaggaaa agggagggca    180

cggcagccag gcttcatatt cctacaagtg catgcttcaa gattactgta cttacagtgt    240

ttccaacatc ttctcataaa aggggaaagc ttcatagcct caaccatgaa ggaaaccagt    300

cgcatagggc atggagctgg agaactataa acagcccgtg gtgctgagag aggacaactg    360

ccgaaggcgc cggaggatga agccgcgcag tgctgcggcc agcctgtcct ccatggagct    420

catccccatc gagttcgtgc tgcccaccag ccagcgcaaa tgcaagagcc ccgaaacggc    480

gctgctgcac gtggccggcc acggcaacgt ggagcagatg aaggcccagg tgtggctgcg    540

agcgctggag accagcgtgg cggcggactt ctaccaccgg ctgggaccgc atcacttcct    600
```

-continued

```
cctgctctat cagaagaagg ggcagtggta cgagatctac gacaagtacc aggtggtgca    660
gactctggac tgcctgcgct actggaaggc cacgcaccgg agcccgggcc agatccacct    720
ggtgcagcgg cacccgccct ccgaggagtc ccaagccttc cagcggcagc tcacggcgct    780
gattggctat gacgtcactg acgtcagcaa cgtgcacgac gatgagctgg agttcacgcg    840
ccgtggcttg gtgaccccgc gcatggcgga ggtggccagc cgcgacccca agctctacgc    900
catgcacccg tgggtgacgt ccaagcccct cccggagtac ctgtggaaga agattgccaa    960
caactgcatc ttcatcgtca ttcaccgcag caccaccagc cagaccatta aggtctcacc   1020
cgacgacacc cccggcgcca tcctgcagag cttcttcacc aagatggcca agaagaaatc   1080
tctgatggat attcccgaaa gccaaagcga acaggatttt gtgctgcgcg tctgtggccg   1140
ggatgagtac ctggtgggcg aaacgcccat caaaaacttc cagtgggtga ggcactgcct   1200
caagaacgga gaagagattc acgtggtact ggacacgcct ccagacccgg ccctagacga   1260
ggtgaggaag gaagagtggc cgctggtgga tgactgcacg ggagtcaccg gctaccatga   1320
gcagcttacc atccacggca aggaccacga gagtgtgttc accgtgtccc tgtgggactg   1380
cgaccgcaag ttcagggtca agatcagagg cattgatatc cccgtcctgc ctcggaacac   1440
cgacctcaca gtttttgtag aggcaaacat ccagcatggg caacaagtcc tttgccaaag   1500
gagaaccagc cccaaaccct tcacagagga ggtgctgtgg aatgtgtggc ttgagttcag   1560
tatcaaaatc aaagacttgc ccaaaggggc tctactgaac ctccagatct actgcggtaa   1620
agctccagca ctgtccagca aggcctctgc agagtccccc agttctgagt ccaagggcaa   1680
agttcagctt ctctattatg tgaacctgct gctgatagac caccgtttcc tcctgcgccg   1740
tggagaatac gtcctccaca tgtggcagat atctgggaag ggagaagacc aaggaagctt   1800
caatgctgac aaactcacgt ctgcaactaa cccagacaag gagaactcaa tgtccatctc   1860
cattcttctg gacaattact gccacccgat agccctgcct aagcatcagc ccacccctga   1920
cccggaaggg gaccgggttc gagcagaaat gcccaaccag cttcgcaagc aattggaggc   1980
gatcatagcc actgatccac ttaaccctct cacagcagag gacaaagaat tgctctggca   2040
ttttagatac gaaagcctta agcacccaaa agcatatcct aagctattta gttcagtgaa   2100
atggggacag caagaaattg tggccaaaac ataccaattg ttggccagaa gggaagtctg   2160
ggatcaaagt gctttggatg ttgggttaac aatgcagctc ctggactgca acttctcaga   2220
tgaaaatgta agagccattg cagttcagaa actggagagc ttggaggacg atgatgttct   2280
gcattacctt ctacaattgg tccaggctgt gaaatttgaa ccataccatg atagcgccct   2340
tgccagattt ctgctgaagc gtggtttaag aaacaaaaga attggtcact tttttgtttg   2400
gttcttgaga agtgagatag cccagtccag acactatcag cagaggttcg ctgtgattct   2460
ggaagcctat ctgaggggct gtggcacagc catgctgcac gactttaccc aacaagtcca   2520
agtaatcgag atgttacaaa aagtcaccct tgatattaaa tcgctctctg ctgaaaagta   2580
tgacgtcagt tcccaagtta tttcacaact taaacaaaag cttgaaaacc tgcagaattc   2640
tcaactcccc gaaagcttta gagttccata tgatcctgga ctgaaagcag gagcgctggc   2700
aattgaaaaa tgtaaagtaa tggcctccaa gaaaaaacca ctatggcttg agtttaaatg   2760
tgccgatcct acagccctat caaatgaaac aattggaatt atctttaaac atggtgatga   2820
tctgcgccaa gacatgctta ttttacagat tctacgaatc atggagtcta tttgggagac   2880
tgaatctttg gatctatgcc tcctgccata tggttgcatt tcaactggtg acaaaatagg   2940
aatgatcgag attgtgaaag acgccacgac aattgccaaa attcagcaaa gcacagtggg   3000
```

```
caacacggga gcatttaaag atgaagtcct gaatcactgg ctcaaagaaa aatcccctac   3060
tgaagaaaag tttcaggcag cagtggagag atttgtttat tcctgtgcag gctactgtgt   3120
ggcaaccttt gttcttggaa taggcgacag acacaatgac aatattatga tcaccgagac   3180
aggaaaccta tttcatattg acttcgggca cattcttggg aattacaaaa gtttcctggg   3240
cattaataaa gagagagtgc catttgtgct aacccctgac ttcctctttg tgatgggaac   3300
ttctggaaag aagacaagcc cacacttcca gaaatttcag gacatctgtg ttaaggctta   3360
tctagccctt cgtcatcaca caaacctact gatcatcctg ttctccatga tgctgatgac   3420
aggaatgccc cagttaacaa gcaaagaaga cattgaatat atccgggatg ccctcacagt   3480
ggggaaaaat gaggaggatg ctaaaaagta ttttcttgat cagatcgaag tttgcagaga   3540
caaaggatgg actgtgcagt ttaattggtt tctacatctt gttcttggca tcaaacaagg   3600
agagaaacat tcagcctaat actttaggct agaatcaaaa acaagttagt gttctatggt   3660
ttaaattagc atagcaatca tcgaacttgg atttcaaatg caatagacat tgtgaaagct   3720
ggcatttcag aagtatagct cttttcctac ctgaactctt ccctggagaa aagatgttgg   3780
cattgctgat tgtttggtta agcaatgtcc agtgctagga ttatttgcag gtttggtttt   3840
ttctcatttg tctgtggcat tggagaatat tctcggttta aacagactaa tgacttcctt   3900
attgtccctg atattttgac tatcttacta ttgagtgctt ctggaaattc tttggaataa   3960
ttgatgacat ctattttcat ctgggtttag tctcaatttt ggttatcttt gtgttcctca   4020
agctctttaa agaaaaagat gtaatcgttg taacctttgt ctcattcctt aaatgatgct   4080
tccaaacatc tccttagtgt ctgcaggtgt tagtggtgtg ctaaaagcaa ggaaagcgag   4140
ttagtctttt cagtgtcttt tgcaattcaa ttcttttgtc atgtataact gagacacaca   4200
aacacagcag gagaaatcta aaccgttgtg ccttgacctt cctctgctgg tcttgttcca   4260
gggttatgaa tatgaaaaaa tagagatgag actttttgtg tcaactctgt ccacaagagt   4320
gagttatcta gtatgattag tatagctttc tccagcatgg cagcaggaag taactacagg   4380
gcctctttta tgcctgacat ttcttccctt cctttttccc tgcctccctt tttcatcaat   4440
tgcaatgctc ccacaactct ttacagactt gtgaaatctt caagaacacc tttactctat   4500
aactcaaaaa ttagttgaaa aataattact tctcaaggat tattagaatc ttaggtactt   4560
atttgtaaag atgtttagtg actttttttt caagtatctt attaaaggag gcattctaga   4620
aaatatgaat tagtttccaa atgccttaat tttaaacttt ggcctgaaca gtttttttctt   4680
tttcttaatg gaagaagata tttaatatct taaaaatatt ccaagttagg aagaacacta   4740
cttgccttat ccatttccca tttaaaggac ttttaaactt tgacacatcc ttcagatttc   4800
ctgaaaataa ttgaaatatc ttactttaaa aatattttca tctctgaaat atctcgttat   4860
ttattggagg tattgtttaa ccttagagag accattaaat tatttataaa atattttgta   4920
attacctgta gctaatacat tacatagaaa aaaactatgt taacagtgtc tctgtttaag   4980
tataatcaga tataaatata tacttaattt tttaatttta aaaatagata cctgtttgac   5040
tttgaggtag tccagacctt ttcttttttt tttttttttt aatgtgtgca aaagcccaaa   5100
ggttcctaag cctggctgca aagaagaatc aacagggaca ctttttaaaa acactcttat   5160
cagcctgggc aacacagtga gactccatct cttaaaaaaa aaattagctg ggtatagtgg   5220
tatgtgcctg tagtcccagg tactcaggag gctgaggcag gaggattgcc tgagcccagg   5280
aggtggaaac tgcagagagt catgatcatg tccttacact ccagcctgga taacagagcg   5340
```

```
agaccctgtc tcaaaaaaat aaaataaaaa ataaaaaca                         5379


<210> SEQ ID NO 242
<211> LENGTH: 3150
<212> TYPE: DNA
<213> ORGANISM: Homo sapiens
<220> FEATURE:
<221> NAME/KEY: misc_feature
<222> LOCATION: (1)..(3150)
<223> OTHER INFORMATION: bone morphogenetic protein 2 (BMP2)

<400> SEQUENCE: 242

ccacaaaggg cacttggccc cagggctagg agagcgaggg gagagcacag ccacccgcct      60

cggcggcccg ggactcggct cgactcgccg gagaatgcgc ccgaggacga cggggcgcca     120

gagccgcggt gctttcaact ggcgagcgcg aatgggggtg cactggagta aggcagagtg     180

atgcgggggg gcaactcgcc tggcaccgag atcgccgccg tgcccttccc tggacccggc     240

gtcgcccagg atggctgccc cgagccatgg gccgcggcgg agctagcgcg gagcgcccga     300

ccctcgaccc ccgagtcccg gagccggccc cgcgcggggc cacgcgtccc tcgggcgctg     360

gttcctaagg aggacgacag caccagcttc tcctttctcc cttcccttcc ctgccccgca     420

ctcctccccc tgctcgctgt tgttgtgtgt cagcacttgg ctggggactt cttgaacttg     480

cagggagaat aacttgcgca ccccactttg cgccggtgcc tttgccccag cggagcctgc     540

ttcgccatct ccgagcccca ccgcccctcc actcctcggc cttgcccgac actgagacgc     600

tgttcccagc gtgaaaagag agactgcgcg gccggcaccc gggagaagga ggaggcaaag     660

aaaaggaacg gacattcggt ccttgcgcca ggtcctttga ccagagtttt tccatgtgga     720

cgctctttca atggacgtgt ccccgcgtgc ttcttagacg gactgcggtc tcctaaaggt     780

cgaccatggt ggccgggacc cgctgtcttc tagcgttgct gcttccccag gtcctcctgg     840

gcggcgcggc tggcctcgtt ccggagctgg gccgcaggaa gttcgcggcg gcgtcgtcgg     900

gccgcccctc atcccagccc tctgacgagg tcctgagcga gttcgagttg cggctgctca     960

gcatgttcgg cctgaaacag agacccaccc ccagcaggga cgccgtggtg ccccccctaca   1020

tgctagacct gtatcgcagg cactcaggtc agccgggctc acccgcccca gaccaccggt    1080

tggagagggc agccagccga gccaacactg tgcgcagctt ccaccatgaa gaatctttgg    1140

aagaactacc agaaacgagt gggaaaacaa cccggagatt cttctttaat ttaagttcta    1200

tccccacgga ggagtttatc acctcagcag agcttcaggt tttccgagaa cagatgcaag    1260

atgctttagg aaacaatagc agtttccatc accgaattaa tatttatgaa atcataaaac    1320

ctgcaacagc caactcgaaa ttccccgtga ccagactttt ggacaccagg ttggtgaatc    1380

agaatgcaag caggtgggaa agttttgatg tcacccccgc tgtgatgcgg tggactgcac    1440

agggacacgc caaccatgga ttcgtggtgg aagtggccca cttggaggag aaacaaggtg    1500

tctccaagag acatgttagg ataagcaggt ctttgcacca agatgaacac agctggtcac    1560

agataaggcc attgctagta acttttggcc atgatggaaa agggcatcct ctccacaaaa    1620

gagaaaaacg tcaagccaaa cacaaacagc ggaaacgcct taagtccagc tgtaagagac    1680

accctttgta cgtggacttc agtgacgtgg ggtggaatga ctggattgtg gctcccccgg    1740

ggtatcacgc cttttactgc cacggagaat gcccttttcc tctggctgat catctgaact    1800

ccactaatca tgccattgtt cagacgttgg tcaactctgt taactctaag attcctaagg    1860

catgctgtgt cccgacagaa ctcagtgcta tctcgatgct gtaccttgac gagaatgaaa    1920

aggttgtatt aaagaactat caggacatgg ttgtggaggg ttgtgggtgt cgctagtaca    1980
```

```
gcaaaattaa atacataaat atatatatat atatatattt tagaaaaaag aaaaaaacaa   2040

acaaacaaaa aaaccccacc ccagttgaca ctttaatatt tcccaatgaa gactttattt   2100

atggaatgga atggaaaaaa aaacagctat tttgaaaata tatttatatc tacgaaaaga   2160

agttgggaaa acaaatattt taatcagaga attattcctt aaagatttaa aatgtattta   2220

gttgtacatt ttatatgggt tcaaccccag cacatgaagt ataatggtca gatttatttt   2280

gtatttattt actattataa ccacttttta ggaaaaaaat agctaatttg tatttatatg   2340

taatcaaaag aagtatcggg tttgtacata attttccaaa aattgtagtt gttttcagtt   2400

gtgtgtattt aagatgaaaa gtctacatgg aaggttactc tggcaaagtg cttagcacgt   2460

ttgctttttt gcagtgctac tgttgagttc acaagttcaa gtccagaaaa aaaaagtgga   2520

taatccactc tgctgacttt caagattatt atattattca attctcagga atgttgcaga   2580

gtgattgtcc aatccatgag aatttacatc cttattaggt ggaatatttg gataagaacc   2640

agacattgct gatctattat agaaactctc ctcctgcccc ttaatttaca gaaagaataa   2700

agcaggatcc atagaaataa ttaggaaaac gatgaacctg caggaaagtg aatgatggtt   2760

tgttgttctt ctttcctaaa ttagtgatcc cttcaaaggg gctgatctgg ccaaagtatt   2820

caataaaacg taagatttct tcattattga tattgtggtc atatatattt aaaattgata   2880

tctcgtggcc ctcatcaagg gttggaaatt tatttgtgtt ttacctttac ctcatctgag   2940

agctctttat tctccaaaga acccagtttt ctaacttttt gcccaacacg cagcaaaatt   3000

atgcacatcg tgttttctgc ccaccctctg ttctctgacc tatcagcttg cttttctttc   3060

caaggttgtg tgtttgaaca catttctcca aatgttaaac ctatttcaga taataaatat   3120

caaatctctg gcatttcatt ctataaagtc                                    3150
```

<210> SEQ ID NO 243
<211> LENGTH: 3373
<212> TYPE: DNA
<213> ORGANISM: Homo sapiens
<220> FEATURE:
<221> NAME/KEY: misc_feature
<222> LOCATION: (1)..(3373)
<223> OTHER INFORMATION: dopamine receptor d1 (drd1)

<400> SEQUENCE: 243

```
ggctcgctgc ctcgcattgc cacaggctcc tgagaggtcg cgggcagtgc ctgcggggag     60

gcgcggggcc ctgctctgta gggctgaagg ccgcccgagg ttcgccaagg ctctgggctc    120

tcgaaaggaa gccaagaaaa gaagctgccc aggtgaccag tcctgggagt gctctctccc    180

aaggaagctc cgagcgccca ggagccctta gccggggtct agtgcccttt gaacaatctc    240

cagctcttca aggaagtggg ctgccgccgc ctctcttggg acctggcctg ggatcctttc    300

cccaaacgca ccccggcgat tttgcgcac cgggagccga acccctgctg cgcgcagctg    360

gctgggctca ggcgcgcttc ctcaacgttt cggagccgct gcccccagcg aagtccacat    420

tccaagctcc aggggctttg agagagacga ccccaaggca aggcgtttgg agagctgctg    480

aggagccagg ggcttggagg agcgagaaga catgtatttt cagctgagtc tcagaagggg    540

agaatctcct gtcaccacca gaaaagcaac agccccgaaa tgtgattgca actgactagc    600

agagcagagg cccaggagtc actggattga tgatttagaa tatgctaaaa agccagtgct    660

ttatttgggg aattcagggg ctttctggtg cccaagacag tgacctgcag caagggagtc    720

agaagacaga tgtagaaatc aagagtgacc atccacggga ttgacttgga ttgccactca    780
```

-continued

```
agcggtcctc tcatggaatg ttggtgaggc cctctgccag ggaagcaatc tggctgtgca    840
aagtgctgcc tggtggggag gactcctgga aatctgactg acccctattc cctgcttggg    900
aacttgaggg gtgtcagagc ccctgatgtg ctttctctta ggaagatgag gactctgaac    960
acctctgcca tggacgggac tgggctggtg gtggagaggg acttctctgt tcgtatcctc   1020
actgcctgtt tcctgtcgct gctcatcctg tccacgctcc tggggaacac gctggtctgt   1080
gctgccgtta tcaggttccg acacctgcgg tccaaggtga ccaacttctt tgtcatctcc   1140
ttggctgtgt cagatctctt ggtggccgtc ctggtcatgc cctggaaggc agtggctgag   1200
attgctggct tctggccctt tgggtccttc tgtaacatct gggtggcctt tgacatcatg   1260
tgctccactg catccatcct caacctctgt gtgatcagcg tggacaggta ttgggctatc   1320
tccagccctt tccggtatga gagaaagatg acccccaagg cagccttcat cctgatcagt   1380
gtggcatgga ccttgtctgt actcatctcc ttcatcccag tgcagctcag ctggcacaag   1440
gcaaaaccca caagcccctc tgatggaaat gccacttccc tggctgagac catagacaac   1500
tgtgactcca gcctcagcag gacatatgcc atctcatcct ctgtaataag cttttacatc   1560
cctgtggcca tcatgattgt cacctacacc aggatctaca ggattgctca gaaacaaata   1620
cggcgcattg cggccttgga gagggcagca gtccacgcca agaattgcca gaccaccaca   1680
ggtaatggaa agcctgtcga atgttctcaa ccggaaagtt cttttaagat gtccttcaaa   1740
agagaaacta aagtcctgaa gactctgtcg gtgatcatgg gtgtgtttgt gtgctgttgg   1800
ctacctttct tcatcttgaa ctgcattttg cccttctgtg ggtctgggga gacgcagccc   1860
ttctgcattg attccaacac ctttgacgtg tttgtgtggt ttgggtgggc taattcatcc   1920
ttgaacccca tcatttatgc ctttaatgct gattttcgga aggcattttc aaccctctta   1980
ggatgctaca gactttgccc tgcgacgaat aatgccatag agacggtgag tatcaataac   2040
aatggggccg cgatgttttc cagccatcat gagccacgag gctccatctc caaggagtgc   2100
aatctggttt acctgatccc acatgctgtg ggctcctctg aggacctgaa aaaggaggag   2160
gcagctggca tcgccagacc cttggagaag ctgtccccag ccctatcagt catattggac   2220
tatgacactg acgtctctct ggagaagatc caacccatca cacaaaacgg tcagcaccca   2280
acctgaactc gcagatgaat cctgccacac atgctcatcc caaaagctag aggagattgc   2340
tctggggctt gctattaaga aactaaggta cggtgagact ctgaggtgtc aggagagccc   2400
tctgctgctt tccaacacac aattaactcc gtttccaaat acattccagt gtattttctg   2460
tgttgttcat agtcaatcaa acagggacac tacaaacatg ggagccata agggacatgt    2520
ctttggcttc agaattgttt ttagaaattt attcttatct taggatttac caaatagggc   2580
aaagaatcaa cagtgaacag cttcacttaa aatcaaattt ttctgggaag aaaatgagat   2640
gggttgagtt tgctgtatac aaacaggtgc taacactgtt cccagcaaag ttttcagatt   2700
gtaaaggtag gtgcatgcct tcataaatta tttctaaaac attaattgag gcttacagta   2760
ggagtgagaa attttttttcc agaattgaga gatgttttgt tgatattggt tctatttatt  2820
tattgtatat atggatattt ttaatttatg atataataaa tatatattta tcatatttaa   2880
taggataaat taatgagttt tatccaagac cttacaacca catttctggc catttaacta   2940
gcactttata agccaatgaa gcaaacacac agactctgtg agattctaaa tgttcatgtg   3000
taacttctag aaacacagca gaaactgata gataagggaa taaagttgaa atgattcctt   3060
aaaattcatg gacacagata aatgcaaggt gagaattgac aaatgctata aatgctttct   3120
ttttctgaaa agattttgaa aaatttaaaa aagtatagct actactgtgt tcaaaacgtt   3180
```

```
ttaaatgaca aatgactttc ccaggggaat ttgcagttct gtaaatatct taaataaaag   3240

ccaacttaag aagagcccag cattaaattt acgatcttag gtggtaatga aaagtatatg   3300

ctgctttgta tttatgtaaa ataattggcc ctctccatct tttctcattt catgtgtcag   3360

gtagtttttc tga                                                      3373
```

<210> SEQ ID NO 244
<211> LENGTH: 3650
<212> TYPE: DNA
<213> ORGANISM: Homo sapiens
<220> FEATURE:
<221> NAME/KEY: misc_feature
<222> LOCATION: (1)..(3650)
<223> OTHER INFORMATION: paired box 5 (PAX5)

<400> SEQUENCE: 244

```
agcactgctg ctctcccggc ttcccgctct actccggccg ggccgggtcc gccacgtctg     60

gcgcgctgag caggcccggc cgcgcagcgc ctaccctttc ctcgctccgg gccggcagtg    120

tggggcggcg cgctgggggc gcggcgtgtc tggggacatc ttgtgatgtt ggcgagaaca    180

ggacatgatc tcacatggcg agaagctctt tagttcctta atcatttcac ggtgccttcg    240

gacgcttttt ttccacctaa aacgtttagt ttcagctcag tgatcagcta ccccagctcg    300

gcgggggagc ggaaggcttg aattattccg acctgtgagc ggcccctggc accaaaaaaa    360

aaaaaaaaaa aaaaaaaaaa agaaaaaaaa aggcacaaaa aagtggaaac ttttccctgt    420

ccattccatc aagtcctgaa aaatcaaaat ggatttagag aaaaattatc cgactcctcg    480

gaccagcagg acaggacatg gaggagtgaa tcagcttggg ggggtttttg tgaatggacg    540

gccactcccg gatgtagtcc gccagaggat agtggaactt gctcatcaag gtgtcaggcc    600

ctgcgacatc tccaggcagc ttcgggtcag ccatggttgt gtcagcaaaa ttcttggcag    660

gtattatgag acaggaagca tcaagcctgg ggtaattgga ggatccaaac caaaggtcgc    720

cacacccaaa gtggtggaaa aaatcgctga atataaacgc caaaatccca ccatgtttgc    780

ctgggagatc agggaccggc tgctggcaga gcgggtgtgt gacaatgaca ccgtgcctag    840

cgtcagttcc atcaacagga tcatccggac aaaagtacag cagccaccca accaaccagt    900

cccagcttcc agtcacagca tagtgtccac tggctccgtg acgcaggtgt cctcggtgag    960

cacggattcg gccggctcgt cgtactccat cagcggcatc ctgggcatca cgtcccccag   1020

cgccgacacc aacaagcgca agagagacga aggtattcag gagtctccgg tgccgaacgg   1080

ccactcgctt ccgggcagag acttcctccg gaagcagatg cggggagact tgttcacaca   1140

gcagcagctg gaggtgctgg accgcgtgtt tgagaggcag cactactcag acatcttcac   1200

caccacagag cccatcaagc ccgagcagac cacagagtat tcagccatgg cctcgctggc   1260

tggtgggctg gacgacatga aggccaatct ggccagcccc acccctgctg acatcgggag   1320

cagtgtgcca ggcccgcagt cctaccccat tgtgacaggc cgtgacttgg cgagcacgac   1380

cctccccggg taccctccac acgtcccccc cgctggacag ggcagctact cagcaccgac   1440

gctgacaggg atggtgcctg ggagtgagtt ttccgggagt ccctacagcc accctcagta   1500

ttcctcgtac aacgactcct ggaggttccc caacccgggg ctgcttggct cccccctacta   1560

ttatagcgct gccgcccgag gagccgcccc acctgcagcc gccactgcct atgaccgtca   1620

ctgacccttg gagccaggcg ggcaccaaac actgatggca cctattgagg gtgacagcca   1680

cccagccctc ctgaagatag ccagagagcc catgagaccg tcccccagca tcccccactt   1740
```

```
gcctgaagct cccctcttcc tctcttcctc cagggactct ggggcccttt ggtggggccg   1800
ttggacttct ggatgcttgt ctatttctaa aagccaatct atgagcttct cccgatggcc   1860
actgggtctc tgcaaaccaa tagactgtcc tgcaaataac cgcagcccca gcccagcctg   1920
cctgtcctcc agctgtctga ctatccatcc atcataacca ccccagcctg ggaaggagag   1980
cttgcttttg ttgcttcagc agcacccatg taaatacctt cttgcttttc tgtgggcctg   2040
aaggtccgac tgagaagact gctccaccca tgatgcatct cgcactcttg gtgcatcacc   2100
ggacatctta gacctatggc agagcatcct ctctgccctg ggtgaccctg gcaggtgcgc   2160
tcagagctgt cctcaagatg gaggatgctg cccttgggcc ccagcctcct gctcatccct   2220
ccttctttag tatctttacg aggagtctca ctgggctggt tgtgctgcag gctccccctg   2280
aggcccctct ccaagaggag cacactttgg ggagatgtcc tggtttcctg cctccatttc   2340
tctgggaccg atgcagtatc agcagctctt ttccagatca aagaactcaa agaaaactgt   2400
ctgggagatt cctcagctac ttttccgaag cagaatgtca tccgaggtat tgattacatt   2460
gtggactttg aatgtgaggg ctggatggga cgcaggagat catctgatcc cagccaagga   2520
ggggcctgag gctctcccta ctccctcagc ccctggaacg gtgttttctg aggcatgccc   2580
aggttcaggt cacttcggac acctgccatg gacacttcac ccaccctcca ggaccccagc   2640
aagtggattc tgggcaagcc tgttccggtg atgtagacaa taattaacac agaggacttt   2700
cccccacacc cagatcacaa acagcctaca gccagaactt ctgagcatcc tctcggggca   2760
gaccctcccc gtcctcgtgg agcttagcag gcagctgggc atggaggtgc tggggctggg   2820
gcagatgcct aatttcgcac aatgcatgcc cacctgttga tctaaggggc cgcgatggtc   2880
agggccacgg ccaagggcca cgggaacttg gagagggagc ttggagaact cactgtgggc   2940
tagggtggtc agaggaagcc agcagggaag atctgggggga cagaggaagg cctcctgagg   3000
gaggggcagg agagcagtga ggagctgctg tgtgacctgg gagtgatttt gacatggggg   3060
tgccaggtgc catcatctct ttacctgggg ccttaattcc ttgcatagtc tctcttgtca   3120
agtcagaaca gccaggtaga gcccttgtcc aaacctgggc tgaatgacag tgatgagagg   3180
gggcttggcc ttcttaggtg acaatgtccc ccatatctgt atgtcaccag gatggcagag   3240
agccagggca gagagagact ggacttggga tcagcaggcc aggcaggtct tgtcctggtc   3300
ctggccacat gtctttgctg tgggacctca gacaaaaccc tgcacctctt tgagccttgg   3360
ctgccttggt gcagcagggt catctgtagg gccaccccac agctctttcc ttcccctcct   3420
ctctccaggg agccggggct gtgagaggat catctggggc aggccctcca cttccaagca   3480
agcagatggg ggtgggcacc tgaggcccaa taatatttgg accaagtggg aaacaagaac   3540
actcggaggg gcgggaatca gaagagcctg gaaaaagacc tagcccaact tcccttgtgg   3600
gaaactgagg cccagcttgg ggaaggccag gaccatgcag ggagaaaaag             3650
```

```
<210> SEQ ID NO 245
<211> LENGTH: 683
<212> TYPE: DNA
<213> ORGANISM: Homo sapiens
<220> FEATURE:
<221> NAME/KEY: misc_feature
<222> LOCATION: (1)..(683)
<223> OTHER INFORMATION: S100 calcium binding protein A6 (S100A6)

<400> SEQUENCE: 245

ctgcgcagat gaggggagac tcgtcaccag gcgtgcagtg ggcactgctg ggctccccca     60
tcccgtccta acccggaaca gccccgggca ggaggcgtgg aaagtcgagg gggtaaaccg    120
```

```
cgaatgtgcg ttgtgtaagc cacggcgcag ggtggggcgc gggcgggact tgggcgggcg    180

gggtgggctt ggccgagctg gcctccgggg caccgaccgc tataaggcca gtcggactgc    240

gacacagccc atcccctcga ccgctcgcgt cgcatttggc cgcctcccta ccgctccaag    300

cccagccctc agccatggca tgccccctgg atcaggccat tggcctcctc gtggccatct    360

tccacaagta ctccggcagg gagggtgaca agcacaccct gagcaagaag gagctgaagg    420

agctgatcca gaaggagctc accattggct cgaagctgca ggatgctgaa attgcaaggc    480

tgatggaaga cttggaccgg aacaaggacc aggaggtgaa cttccaggag tatgtcacct    540

tcctgggggc cttggctttg atctacaatg aagccctcaa gggctgaaaa taaataggga    600

agatggagac accctctggg ggtcctctct gagtcaaatc cagtggtggg taattgtaca    660

ataaattttt tttggtcaaa ttt                                            683
```

```
<210> SEQ ID NO 246
<211> LENGTH: 2713
<212> TYPE: DNA
<213> ORGANISM: Homo sapiens
<220> FEATURE:
<221> NAME/KEY: misc_feature
<222> LOCATION: (1)..(2713)
<223> OTHER INFORMATION: dopamine receptor D2 (DRD2)

<400> SEQUENCE: 246

actgctcccc gcgggccaga gccggccgag ctgctgcccg ccggggctct gaacggcgcg     60

gcggggccgg gagccaggga ccggccgagg agagtggcgg ccccggacgg ctgccggagg    120

ggcggccgcg cgtggatgcg gcgggagctg gaagcctcaa gcagccggcg ccgtctctgc    180

ccccgggcgc cctatggctt gaagagcctg gccacccagt ggctccaccg ccctgatgga    240

tccactgaat ctgtcctggt atgatgatga tctggagagg cagaactgga gccggccctt    300

caacgggtca gacgggaagg cggacagacc ccactacaac tactatgcca cactgctcac    360

cctgctcatc gctgtcatcg tcttcggcaa cgtgctggtg tgcatggctg tgtcccgcga    420

gaaggcgctg cagaccacca ccaactacct gatcgtcagc ctcgcagtgg ccgacctcct    480

cgtcgccaca ctggtcatgc cctgggttgt ctacctggag gtggtaggtg agtggaaatt    540

cagcaggatt cactgtgaca tcttcgtcac tctggacgtc atgatgtgca cggcgagcat    600

cctgaacttg tgtgccatca gcatcgacag gtacacagct gtggccatgc ccatgctgta    660

caatacgcgc tacagctcca agcgccgggt caccgtcatg atctccatcg tctgggtcct    720

gtccttcacc atctcctgcc cactcctctt cggactcaat aacgcagacc agaacgagtg    780

catcattgcc aacccggcct tcgtggtcta ctcctccatc gtctccttct acgtgccctt    840

cattgtcacc ctgctggtct acatcaagat ctacattgtc ctccgcagac gccgcaagcg    900

agtcaacacc aaacgcagca gccgagcttt cagggcccac ctgagggctc cactaaaggg    960

caactgtact caccccgagg acatgaaact ctgcaccgtt atcatgaagt ctaatgggag   1020

tttcccagtg aacaggcgga gagtggaggc tgcccggcga gcccaggagc tggagatgga   1080

gatgctctcc agcaccagcc cacccgagag gacccggtac agccccatcc cacccagcca   1140

ccaccagctg actctccccg acccgtccca ccatggtctc cacagcactc ccgacagccc   1200

cgccaaacca gagaagaatg ggcatgccaa agaccacccc aagattgcca agatctttga   1260

gatccagacc atgcccaatg gcaaaacccg gacctccctc aagaccatga gccgtaggaa   1320

gctctcccag cagaaggaga agaaagccac tcagatgctc gccattgttc tcggcgtgtt   1380
```

```
catcatctgc tggctgccct tcttcatcac acacatcctg aacatacact gtgactgcaa   1440

catcccgcct gtcctgtaca gcgccttcac gtggctgggc tatgtcaaca gcgccgtgaa   1500

ccccatcatc tacaccacct tcaacattga gttccgcaag gccttcctga agatcctcca   1560

ctgctgactc tgctgcctgc ccgcacagca gcctgcttcc cacctccctg cccaggccgg   1620

ccagcctcac ccttgcgaac cgtgagcagg aaggcctggg tggatcggcc tcctcttcac   1680

cccggcaggc cctgcagtgt tcgcttggct ccatgctcct cactgcccgc acaccctcac   1740

tctgccaggg cagtgctagt gagctgggca tggtaccagc cctggggctg ggcccccag   1800

ctcaggggca gctcatagag tccccctcc cacctccagt cccctatcc ttggcaccaa   1860

agatgcagcc gccttccttg accttcctct ggggctctag ggttgctgga gcctgagtca   1920

gggcccagag gctgagtttt ctctttgtgg ggcttggcgt ggagcaggcg gtggggagag   1980

atggacagtt cacaccctgc aaggcccaca ggaggcaagc aagctctctt gccgaggagc   2040

caggcaactt cagtcctggg agacccatgt aaataccaga ctgcaggttg gaccccagag   2100

attcccaagc caaaaacctt agctccctcc cgcaccccga tgtggacctc tactttccag   2160

gctagtccgg acccacctca ccccgttaca gctccccaag tggtttccac atgctctgag   2220

aagaggagcc ctcatcttga agggcccagg agggtctatg ggagaggaa ctccttggcc   2280

tagcccaccc tgctgccttc tgacggccct gcaatgtatc ccttctcaca gcacatgctg   2340

gccagcctgg ggcctggcag ggaggtcagg ccctggaact ctatctgggc ctgggctagg   2400

ggacatcaga ggttctttga gggactgcct ctgccacact ctgacgcaaa accactttcc   2460

ttttctattc cttctggcct ttcctctctc ctgtttccct tcccttccac tgcctctgcc   2520

ttagaggagc ccacggctaa gaggctgctg aaaaccatct ggcctggcct ggccctgccc   2580

tgaggaagga ggggaagctg cagcttggga gagcccctgg ggcctagact ctgtaacatc   2640

actatccatg caccaaacta ataaaacttt gacgagtcac cttccaggac ccctgggtaa   2700

aaaaaaaaaa aaa                                                      2713
```

```
<210> SEQ ID NO 247
<211> LENGTH: 4190
<212> TYPE: DNA
<213> ORGANISM: Homo sapiens
<220> FEATURE:
<221> NAME/KEY: misc_feature
<222> LOCATION: (1)..(4190)
<223> OTHER INFORMATION: histone deacetylase 7 (HDAC7)

<400> SEQUENCE: 247

agataaagca tttccttcca ttgtcatcct acccggccgg ccgggctgcc agggccctcc     60

ccctcccggc cccctccctt cctctcgccg tctcacagtc gctctgcagc ctccggcgac    120

tggggggatg tgaggccggc gccccagccc cccgccccgc catgagcccc ccgctctgag    180

ggccccggcc cctggatgca cagccccggc gctgatggga cccaggtgag cccgggtgcc    240

cactactgca gccccactgg cgcaggctgc cccaggccct gtgcagacac accaggccct    300

cagccgcagc ccatggacct gcgggtgggc cagcggcccc cagtggagcc cccaccagag    360

cccacattgc tggccctgca gcgtccccag cgcctgcacc accacctctt cctagcaggc    420

ctgcagcagc agcgctcggt ggagcccatg aggctctcca tggacacgcc gatgcccgag    480

ttgcaggtgg gaccccagga acaagagctg cggcagcttc tccacaagga caagagcaag    540

cgaagtgctg tagccagcag cgtggtcaag cagaagctag cggaggtgat tctgaaaaaa    600

cagcaggcgg ccctagaaag aacagtccat cccaacagcc ccggcattcc ctacagaacc    660
```

```
ctggagcccc tggagacgga aggagccacc cgctccatgc tcagcagctt tttgcctcct    720
gttcccagcc tgcccagtga ccccccagag cacttccctc tgcgcaagac agtctctgag    780
cccaacctga agctgcgcta taagcccaag aagtccctgg agcggaggaa gaatccactg    840
ctccgaaagg agagtgcgcc ccccagcctc cggcggcggc ccgcagagac cctcggagac    900
tcctccccaa gtagtagcag cacgcccgca tcagggtgca gctcccccaa tgacagcgag    960
cacggcccca atcccatcct gggctcggag gctgacagtg accgcaggac ccatccgact   1020
ctgggccctc gggggccaat cctggggagc cccccacactc ccctcttcct gccccatggc   1080
ttggagcccg aggctggggg caccttgccc tctcgcctgc agcccattct cctcctggac   1140
ccctcaggct ctcatgcccc gctgctgact gtgcccgggc ttgggccctt gcccttccac   1200
tttgcccagt ccttaatgac caccgagcgg ctctctgggt caggcctcca ctggccactg   1260
agccggactc gctcagagcc cctgcccccc agtgccaccg ctcccccacc gccgggcccc   1320
atgcagcccc gcctggagca gctcaaaact cacgtccagg tgatcaagag gtcagccaag   1380
ccgagtgaga agccccggct gcggcagata ccctcggctg aagacctgga gacagatggc   1440
gggggaccgg gccaggtggt ggacgatggc ctggagcaca gggagctggg ccatgggcag   1500
cctgaggcca gaggccccgc tcctctccag cagcaccctc aggtgttgct ctgggaacag   1560
cagcgactgg ctgggcggct cccccggggc agcaccgggg acactgtgct gcttcctctg   1620
gcccagggtg ggcaccggcc tctgtcccgg gctcagtctt ccccagccgc acctgcctca   1680
ctgtcagccc cagagcctgc cagccaggcc cgagtcctct ccagctcaga gacccctgcc   1740
aggaccctgc ccttcaccac aggctgatc tatgactcgg tcatgctgaa gcaccagtgc   1800
tcctgcggtg acaacagcag gcacccggag cacgccggcc gcatccagag catctggtcc   1860
cggctgcagg agcgggggct ccggagccag tgtgagtgtc tccgaggccg gaaggcctcc   1920
ctggaagagc tgcagtcggt ccactctgag cggcacgtgc tcctctacgg caccaacccg   1980
ctcagccgcc tcaaactgga caacgggaag ctggcagggc tcctggcaca gcggatgttt   2040
gtgatgctgc cctgtggtgg ggttggggtg gacactgaca ccatctggaa tgagcttcat   2100
tcctccaatg cagcccgctg ggccgctggc agtgtcactg acctcgcctt caaagtggct   2160
tctcgtgagc taaagaatgg tttcgctgtg gtgcggcccc caggacacca tgcagatcat   2220
tcaacagcca tgggcttctg cttcttcaac tcagtggcca tcgcctgccg gcagctgcaa   2280
cagcagagca aggccagcaa gatcctcatt gtagactggg acgtgcacca tggcaacggc   2340
acccagcaaa ccttctacca agaccccagt gtgctctaca tctccctgca tcgccatgac   2400
gacggcaact tcttcccggg gagtggggct gtggatgagg taggggctgg cagcggtgag   2460
ggcttcaatg tcaatgtggc ctgggctgga ggtctggacc cccccatggg ggatcctgag   2520
tacctggctg ctttcaggat agtcgtgatg cccatcgccc gagagttctc tccagaccta   2580
gtcctggtgt ctgctggatt tgatgctgct gagggtcacc cggcccccact gggtggctac   2640
catgtttctg ccaaatgttt tggatacatg acgcagcaac tgatgaacct ggcaggaggc   2700
gcagtggtgc tggccttgga gggtggccat gacctcacag ccatctgtga cgcctctgag   2760
gcctgtgtgg ctgctcttct gggtaacagg gtggatcccc tttcagaaga aggctggaaa   2820
cagaaaccca acctcaatgc catccgctct ctggaggccg tgatccgggt gcacagtaaa   2880
tactggggct gcatgcagcg cctggcctcc tgtccagact cctgggtgcc tagagtgcca   2940
ggggctgaca aagaagaagt ggaggcagtg accgcactgg cgtccctctc tgtgggcatc   3000
```

```
ctggctgaag ataggccctc ggagcagctg gtggaggagg aagaacctat gaatctctaa   3060

ggctctggaa ccatctgccc gcccaccatg cccttgggac ctggttctct tctaacccct   3120

ggcaatagcc cccattcctg ggtctttaga gatcctgtgg gcaagtagtt ggaaccagag   3180

aacagcctgc ctgctttgac agttatccca gggagcgtga gaaaatccct gggtctagaa   3240

tgggaactgg agaggaccct gagaggagac gggctgggcg gcgaccccca cagggctctc   3300

gagaacagat tctcccctcc agtatgggcc ctggctgtgg cccccattcc tcaggactgc   3360

acagaggagg actggctccg gctccgtcgg gctcaccctt aaccactatt cctggctctg   3420

caaaccccag actttgcaca cagcctcagg ctccacacag aaatgtgaac ttggcctcag   3480

acaggctggc ccttcctagg ctctaggggc tagggggag tggggagcca agaggtccca   3540

tattcctgag tgcaggggta gtccctctca cctgcttcct cagacgactc tggaagcttc   3600

cctctaccac tgggcactga gacgaagctc cctgacagcc gagactggca gccctccatc   3660

tggtccgtac cctcgccaga ggcccccta catcaacctc ctggcgatgc cctggtggag   3720

cagatgggtg ctctgggagt cctgtgcttc ctgatccaat ggtgccaaac ccttcatctc   3780

cccaagaagc gcagcatacc cctgggaccc ctcggccact gcccactcgg ggagccttct   3840

ctgtttctgg ggcctccccc accatagctc tgattcccac cccacatagg agtagcctga   3900

ctgaggggga aggggtggga gagaagatac agacatggag gaggggaggc tgctctggca   3960

aagtcttcaa ggcttttggg ggtccaggcc tggggtcaag aaggaaaatg tgtgtgagca   4020

tgtgtgtgag tgaggcgtgt gtgtgagcgt gtgtgtgagt gaggcgtgtg tgtgtgtctt   4080

tcctaggacc caccataccc tgtgtatgta tgcatgtttt tgtaaaaagg aagaaaatgg   4140

aaaaaaatct gaacaataaa tgttttattt gctttaaaaa aaaaaaaaaa              4190
```

<210> SEQ ID NO 248
<211> LENGTH: 2672
<212> TYPE: DNA
<213> ORGANISM: Homo sapiens
<220> FEATURE:
<221> NAME/KEY: misc_feature
<222> LOCATION: (1)..(2672)
<223> OTHER INFORMATION: hairy/enhancer-of-split related with YRPW motif 2 (HEY2)

<400> SEQUENCE: 248

```
gcgtggccgg cgccggctct tgcggccgag cagagttgcg gcgtgggaaa gagccgctag     60

gagcagaccg cgccgccgcc ggagccgcgc ctgcccaggc ccggggaggg aggaggcggg    120

cgtcagggtg ctgcgccccg ctcggcgtcc gagcttccgg ccgggctgtg ccccgcgcgg    180

tcttcgccgg gatgaagcgc ccctgcgagg agacgacctc cgagagcgac atggacgaga    240

ccatcgacgt ggggagcgag aacaattact cggggcaaag tactagctct gtgattagat    300

tgaattctcc aacaacaaca tctcagatta tggcaagaaa gaaaaggaga gggattatag    360

agaaaaggcg tcgggatcgg ataaataaca gtttatctga gttgagaaga cttgtgccaa    420

ctgcttttga aaaacaagga tctgcaaagt tagaaaaagc tgaaatattg caaatgacag    480

tggatcattt gaagatgctt caggcaacag gggtaaagg ctactttgac gcacacgctc    540

ttgccatgga cttcatgagc ataggattcc gagagtgcct aacagaagtt gcgcggtacc    600

tgagctccgt ggaaggcctg gactcctcgg atccgctgcg ggtgcggctt gtgtctcatc    660

tcagcacttg cgccacccag cgggaggcgg cggccatgac atcctccatg gcccaccacc    720

atcatccgct ccacccgcat cactgggccg ccgccttcca ccacctgccc gcagccctgc    780
```

```
tccagcccaa cggcctccat gcctcagagt caacccccttg tcgcctctcc acaacttcag    840

aagtgcctcc tgcccacggc tctgctctcc tcacggccac gtttgcccat gcggattcag    900

ccctccgaat gccatccacg ggcagcgtcg ccccctgcgt gccacctctc tccacctctc    960

tcttgtccct ctctgccacc gtccacgccg cagccgcagc agccaccgcg gctgcacaca   1020

gcttccctct gtccttcgcg ggggcattcc ccatgcttcc cccaaacgca gcagcagcag   1080

tggccgcggc cacagccatc agcccgccct tgtcagtatc agccacgtcc agtcctcagc   1140

agaccagcag tggaacaaac aataaacctt accgaccctg gggacagaa gttggagctt   1200

tttaaatttt tcttgaactt cttgcaatag taactgaatg tcctccattt cagagtcagc   1260

ttaaaacctc tgcaccctga aggtagccat acagatgccg acagatccac aaaggaacaa   1320

taaagctatt tgagacacaa acctcacgag tggaaatgtg gtattctctt ttttttctct   1380

cccttttttg tttggttcaa ggcagctcgg taactgacat cagcaacttt tgaaaacttc   1440

acacttgtta ccatttagaa gtttcctgga aaatatatgg accgtaccat ccagcagtgc   1500

atcagtatgt ctgaattggg gaagtaaaat gccctgactg aattctcttg agactagatg   1560

ggacatacat atatagagag agagtgagag agtcgtgttt cgtaagtgcc tgagcttagg   1620

aagttttctt ctggatatat aacattgcac aagggaagac gagtgtggag gataggttaa   1680

gaaaggaaag ggacagaagt cttgcaatag gctgcagaca ttttaatacc atgccagaga   1740

agagtattct gctgaaacca acaggtttta ctggtcaaaa tgactgctga aaataatttt   1800

caagttgaaa gatctagttt tatcttagtt tgccttcttt gtacagacat gccaagaggt   1860

gacatttagc agtgcattgg tataagcaat tatttcatca gttctcagat taacaagcat   1920

ttctgctctg cctgcaggcc cccaggcact tttttttttg gatggctcaa aatatggtgc   1980

tgctttatat aaaccttaca tttatatagt gcacctatga gcagttgcct accatgtgtc   2040

caccagaggc tatttaattc atgccaactt gaaaactctc cagtttgtag gagtttggtt   2100

taatttattc agtttcatta ggactatttt tatatattta tcctcttcat tttctcctaa   2160

tgatgcaaca tctattcttg tcacccttttg ggagaagtta catttctgga ggtgatgaag   2220

caaggaggga gcactaggaa gagaaaagct acaattttta aagctctttg tcaagttagt   2280

gattgcattt gatcccaaaa caagatgaat gtatgcaatg ggatgtacat aagttatttt   2340

tgcccatgcc taaactagtg ctatgtaatg gggttgtggt tttgtttttt tcgatttcgt   2400

ttaatgacaa aataatctct taatatgctg aaatcaagca cgtgagagtt tttgtttaaa   2460

agataagaga cacagcatgt attatgcact tcatttctct actgtgtgga gaaagcaata   2520

aacattatga gaatgttaaa cgttatgcaa aattatactt ttaaatattt gttttgaaat   2580

tactgtacct agtctttttt gcattacttt gtaacctttt tctatgcaag agtctttaca   2640

taccactaat taaatgaagt cctttttgac ta                                 2672
```

```
<210> SEQ ID NO 249
<211> LENGTH: 2175
<212> TYPE: DNA
<213> ORGANISM: Homo sapiens
<220> FEATURE:
<221> NAME/KEY: misc_feature
<222> LOCATION: (1)..(2175)
<223> OTHER INFORMATION: inhibin, beta A (INHBA)

<400> SEQUENCE: 249

agtacagtat aaaacttcac agtgccaata ccatgaagag gagctcagac agctcttacc     60

acatgataca agagccggct ggtggaagag tggggaccag aaagagaatt tgctgaagag    120
```

```
gagaaggaaa aaaaaaacac caaaaaaaaa aataaaaaaa tccacacaca caaaaaaacc    180
tgcgcgtgag gggggaggaa aagcagggcc ttttaaaaag gcaatcacaa caacttttgc    240
tgccaggatg cccttgcttt ggctgagagg atttctgttg gcaagttgct ggattatagt    300
gaggagttcc cccaccccag gatccgaggg gcacagcgcg gcccccgact gtccgtcctg    360
tgcgctggcc gccctcccaa aggatgtacc caactctcag ccagagatgg tggaggccgt    420
caagaagcac attttaaaca tgctgcactt gaagaagaga cccgatgtca cccagccggt    480
acccaaggcg gcgcttctga acgcgatcag aaagcttcat gtgggcaaag tcggggagaa    540
cgggtatgtg gagatagagg atgacattgg aaggagggca gaaatgaatg aacttatgga    600
gcagacctcg gagatcatca cgtttgccga gtcaggaaca gccaggaaga cgctgcactt    660
cgagatttcc aaggaaggca gtgacctgtc agtggtggag cgtgcagaag tctggctctt    720
cctaaaagtc cccaaggcca acaggaccag gaccaaagtc accatccgcc tcttccagca    780
gcagaagcac ccgcagggca gcttggacac aggggaagag gccgaggaag tgggcttaaa    840
gggggagagg agtgaactgt tgctctctga aaaagtagta gacgctcgga agagcacctg    900
gcatgtcttc cctgtctcca gcagcatcca gcggttgctg gaccagggca agagctccct    960
ggacgttcgg attgcctgtg agcagtgcca ggagagtggc gccagcttgg ttctcctggg   1020
caagaagaag aagaaaagaag aggagggga agggaaaaag aagggcggag gtgaaggtgg   1080
ggcaggagca gatgaggaaa aggagcagtc gcacagacct ttcctcatgc tgcaggcccg   1140
gcagtctgaa gaccaccctc atcgccggcg tcggcggggc ttggagtgtg atggcaaggt   1200
caacatctgc tgtaagaaac agttctttgt cagtttcaag gacatcggct ggaatgactg   1260
gatcattgct ccctctggct atcatgccaa ctactgcgag ggtgagtgcc cgagccatat   1320
agcaggcacg tccgggtcct cactgtcctt ccactcaaca gtcatcaacc actaccgcat   1380
gcggggccat agcccctttg ccaacctcaa atcgtgctgt gtgcccacca agctgagacc   1440
catgtccatg ttgtactatg atgatggtca aaacatcatc aaaaaggaca ttcagaacat   1500
gatcgtggag gagtgtgggt gctcatagag ttgcccagcc caggggggaaa gggagcaaga   1560
gttgtccaga gaagacagtg gcaaaatgaa gaaattttta aggtttctga gttaaccaga   1620
aaaatagaaa ttaaaaacaa aacaaaaaaa aaaacaaaaa aaaacaaaag taaattaaaa   1680
acaaaacctg atgaaacaga tgaaggaaga tgtggaaaaa atccttagcc agggctcaga   1740
gatgaagcag tgaaagagac aggaattggg agggaaaggg agaatggtgt accctttatt   1800
tcttctgaaa tcacactgat gacatcagtt gtttaaacgg ggtattgtcc tttccccccct   1860
tgaggttccc ttgtgagcct tgaatcaacc aatctagtct gcagtagtgt ggactagaac   1920
aacccaaata gcatctagaa agccatgagt ttgaaagggc ccatcacagg cactttccta   1980
cccaattacc caggtcataa ggtatgtctg tgtgacactt atctctgtgt atatcagcat   2040
acacacacac acacacacac acacacacac acacaggcat ttccacacat tacatatata   2100
cacatactgg taaaagaaca atcgtgtgca ggtggtcaca cttccttttt ctgtaccact   2160
tttgcaacaa aacaa                                                    2175
```

```
<210> SEQ ID NO 250
<211> LENGTH: 1576
<212> TYPE: DNA
<213> ORGANISM: Homo sapiens
<220> FEATURE:
<221> NAME/KEY: misc_feature
<222> LOCATION: (1)..(1576)
```

<223> OTHER INFORMATION: sonic hedgehog (SHH)

<400> SEQUENCE: 250

```
gcgaggcagc cagcgaggga gagagcgagc gggcgagccg gagcgaggaa gggaaagcgc     60
aagagagagc gcacacgcac acacccgccg cgcgcactcg cgcacggacc cgcacgggga    120
cagctcggaa gtcatcagtt ccatgggcga gatgctgctg ctggcgagat gtctgctgct    180
agtcctcgtc tcctcgctgc tggtatgctc gggactggcg tgcggaccgg gcagggggtt    240
cgggaagagg aggcacccca aaaagctgac ccctttagcc tacaagcagt ttatccccaa    300
tgtggccgag aagaccctag gcgccagcgg aaggtatgaa gggaagatct ccagaaactc    360
cgagcgattt aaggaactca cccccaatta caaccccgac atcatattta aggatgaaga    420
aaacaccgga gcggacaggc tgatgactca gaggtgtaag gacaagttga acgctttggc    480
catctcggtg atgaaccagt ggccaggagt gaaactgcgg gtgaccgagg gctgggacga    540
agatggccac cactcagagg agtctctgca ctacgagggc cgcgcagtgg acatcaccac    600
gtctgaccgc gaccgcagca agtacggcat gctggcccgc ctggcggtgg aggccggctt    660
cgactgggtg tactacgagt ccaaggcaca tatccactgc tcggtgaaag cagagaactc    720
ggtggcggcc aaatcgggag gctgcttccc gggctcggcc acggtgcacc tggagcaggg    780
cggcaccaag ctggtgaagg acctgagccc cggggaccgc gtgctggcgg cggacgacca    840
gggccggctg ctctacagcg acttcctcac tttcctggac cgcgacgacg gcgccaagaa    900
ggtcttctac gtgatcgaga cgcgggagcc gcgcgagcgc ctgctgctca ccgccgcgca    960
cctgctcttt gtggcgccgc acaacgactc ggccaccggg gagcccgagg cgtcctcggg   1020
ctcggggccg ccttccgggg gcgcactggg gcctcgggcg ctgttcgcca gccgcgtgcg   1080
cccgggccag cgcgtgtacg tggtggccga gcgtgacggg gaccgccggc tcctgcccgc   1140
cgctgtgcac agcgtgaccc taagcgagga ggccgcgggc gcctacgcgc cgctcacggc   1200
ccagggcacc attctcatca accgggtgct ggcctcgtgc tacgcggtca tcgaggagca   1260
cagctgggcg caccgggcct tcgcgccctt ccgcctggcg cacgcgctcc tggctgcact   1320
ggcgcccgcg cgcacggacc gcggcgggga cagcggcggc ggggaccgcg ggggcggcgg   1380
cggcagagta gccctaaccg ctccaggtgc tgccgacgct ccgggtgcgg gggccaccgc   1440
gggcatccac tggtactcgc agctgctcta ccaaataggc acctggctcc tggacagcga   1500
ggccctgcac ccgctgggca tggcggtcaa gtccagctga agccgggggg ccgggggagg   1560
ggcgcgggag ggggcg                                                   1576
```

<210> SEQ ID NO 251
<211> LENGTH: 2611
<212> TYPE: DNA
<213> ORGANISM: Homo sapiens
<220> FEATURE:
<221> NAME/KEY: misc_feature
<222> LOCATION: (1)..(2611)
<223> OTHER INFORMATION: Bruton agammaglobulinemia tyrosine kinase (BTK)

<400> SEQUENCE: 251

```
aactgagtgg ctgtgaaagg gtggggtttg ctcagactgt ccttcctctc tggactgtaa     60
gaatatgtct ccagggccag tgtctgctgc gatcgagtcc caccttccaa gtcctggcat    120
ctcaatgcat ctgggaagct acctgcatta agtcaggact gagcacacag gtgaactcca    180
gaaagaagaa gctatggccg cagtgattct ggagagcatc tttctgaagc gatcccaaca    240
gaaaaagaaa acatcacctc taaacttcaa gaagcgcctg tttctcttga ccgtgcacaa    300
```

```
actctcctac tatgagtatg actttgaacg tgggagaaga ggcagtaaga agggttcaat    360
agatgttgag aagatcactt gtgttgaaac agtggttcct gaaaaaaatc ctcctccaga    420
aagacagatt ccgagaagag gtgaagagtc cagtgaaatg gagcaaattt caatcattga    480
aaggttccct tatcccttcc aggttgtata tgatgaaggg cctctctacg tcttctcccc    540
aactgaagaa ctaaggaagc ggtggattca ccagctcaaa aacgtaatcc ggtacaacag    600
tgatctggtt cagaaatatc acccttgctt ctggatcgat gggcagtatc tctgctgctc    660
tcagacagcc aaaaatgcta tgggctgcca aattttggag aacaggaatg gaagcttaaa    720
acctgggagt tctcaccgga agacaaaaaa gcctcttccc ccaacgcctg aggaggacca    780
gatcttgaaa aagccactac cgcctgagcc agcagcagca ccagtctcca caagtgagct    840
gaaaaaggtt gtggcccttt atgattacat gccaatgaat gcaaatgatc tacagctgcg    900
gaagggtgat gaatatttta tcttggagga aagcaactta ccatggtgga gagcacgaga    960
taaaaatggg caggaaggct acattcctag taactatgtc actgaagcag aagactccat   1020
agaaatgtat gagtggtatt ccaaacacat gactcggagt caggctgagc aactgctaaa   1080
gcaagagggg aaagaaggag gtttcattgt cagagactcc agcaaagctg gcaaatatac   1140
agtgtctgtg tttgctaaat ccacagggga ccctcaaggg gtgatacgtc attatgttgt   1200
gtgttccaca cctcagagcc agtattacct ggctgagaag caccttttca gcaccatccc   1260
tgagctcatt aactaccatc agcacaactc tgcaggactc atatccaggc tcaaatatcc   1320
agtgtctcaa caaaacaaga atgcaccttc cactgcaggc ctgggatacg gatcatggga   1380
aattgatcca aaggacctga ccttcttgaa ggagctgggg actggacaat ttggggtagt   1440
gaagtatggg aaatggagag gccagtacga cgtggccatc aagatgatca aagaaggctc   1500
catgtctgaa gatgaattca ttgaagaagc caaagtcatg atgaatcttt cccatgagaa   1560
gctggtgcag ttgtatggcg tctgcaccaa gcagcgcccc atcttcatca tcactgagta   1620
catggccaat ggctgcctcc tgaactacct gagggagatg cgccaccgct tccagactca   1680
gcagctgcta gagatgtgca aggatgtctg tgaagccatg gaatacctgg agtcaaagca   1740
gttccttcac cgagacctgg cagctcgaaa ctgtttggta aacgatcaag gagttgttaa   1800
agtatctgat ttcggcctgt ccaggtatgt cctggatgat gaatacacaa gctcagtagg   1860
ctccaaattt ccagtccggt ggtccccacc ggaagtcctg atgtatagca agttcagcag   1920
caaatctgac atttgggctt ttggggtttt gatgtgggaa atttactccc tggggaagat   1980
gccatatgag agatttacta acagtgagac tgctgaacac attgcccaag gcctacgtct   2040
ctacaggcct catctggctt cagagaaggt atataccatc atgtacagtt gctggcatga   2100
gaaagcagat gagcgtccca ctttcaaaat tcttctgagc aatattctag atgtcatgga   2160
tgaagaatcc tgagctcgcc aataagcttc ttggttctac ttctcttctc cacaagcccc   2220
aatttcactt tctcagagga aatcccaagc ttaggagccc tggagccttt gtgctcccac   2280
tcaatacaaa aaggcccctc tctacatctg ggaatgcacc tcttctttga ttccctggga   2340
tagtggcttc tgagcaaagg ccaagaaatt attgtgcctg aaatttcccg agagaattaa   2400
gacagactga atttgcgatg aaaatatttt ttaggaggga ggatgtaaat agccgcacaa   2460
aggggtccaa cagctctttg agtaggcatt tggtagagct tgggggtgtg tgtgtggggg   2520
tggaccgaat ttggcaagaa tgaaatggtg tcataaagat gggaggggag ggtgttttga   2580
taaaataaaa ttactagaaa gcttgaaagt c                                  2611
```

<210> SEQ ID NO 252
<211> LENGTH: 2158
<212> TYPE: DNA
<213> ORGANISM: Homo sapiens
<220> FEATURE:
<221> NAME/KEY: misc_feature
<222> LOCATION: (1)..(2158)
<223> OTHER INFORMATION: FBJ murine osteosarcoma viral oncogene homolog (FOS)

<400> SEQUENCE: 252

```
attcataaaa cgcttgttat aaaagcagtg gctgcggcgc ctcgtactcc aaccgcatct     60
gcagcgagca tctgagaagc caagactgag ccggcggccg cggcgcagcg aacgagcagt    120
gaccgtgctc ctacccagct ctgctccaca gcgcccacct gtctccgccc ctcggcccct    180
cgcccggctt tgcctaaccg ccacgatgat gttctcgggc ttcaacgcag actacgaggc    240
gtcatcctcc cgctgcagca gcgcgtcccc ggccggggat agcctctctt actaccactc    300
acccgcagac tccttctcca gcatgggctc gcctgtcaac gcgcaggact tctgcacgga    360
cctggccgtc tccagtgcca acttcattcc cacggtcact gccatctcga ccagtccgga    420
cctgcagtgg ctggtgcagc ccgccctcgt ctcctccgtg gccccatcgc agaccagagc    480
ccctcaccct ttcggagtcc ccgccccctc cgctggggct tactccaggg ctggcgttgt    540
gaagaccatg acaggaggcc gagcgcagag cattggcagg aggggcaagg tggaacagtt    600
atctccagaa gaagaagaga aaaggagaat ccgaagggaa aggaataaga tggctgcagc    660
caaatgccgc aaccggagga gggagctgac tgatacactc caagcggaga cagaccaact    720
agaagatgag aagtctgctt tgcagaccga gattgccaac ctgctgaagg agaaggaaaa    780
actagagttc atcctggcag ctcaccgacc tgcctgcaag atccctgatg acctgggctt    840
cccagaagag atgtctgtgg cttcccttga tctgactggg ggcctgccag aggttgccac    900
ccggagtctt gaggaggcct tcaccctgcc tctcctcaat gaccctgagc ccaagccctc    960
agtggaacct gtcaagagca tcagcagcat ggagctgaag accgagccct ttgatgactt   1020
cctgttccca gcatcatcca ggcccagtgg ctctgagaca gcccgctccg tgccagacat   1080
ggacctatct gggtccttct atgcagcaga ctgggagcct ctgcacagtg gctccctggg   1140
gatggggccc atggccacag agctggagcc cctgtgcact ccggtggtca cctgtactcc   1200
cagctgcact gcttacacgt cttccttcgt cttcacctac cccgaggctg actccttccc   1260
cagctgtgca gctgcccacc gcaagggcag cagcagcaat gagccttcct ctgactcgct   1320
cagctcaccc acgctgctgg ccctgtgagg gggcagggaa ggggaggcag ccggcaccca   1380
caagtgccac tgcccgagct ggtgcattac agagaggaga aacacatctt ccctagaggg   1440
ttcctgtaga cctagggagg accttatctg tgcgtgaaac acaccaggct gtgggcctca   1500
aggacttgaa agcatccatg tgtggactca agtccttacc tcttccggag atgtagcaaa   1560
acgcatggag tgtgtattgt tcccagtgac acttcagaga gctggtagtt agtagcatgt   1620
tgagccaggc ctgggtctgt gtctcttttc tctttctcct tagtcttctc atagcattaa   1680
ctaatctatt gggttcatta ttggaattaa cctggtgctg gatattttca aattgtatct   1740
agtgcagctg attttaacaa taactactgt gttcctggca atagtgtgtt ctgattagaa   1800
atgaccaata ttatactaag aaaagatacg actttatttt ctggtagata gaaataaata   1860
gctatatcca tgtactgtag tttttcttca acatcaatgt tcattgtaat gttactgatc   1920
atgcattgtt gaggtggtct gaatgttctg acattaacag ttttccatga aaacgtttta   1980
```

```
ttgtgttttt aatttattta ttaagatgga ttctcagata tttatatttt tattttattt   2040

ttttctacct tgaggtcttt tgacatgtgg aaagtgaatt tgaatgaaaa atttaagcat   2100

tgtttgctta ttgttccaag acattgtcaa taaaagcatt taagttgaat gcgaccaa     2158


<210> SEQ ID NO 253
<211> LENGTH: 18
<212> TYPE: DNA
<213> ORGANISM: Artificial Sequence
<220> FEATURE:
<223> OTHER INFORMATION: ROBO1 Forward primer

<400> SEQUENCE: 253

gtgtggtgtg tggcttca                                                   18


<210> SEQ ID NO 254
<211> LENGTH: 17
<212> TYPE: DNA
<213> ORGANISM: Artificial Sequence
<220> FEATURE:
<223> OTHER INFORMATION: ROBO1 Backward primer

<400> SEQUENCE: 254

gtatacagtc tcatgcc                                                    17


<210> SEQ ID NO 255
<211> LENGTH: 17
<212> TYPE: DNA
<213> ORGANISM: Artificial Sequence
<220> FEATURE:
<223> OTHER INFORMATION: POU4F1 Forward primer

<400> SEQUENCE: 255

ccctccctga gcacaag                                                    17


<210> SEQ ID NO 256
<211> LENGTH: 16
<212> TYPE: DNA
<213> ORGANISM: Artificial Sequence
<220> FEATURE:
<223> OTHER INFORMATION: POU4F1 Backward primer

<400> SEQUENCE: 256

gtgggcaggc aggccc                                                     16


<210> SEQ ID NO 257
<211> LENGTH: 19
<212> TYPE: DNA
<213> ORGANISM: Artificial Sequence
<220> FEATURE:
<223> OTHER INFORMATION: PTN Forward primer

<400> SEQUENCE: 257

ggcaagaaac aggagaaga                                                  19


<210> SEQ ID NO 258
<211> LENGTH: 17
<212> TYPE: DNA
<213> ORGANISM: Artificial Sequence
<220> FEATURE:
<223> OTHER INFORMATION: PTN Backward primer

<400> SEQUENCE: 258

gtttgctgat gtccttt                                                    17
```

<210> SEQ ID NO 259
<211> LENGTH: 18
<212> TYPE: DNA
<213> ORGANISM: Artificial Sequence
<220> FEATURE:
<223> OTHER INFORMATION: PARD6B Forward primer

<400> SEQUENCE: 259
catatagtca ttagtatg 18

<210> SEQ ID NO 260
<211> LENGTH: 17
<212> TYPE: DNA
<213> ORGANISM: Artificial Sequence
<220> FEATURE:
<223> OTHER INFORMATION: PARD6B Backward primer

<400> SEQUENCE: 260
ctgggagaat atccacg 17

<210> SEQ ID NO 261
<211> LENGTH: 18
<212> TYPE: DNA
<213> ORGANISM: Artificial Sequence
<220> FEATURE:
<223> OTHER INFORMATION: PAFAH1B1 Forward primer

<400> SEQUENCE: 261
cggcaagctt ctggcttc 18

<210> SEQ ID NO 262
<211> LENGTH: 15
<212> TYPE: DNA
<213> ORGANISM: Artificial Sequence
<220> FEATURE:
<223> OTHER INFORMATION: PAFAH1B1 Backward primer

<400> SEQUENCE: 262
gcattcaaag ccctg 15

<210> SEQ ID NO 263
<211> LENGTH: 20
<212> TYPE: DNA
<213> ORGANISM: Artificial Sequence
<220> FEATURE:
<223> OTHER INFORMATION: PIK3CG Forward primer

<400> SEQUENCE: 263
cgagatctac gacaagtacc 20

<210> SEQ ID NO 264
<211> LENGTH: 20
<212> TYPE: DNA
<213> ORGANISM: Artificial Sequence
<220> FEATURE:
<223> OTHER INFORMATION: PIK3CG Backward primer

<400> SEQUENCE: 264
ccggtgcgtg gccttccagt 20

<210> SEQ ID NO 265
<211> LENGTH: 19
<212> TYPE: DNA
<213> ORGANISM: Artificial Sequence
<220> FEATURE:
<223> OTHER INFORMATION: BMP2 Forward primer

<400> SEQUENCE: 265
ccaccatgaa gaatctttg 19

<210> SEQ ID NO 266
<211> LENGTH: 19
<212> TYPE: DNA
<213> ORGANISM: Artificial Sequence
<220> FEATURE:
<223> OTHER INFORMATION: BMP2 Backward primer

<400> SEQUENCE: 266
attaaagaag aatctccgg 19

<210> SEQ ID NO 267
<211> LENGTH: 20
<212> TYPE: DNA
<213> ORGANISM: Artificial Sequence
<220> FEATURE:
<223> OTHER INFORMATION: DRD1 Forward primer

<400> SEQUENCE: 267
gtgtcagagc ccctgatgtg 20

<210> SEQ ID NO 268
<211> LENGTH: 18
<212> TYPE: DNA
<213> ORGANISM: Artificial Sequence
<220> FEATURE:
<223> OTHER INFORMATION: DRD1 Backward primer

<400> SEQUENCE: 268
gtcccgtcca tggcagag 18

<210> SEQ ID NO 269
<211> LENGTH: 19
<212> TYPE: DNA
<213> ORGANISM: Artificial Sequence
<220> FEATURE:
<223> OTHER INFORMATION: PAX5 Forward primer

<400> SEQUENCE: 269
cgtcagttcc atcaacagg 19

<210> SEQ ID NO 270
<211> LENGTH: 18
<212> TYPE: DNA
<213> ORGANISM: Artificial Sequence
<220> FEATURE:
<223> OTHER INFORMATION: PAX5 Backward primer

<400> SEQUENCE: 270
ggaagctggg actggttg 18

<210> SEQ ID NO 271
<211> LENGTH: 17
<212> TYPE: DNA
<213> ORGANISM: Artificial Sequence
<220> FEATURE:
<223> OTHER INFORMATION: S100A6 Forward primer

<400> SEQUENCE: 271
caccgaccgc tataagg 17

<210> SEQ ID NO 272
<211> LENGTH: 19

<212> TYPE: DNA
<213> ORGANISM: Artificial Sequence
<220> FEATURE:
<223> OTHER INFORMATION: S100A6 Backward primer

<400> SEQUENCE: 272
gccaaatgcg acgcgagcg 19

<210> SEQ ID NO 273
<211> LENGTH: 19
<212> TYPE: DNA
<213> ORGANISM: Artificial Sequence
<220> FEATURE:
<223> OTHER INFORMATION: DRD2 Forward primer

<400> SEQUENCE: 273
cattgtcacc ctgctggtc 19

<210> SEQ ID NO 274
<211> LENGTH: 17
<212> TYPE: DNA
<213> ORGANISM: Artificial Sequence
<220> FEATURE:
<223> OTHER INFORMATION: DRD2 Backward primer

<400> SEQUENCE: 274
ggtgttgact cgcttgc 17

<210> SEQ ID NO 275
<211> LENGTH: 18
<212> TYPE: DNA
<213> ORGANISM: Artificial Sequence
<220> FEATURE:
<223> OTHER INFORMATION: HDHC7 Forward primer

<400> SEQUENCE: 275
gtagtagcag cacgcccg 18

<210> SEQ ID NO 276
<211> LENGTH: 16
<212> TYPE: DNA
<213> ORGANISM: Artificial Sequence
<220> FEATURE:
<223> OTHER INFORMATION: HDAC7 Backward primer

<400> SEQUENCE: 276
aggatgggat tggggc 16

<210> SEQ ID NO 277
<211> LENGTH: 19
<212> TYPE: DNA
<213> ORGANISM: Artificial Sequence
<220> FEATURE:
<223> OTHER INFORMATION: HEY2 Forward Primer

<400> SEQUENCE: 277
gcagccctgc tccagccca 19

<210> SEQ ID NO 278
<211> LENGTH: 17
<212> TYPE: DNA
<213> ORGANISM: Artificial Sequence
<220> FEATURE:
<223> OTHER INFORMATION: HEY2 Backward Primer

<400> SEQUENCE: 278
ctgaagttgt ggagagg 17

<210> SEQ ID NO 279
<211> LENGTH: 19
<212> TYPE: DNA
<213> ORGANISM: Artificial Sequence
<220> FEATURE:
<223> OTHER INFORMATION: INHBA Forward primer

<400> SEQUENCE: 279
gggggagagg agtgaactg 19

<210> SEQ ID NO 280
<211> LENGTH: 17
<212> TYPE: DNA
<213> ORGANISM: Artificial Sequence
<220> FEATURE:
<223> OTHER INFORMATION: INHBA Backward primer

<400> SEQUENCE: 280
gaagacatgc caggtgc 17

<210> SEQ ID NO 281
<211> LENGTH: 20
<212> TYPE: DNA
<213> ORGANISM: Artificial Sequence
<220> FEATURE:
<223> OTHER INFORMATION: SHH Forward primer

<400> SEQUENCE: 281
gctggcccgc ctggcggtgg 20

<210> SEQ ID NO 282
<211> LENGTH: 20
<212> TYPE: DNA
<213> ORGANISM: Artificial Sequence
<220> FEATURE:
<223> OTHER INFORMATION: SHH Backward primer

<400> SEQUENCE: 282
gcagtggata tgtgccttgg 20

<210> SEQ ID NO 283
<211> LENGTH: 20
<212> TYPE: DNA
<213> ORGANISM: Artificial Sequence
<220> FEATURE:
<223> OTHER INFORMATION: BTK Forward primer

<400> SEQUENCE: 283
gaatatttta tcttggagga 20

<210> SEQ ID NO 284
<211> LENGTH: 19
<212> TYPE: DNA
<213> ORGANISM: Artificial Sequence
<220> FEATURE:
<223> OTHER INFORMATION: BTK Backward primer

<400> SEQUENCE: 284
agccttcctg cccattttt 19

<210> SEQ ID NO 285
<211> LENGTH: 20
<212> TYPE: DNA
<213> ORGANISM: Artificial Sequence
<220> FEATURE:
<223> OTHER INFORMATION: FOS Forward primer

<400> SEQUENCE: 285
gaggaggcct tcaccctgcc 20

<210> SEQ ID NO 286
<211> LENGTH: 20
<212> TYPE: DNA
<213> ORGANISM: Artificial Sequence
<220> FEATURE:
<223> OTHER INFORMATION: FOS Backward primer

<400> SEQUENCE: 286
tgctcttgac aggttccact 20

<210> SEQ ID NO 287
<211> LENGTH: 1575
<212> TYPE: DNA
<213> ORGANISM: Rabies virus
<220> FEATURE:
<221> NAME/KEY: CDS
<222> LOCATION: (1)..(1575)

<400> SEQUENCE: 287

```
atg gtt cct cag gtt ctt ttg ttt gta ctc ctt ctg ggt ttt tcg ttg      48
Met Val Pro Gln Val Leu Leu Phe Val Leu Leu Leu Gly Phe Ser Leu
1               5                   10                  15

tgt ttc ggg aag ttc ccc att tac acg ata cca gac aaa ctt ggt ccc      96
Cys Phe Gly Lys Phe Pro Ile Tyr Thr Ile Pro Asp Lys Leu Gly Pro
            20                  25                  30

tgg agc cct att gac ata cac cat ctc cgc tgt cca aat aac ctg gtt     144
Trp Ser Pro Ile Asp Ile His His Leu Arg Cys Pro Asn Asn Leu Val
        35                  40                  45

gtg gag gat gaa gga tgt atc aac ctg tcc ggg ttc tcc tac atg gaa     192
Val Glu Asp Glu Gly Cys Ile Asn Leu Ser Gly Phe Ser Tyr Met Glu
    50                  55                  60

ctc aaa gtg gga tac atc tca gcc atc aaa gtg aac ggg ttc act tgc     240
Leu Lys Val Gly Tyr Ile Ser Ala Ile Lys Val Asn Gly Phe Thr Cys
65                  70                  75                  80

aca ggt gtt gtg aca gag gca gag acc tac acc aac ttt gtt ggt tat     288
Thr Gly Val Val Thr Glu Ala Glu Thr Tyr Thr Asn Phe Val Gly Tyr
                85                  90                  95

gtc aca acc aca ttc aag aga aag cat ttc cgc ccc acc cca gac gca     336
Val Thr Thr Thr Phe Lys Arg Lys His Phe Arg Pro Thr Pro Asp Ala
            100                 105                 110

tgt aga gcc gcg tat aac tgg aag atg gcc ggt gac ccc aga tat gaa     384
Cys Arg Ala Ala Tyr Asn Trp Lys Met Ala Gly Asp Pro Arg Tyr Glu
        115                 120                 125

gag tcc cta caa aat cca tac ccc gac tac cac tgg ctt cga act gta     432
Glu Ser Leu Gln Asn Pro Tyr Pro Asp Tyr His Trp Leu Arg Thr Val
    130                 135                 140

aga acc acc aaa gag tcc ctc att atc ata tcc cca agt gtg aca gat     480
Arg Thr Thr Lys Glu Ser Leu Ile Ile Ile Ser Pro Ser Val Thr Asp
145                 150                 155                 160

ttg gac cca tat gac aaa tcc ctt cac tca agg gtc ttc cct ggc gga     528
Leu Asp Pro Tyr Asp Lys Ser Leu His Ser Arg Val Phe Pro Gly Gly
                165                 170                 175

aag tgc tca gga ata acg gtg tcc tct acc tac tgc tca act aac cat     576
Lys Cys Ser Gly Ile Thr Val Ser Ser Thr Tyr Cys Ser Thr Asn His
            180                 185                 190

gat tac acc att tgg atg ccc gag aat ccg aga cca ggg aca cct tgt     624
```

```
Asp Tyr Thr Ile Trp Met Pro Glu Asn Pro Arg Pro Gly Thr Pro Cys
        195                 200                 205

gac att ttt acc aat agc aga ggg aag aga gca tcc aac ggg aac aag      672
Asp Ile Phe Thr Asn Ser Arg Gly Lys Arg Ala Ser Asn Gly Asn Lys
    210                 215                 220

act tgc ggc ttt gtg gat gaa aga ggc ctg tat aag tct cta aaa gga      720
Thr Cys Gly Phe Val Asp Glu Arg Gly Leu Tyr Lys Ser Leu Lys Gly
225                 230                 235                 240

gca tgc agg ctc aag tta tgt gga gtt ctt gga ctt aga ctt atg gat      768
Ala Cys Arg Leu Lys Leu Cys Gly Val Leu Gly Leu Arg Leu Met Asp
                245                 250                 255

gga aca tgg gtc gcg atg caa aca tca gat gag acc aaa tgg tgc tct      816
Gly Thr Trp Val Ala Met Gln Thr Ser Asp Glu Thr Lys Trp Cys Ser
            260                 265                 270

cca gat cag ttg gtg aat ttg cac gac ttt cgc tca gac gag att gag      864
Pro Asp Gln Leu Val Asn Leu His Asp Phe Arg Ser Asp Glu Ile Glu
        275                 280                 285

cat ctc gtt gtg gag gag tta gtc aag aaa aga gag gaa tgt ctg gat      912
His Leu Val Val Glu Glu Leu Val Lys Lys Arg Glu Glu Cys Leu Asp
    290                 295                 300

aca tta gag tcc atc atg acc acc aag tca gta agt ttc aga cgt ctc      960
Thr Leu Glu Ser Ile Met Thr Thr Lys Ser Val Ser Phe Arg Arg Leu
305                 310                 315                 320

agt cac ctg aga aaa ctt gtc cca ggg ttt gga aaa gca tat acc ata     1008
Ser His Leu Arg Lys Leu Val Pro Gly Phe Gly Lys Ala Tyr Thr Ile
                325                 330                 335

ttc aac aaa acc ttg atg gag gct gat gct cac tac aag tca gtc cgg     1056
Phe Asn Lys Thr Leu Met Glu Ala Asp Ala His Tyr Lys Ser Val Arg
            340                 345                 350

acc tgg aat gag atc atc ccc tca aaa ggg tgt ttg aaa gtt gga gga     1104
Thr Trp Asn Glu Ile Ile Pro Ser Lys Gly Cys Leu Lys Val Gly Gly
        355                 360                 365

agg tgc cat cct cat gtg aac ggg gtg ttt ttc aat ggt ata ata tta     1152
Arg Cys His Pro His Val Asn Gly Val Phe Phe Asn Gly Ile Ile Leu
    370                 375                 380

ggg cct gac gac cgt gtc cta atc cca gag atg caa tca tcc ctc ctc     1200
Gly Pro Asp Asp Arg Val Leu Ile Pro Glu Met Gln Ser Ser Leu Leu
385                 390                 395                 400

cgg caa cat atg gag ttg ttg gaa tct tca gtt atc ccc ctg atg cac     1248
Arg Gln His Met Glu Leu Leu Glu Ser Ser Val Ile Pro Leu Met His
                405                 410                 415

ccc ctg gct gac cct tct aca gtt ttc aaa gaa ggt gat gag gct gag     1296
Pro Leu Ala Asp Pro Ser Thr Val Phe Lys Glu Gly Asp Glu Ala Glu
            420                 425                 430

gat ttt gtt gaa gtt cac ctc ccc gat gtg tac aaa cag atc tca ggg     1344
Asp Phe Val Glu Val His Leu Pro Asp Val Tyr Lys Gln Ile Ser Gly
        435                 440                 445

gtt gac ctg ggt ctc ccg aac tgg gga aag tat gta ttg atg act gca     1392
Val Asp Leu Gly Leu Pro Asn Trp Gly Lys Tyr Val Leu Met Thr Ala
    450                 455                 460

ggg gcc atg att ggc ctg gtg ttg ata ttt tcc cta atg aca tgg tgc     1440
Gly Ala Met Ile Gly Leu Val Leu Ile Phe Ser Leu Met Thr Trp Cys
465                 470                 475                 480

aga aga gcc aat cga cca gaa tcg aaa caa cgc agt ttt gga ggg aca     1488
Arg Arg Ala Asn Arg Pro Glu Ser Lys Gln Arg Ser Phe Gly Gly Thr
                485                 490                 495

ggg ggg aat gtg tca gtc act tcc caa agc gga aaa gtc ata cct tca     1536
Gly Gly Asn Val Ser Val Thr Ser Gln Ser Gly Lys Val Ile Pro Ser
            500                 505                 510
```

```
tgg gaa tca tat aag agt gga ggt gag atc aga ctg tga              1575
Trp Glu Ser Tyr Lys Ser Gly Gly Glu Ile Arg Leu
        515                 520


<210> SEQ ID NO 288
<211> LENGTH: 524
<212> TYPE: PRT
<213> ORGANISM: Rabies virus

<400> SEQUENCE: 288

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Arg Cys Pro Asn Asn Leu Val
        35                  40                  45

Val Glu Asp Glu Gly Cys Ile Asn Leu Ser Gly Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu Gln Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Gly Thr Pro Cys
        195                 200                 205

Asp Ile Phe Thr Asn Ser Arg Gly Lys Arg Ala Ser Asn Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Ser
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Thr Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
```

-continued

```
        355                 360                 365

Arg Cys His Pro His Val Asn Gly Val Phe Phe Asn Gly Ile Ile Leu
    370                 375                 380

Gly Pro Asp Asp Arg Val Leu Ile Pro Glu Met Gln Ser Ser Leu Leu
385                 390                 395                 400

Arg Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
        435                 440                 445

Val Asp Leu Gly Leu Pro Asn Trp Gly Lys Tyr Val Leu Met Thr Ala
    450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Gly Asn Val Ser Val Thr Ser Gln Ser Gly Lys Val Ile Pro Ser
            500                 505                 510

Trp Glu Ser Tyr Lys Ser Gly Gly Glu Ile Arg Leu
        515                 520
```

HIGH MAST2-AFFINITY POLYPEPTIDES AND USES THEREOF

CROSS REFERENCE TO RELATED APPLICATIONS

This application is a §371 National Stage Application of PCT/EP2012/072073, filed Nov. 7, 2012 which claims priority to EP 11306454.7, filed Nov. 8, 2011.

BACKGROUND

1. Field of the Invention

The invention relates to polypeptides containing a cytoplasmic domain ending with a MAST-2 binding domain, the first two residues of which are S and W, and the last four residues of which are Q, T, R and L, said polypeptides presenting a high affinity for the PDZ domain of the human MAST2 protein. The invention also relates to polynucleotides, vectors, lentiviral particles, cells as well as compositions comprising the same. The invention is also directed to the use of said polypeptides, polynucleotides, vectors, lentiviral particles, cells and compositions in the treatment and/or prevention of a disease, disorder or condition, which alters the Central Nervous System (CNS) and/or the Peripheral Nervous System (PNS). The invention also concerns molecular signatures of cellular genes to determine the neurosurvival and/or neuroprotection activity of a molecule.

2. Description of Related Art

During development of the nervous system, neurons extend axons over considerable distances in order to innervate their targets in an appropriate manner. This involves the stimulation in the cells of specific signaling pathways which can stimulate the activity of the growth cone.

While the developing nervous system, more particularly the developing central nervous system, is highly plastic, the adult nervous system, more particularly the adult brain, has more limited repair potential. Therefore, neurite-axon outgrowth and protection against degeneration are important factors to be considered to improve the outcome of a neurodegenerative disease, disorder or condition, such as an acute injury of the nervous system or a chronic neurodegenerative disorder. Products, which would be capable of inducing neurite outgrowth from such neuronal cells, would bring a very useful therapeutic and/or preventive and/or palliative solution to such diseases, disorders or conditions.

At the other side of the neuron developmental process, the proliferation of neuronal progenitors, which do not differentiate into matured neuronal structures, leads to nervous system neoplasm. Products, which would be capable of inducing neurite outgrowth from such progenic cells, would bring a therapeutic and/or preventive and/or palliative solution to such neoplasms.

It has been described that the pathogenicity of a rabies virus strain is inversely correlated with its ability to induce apoptosis (WO 03/048198; Ugolini 1995; Sarmento et al. 2005; Ugolini 2008; Jackson et al. 2008). Therefore, the more virulent a rabies virus strain is, the less apoptotic. The findings that virulent rabies virus strains, such as CVS strains, do not induce neuron apoptosis and explain why virulent rabies virus strains can propagate so extensively within the CNS before the appearance of signs and symptoms of the disease More recently, Préhaud et al. (2010) reported that the C-terminal region of the cytoplasmic domain of the G protein of rabies viruses is involved in the binding of the G protein to the PDZ domain of the human microtubule associated serine threonine kinase 2 MAST2 protein. This C-terminal region bears a four amino-acid motif called PDZ-BS (PDZ binding site) which has the sequence QTRL in virulent rabies strains and the sequence ETRL in attenuated strains. Thus, the G protein of virulent rabies virus strain has been shown to bind with a high affinity to MAST-1 and MAST-2 but to not bind PTPN4, DLG2 and MPDZ. In contrast, the G protein of attenuated rabies virus strain has been shown to bind with MAST-1, MAST-2, PTPN4, DLG2 and MPDZ. This difference regarding the binding partners of the G protein of virulent and attenuated rabies virus strains seems to be correlated with the difference of virulence of these strains (FIG. 2).

Thus, as demonstrated in application WO2010/116258, the nature of the amino acid residues at positions 491(H/L) and 521(Q/E) of the G protein of rabies viruses is important for the effects on neuron survival and on neurite outgrowth. The G protein of a virulent rabies virus strain presenting a H residue at position 491 and a Q residue at position 521 is non-apoptotic and favours neurite outgrowth. In contrast, the G protein of an attenuated rabies virus strain presenting a L residue at position 491 and a E residue at position 521 is apoptotic and does not promote neurite outgrowth.

Based on these results, there is a need in the art to identify and to design means having improved properties in the promotion of neurite outgrowth and in neurosurvival. The invention provides means for the regeneration and protection of neurons, which derive from the G protein of rabies virus strains, and which show unexpected properties. The invention also concerns means for the screening of molecules suitable for the regeneration and protection of neurons.

Figure 5:
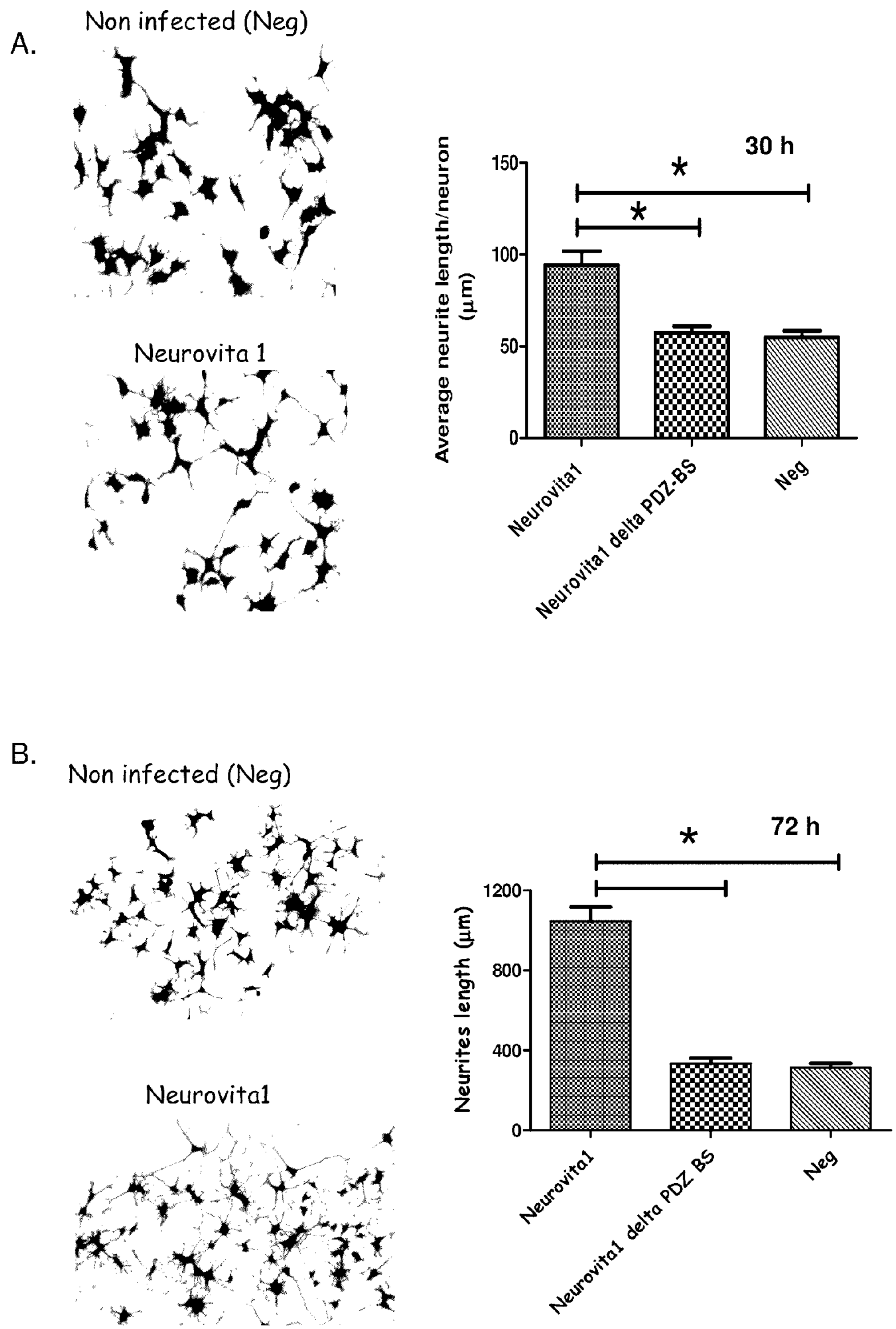

FIG. 5. Neurovita 1 triggers neurite outgrowth in NS and SH-SY5Y in a PDZ-BS dependent manner (A) Neurite outgrowth assay in SH-SY-5Y human neuroblastoma cells following lentiviral vectors infection (30 h, p.i.). Cells were treated with db c-AMP (10 μM) (B) Neurite outgrowth assay in NS cells following lentiviral vectors infection (72 h p.i.). Cells were treated with NGF (200 ng/ml) (*: $p<0.05$ student's t test).

Figure 6:
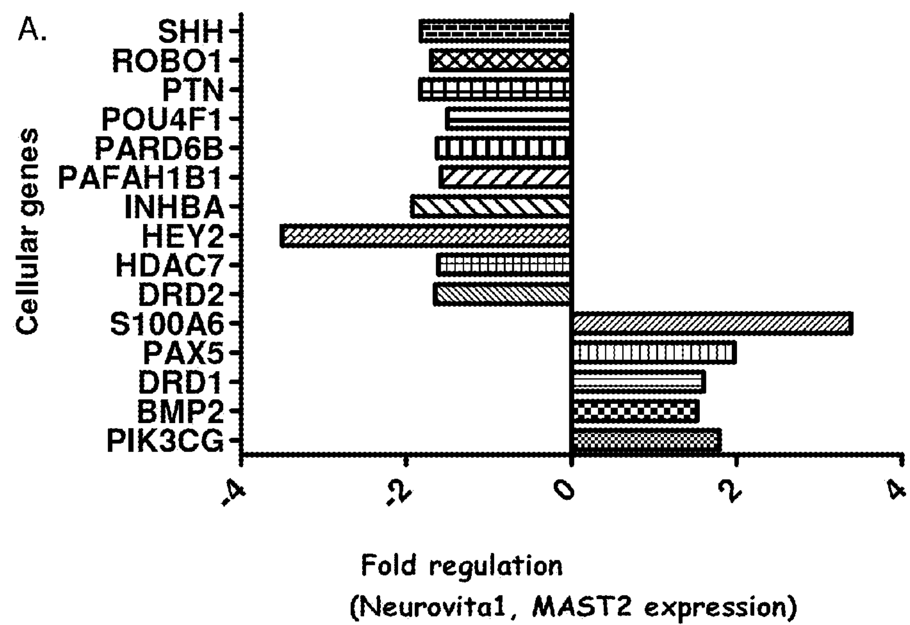
Figure 6:
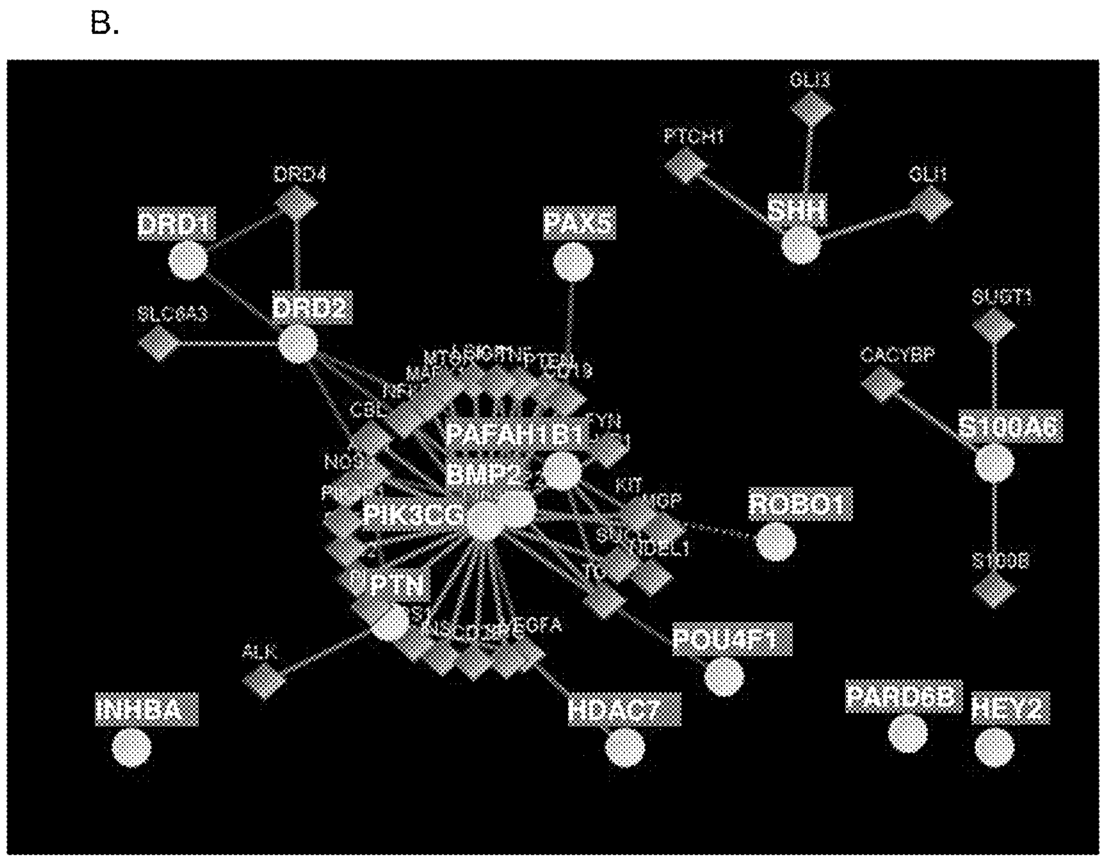

FIG. 6. (A) Identification of the genetic molecular signature of Neurovita1-mediated neuroprotection; the gene expression was measured in NT2-N cells, 24 h p.i., with Neurovita1-expressing lentiviral vectors, on a Human Neurogenesis and Neural Stem Cell PCR and PI3K-Akt Signaling Pathway Arrays (B) Schematic representation of the Neurovita1 genetic molecular signature obtained with the pathway-focused gene expression profiling (qRT-PCR). The cluster of genes represents the genes regulated following Neurovita1 infection but not regulated in non-infected culture or culture infected with Neurovita1 delta PDZ-BS (dots are Neurovita 1 specific genes; diamonds are connected genes).

Figure 7:
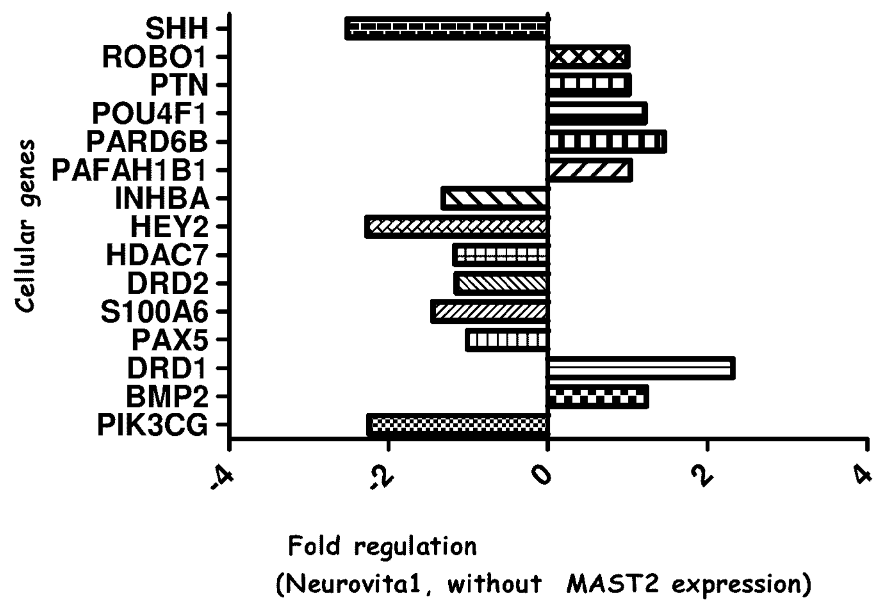

FIG. 7. Molecular signature of Neurovita 1 in absence of MAST2; Genetic molecular signature (24 h p.i.) following infection by Neurovita1-expressing lentivector of NT2-N cells in which the MAST2 expression was knocked out by infection with Sh RNA MAST2 specific recombinant lentiviruses, 48 h before infection with lentivector Neurovita1 on Human Neurogenesis and Neural Stem Cell PCR and PI3K-Akt Signaling Pathway Arrays.

Figure 8:
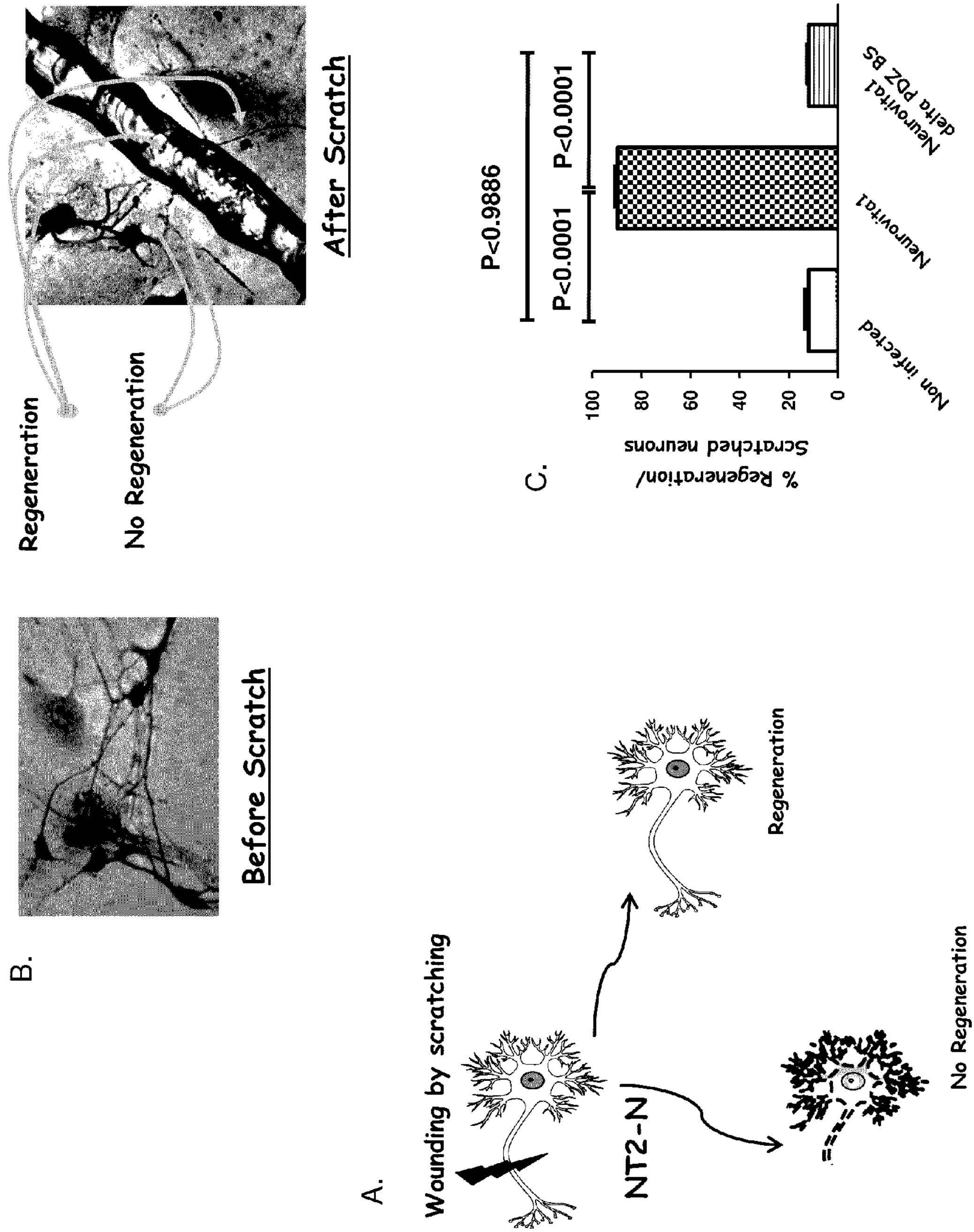

FIG. 8. Lentivector Neurovita 1 favours wound healing of NT2-N axons (A) Representation of the scratch assay (B) Illustration of regeneration 6 days post wounding (C) Comparison of axon regeneration after lentivector Neurovita1 or Neurovita 1 delta PDZ-BS infection.

Figure 9:
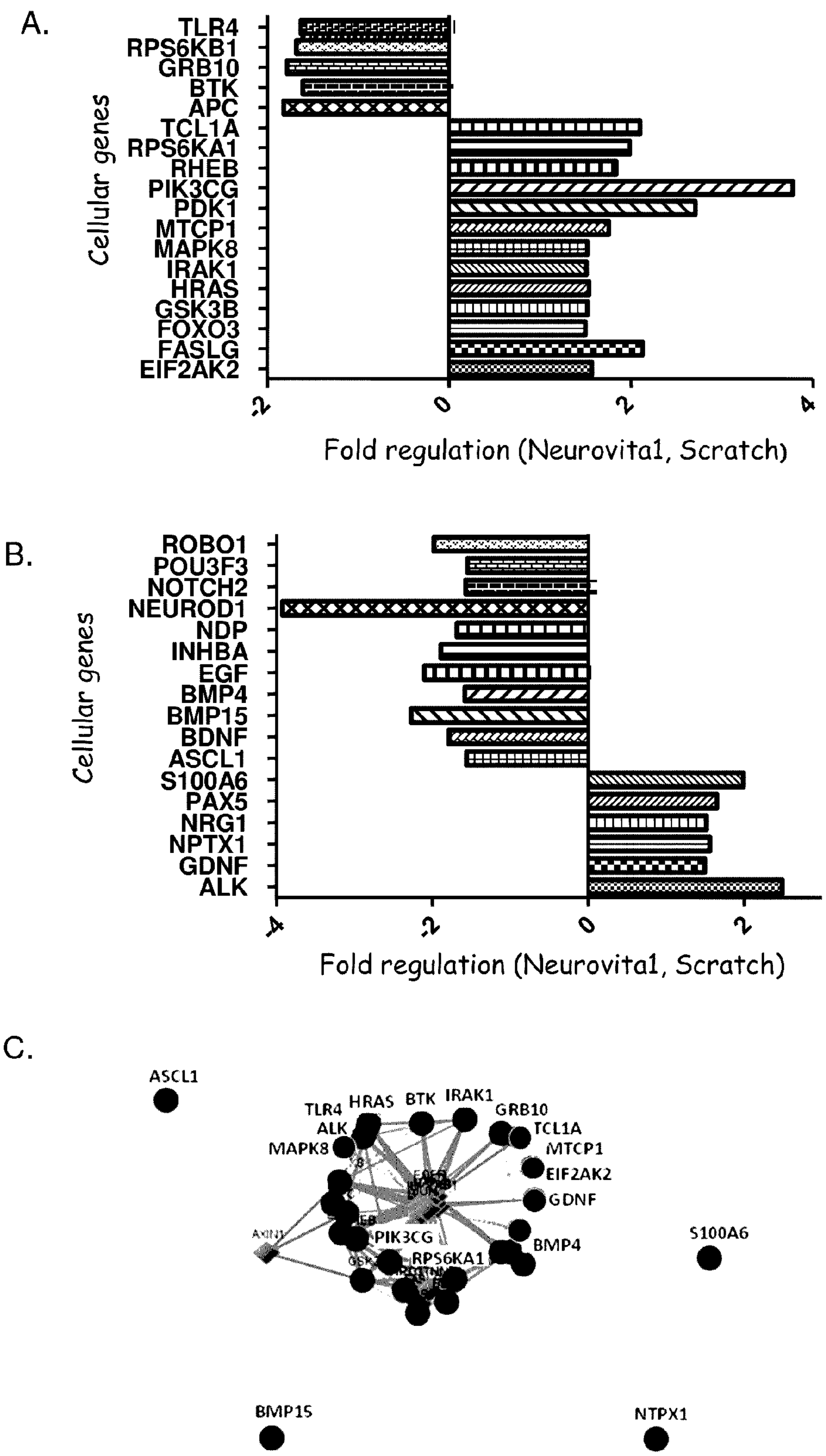

FIG. 9. Molecular signatures of Neurovita1 mediated axon regeneration; the pathway-focused gene expression profiling was established on NT2-N cell culture two days post wounding. (A) genes involved in PI3K/Akt signalling pathway (Human PI3K-AKT Signaling PCR array) (B) genes involved in cell proliferation, adhesion, differentiation, growth factors and synaptic functions (Human Neurogenesis and Neural Stem Cell PCR Array). (C) Schematic representation of the gene cluster involved in Neurovita1 mediated axon regeneration (dots are neurovita-specific genes; diamonds are related genes).

Figure 10:
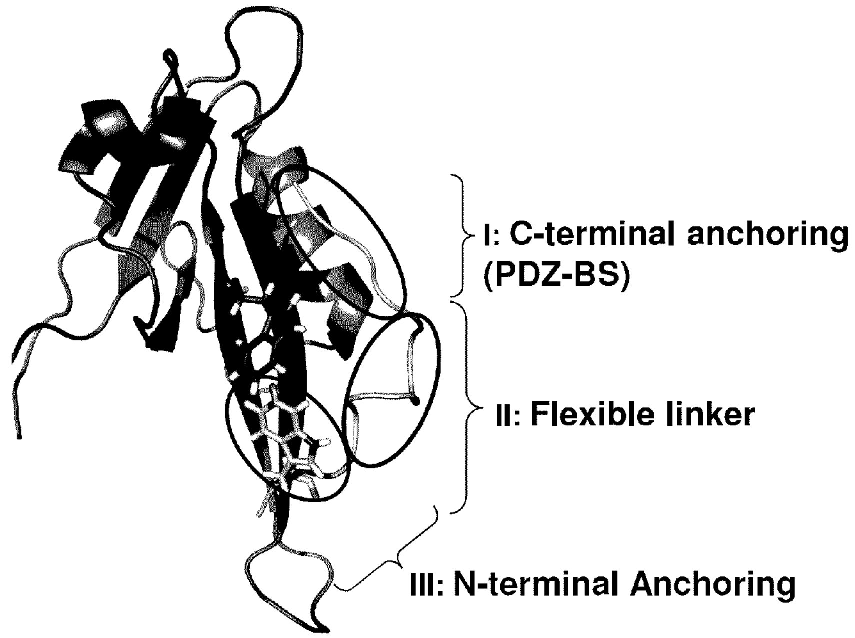
Figure 10:
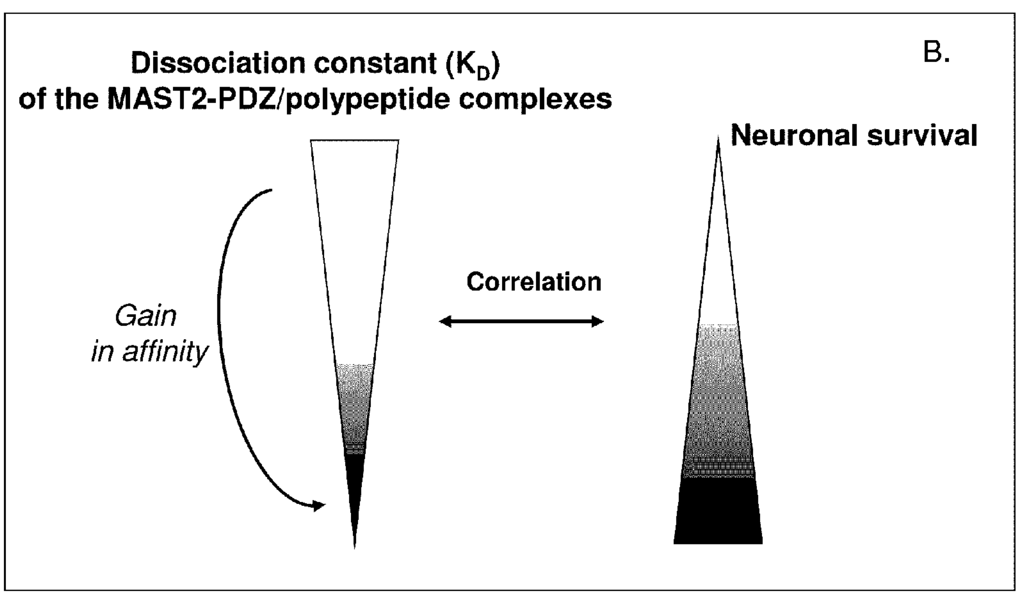

FIG. 10. Structure/function analysis (A) Sequence and three-dimensional organization of the Neurovita 1 sequence (SEQ ID NO:1). (B) Relationship between the affinity of the polypeptides of the invention (Neurovita polypeptides) for MAST2-PDZ and their neurosurvival properties.

Figure 11:
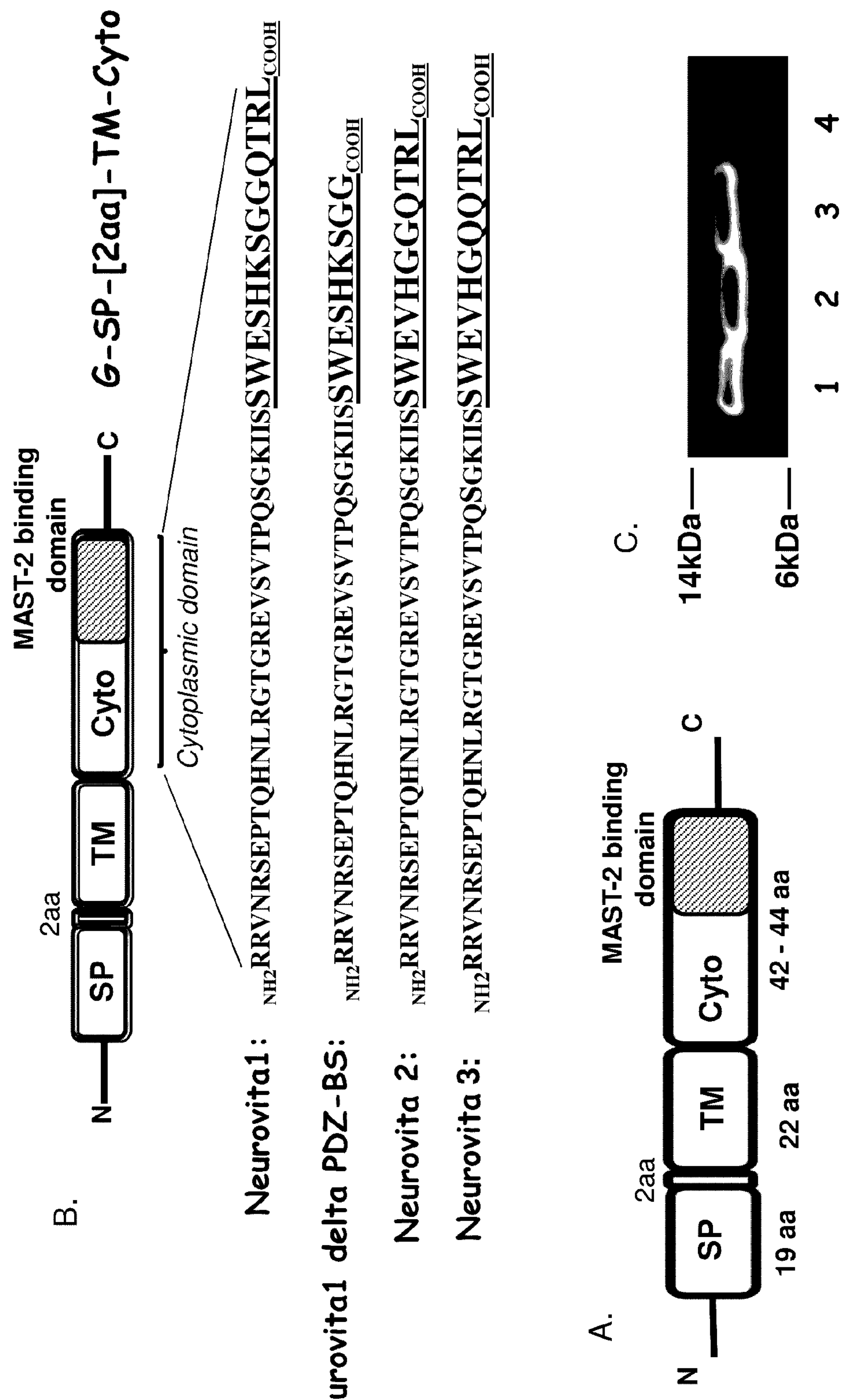

FIG. 11. (A) Schematic representation of the polypeptides of the invention; SP: Signal peptide, EC: extracellular domain, TM: transmembrane domain, Cyto: Cytoplasmic domain. The number of amino acid residues (aa) for each domain is also indicated (B) Protein sequence of 2 particular polypeptides of the invention (Neurovita2 (amino acids 44-85 of SEQ ID NO:210)and Neurovita3(amino acids 44-85 of SEQ ID NO:211)) and comparison with the sequences of Neurovita1 (amino acids 44-87 SEQ ID NO:9) and Neurovita1 delta PDZ-BS polypeptides (amino acids 44-83 of SEQ ID NO:11) (C) Expression of Neurovita1, Neurovita1 delta PDZ-BS and Neurovita2 by lentiviral vectors (lentivectors) in NS cells, measured by western blotting 48 h p.i., with antibodies specific for RABV Cyto-G (1: Neurovita2; 2: Neurovita1 delta PDZ-BS; 3: Neurovita1, and 4: negative control).

Figure 12:
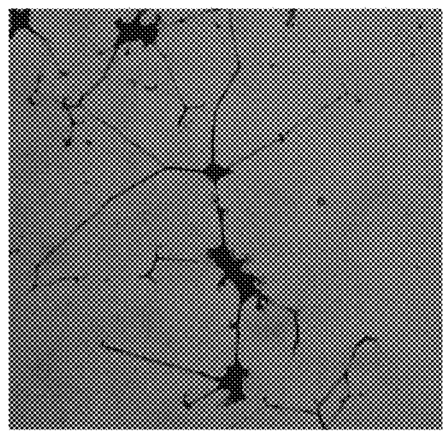
Figure 12:
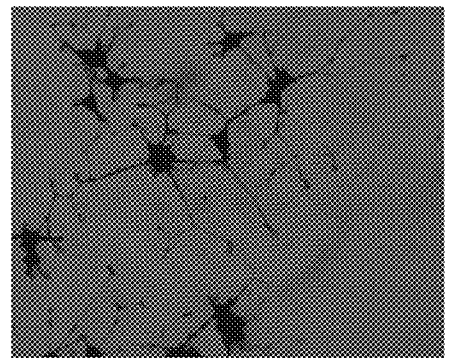
Figure 12:
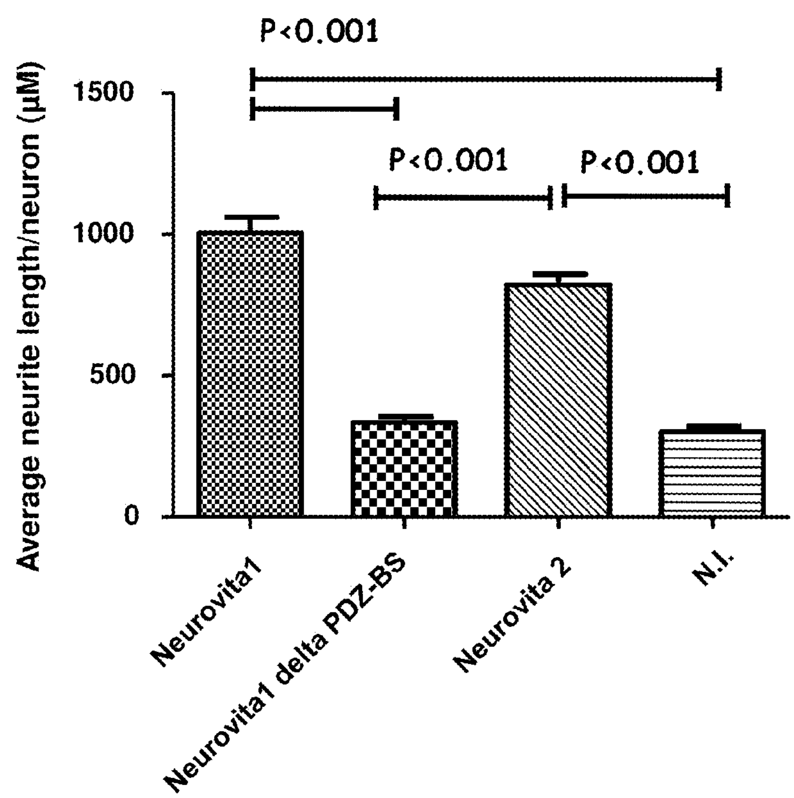

FIG. 12. Neurite outgrowth assay in NS cells following lentivectors infection (72 h p.i.). Cells were treated with NGF (200 ng/ml) (NJ. non-infected cells).

Figure 13:
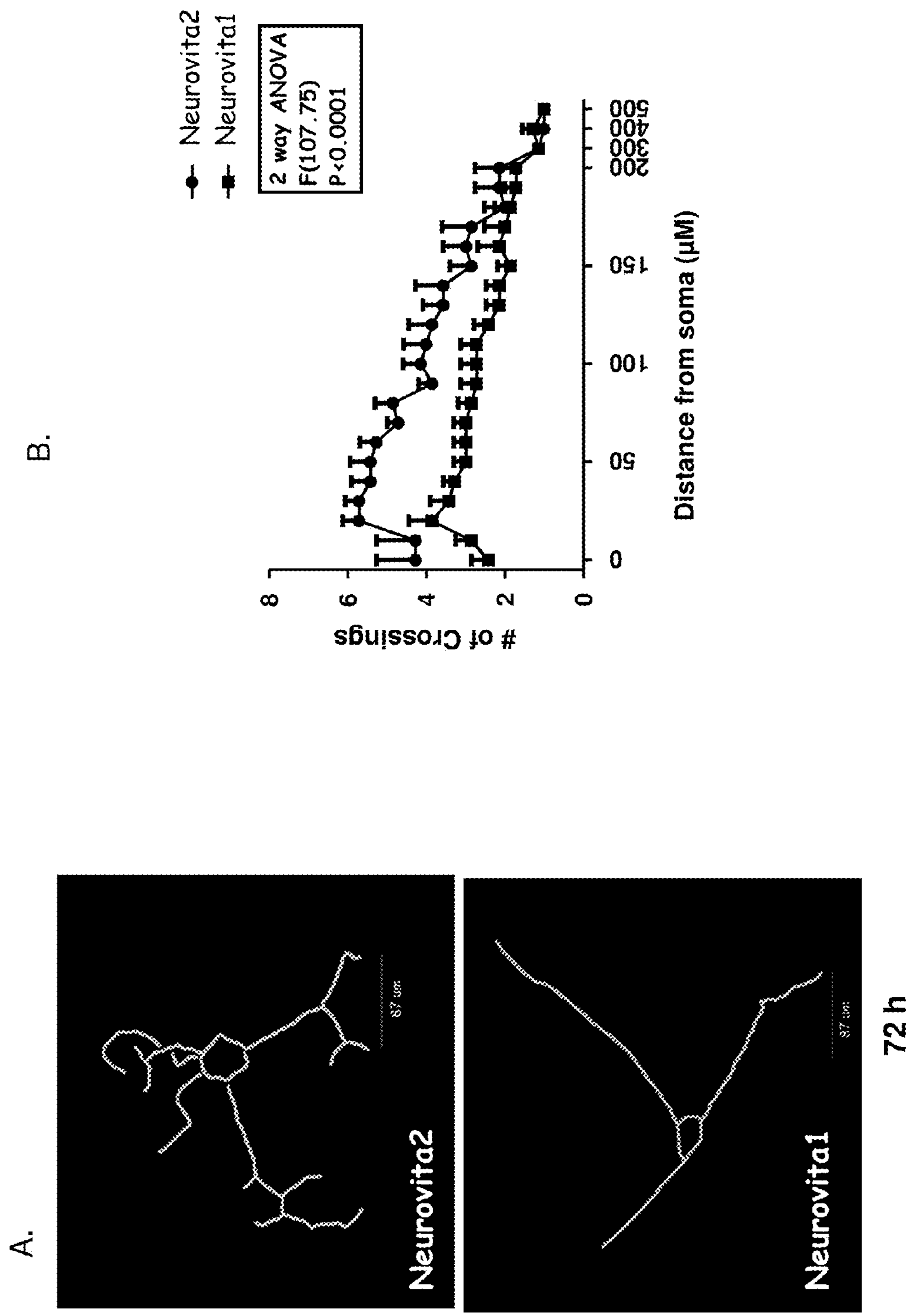

FIG. 13. Neurovitas induce neurite arborisation in NS cells (A) Schematic redrawing of the arborisation of representative NS cells either infected with Neurovita2 (upper photo) or Neurovita1 (lower photo) (B) Complexity of the neurite tree measured by Sholl analysis on NS culture infected for 72 h with Neurovita1 (black squares) and Neurovita2 (black circles) lentivectors.

Figure 14:
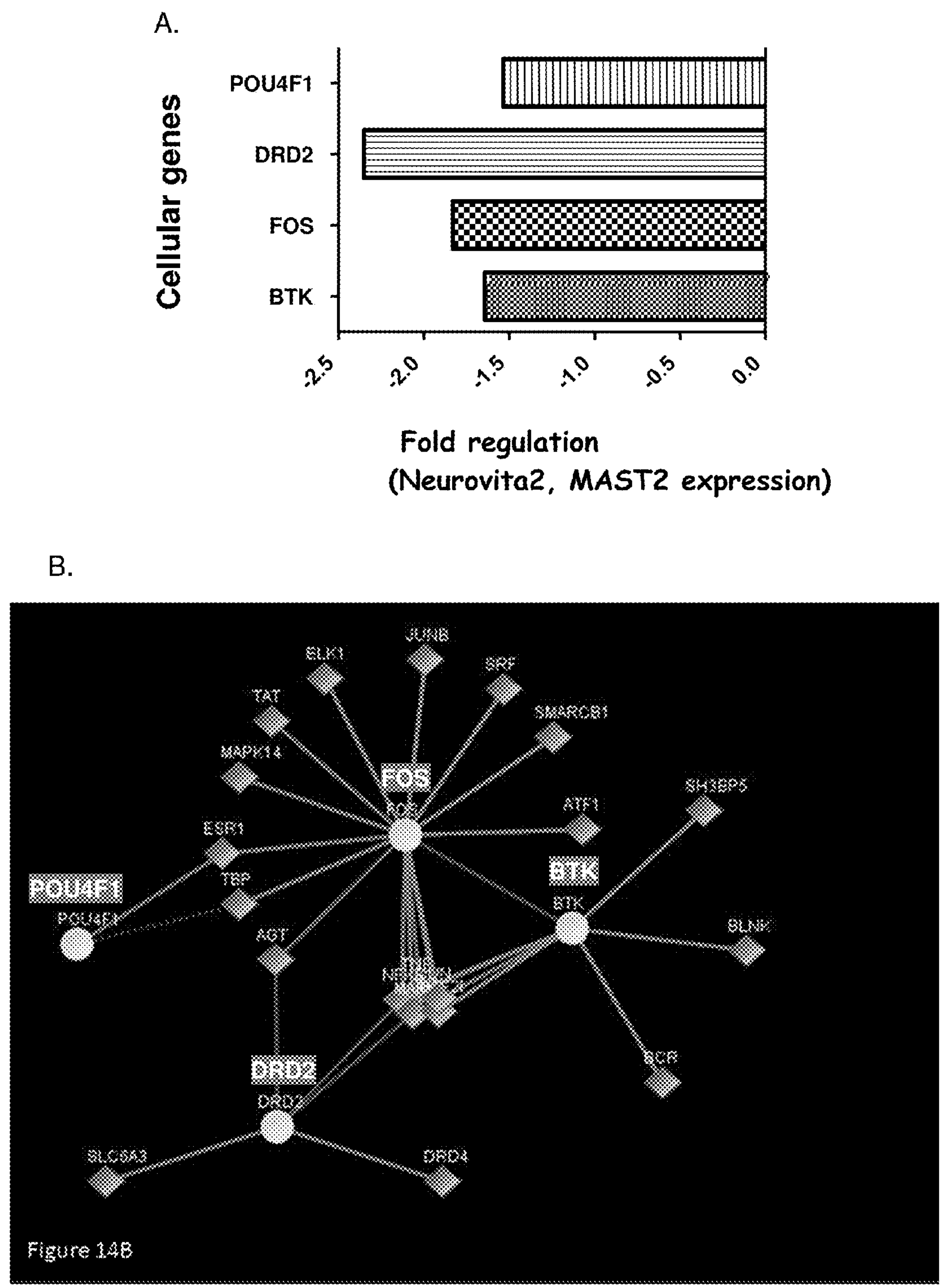

FIG. 14. Identification of the genetic molecular signature of Neurovita2. (A) Down regulation of POU4F1, DRD2, FOS and BTK, in NT2-N cells, 24 h p.i., by lentivectors (B) Schematic representation of the Neurovita2 genetic molecular signature obtained with the pathway-focused gene expression profiling (qRT-PCR). The cluster of genes represents the genes regulated following Neurovita2 infection but not regulated in non-infected culture or culture infected with Neurovita1 delta PDZ-BS (dots are neurovita specific genes; diamonds are related genes).

Figure 15:
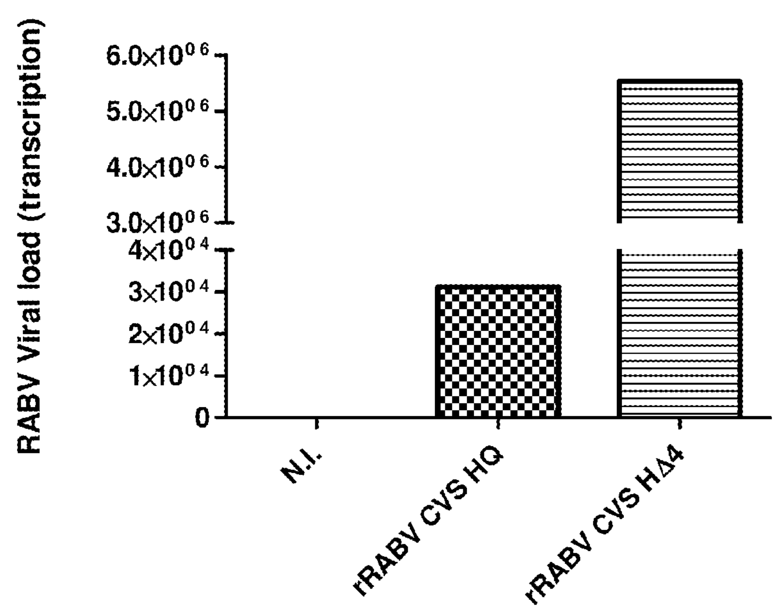
Figure 15:
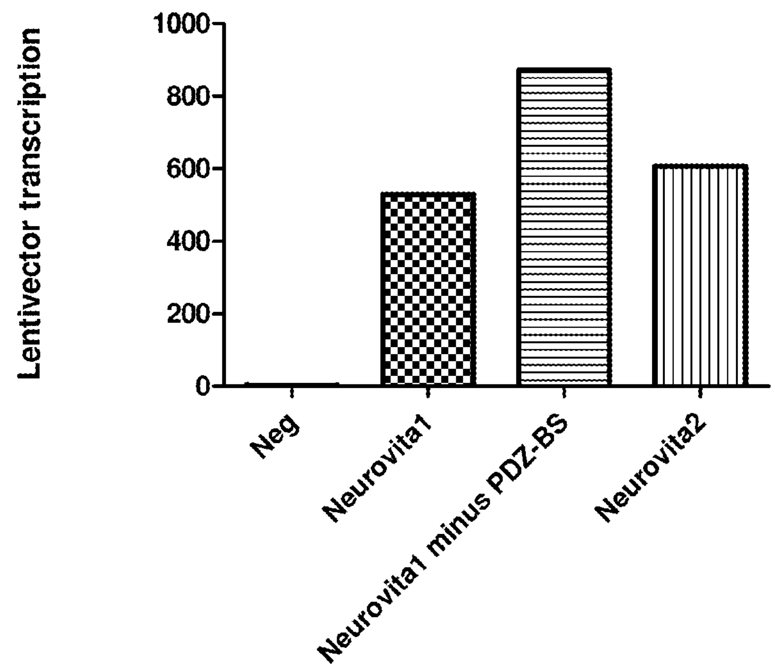

FIG. 15. Transcription of (A) the rRABV at 24 h p.i. and (B) of the lentivectors at 48 h p.i., in NT2-N cells following Neurovita lentiviral vectors infection. Transcription was measured by RT-QPCR.

Figure 16:
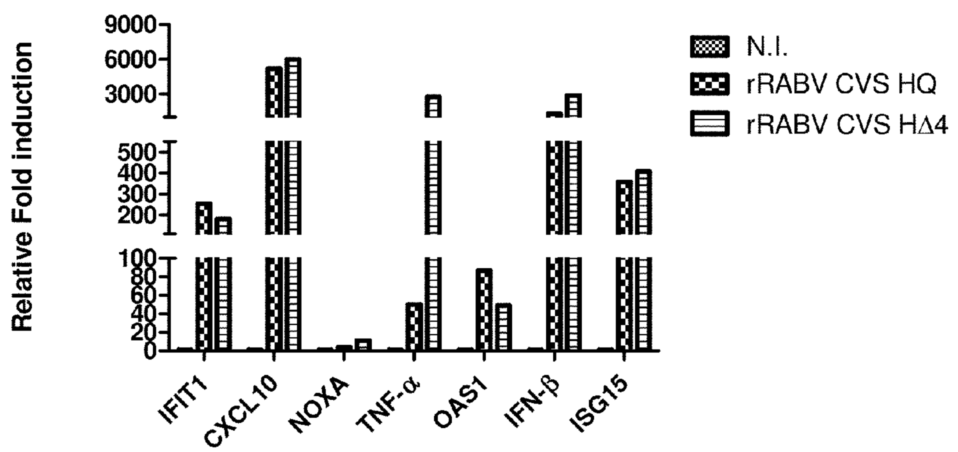
Figure 16:
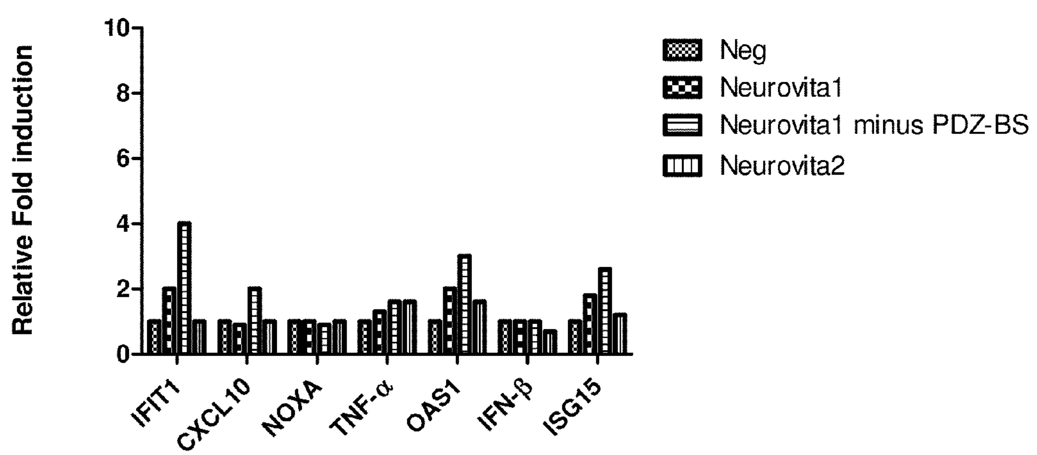

FIG. 16. Activation of innate immune genes (A) Transcription of a representative set of immunity genes (in NT2-N cells), (A) after infection with rRABV CVS HQ and rRABV CVS HΔ4 (N.I.: non-infected) or (B) after infection with Neurovita1, Neurovita1 delta PDZ-BS and Neurovita2 lentivectors (neg: negative control).

Figure 17:
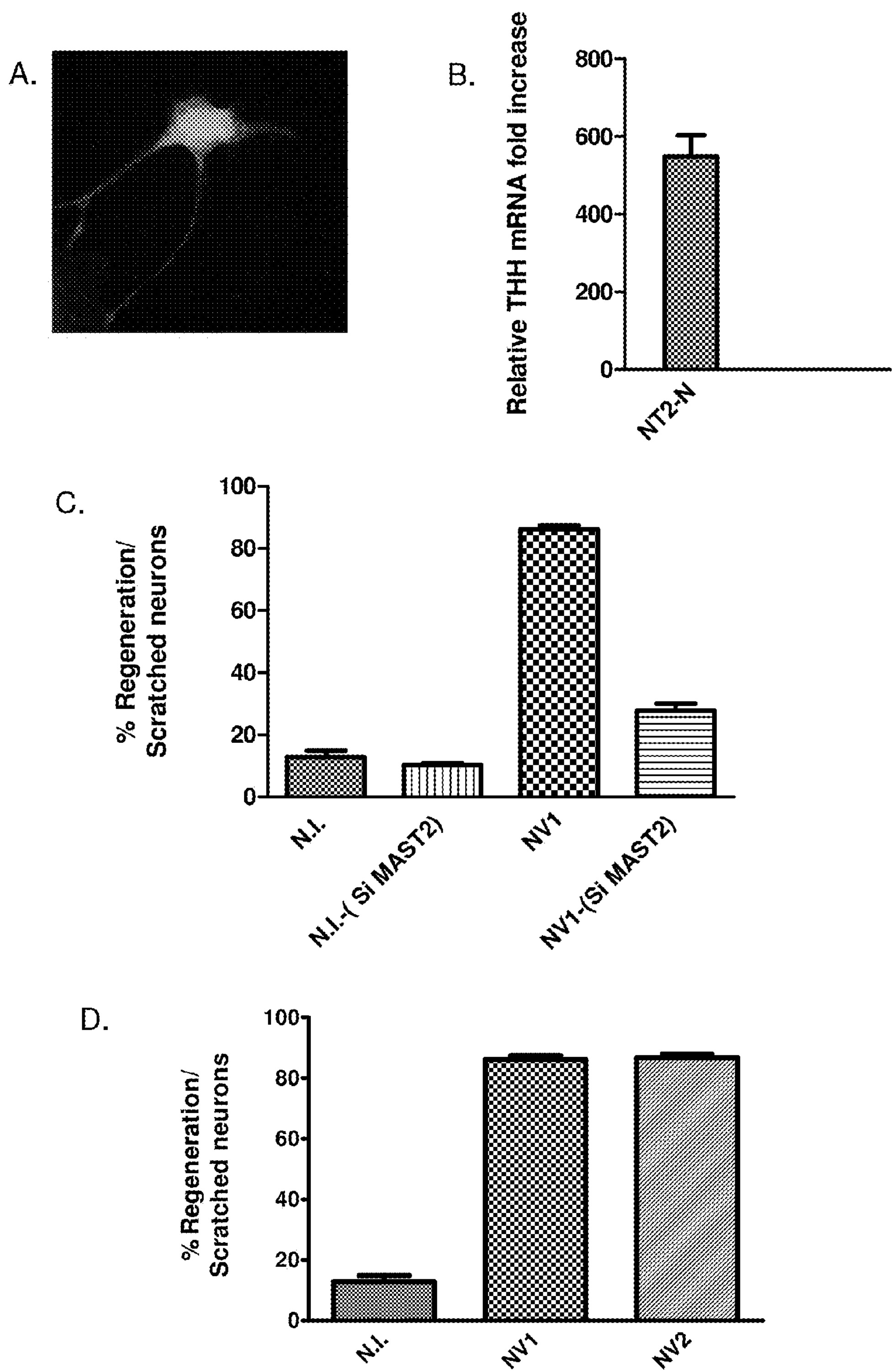

FIG. 17. Axon regeneration post wounding in NT2-N cells (A) expression of tyrosine hydroxylase (TH), a marker of dopaminergic neuron in a NT2-N cell (B) TH mRNA transcription in NT2-N culture, 18S as a standard (C) Axon regeneration after lentivector infection with Neurovita 1, in presence or absence of SHRNA against MAST-2 (si MAST2); N.I.: non-infected. Results are expressed as percentages of scratched neurons which regenerate (D) Axon regeneration after infection with Neurovita 1 or Neurovita2 lentivectors; N.I.: non-infected.

Figure 18:
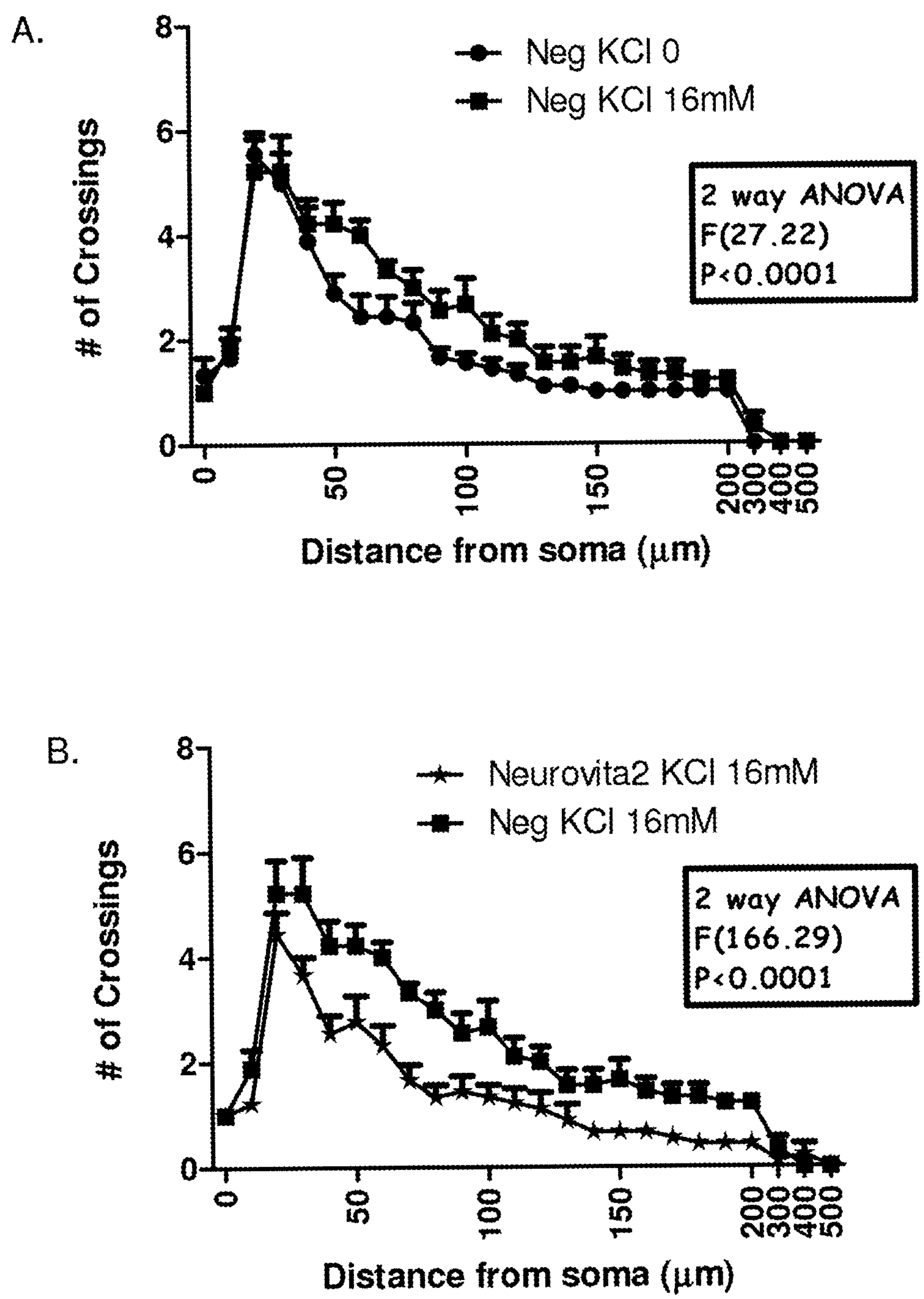

FIG. 18. Complexity of the neurite tree measured by Sholl analysis on NS culture, 27 h post lentivirus infection (A) with a negative control in absence (circles) or presence (squares) of KCl, or (B) after infection with Neurovita2 lentivector in presence of KCl (stars).

Figure 19:
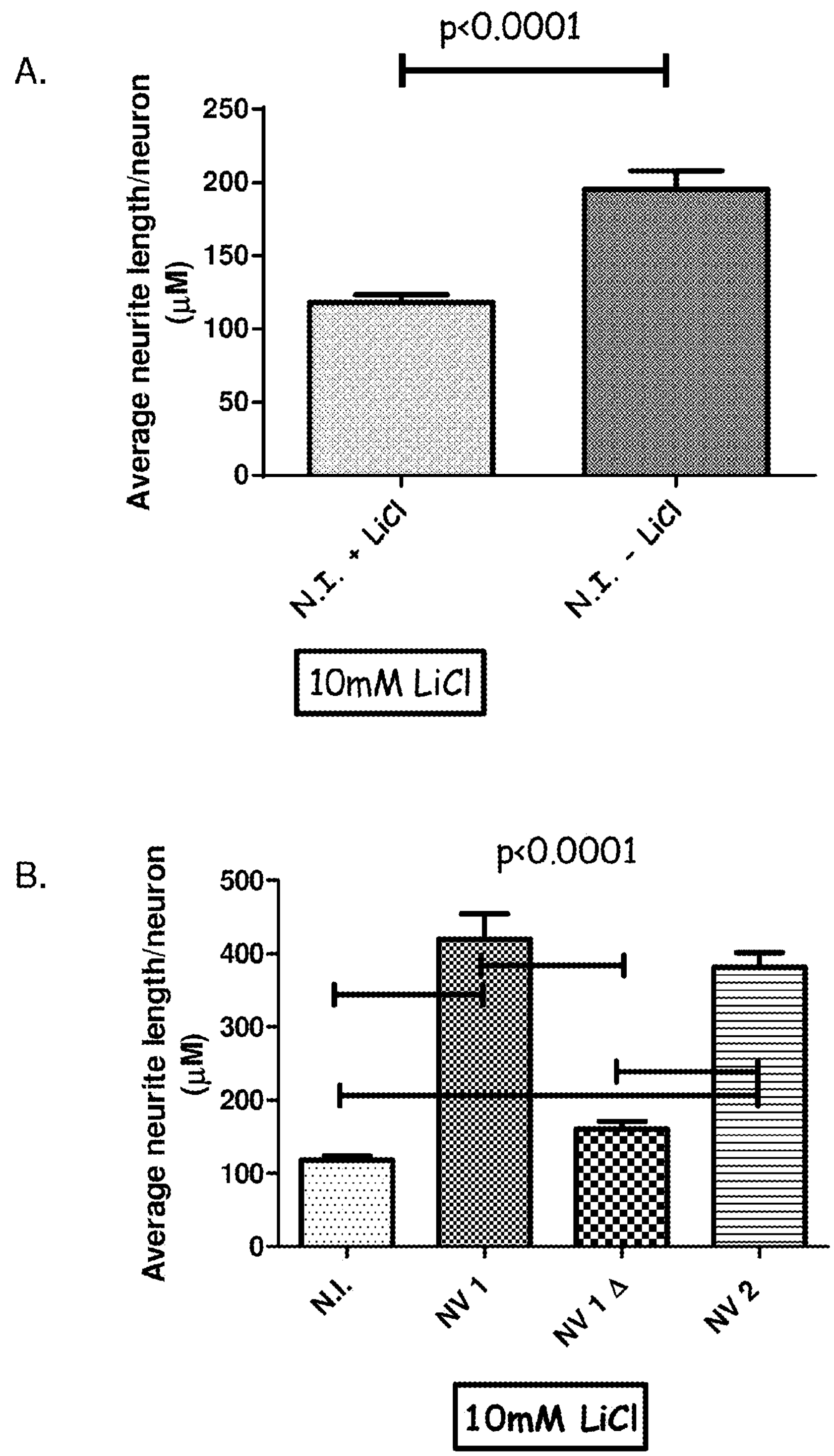

FIG. 19. Neurite outgrowth assay (A) in non-infected (N.I.) NS cells in absence or presence of LiCl and (B) in LiCl-treated NS cells, non-infected (N.I.) or after infection with Neurovita1 (NV1), Neurovita1 delta PDZ-BS (NV1Δ) or Neurovita2 (NV2) lentivectors.

FIG. 20. Comparison of neurite outgrowth triggered by G full, NV1 and NV1 cyto (A) Schematic representation of RABV G full, Neurovita 1 and cytosolic form of Neurovita 1 (NV1 cyto); SP: Signal peptide, EC: extracellular domain, TM: transmembrane domain, Cyto: Cytoplasmic domain, PDZ-BS: PDZ binding site. The number of amino acid residues (aa) for each domain is also indicated. (B) Neurite outgrowth assay after infection of NS with Neurovita 1, Neurovita1 delta PDZ-BS, RABV Gfull, RABV Gfull delta PDZ-BS, Neurovita1-cyto and Neurovita1-cyto delta PDZ-BS (N.I.: non-infected).

Figure 21:
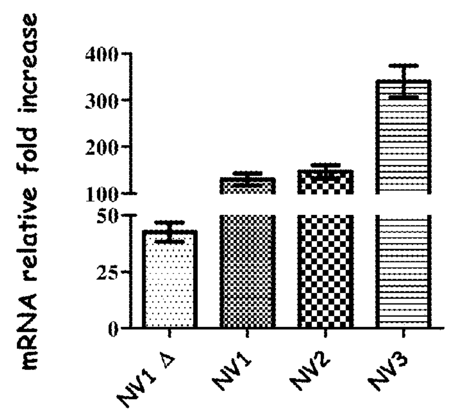
Figure 21:
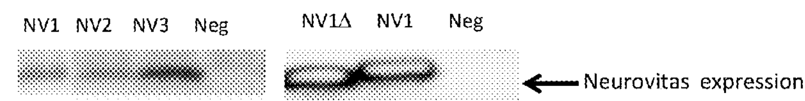
Figure 21:
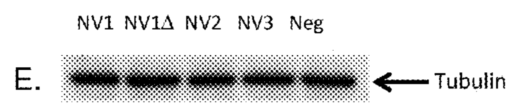

FIG. 21. Expression of Neurovita molecules from a bicistronic lentivector in NS cells (A) schematic representation of the pLenti7.3 Neurovita bicistronic lentivector (B) mRNA relative fold increase of Neurovita1 delta PDZ-BS (NV1Δ), Neurovita1 (NV1), Neurovita2 (NV2) or Neurovita3 (NV3), 18S as a standard (C) GFP expression after infection of NS cells with NV1Δ-, NV1-, NV2- or NV3-expressing lentivector by flow cytometry; results are expressed as percentages of cells expressing GFP in the culture; Neg is non-infected cells. (D) Expression of NV1Δ, NV1, NV2, or NV3 in NS cells by Western blotting. (E) Expression of tubulin as a internal protein loading control, in the corresponding lysates.

Figure 22:
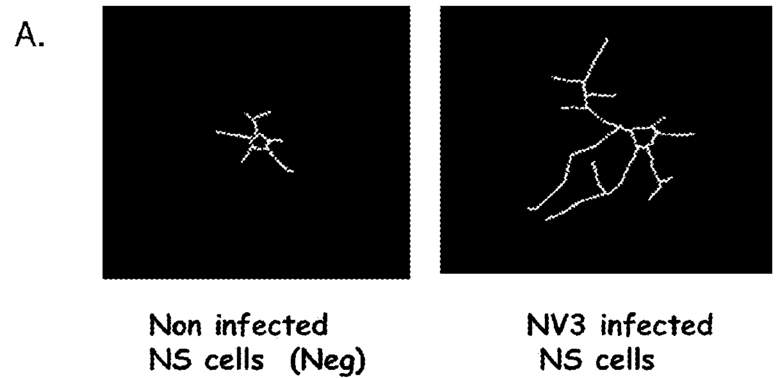
Figure 22:
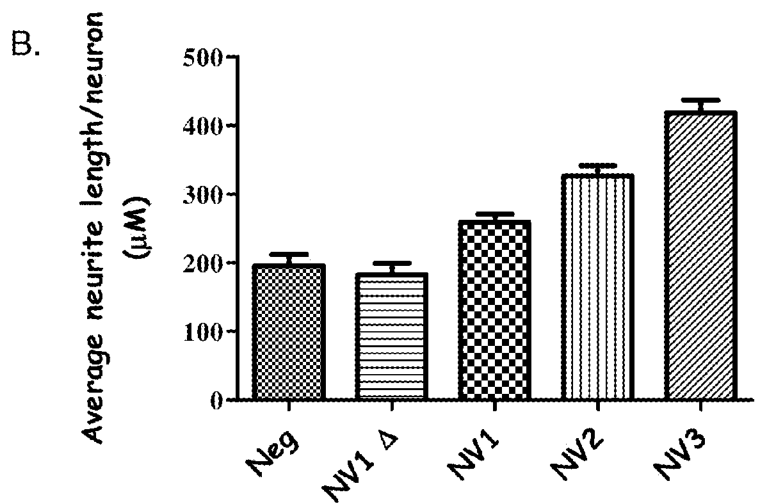

FIG. 22. Neurite outgrowth triggered by NV3 in NS cultures (A) Schematic redrawing of the arborisation of representative NS cells either non-infected (left panel) or infected with Neurovita3 (right panel); (B) Neurite outgrowth assay in NS cells following infection with NV1Δ, NV1, NV2, or NV3 lentivectors; (C) Student's t-test ($p<0.05$).

Figure 23:
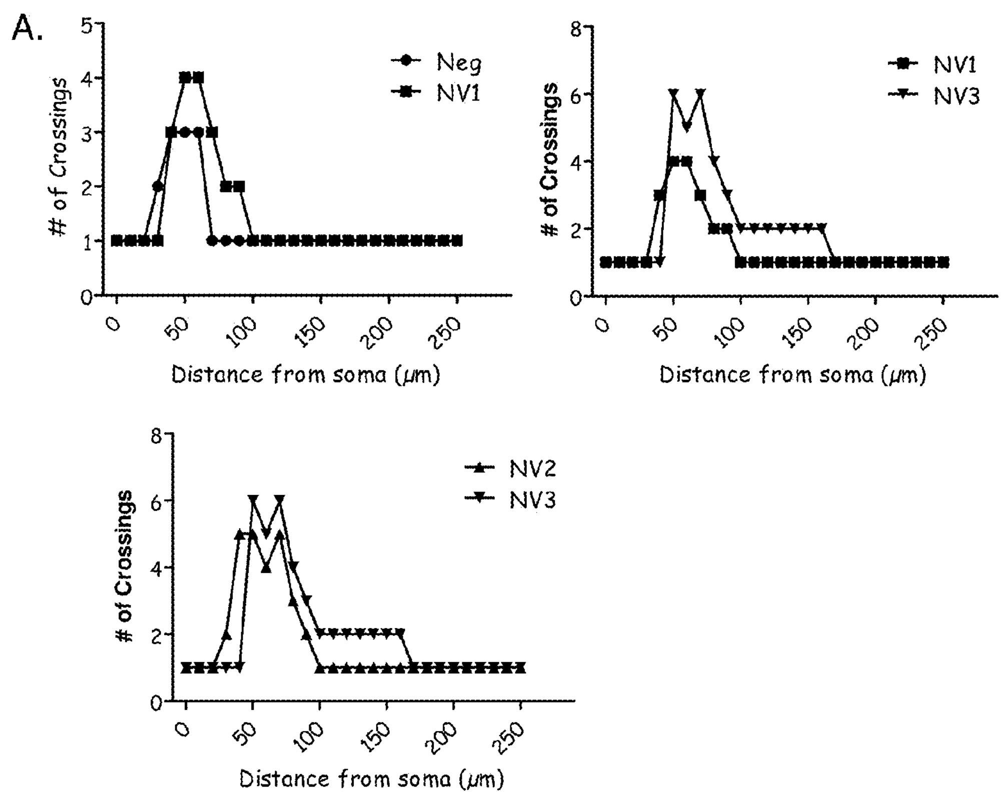

FIG. 23. Tree arborisation triggered by NV3 in NS cultures (A) Complexity of the neurite tree measured by Sholl analysis on NS cells, either non-infected versus infected with Neurovita1, infected with Neurovita1 versus infected with Neurovita3 or infected with Neurovita2 versus infected with Neurovita3; (B) two way ANOVA ($p<0.05$).

Figure 24:
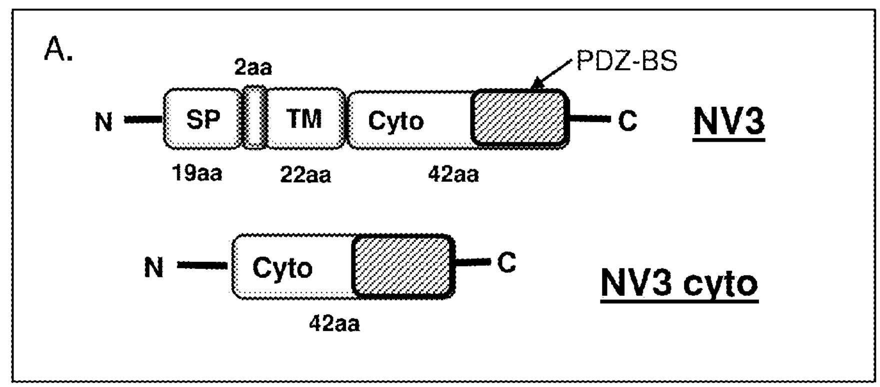
Figure 24:
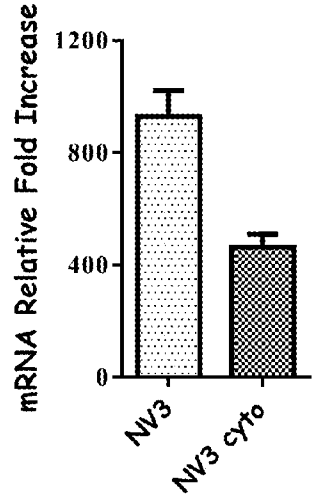

FIG. 24. Construction of NV3 cytosolic (NV3 cyto) lentivector (A) Schematic representation of Neurovita 3 and cytosolic form of Neurovita 3 (NV3 cyto); SP: Signal peptide, EC: extracellular domain, TM: transmembrane domain, Cyto: Cytoplasmic domain, PDZ-BS: PDZ binding site. The number of amino acid residues (aa) for each domain is also indicated; (B) schematic representation of the pLenti7.3 Neurovita bicistronic lentivector expressing NV3 or NV3-cyto; (C) relative fold increase of NV3 and NV3cyto, 18S as a standard; (D) GFP expression after infection with NV3 or NV3cyto-expressing lentivector by cytofluorimetry; results are expressed as percentages of GFP positive cells in the culture; neg is non-infected cells.

Figure 25:
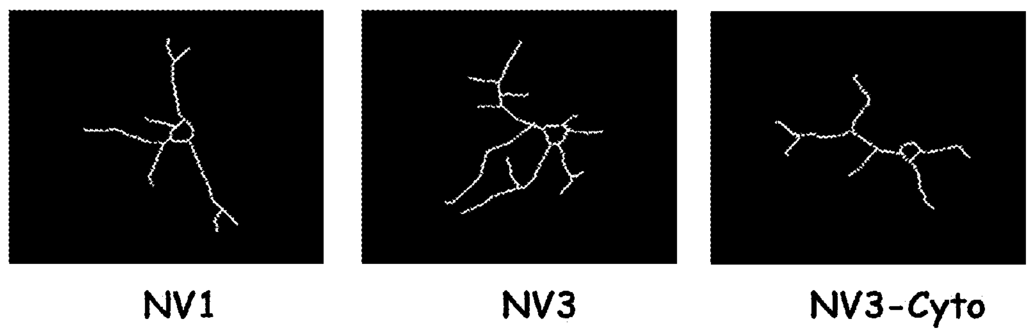
Figure 25:
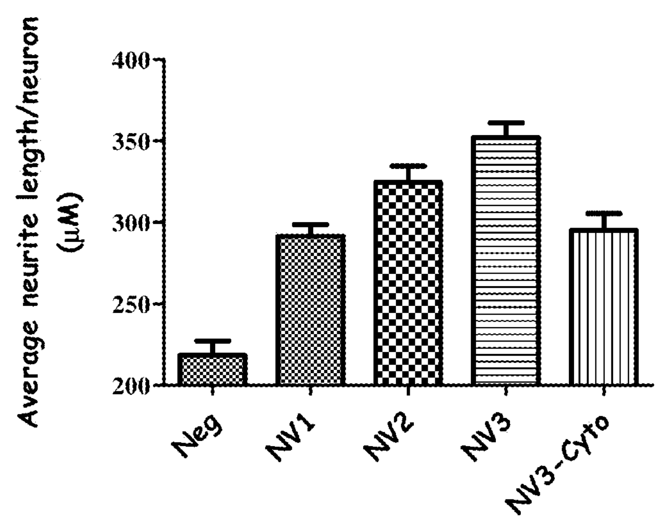

FIG. 25. Comparison of NV3-cyto induced neurite outgrowth with those of NV1 and NV3 (A) Schematic redrawing of the arborisation of representative NS cells infected with NV1, NV3 or NV3-cyto; (B) Neurite outgrowth assay in NS cells following infection with NV1, NV2, NV3 or NV3-cyto lentivectors; (C) Student's t-test ($p<0.05$).

Figure 26:
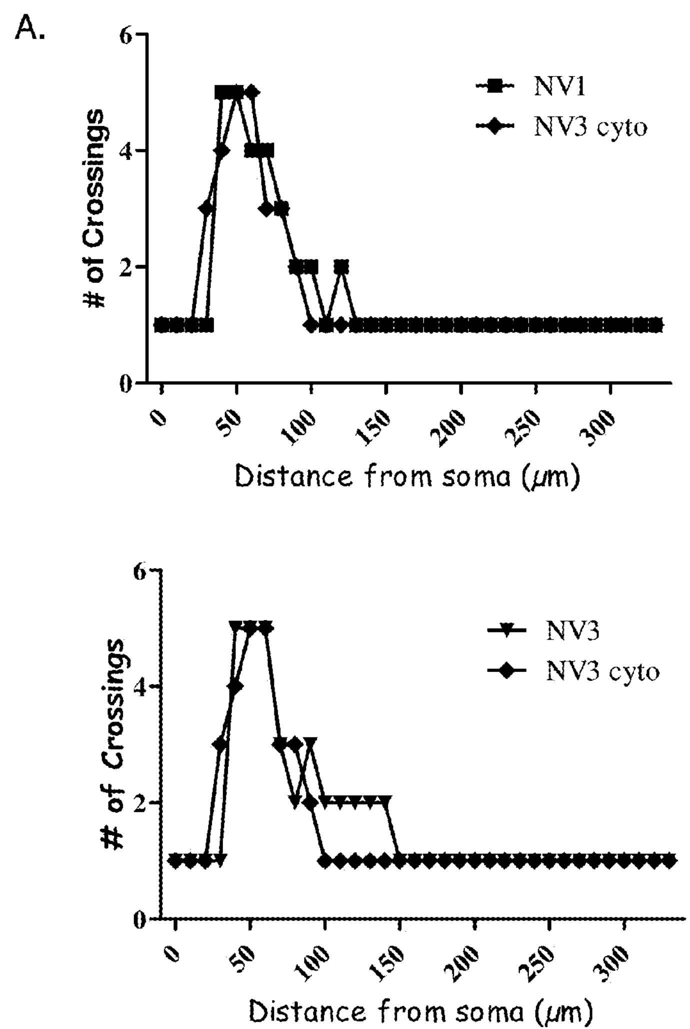

FIG. 26. Comparison of NV3-cyto induced neurite trees with those of NV1 and NV3 (A) Complexity of the neurite tree measured by Sholl analysis on NS culture, either infected with NV1 versus infected with NV3cyto or infected with NV3 versus infected with NV3cyto; (B) two way ANOVA ($p<0.05$).

Figure 27:
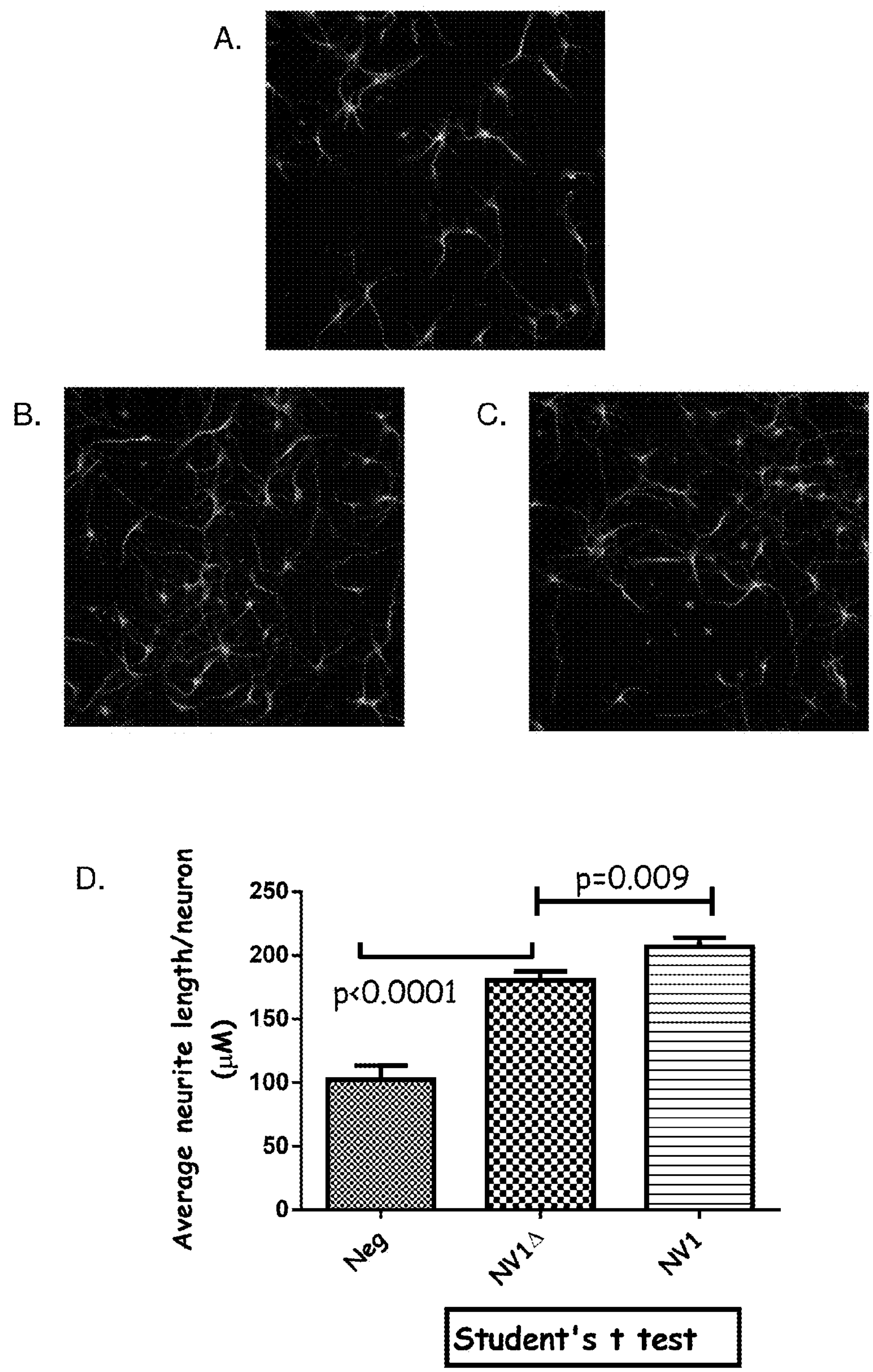

FIG. 27. Neuritogenesis in culture of E16 mouse foetal cortical neurons induced by NV1 and NV1 delta. Representative pictures of 6111 tubulin (neuronal form) stain E16 mouse cortical neurons 3 days in vitro (A) non-infected or 3 days infected by NV1 (B) or NV1Δ (C) lentivectors; (D) Neurite outgrowth assay in cortical neurons following infection with NV1 or NV1Δ lentivectors.

Figure 28:
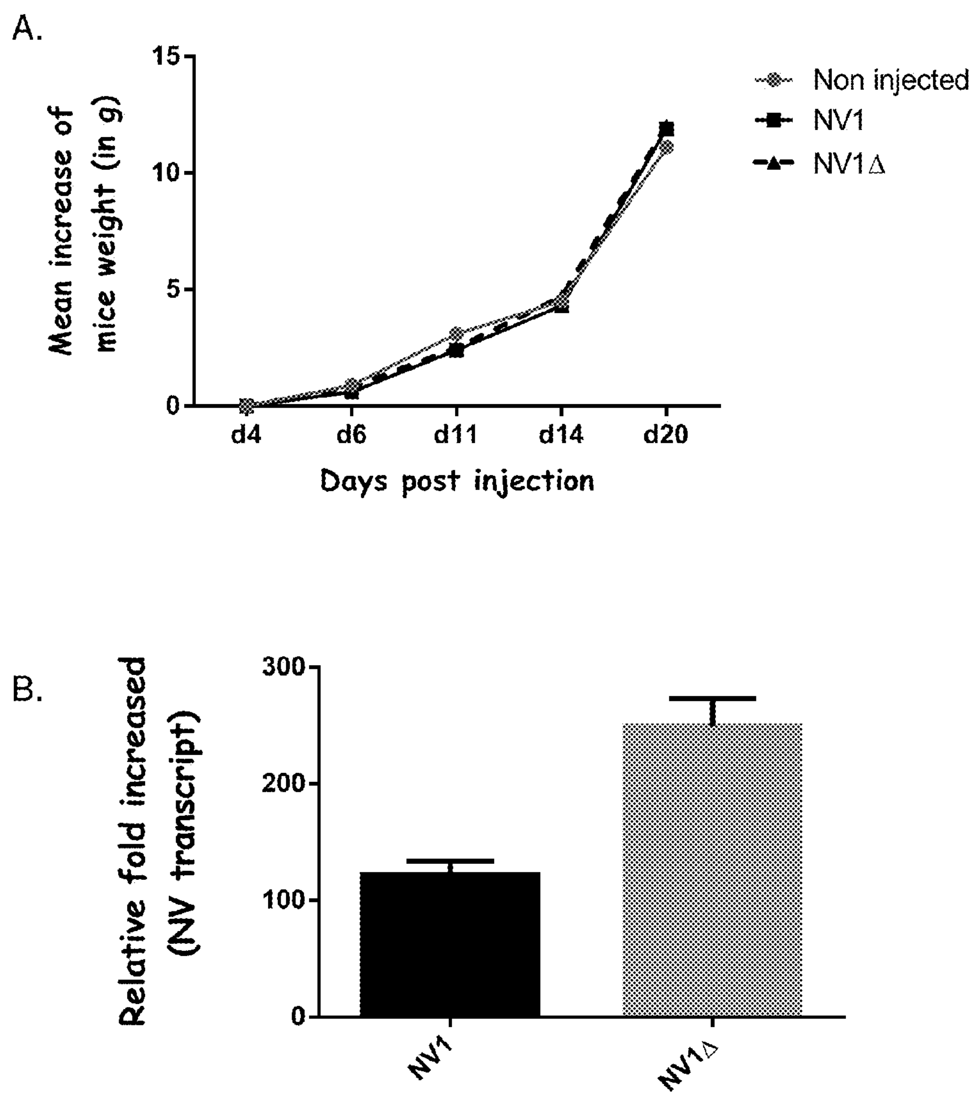

FIG. 28. Toxicity assays in new born mice injected by the intracerebral route with NV1 or NV1 delta lentivectors (A) Weight determined in non-injected mice or mice injected with NV1 or NV1Δlentivectors; (B) Expression of NV1 or NV1Δtranscripts in brain, 3 months after lentivirus infection, 18S as a standard.

Figure 29:
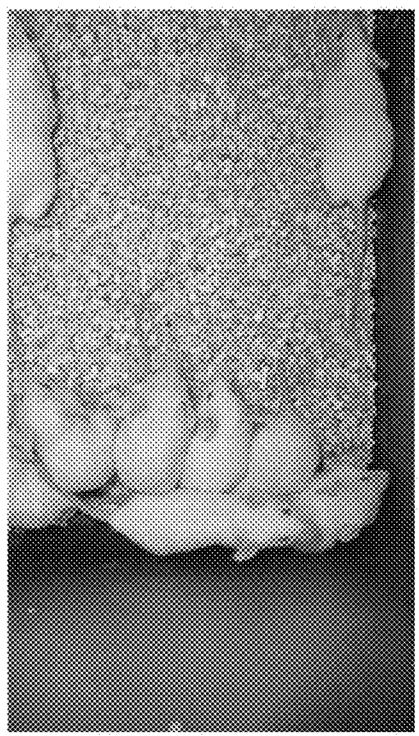
Figure 29:
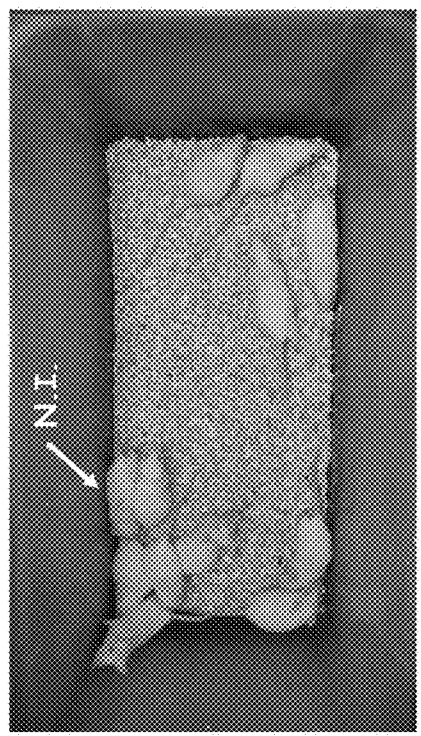
Figure 29:
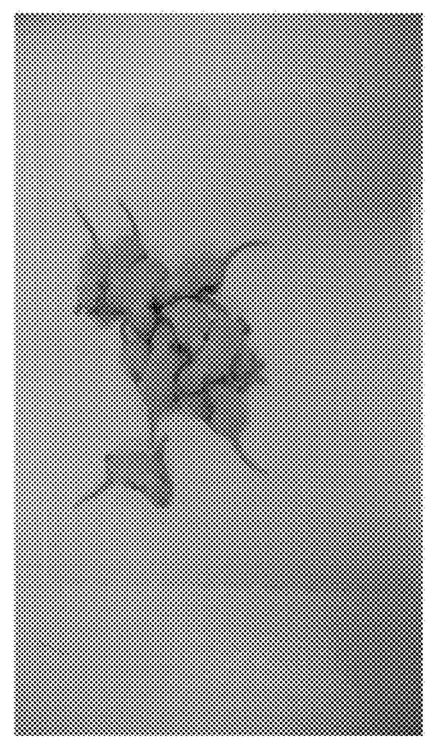

FIG. 29. Phenotype of mice injected with NV1 or NV1Δlentivectors into brain. (A) NV1, day 4 post injection (pi); (B) mice injected with NV1, day 20 pi; (C) mice injected with NV1Δ, day 4 pi; (D) mice injected with NV1Δ, day 20 pi; Arrow represents a non injected (N.I.) mouse (cut tail).

Figure 30:
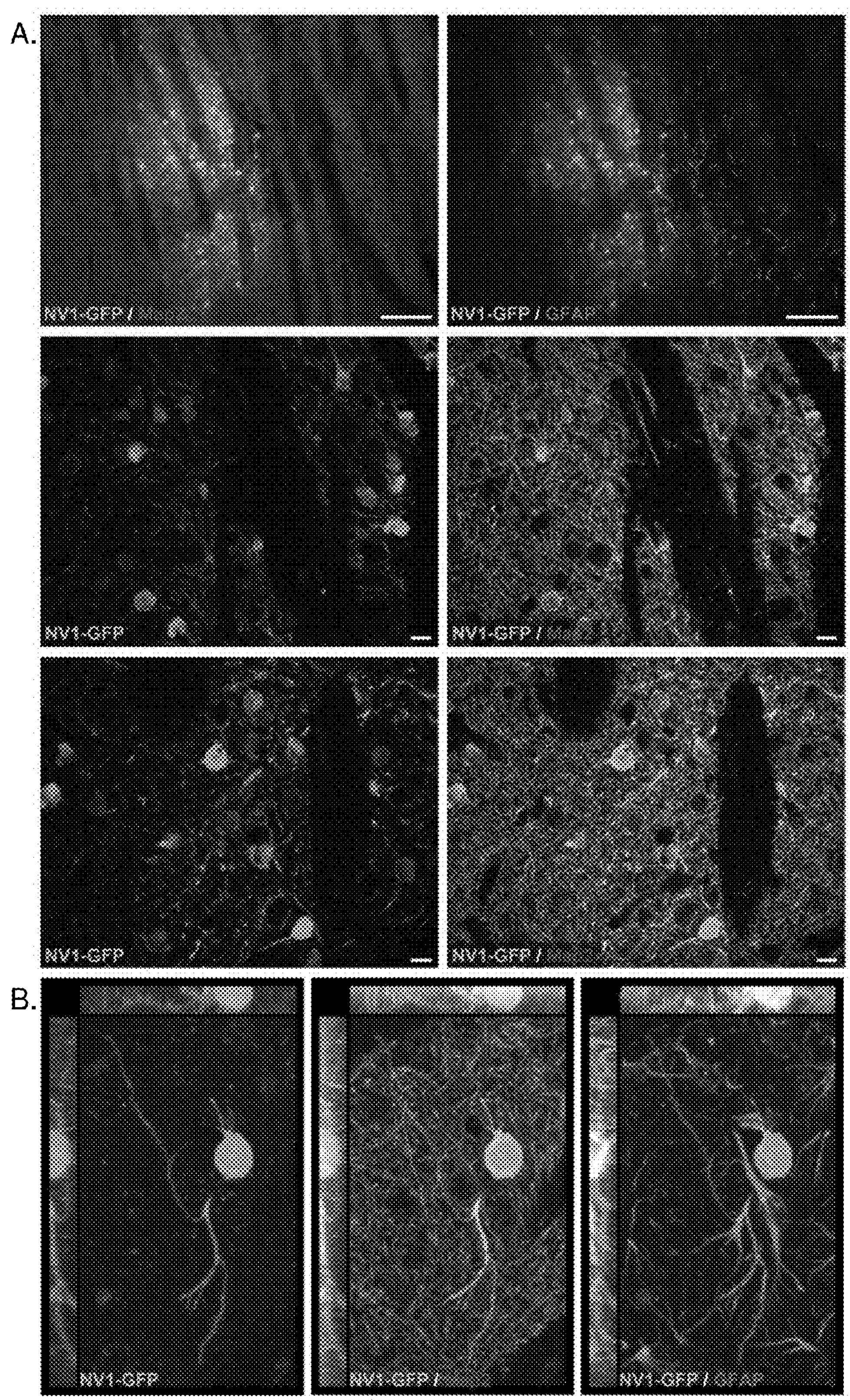

FIG. 30. Immunostaining of brains (striatum) of mice injected by the intracerebral route with NV1 lentivectors. (A) immunostaining of striatum with GFP fluorescence (green), Map2 staining (red) and GFAP staining (purple) (B) immunostaining of dendritic-axonal tree with GFP fluorescence (green), Map2 staining (red) and GFAP staining (purple).

Figure 31:
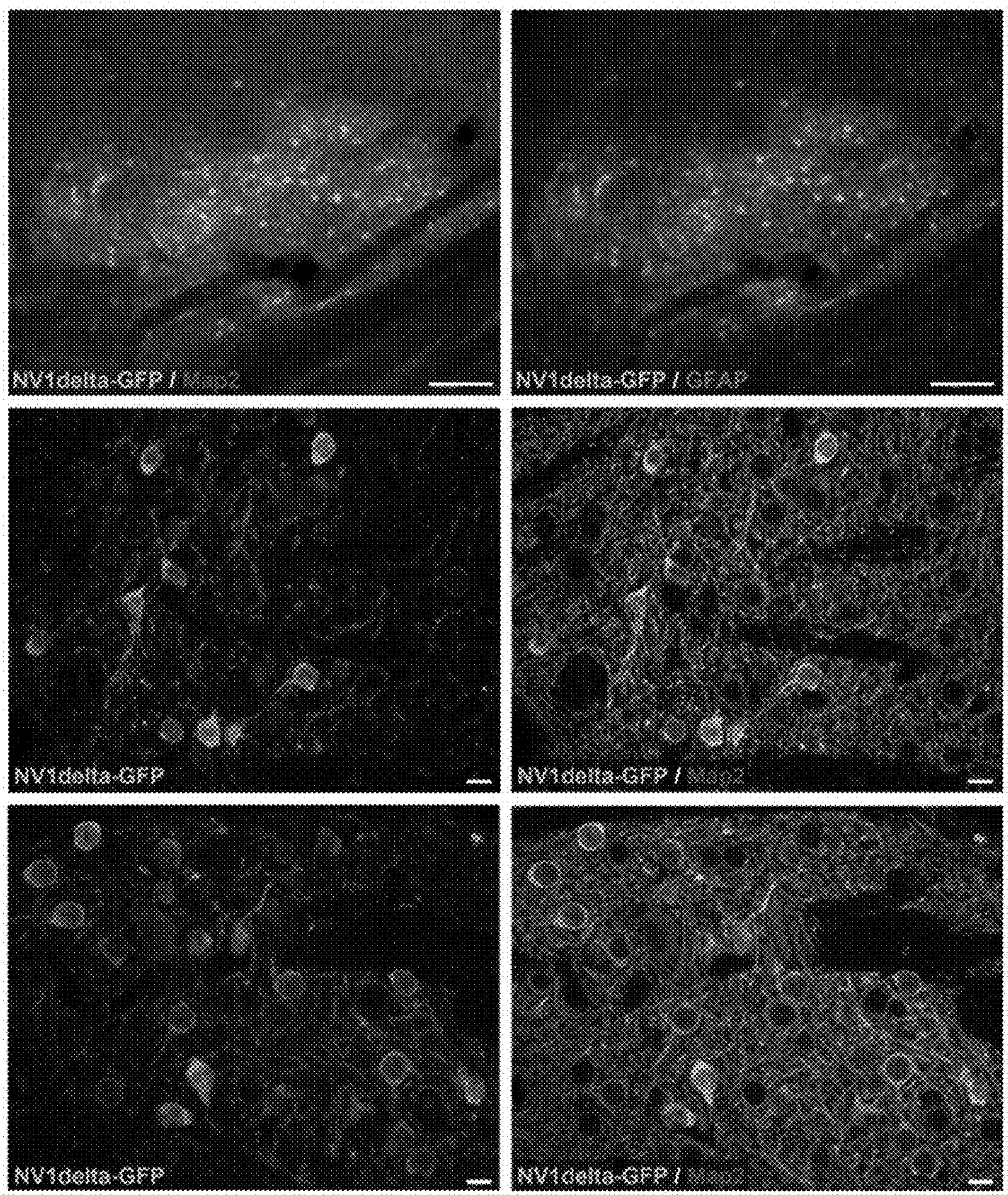

FIG. 31. Striatum immunostaining of mice injected with NV1Δlentivectors into brain; GFP fluorescence (green), Map2 staining (red) and GFAP staining (purple).

SUMMARY

In the present application, the inventors have unexpectedly shown that polypeptides, the sequence of which comprises the residues SW and the residues QTRL, (residues 10-13 of SEQ ID NO:1), having a high affinity for the PDZ domain of the human MAST2 protein, have particular interesting effect on the promotion of neurite outgrowth and on neurosurvival properties. Thus, the lower the constant of dissociation ($K_D$) of the complex formed by the polypeptides of the invention with the PDZ domain of the human MAST2 protein, the higher the neurosurvival properties of the polypeptide of the invention.

The invention is directed to a polypeptide as defined herein which presents a high affinity for the PDZ domain of the human MAST2 protein (SEQ ID NO: 6 for the full length human MAST2 protein and SEQ ID NO:7 for its PDZ domain).

In other words, the polypeptide of the invention as defined herein is designed in such a way that the constant of dissociation ($K_D$) of the complex that it forms with the PDZ domain of the human MAST2 protein is very low and as a consequence that its affinity for the PDZ domain of the human MAST2 protein is very high (the affinity being inverse to the $K_D$).

DETAILED DESCRIPTION OF A PREFERRED EMBODIMENT

Accordingly, in a first embodiment, the polypeptide of the invention presents a binding affinity for the PDZ domain of the human MAST2 protein which is higher than the binding affinity for the PDZ domain of the MAST2 protein of a rabies virus G protein comprising the SWESHKSGGQTRL sequence (SEQ ID NO:1).

In a particular embodiment, the gain in affinity of the polypeptides of the invention as compared to a polypeptide having a MAST-2 binding domain consisting of SWESHKSGGQTRL (SEQ ID NO:1) (for example, ratio of $K_D$) ranges from 2.5 to 20, and in particular ranges from 5 to 20, from 5 to 15 or from 5 to 10.

In particular embodiment, the constant of dissociation ($K_D$) of the complex formed by the polypeptide of the invention with the PDZ domain of the human MAST2 protein is less than 1 μM, less than 0.8 μM, less than 0.5 μM, less than 0.4 μM or less than 0.3 μM. In a preferred embodiment, the constant of dissociation of the complex formed by the polypeptide of the invention with the PDZ domain of the human MAST2 protein is less than 0.2 μM, preferably less than 0.15 μM, more preferably less than 0.1 μM.

In a particular embodiment, the constant of dissociation ($K_D$) of the complex formed by the polypeptide of the invention with the PDZ domain of the human MAST2 protein (MAST2-PDZ) is measured by Isothermal Titration Calorimetry (ITC).

As a particular embodiment of ITC, the constant of dissociation of the complex formed by the polypeptide of the invention with the PDZ domain of the human MAST2 protein (MAST2-PDZ) is determined for a concentration of the polypeptide ranging from 250 μM to 350 μM (preferably in buffer containing 50 mM Tris-HCl, 150 mM NaCl, pH7.5) and an initial concentration of the MAST2-PDZ domain of 30 μM.

As a particular embodiment of ITC, the constant of dissociation of the complex formed by the polypeptide of the invention with the PDZ domain of the human MAST2 protein is measured as follows: the polypeptide of the invention is prepared, in a buffer containing 50 mM Tris-HCl, 150 mM NaCl, pH7.5, at initial concentrations ranging from 250 μM to 350 μM. ITC (Isothermal Titration Calorimetry) measurements are made using Microcal VP ITC200 isothermal titration calorimeter from Microcal (Northampton, Mass.), by titrating the MAST2-PDZ (at an initial concentration of 30 μM), at 298 K, by injection of the polypeptide of the invention as prepared above (each titration of a particular polypeptide involves 25-45 consecutive injections of aliquots of 5-7 μL at 6-min intervals). Raw data are normalized and corrected for heats of dilution of the polypeptides. Equilibrium dissociation constants are determined performing nonlinear curve fitting of the corrected data to a model with one set of sites using the Origin7.0 software (OriginLab).

The affinity of the polypeptides of the invention for the PDZ domain of the human PTPN4 protein is low, i.e., the constant of dissociation ($K_D$) of the complex formed by the polypeptide of the invention with the PDZ domain of the human PTPN4 protein is high, in particular is more than 500 μM (for example as measured by ITC, in particular in the same conditions and with the same concentrations as for the MAST2-PDZ above). This high value of $K_D$ (for the PDZ domain of the human PTPN4 protein) has been shown to be reached with the polypeptides of the invention in which the last four residues are Q, T, R and L.

Thus, polypeptides, having a high affinity for the PDZ domain of the human MAST2 protein and/or designed in such a way that the constant of dissociation (Kd) of the complex that it forms with the PDZ domain of the human MAST2 protein is within the above ranges, are herein described by the following structural features.

The invention accordingly relates to a polypeptide, of at most 350 amino acid residues, comprising or consisting of a cytoplasmic domain. The expression "cytoplasmic domain" means a protein domain ending with a MAST-2 binding domain as defined herein, and which is exposed in the cytoplasm of a cell, preferably when the polypeptide possesses a structure or sequence enabling its anchoring in the cell membrane. According to the invention, the polypeptide may comprise or not a structure or sequence enabling the anchoring of the polypeptide of the invention in the membrane. When the polypeptide does not possess the structure or sequence enabling the anchoring in the membrane, for example when the polypeptide consists of the cytoplasmic domain as defined herein, the polypeptide of the invention is cytosolic.

In a particular embodiment, the constant of dissociation ($K_D$) of the complex formed between the PDZ domain of the human MAST2 protein and a polypeptide of the invention which does not possess the structure or sequence enabling the anchoring in the membrane, in particular a polypeptide consisting of the cytoplasmic domain as defined herein, is less than 1 μM, less than 0.5 μM, less than 0.4 μM or less than 0.3 μM, preferably less than 0.2 μM, less than 0.15 μM, and more preferably less than 0.1 μM.

In a particular embodiment, the invention relates to a polypeptide, of at most 350 amino acid residues, comprising (1) a signal peptide, (2) a domain for anchoring said polypeptide into the reticulum membrane and/or Golgi membrane (also called the anchoring domain), and (3) a domain which is exposed in the cytoplasm when the polypeptide is anchored in the membrane (also called the cytoplasmic domain). These domains are organised structurally in such a way that the signal peptide is N-terminal to the anchoring domain, which is itself N-terminal to the cytoplasmic domain. According to this embodiment, the polypeptide of the invention comprises, from N-terminal to C-terminal, (1) a signal peptide, (2) an anchoring domain, and (3) a cytoplasmic domain.

The cytoplasmic domain of the polypeptide of the invention ends with a MAST-2 binding domain, whose size is from 11 to 13 amino acid residues. By "ends with", it is meant that the 11 to 13 successive residues of the MAST-2 binding domain are the last C-terminal residues of the cytoplasmic domain, and in a particular embodiment the last C-terminal residues of the polypeptides of the invention.

The MAST-2 binding domain of the polypeptide of the invention consists of a sequence, whose size is from 11 to 13 residues, the first two residues of which are S and W, and the fourth last residues of which are Q, T, R and L (these 4 last amino acid residues represent the so-called PDZ-BS). The MAST-2 binding domain is defined according to one of the following groups, knowing that, whatever the group, the first two amino acid residues of the MAST-2 binding domain are S and W and the last four amino acid residues of the MAST-2 binding domain are Q, T, R and L.

(A) in a first group, the MAST-2 binding domain consists of a sequence, whose size is 11 residues, the first two residues of which are S and W, and the last four residues of which are Q, T, R and L, consisting of SWX$_1$X$_2$X$_3$X$_4$X$_5$QTRL, wherein each of $X_1$, $X_2$, $X_3$, $X_4$ and $X_5$ is any amino acid residue (SEQ ID NO:19).

In a particular embodiment, $X_1$ is E or A, more preferably E, such that the MAST-2 binding domain consists of a sequence, whose size is 11 residues, the first two residues of which are S, W and E, and the last four residues of which are Q, T, R and L, consisting of SWEX$_2$X$_3$X$_4$X$_5$QTRL (SEQ ID NO:20) or SWAX$_2$X$_3$X$_4$X$_5$QTRL (SEQ ID NO:21), wherein each of $X_2$, $X_3$, $X_4$ and $X_5$ is any amino acid residue.

In another embodiment, $X_2$ is S, E or V, more preferably V, such that the MAST-2 binding domain consists of a sequence, whose size is 11 residues, the first two residues of which are S and W and the last four residues of which are Q, T, R and L, consisting of SWX$_1$VX$_3$X$_4$X$_5$QTRL (SEQ ID NO:22), SWX$_1$EX$_3$X$_4$X$_5$QTRL (SEQ ID NO:23) or SWX$_1$SX$_3$X$_4$X$_5$QTRL (SEQ ID NO:24), wherein each of $X_1$, $X_3$, $X_4$ and $X_5$ is any amino acid residue.

In a particular embodiment, $X_3$ is H, A or Y such that the MAST-2 binding domain consists of a sequence, whose size is 11 residues, the first two residues of which are S and W and the last four residues of which are Q, T, R and L, consisting of SWX$_1$X$_2$HX$_4$X$_5$QTRL (SEQ ID NO:25), SWX$_1$X$_2$AX$_4$X$_5$QTRL (SEQ ID NO:26) or SWX$_1$X$_2$YX$_4$X$_5$QTRL (SEQ ID NO:27), wherein each of $X_1$, $X_2$, $X_4$ and $X_5$ is any amino acid residue.

In a particular embodiment, $X_4$ is G or T such that the MAST-2 binding domain consists of a sequence, whose size is 11 residues, the first two residues of which are S and W and the last four residues of which are Q, T, R and L, consisting of $SWX_1X_2X_3GX_5QTRL$ (SEQ ID NO:28) or $SWX_1X_2X_3TX_5QTRL$ (SEQ ID NO:29), wherein each of $X_1$, $X_2$, $X_3$ and $X_5$ is any amino acid residue.

In a particular embodiment, $X_5$ is G or Q such that the MAST-2 binding domain consists of a sequence, whose size is 11 residues, the first two residues of which are S and W and the last four residues of which are Q, T, R and L, consisting of $SWX_1X_2X_3X_4GQTRL$ (SEQ ID NO:30) or $SWX_1X_2X_3X_4QQTRL$ (SEQ ID NO:31), wherein each of $X_1$, $X_2$, $X_3$ and $X_4$ is any amino acid residue.

In a particular embodiment, $X_1$ is E and $X_2$ is S, E or V, more preferably V, such that the MAST-2 binding domain consists of a sequence, whose size is 11 residues, the first three residues of which are S, W and E, and the last four residues of which are Q, T, R and L, consisting of $SWEVX_3X_4X_5QTRL$ (SEQ ID NO:32), $SWESX_3X_4X_5QTRL$ (SEQ ID NO:33) or $SWEEX_3X_4X_5QTRL$ (SEQ ID NO:34), wherein each of $X_3$, $X_4$ and $X_5$ is any amino acid residue.

In a particular embodiment, $X_1$ is E and $X_3$ is H, A or Y, such that the MAST-2 binding domain consists of a sequence, whose size is 11 residues, the first three residues of which are S, W and E, and the last four residues of which are Q, T, R and L, consisting of $SWEX_2HX_4X_5QTRL$ (SEQ ID NO:35), $SWEX_2AX_4X_5QTRL$ (SEQ ID NO:36) or $SWEX_2YX_4X_5QTRL$ (SEQ ID NO:37), wherein each of $X_2$, $X_4$ and $X_5$ is any amino acid residue.

In a particular embodiment, $X_1$ is E and $X_4$ is G or T, such that the MAST-2 binding domain consists of a sequence, whose size is 11 residues, the first three residues of which are S, W and E, and the last four residues of which are Q, T, R and L, consisting of $SWEX_2X_3GX_5QTRL$ (SEQ ID NO:38) or $SWEX_2X_3TX_5QTRL$ (SEQ ID NO:39), wherein each of $X_2$, $X_3$ and $X_5$ is any amino acid residue.

In a particular embodiment, $X_1$ is E and $X_5$ is G or Q, such that the MAST-2 binding domain consists of a sequence, whose size is 11 residues, the first three residues of which are S, W and E, and the last four residues of which are Q, T, R and L, consisting of $SWEX_2X_3X_4GQTRL$ (SEQ ID NO:40) and $SWEX_2X_3X_4QQTRL$ (SEQ ID NO:41), wherein each of $X_2$, $X_3$ and $X_4$ is any amino acid residue.

In a particular embodiment, $X_1$ is E, $X_2$ is V and $X_3$ is H, A or Y, such that the MAST-2 binding domain consists of a sequence, whose size is 11 residues, the first four residues of which are S, W, E and V and the last four residues of which are Q, T, R and L, consisting of $SWEVHX_4X_5QTRL$ (SEQ ID NO:42), $SWEVAX_4X_5QTRL$ (SEQ ID NO:43) or $SWEVYX_4X_5QTRL$ (SEQ ID NO:44), wherein each of $X_4$ and $X_5$ is any amino acid residue.

In a particular embodiment, $X_1$ is E, $X_2$ is V and $X_4$ is G or T, such that the MAST-2 binding domain consists of a sequence, whose size is 11 residues, the first four residues of which are S, W, E and V and the last four residues of which are Q, T, R and L, consisting of $SWEVX_3GX_5QTRL$ (SEQ ID NO:45) or $SWEVX_3TX_5QTRL$ (SEQ ID NO:46), wherein each of $X_3$ and $X_5$ is any amino acid residue.

In a particular embodiment, $X_1$ is E, $X_2$ is V and $X_5$ is G or Q, such that the MAST-2 binding domain consists of a sequence, whose size is 11 residues, the first four residues of which are S, W, E and V and the last four residues of which are Q, T, R and L, consisting of $SWEVX_3X_4GQTRL$ (SEQ ID NO:47) or $SWEVX_3X_4QQTRL$ (SEQ ID NO:48), wherein each of $X_3$ and $X_4$ is any amino acid residue.

In a particular embodiment, $X_1$ is E, $X_2$ is V, $X_3$ is H, A or Y and $X_4$ is G or T, such that the MAST-2 binding domain consists of a sequence, whose size is 11 residues, the first four residues of which are S, W, E and V and the last four residues of which are Q, T, R and L, consisting of $SWEVHGX_5QTRL$ (SEQ ID NO:49), $SWEVHTX_5QTRL$ (SEQ ID NO:50), $SWEVAGX_5QTRL$ (SEQ ID NO:51), $SWEVATX_5QTRL$ (SEQ ID NO:52), $SWEVYGX_5QTRL$ (SEQ ID NO:53) or $SWEVYTX_5QTRL$ (SEQ ID NO:54), wherein $X_5$ is any amino acid residue.

In a particular embodiment, $X_1$ is E, $X_2$ is V, $X_3$ is H, A or Y and $X_5$ is G or Q, such that the MAST-2 binding domain consists of a sequence, whose size is 11 residues, the first four residues of which are S, W, E and V and the last four residues of which are Q, T, R and L, consisting of $SWEVHX_4GQTRL$ (SEQ ID NO:55), $SWEVHX_4QQTRL$ (SEQ ID NO:56), $SWEVAX_4GQTRL$ (SEQ ID NO:57), $SWEVAX_4QQTRL$ (SEQ ID NO:58), $SWEVYX_4GQTRL$ (SEQ ID NO:59) or $SWEVYX_4QQTRL$ (SEQ ID NO:60), wherein $X_4$ is any amino acid residue.

In a particular embodiment, the MAST-2 binding domain consists of a sequence, whose size is 11 residues, the first two residues of which are S and W, and the last four residues of which are Q, T, R and L, consisting of $SWX_1X_2X_3X_4X_5QTRL$, wherein $X_1$ is E or A, $X_2$ is S, E or V, $X_3$ is H, A or Y, $X_4$ is G or T and $X_5$ is G or Q (SEQ ID NO:61). In this embodiment, the MAST-2 binding domain consists of S-W-E/A-S/EN-H/A/Y-G/T-G/Q-Q-T-R-L (SEQ ID NO:61).

In a particular embodiment, the MAST-2 binding domain consists of a sequence, whose size is 11 residues, the first two residues of which are S and W, and the last four residues of which are Q, T, R and L, consisting of $SWX_1X_2X_3X_4X_5QTRL$, wherein $X_1$ is E, $X_2$ is S, E or V, $X_3$ is H, A or Y, $X_4$ is G or T and $X_5$ is G or Q (SEQ ID NO:62). In this embodiment, the MAST-2 binding domain consists of S-W-E-S/EN-H/A/Y-G/T-G/Q-Q-T-R-L (SEQ ID NO:62).

In a particular embodiment, the MAST-2 binding domain consists of a sequence, whose size is 11 residues, the first two residues of which are S and W, and the last four residues of which are Q, T, R and L, consisting of $SWX_1X_2X_3X_4X_5QTRL$, wherein $X_1$ is E, $X_2$ is V, $X_3$ is H, A or Y, $X_4$ is G or T and $X_5$ is G or Q (SEQ ID NO:63). In this embodiment, the MAST-2 binding domain consists of S-W-E-V-H/NY-G/T-G/Q-Q-T-R-L (SEQ ID NO:63). In a more particular embodiment, the MAST-2 binding domain consists of a sequence, whose size is 11 residues, the first four residues of which are S, W, E and V and the last four residues of which are Q, T, R and L, consisting of SWEVHGGQTRL (SEQ ID NO:64), SWEVHGQQTRL (SEQ ID NO:65), SWEVHTGQTRL (SEQ ID NO:66), SWEVHTQQTRL (SEQ ID NO:67), SWEVAGGQTRL (SEQ ID NO:68), SWEVAGQQTRL (SEQ ID NO:69), SWEVATGQTRL (SEQ ID NO:70), SWEVATQQTRL (SEQ ID NO:71), SWEVYGGQTRL (SEQ ID NO:72), SWEVYGQQTRL (SEQ ID NO:73), SWEVYTGQTRL (SEQ ID NO:74) or SWEVYTQQTRL (SEQ ID NO:75).

The polypeptides fulfilling one of the definitions as described in this group are preferred, in particular when the constant of dissociation of the complex formed by a polypeptide of this group with the PDZ domain of the human MAST2 protein is less than 0.3 μM, preferably less than 0.25 μM, preferably less than 0.2 μM preferably less than 0.15 μM, more preferably less than 0.1 μM, as measured by the method defined above. In a more preferred embodiment, the polypeptides fulfilling one of the definitions described in this group have a constant of dissociation of the complex formed by the polypeptide of the invention with the PDZ domain of the human MAST2 protein which is less than 0.09 μM, less than 0.08 μM, less than 0.07 μM, less than 0.06 μM or less than 0.05 μM, as measured by the method defined above.

(B) in a second group, the MAST-2 binding domain consists of a sequence, whose size is 11 residues, the first two residues of which are S and W, and the last four residues of which are Q, T, R and L, said domain being selected from the group consisting of: $SWX_1KSGGQTRL$ (SEQ ID NO:76), $SWX_1SSGGQTRL$ (SEQ ID NO:77), $SWX_1SHGGQTRL$ (SEQ ID NO:78), $SWX_1SHKGQTRL$ (SEQ ID NO:79), $SWX_1SHKSQTRL$ (SEQ ID NO:80), $SWX_1HSGGQTRL$ (SEQ ID NO:86), $SWX_1HKGGQTRL$ (SEQ ID NO:87), $SWX_1HKSGQTRL$ (SEQ ID NO:88), $SWX_1SKGGQTRL$ (SEQ ID NO:89), $SWX_1SKSGQTRL$ (SEQ ID NO:90), $SWX_1SHSGQTRL$ (SEQ ID NO:91), $SWX_1SHKGQTRL$ (SEQ ID NO:92) and $SWX_1SKGGQTRL$ (SEQ ID NO:93), wherein $X_1$ is any amino acid, preferably E or A, more preferably E. Thus, in a particular embodiment, the MAST-2 binding domain consists of the sequence, whose size is 11 residues, the first three residues of which are S, W and E, and the last four residues of which are Q, T, R and L, said domain being selected from the group consisting of: SWEKSGGQTRL (SEQ ID NO:81), SWESSGGQTRL (SEQ ID NO:82), SWESHGGQTRL (SEQ ID NO:83), SWESHKGQTRL (SEQ ID NO:84), SWESHKSQTRL (SEQ ID NO:85), SWEHSGGQTRL (SEQ ID NO:94), SWEHKGGQTRL (SEQ ID NO:95), SWEHKSGQTRL (SEQ ID NO:96), SWESKGGQTRL (SEQ ID NO:97), SWESKSGQTRL (SEQ ID NO:98), SWESHSGQTRL (SEQ ID NO:99), SWESHKGQTRL (SEQ ID NO:100) and SWESKGGQTRL (SEQ ID NO:101). In a particular embodiment, the MAST-2 binding domain of the cytoplasmic domain is SWESHGGQTRL (SEQ ID NO:83).

MAST-2 binding domain of this second group may be obtained by deletion of two amino acid residues, consecutive or not, from the SWESHKSGGQTRL sequence (SEQ ID NO:1).

(C) In a third group, the MAST-2 binding domain consists of a sequence, whose size is 12 residues, the first two residues of which are S and W, and the last four residues of which are Q, T, R and L, consisting of $SWX_1X_2X_3X_4X_5X_6QTRL$, wherein each of $X_1$, $X_2$, $X_3$, $X_4$, $X_5$ and $X_6$ is any amino acid residue (SEQ ID NO:112).

In a particular embodiment, $X_1$ is E, A, V or S, such that the MAST-2 binding domain consists of a sequence, whose size is 12 residues, the first two residues of which are S and W and the last four residues of which are Q, T, R and L, consisting of $SWEX_2X_3X_4X_5X_6QTRL$ (SEQ ID NO:113), $SWAX_2X_3X_4X_5X_6QTRL$ (SEQ ID NO:114), $SWVX_2X_3X_4X_5X_6QTRL$ (SEQ ID NO:115) or $SWSX_2X_3X_4X_5X_6QTRL$ (SEQ ID NO:116), wherein each of $X_2$, $X_3$, $X_4$, $X_5$ and $X_6$ is any amino acid residue.

In a particular embodiment, $X_2$ is 5, V, H, A or Y, such that the MAST-2 binding domain consists of a sequence, whose size is 12 residues, the first two residues of which are S and W and the last four residues of which are Q, T, R and L, consisting of $SWX_1SX_3X_4X_5X_6QTRL$ (SEQ ID NO:117), $SWX_1VX_3X_4X_5X_6QTRL$ (SEQ ID NO:118), $SWX_1HX_3X_4X_5X_6QTRL$ (SEQ ID NO:119), $SWX_1AX_3X_4X_5X_6QTRL$ (SEQ ID NO:120) or $SWX_1YX_3X_4X_5X_6QTRL$ (SEQ ID NO:121), wherein each of $X_1$, $X_3$, $X_4$, $X_5$ and $X_6$ is any amino acid.

In a particular embodiment, $X_3$ is H, A, Y, K or Q, such that the MAST-2 binding domain consists of a sequence, whose size is 12 residues, the first two residues of which are S and W and the last four residues of which are Q, T, R and L, consisting of $SWX_1X_2HX_4X_5X_6QTRL$ (SEQ ID NO:122), $SWX_1X_2AX_4X_5X_6QTRL$ (SEQ ID NO:123), $SWX_1X_2YX_4X_5X_6QTRL$ (SEQ ID NO:124), $SWX_1X_2KX_4X_5X_6QTRL$ (SEQ ID NO:125) or $SWX_1X_2QX_4X_5X_6QTRL$ (SEQ ID NO:126), wherein each of $X_1$, $X_2$, $X_4$, $X_5$ and $X_6$ is any amino acid.

In a particular embodiment, $X_4$ is K, A, Q, S or H, such that the MAST-2 binding domain consists of a sequence, whose size is 12 residues, the first two residues of which are S and W and the last four residues of which are Q, T, R and L, consisting of $SWX_1X_2X_3KX_5X_6QTRL$ (SEQ ID NO:127), $SWX_1X_2X_3AX_5X_6QTRL$ (SEQ ID NO:128), $SWX_1X_2X_3QX_5X_6QTRL$ (SEQ ID NO:129), $SWX_1X_2X_3SX_5X_6QTRL$ (SEQ ID NO:130) or $SWX_1X_2X_3HX_5X_6QTRL$ (SEQ ID NO:131), wherein each of $X_1$, $X_2$, $X_3$, $X_5$ and $X_6$ is any amino acid.

In a particular embodiment, $X_5$ is S, H, G or T, such that the MAST-2 binding domain consists of a sequence, whose size is 12 residues, the first two residues of which are S and W and the last four residues of which are Q, T, R and L, consisting of $SWX_1X_2X_3X_4SX_6QTRL$ (SEQ ID NO:132), $SWX_1X_2X_3X_4HX_6QTRL$ (SEQ ID NO:133), $SWX_1X_2X_3X_4GX_6QTRL$ (SEQ ID NO:134) or $SWX_1X_2X_3X_4TX_6QTRL$ (SEQ ID NO:135), wherein each of $X_1$, $X_2$, $X_3$, $X_4$ and $X_6$ is any amino acid.

In a particular embodiment, $X_6$ is G, T or Q, such that the MAST-2 binding domain consists of a sequence, whose size is 12 residues, the first two residues of which are S and W and the last four residues of which are Q, T, R and L, consisting of $SWX_1X_2X_3X_4X_5GQTRL$ (SEQ ID NO:136), $SWX_1X_2X_3X_4X_5TQTRL$ (SEQ ID NO:137) or $SWX_1X_2X_3X_4X_5QQTRL$ (SEQ ID NO:138), wherein each of $X_1$, $X_2$, $X_3$, $X_4$ and $X_5$ is any amino acid.

In a particular embodiment, regarding the polypeptides of SEQ ID NO:112 and SEQ ID NO:122 to SEQ ID NO:138 as defined above, $X_1$ is E and/or $X_2$ is V, as disclosed in Table 1 (next page).

In a particular embodiment, the MAST-2 binding domain consists of 12 residues, its first two residues are S and W and its last four residues are Q, T, R and L, consisting of the sequence $SWX_1X_2X_3X_4X_5X_6QTRL$, wherein $X_1$ is E, A, V or S, $X_2$ is S, V, H, A or Y, $X_3$ is H, A, Y, K or Q, $X_4$ is K, A, Q, S or H, $X_5$ is S, H, G or T and $X_6$ is G, T or Q (SEQ ID NO:191). In this embodiment, the MAST-2 binding domain consists of the sequence S-W-E/A/V/S-S/V/H/A/Y-H/A/Y/K/Q-K/A/Q/S/H-S/H/G/T-G/T/Q-QTRL (SEQ ID NO:191).

(D) In a fourth group, the MAST-2 binding domain consists of a sequence, whose size is 12 residues, the first two residues of which are S and W, and the last four residues of which are Q, T, R and L, said domain being selected from the group consisting of: $SWX_1HKSGGQTRL$ (SEQ ID NO:102), $SWX_1SKSGGQTRL$ (SEQ ID NO:103), $SWX_1SHSGGQTRL$ (SEQ ID NO:104), $SWX_1SHKGGQTRL$ (SEQ ID NO:105) and $SWX_1SHKSGQTRL$ (SEQ ID NO:106), wherein $X_1$ is any amino acid, preferably E or A, more preferably E. Thus, in a particular embodiment, the MAST-2 binding domain consists of the sequence, whose size is 12 residues, the first three residues of which are S, W and E, and the last four residues of which are Q, T, R and L, said domain being selected from the group consisting of: SWEHKSGGQTRL (SEQ ID NO:107), SWESKSGGQTRL (SEQ ID NO:108), SWESHSGGQTRL (SEQ ID NO:109), SWESHKGGQTRL (SEQ ID NO:110) and SWESHKSGQTRL (SEQ ID NO:111).

MAST-2 binding domain of this fourth group may be obtained by deletion of one amino acid residue from the SWESHKSGGQTRL sequence (SEQ ID NO:1).

TABLE 1

| | with X$_1$ is E | with X$_2$ is V | with X$_1$ is E and X$_2$ is V |
|---|---|---|---|
| SEQ ID NO: 112 | SWEX$_2$X$_3$X$_4$X$_5$X$_6$QTRL (SEQ ID NO: X113) | SWX$_1$VX$_3$X$_4$X$_5$X$_6$QTRL (SEQ ID NO: 118) | SWEVX$_3$X$_4$X$_5$X$_6$QTRL (SEQ ID NO: 190) |
| SEQ ID NO: 122 | SWEX$_2$HX$_4$X$_5$X$_6$QTRL (SEQ ID NO: 139) | SWX$_1$VHX$_4$X$_5$X$_6$QTRL (SEQ ID NO: 140) | SWEVHX$_4$X$_5$X$_6$QTRL (SEQ ID NO: 141) |
| SEQ ID NO: 123 | SWEX$_2$AX$_4$X$_5$X$_6$QTRL (SEQ ID NO: 142) | SWX$_1$VAX$_4$X$_5$X$_6$QTRL (SEQ ID NO: 143) | SWEVAX$_4$X$_5$X$_6$QTRL (SEQ ID NO: 144) |
| SEQ ID NO: 124 | SWEX$_2$YX$_4$X$_5$X$_6$QTRL (SEQ ID NO: 145) | SWX$_1$VYX$_4$X$_5$X$_6$QTRL (SEQ ID NO: 146) | SWEVYX$_4$X$_5$X$_6$QTRL (SEQ ID NO: 147) |
| SEQ ID NO: 125 | SWEX$_2$KX$_4$X$_5$X$_6$QTRL (SEQ ID NO: 148) | SWX$_1$VKX$_4$X$_5$X$_6$QTRL (SEQ ID NO: 149) | SWEVKX$_4$X$_5$X$_6$QTRL (SEQ ID NO: 150) |
| SEQ ID NO: 126 | SWEX$_2$QX$_4$X$_5$X$_6$QTRL (SEQ ID NO: 151) | SWX$_1$VQX$_4$X$_5$X$_6$QTRL (SEQ ID NO: 152) | SWEVQX$_4$X$_5$X$_6$QTRL (SEQ ID NO: 153) |
| SEQ ID NO: 127 | SWEX$_2$X$_3$KX$_5$X$_6$QTRL (SEQ ID NO: 154) | SWX$_1$VX$_3$KX$_5$X$_6$QTRL (SEQ ID NO: 155) | SWEVX$_3$KX$_5$X$_6$QTRL (SEQ ID NO: 156) |
| SEQ ID NO: 128 | SWEX$_2$X$_3$AX$_5$X$_6$QTRL (SEQ ID NO: 157) | SWX$_1$VX$_3$AX$_5$X$_6$QTRL (SEQ ID NO: 158) | SWEVX$_3$AX$_5$X$_6$QTRL (SEQ ID NO: 159) |
| SEQ ID NO: 129 | SWEX$_2$X$_3$QX$_5$X$_6$QTRL (SEQ ID NO: 160) | SWX$_1$VX$_3$QX$_5$X$_6$QTRL (SEQ ID NO: 161) | SWEVX$_3$QX$_5$X$_6$QTRL (SEQ ID NO: 162) |
| SEQ ID NO: 130 | SWEX$_2$X$_3$SX$_5$X$_6$QTRL (SEQ ID NO: 163) | SWX$_1$VX$_3$SX$_5$X$_6$QTRL (SEQ ID NO: 164) | SWEVX$_3$SX$_5$X$_6$QTRL (SEQ ID NO: 165) |
| SEQ ID NO: 131 | SWEX$_2$X$_3$HX$_5$X$_6$QTRL (SEQ ID NO: 166) | SWX$_1$VX$_3$HX$_5$X$_6$QTRL (SEQ ID NO: 167) | SWEVX$_3$HX$_5$X$_6$QTRL (SEQ ID NO: 168) |
| SEQ ID NO: 132 | SWEX$_2$X$_3$X$_4$SX$_6$QTRL (SEQ ID NO: 169) | SWX$_1$VX$_3$X$_4$SX$_6$QTRL (SEQ ID NO: 170) | SWEVX$_3$X$_4$SX$_6$QTRL (SEQ ID NO: 171) |
| SEQ ID NO: 133 | SWEX$_2$X$_3$X$_4$HX$_6$QTRL (SEQ ID NO: 172) | SWX$_1$VX$_3$X$_4$HX$_6$QTRL (SEQ ID NO: 173) | SWEVX$_3$X$_4$HX$_6$QTRL (SEQ ID NO: 174) |
| SEQ ID NO: 134 | SWEX$_2$X$_3$X$_4$GX$_6$QTRL (SEQ ID NO: 175) | SWX$_1$VX$_3$X$_4$GX$_6$QTRL (SEQ ID NO: 176) | SWEVX$_3$X$_4$GX$_6$QTRL (SEQ ID NO: 177) |
| SEQ ID NO: 135 | SWEX$_2$X$_3$X$_4$TX$_6$QTRL (SEQ ID NO: 178) | SWX$_1$VX$_3$X$_4$TX$_6$QTRL (SEQ ID NO: 179) | SWEVX$_3$X$_4$TX$_6$QTRL (SEQ ID NO: 180) |
| SEQ ID NO: 136 | SWEX$_2$X$_3$X$_4$X$_5$GQTRL (SEQ ID NO: 181) | SWX$_1$VX$_3$X$_4$X$_5$GQTRL (SEQ ID NO: 182) | SWEVX$_3$X$_4$X$_5$GQTRL (SEQ ID NO: 183X) |
| SEQ ID NO: 137 | SWEX$_2$X$_3$X$_4$X$_5$TQTRL (SEQ ID NO: 184) | SWX$_1$VX$_3$X$_4$X$_5$TQTRL (SEQ ID NO: 185) | SWEVX$_3$X$_4$X$_5$TQTRL (SEQ ID NO: 186) |
| SEQ ID NO: 138 | SWEX$_2$X$_3$X$_4$X$_5$QQTRL (SEQ ID NO: 187) | SWX$_1$VX$_3$X$_4$X$_5$QQTRL (SEQ ID NO: 188) | SWEVX$_3$X$_4$X$_5$QQTRL (SEQ ID NO: 189) |

wherein each of X$_1$, X$_2$, X$_3$, X$_4$, X$_5$ and X$_6$, when applicable, is any amino acid residue (E) In a fifth group, the MAST-2 binding domain consists of a sequence, whose size is 13 residues, the first two residues of which are S and W, and the last four residues of which are Q, T, R and L, consisting of SWX$_1$X$_2$X$_3$X$_4$X$_5$X$_6$X$_7$QTRL, wherein each of X$_1$, X$_2$, X$_3$, X$_4$, X$_5$, X$_6$ and X$_7$, is any amino acid residue (SEQ ID NO:192), wherein said MAST-2 binding domain does not consist of SWESHKSGGQTRL (SEQ ID NO:1). In a particular embodiment, the MAST-2 binding domain, whose size is 13 residues, is neither SWESHKSGGQTRL (SEQ ID NO:1) nor SWESYKSGGQTRL (SEQ ID NO:16).

In a particular embodiment, the MAST-2 binding domain of 13 residues differs from SWESHKSGGQTRL (SEQ ID NO:1) by at least 1 substitution of amino acid residue, by at least 2 substitutions or by at least 3 substitutions, provided that the first two residues are S and W, and the fourth last residues are Q, T, R and L; in a more particular embodiment, the MAST-2 binding domain of 13 residues differing from SWESHKSGGQTRL (SEQ ID NO:1) by at least 1 substitution is not SWESYKSGGQTRL (SEQ ID NO:16).

In a particular embodiment, the MAST-2 binding domain consists of 13 residues and differs from SWESHKSGGQTRL (SEQ ID NO:1) by 1 substitution in a residue located between SW and QTRL; in particular embodiment, this is not the substitution of the histidine residue (H) in a tyrosine residue (Y).

In a particular embodiment of $SWX_1X_2X_3X_4X_5X_6X_7QTRL$, $X_1$ is E or A, and each of $X_2$, $X_3$, $X_4$, $X_5$, $X_6$ and $X_7$, is any amino acid residue (SEQ ID NO:193).

In a particular embodiment of $SWX_1X_2X_3X_4X_5X_6X_7QTRL$, $X_2$ is selected from polar neutral residues, negatively charged residues or hydrophobic residues (SEQ ID NO:194) and is preferably S, V or E (SEQ ID NO:195), wherein $X_1$, $X_3$, $X_4$, $X_5$, $X_6$ and $X_7$, is any amino acid residue.

In a particular embodiment of $SWX_1X_2X_3X_4X_5X_6X_7QTRL$, $X_3$ is selected from positively charged residues, non polar residues with small volume and polar aromatic residues (SEQ ID NO:196), and is preferably H, A or Y (SEQ ID NO:197), wherein $X_1$, $X_2$, $X_4$, $X_5$, $X_6$ and $X_7$, is any amino acid residue.

In a particular embodiment of $SWX_1X_2X_3X_4X_5X_6X_7QTRL$, $X_4$ is selected from non polar residues with small volume, polar neutral residues and positively charged residues (SEQ ID NO:198) and is preferably K, A or Q (SEQ ID NO:199), wherein $X_1$, $X_2$, $X_3$, $X_5$, $X_6$ and $X_7$, is any amino acid residue.

In a particular embodiment of $SWX_1X_2X_3X_4X_5X_6X_7QTRL$, $X_5$ is selected from polar neutral residues and positively charged residues (SEQ ID NO:200), and is preferably S or H (SEQ ID NO:201), wherein $X_1$, $X_2$, $X_3$, $X_4$, $X_6$ and $X_7$, is any amino acid residue.

In a particular embodiment of $SWX_1X_2X_3X_4X_5X_6X_7QTRL$, $X_6$ is selected from non polar residues with small volume, preferably flexible, and polar neutral residues (SEQ ID NO:202), and is preferably G or T (SEQ ID NO:203), wherein $X_1$, $X_2$, $X_3$, $X_4$, $X_5$ and $X_7$, is any amino acid residue.

In a particular embodiment of $SWX_1X_2X_3X_4X_5X_6X_7QTRL$, $X_7$ is selected from non polar residues with small volume, preferably flexible, and polar neutral residues (SEQ ID NO:204), and is preferably G or Q (SEQ ID NO:205), wherein $X_1$, $X_2$, $X_3$, $X_4$, $X_5$ and $X_6$, is any amino acid residue.

The amino acid residues corresponding to the polar neutral residues, positively charged residues, negatively charged residues, hydrophobic residues, non polar residues with small volume and polar aromatic residues are according to the conventional literature, and confirmed in the lists below.

In a more particular embodiment, said MAST-2 binding domain consists of the sequence $SWX_1X_2X_3X_4X_5X_6X_7QTRL$, wherein $X_1$ is E or A and/or $X_2$ is S, V or E and/or $X_3$ is H, A or Y and/or $X_4$ is K, A or Q and/or $X_5$ is S or H and/or $X_6$ is G or T and/or $X_7$ is G or Q, wherein $X_1$, $X_2$, $X_3$, $X_4$, $X_5$, $X_6$ and $X_7$ are not, together, E, S, H, K, S, G and G. In a particular embodiment, $X_1$, $X_2$, $X_3$, $X_4$, $X_5$, $X_6$ and $X_7$ are neither together E, S, H, K, S, G and G respectively, nor together E, S, Y, K, S, G and G respectively (SEQ ID NO:206).

Thus, in a preferred embodiment, the sequence of the MAST-2 binding domain is S-W-E/A-S/V/E-H/A/Y-K/A/Q-S/H-G/T-G/Q-QTRL as defined in SEQ ID NO:206, provided the MAST-2 binding domain is not SWESHKSGGQTRL (SEQ ID NO:1); in a more particular embodiment, the MAST-2 binding domain of sequence S-W-E/A-S/V/E-H/A/Y-K/A/Q-S/H-G/T-G/Q-QTRL (SEQ ID NO:206) is neither SWESHKSGGQTRL (SEQ ID NO:1) nor SWESYKSGGQTRL (SEQ ID NO:16). In another preferred embodiment, the sequence of the MAST-2 binding domain is S-W-E/A-V/E-H/A-NQ-S/H-G/T-G/Q-QTRL as defined in SEQ ID NO:207. Preferred MAST-2 binding domains consist of the sequence SWAEAQHTQQTRL (SEQ ID NO:208) or SWEVHASGGQTRL (SEQ ID NO:209)

In a particular embodiment, the MAST-2 binding domain consists of a sequence, whose size is 11 or 12 residues, the first two residues of which are S and W, and the fourth last residues of which are Q, T, R and L, selected in the groups (A), (B), (C) and (D) as detailed above.

In another embodiment, the MAST-2 binding domain consists of a sequence, whose size is 11 residues, the first two residues of which are S and W, and the fourth last residues of which are Q, T, R and L, selected in the groups (A) and (B) as detailed above.

In another embodiment, the MAST-2 binding domain consists of a sequence, whose size is 12 residues, the first two residues of which are S and W, and the fourth last residues of which are Q, T, R and L, selected in the groups (C) and (D) as detailed above.

In another embodiment, the MAST-2 binding domain consists of a sequence, whose size is 13 residues, the first two residues of which are S and W, and the fourth last residues of which are Q, T, R and L, selected in the group (E) as detailed above.

In a particular embodiment, the sequence of the cytoplasmic domain upstream of the MAST-2 binding domain of the polypeptide of the invention is either:

- a polypeptide containing 20 to 40 amino acid residues, such that the size of the entire cytoplasmic domain (sequence of the cytoplasmic domain upstream of the MAST-2 binding domain and the MAST-2 binding domain) is from 31 to 53 residues, preferably from 31 to 52 or from 31 to 51 residues. In a particular embodiment, the sequence of the cytoplasmic domain upstream of the MAST-2 binding domain consists of 25 to 45 residues. In another embodiment, the sequence of the cytoplasmic domain upstream of the MAST-2 binding domain is 31 residues, such that the entire cytoplasmic domain is from 42 to 44 residues, preferably 42 residues, 43 residues or 44 residues. Any cytoplasmic domain can be selected as long as this cytoplasmic domain enables the binding of the MAST-2 binding domain to the PDZ domain of the human MAST2 protein. Particular examples of cytoplasmic domains of G protein can be found in Schnell M J et al. (1998) and Owens R J et al (1993). The binding of the MAST-2 binding domain to the PDZ domain of the human MAST2 protein, and thus the affinity of the polypeptide of the invention for the PDZ domain of the human MAST2 protein, may be assayed by the method detailed above for the $K_D$ calculation; or
- the sequence of the cytoplasmic domain upstream of the MAST-2 binding domain is a fragment of the cytoplasmic domain of a rabies virus G protein, in particular a fragment of the cytoplasmic domain of a G protein from an attenuated rabies virus strain or a fragment of the cytoplasmic domain of a G protein from a virulent rabies virus strain; in a particular embodiment, the sequence of the cytoplasmic domain upstream of the MAST-2 binding domain consists of the following sequence RRVNRSEPTQHNLRGTGREVSVTPQS-GKIIS (SEQ ID NO:2) or a variant having at least 80%, at least 85% or at least 90% identity with SEQ ID NO:2, said variant retaining the ability to bind the MAST-2 binding domain of the polypeptide of the invention to the PDZ domain of the human MAST2 protein. The percentage of identity is calculated over the shortest of the two sequences i.e., over the shortest of SEQ ID NO: 2 and of said variant. A variant having at least 80%, at least 85% or at least 90% identity with SEQ ID NO:2 is defined as a variant by one or more addition(s) and/or one or more deletion(s) and/or one or more substitution(s). An example of a variant of SEQ ID NO:2 is a polypeptide consisting of the sequence RRVNRSEPTQLNLRGTGREVSVTPQSGKIIS (SEQ ID NO:5). In a particular embodiment, the variant has at least 90% identity with SEQ ID NO:2 and is obtained by 1, 2 or 3 substitutions in SEQ ID NO:2, preferably by conservative substitution(s) as defined in the literature, or according to the following list:

- the group of the nonpolar (i.e., hydrophobic) amino acid residues: a first subgroup including alanine (A), glycine (G) and proline (P), and a second subgroup including leucine (L), isoleucine (I) and valine (V);
- the group of the polar neutral (uncharged) amino acid residues: a first subgroup including serine (S), threonine (T), cysteine (C) and methionine (M), and a second subgroup including asparagine (N) and glutamine (Q);
- the group of positively charged (i.e., basic) residues, including arginine (R), lysine (K) and histidine (H);
- the group of negatively charged (i.e., acid) residues, including aspartic acid (D) and glutamic acid (E); and
- the group of the aromatic residues, including phenylalanine (F), tryptophan (W) and tyrosine (Y).

In a particular embodiment, when the polypeptide consists of the cytoplasmic domain, the size of the polypeptide is from 31 to 53 residues, preferably from 31 to 52 or from 31 to 51 residues, or from 42 to 44 residues, preferably 42 residues, 43 residues or 44 residues.

Figure 1:
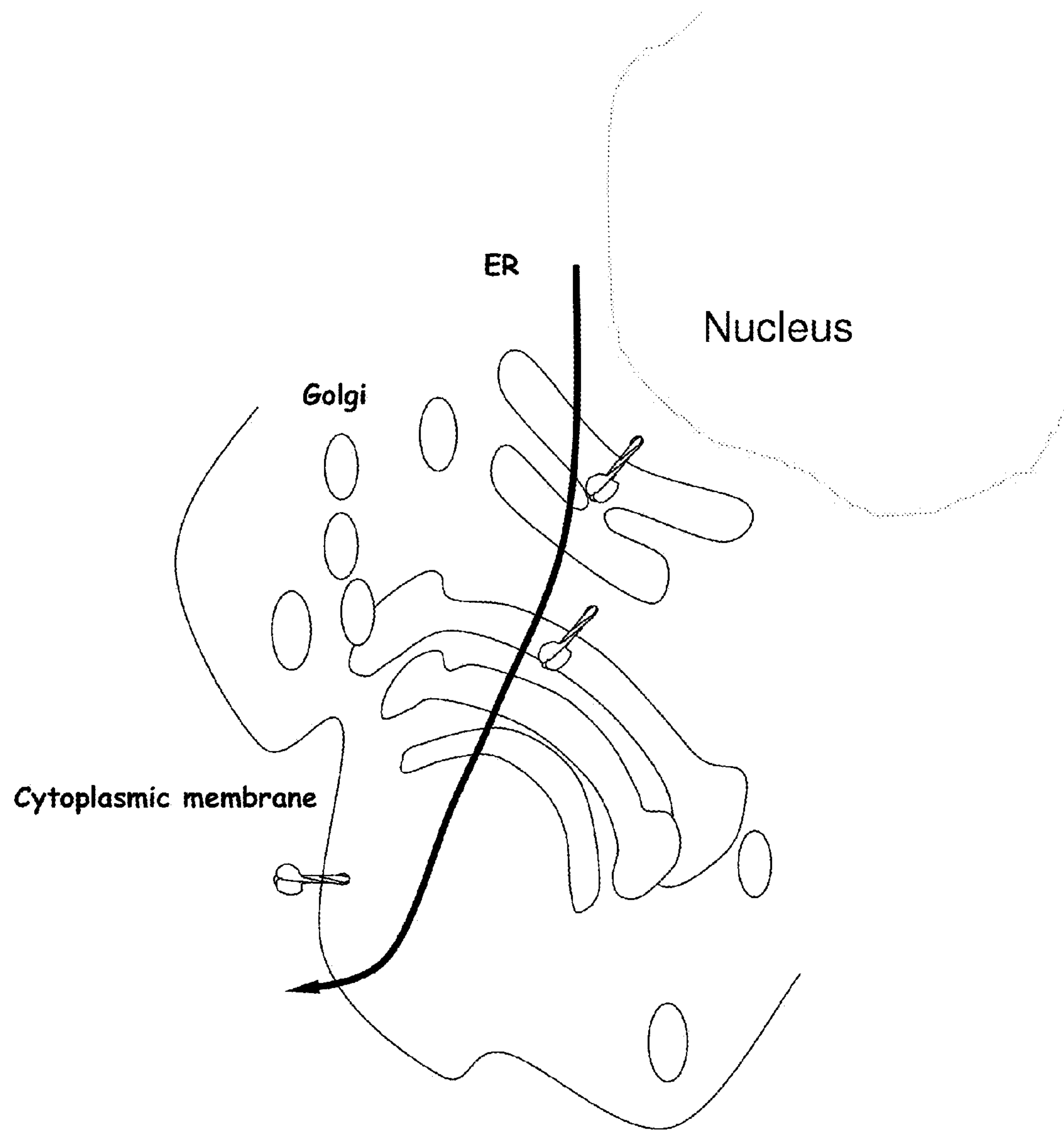
FIG. 1. Rabies virus (RABV) protein G processing inside the cells: upon translation, the protein G, which is a transmembrane type I glycoprotein, is synthesized at the Endoplasmic Reticulum (ER), then processed through the secretory pathway to reach the Golgi apparatus where it is glycosylated on its extracellular domain. Then, the protein is delivered to the cytoplasmic membrane where it is anchored via its transmembrane domain. The cytoplasmic domain of G protein is always in contact with the cytoplasm.
Figure 2:
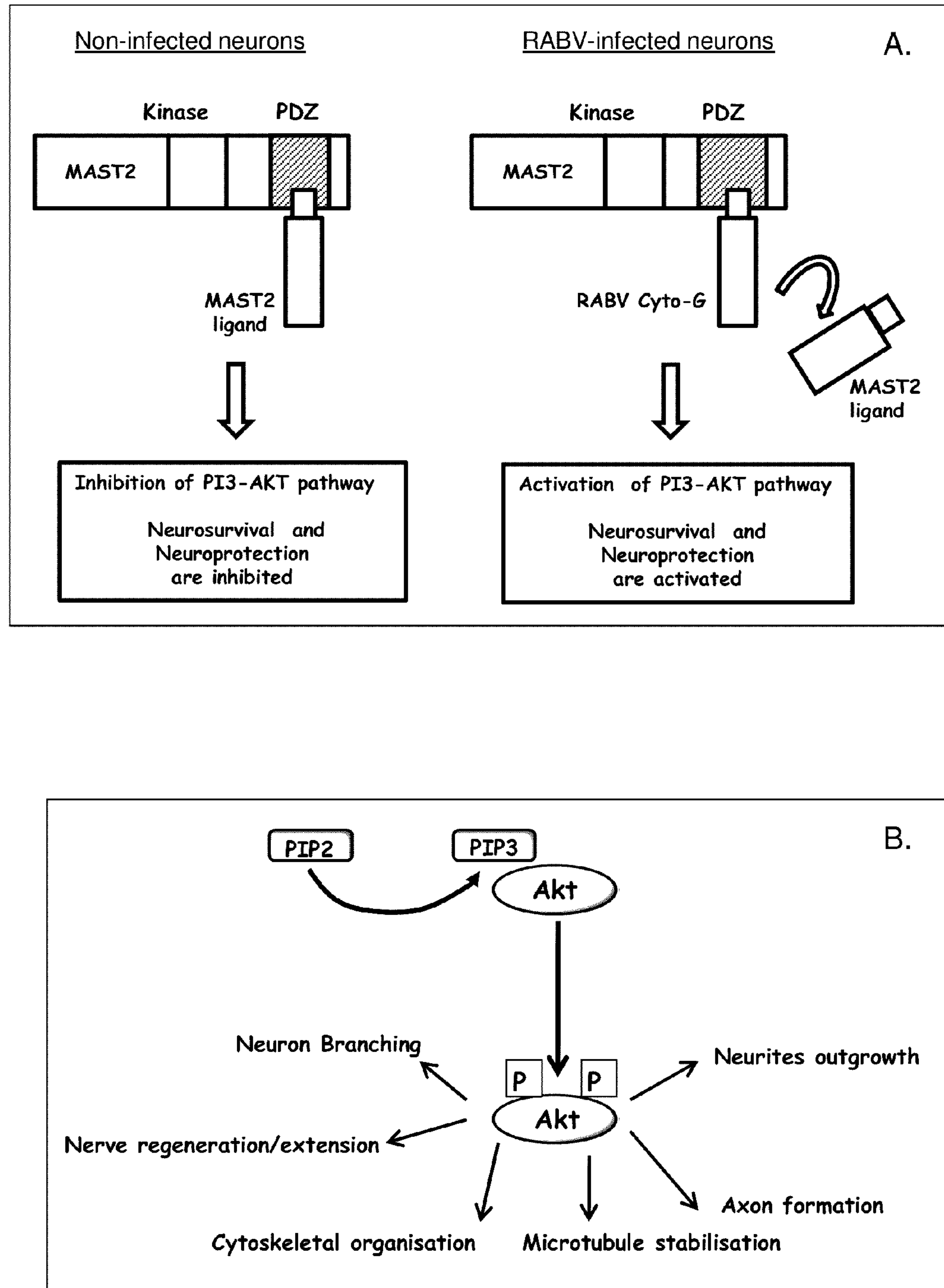
FIG. 2. (A) Schematic representation of the model of action of polypeptides of the invention (Neurovita polypeptides) through the interaction with their cellular partner, the human MAST2 protein (Microtubule associated serine-threonine kinase 2) (B) Schematic representation of the involvement of the PI3K/Akt signalling pathway in neuron physiology.

In a particular embodiment, and whatever the sequence of the cytoplasmic domain upstream of the MAST-2 binding domain and the sequence of the MAST-2 binding domain, the anchoring domain (which may be optional as such or together with the signal peptide) of the polypeptide of the invention is either:

- a peptide, whose size is from 18 to 26 amino acids, which anchors (or has been shown to anchor) a polypeptide in the membrane of the endoplasmic reticulum and/or the membrane of the Golgi apparatus in cells (particularly in neuronal cells, more particularly in human neuronal cells) (FIG. 1). Particular examples of anchoring domains can be found in Schroth-Diez B et al. (2000). In a particular embodiment, the size of the anchoring domain is from 20 to 24 amino acid residues. In a particular embodiment, the size of the anchoring domain is 22 amino acid residues. Any anchoring domain may be selected as long as it anchors the polypeptide of the invention in the membrane of the endoplasmic reticulum and/or the membrane of the Golgi apparatus in cells (particularly in neuronal cells, more particularly in human neuronal cells). In a particular embodiment, the anchoring domain is a transmembrane domain, i.e., any domain able to interact with the lipid bilayer, and in particular able to anchor the polypeptide comprising it, into the lipid bilayer, especially into the cellular membrane. A transmembrane domain is a domain rich in hydrophobic residues (A, G, P, L I and/or V) and stable in a membrane, and is organized in one or several hydrophobic α-helix(es). In a particular embodiment, the transmembrane domain used in the polypeptide described herein is the transmembrane domain (as a fragment) of a known transmembrane protein. Particular examples of transmembrane domains can be found in Schroth-Diez B et al. (2000). The correct anchoring of the polypeptide of the invention may be determined by checking the affinity of the polypeptide of the invention for the PDZ domain of the human MAST2 protein, by implementing the method detailed above for the $K_D$ calculation; or
- the transmembrane domain of a rabies virus G protein, in particular the transmembrane domain of a G protein from an attenuated rabies virus strain or the transmembrane domain of the cytoplasmic domain of a G protein from a virulent rabies virus strain; in a preferred embodiment, the transmembrane domain comprises or consists of the sequence YVLLSAGALTALMLIIFLMTCC (SEQ ID NO:4) or a variant having at least 81%, at least 86%, at least 90% or at least 95% identity with said SEQ ID NO:4, said variant retaining the capacity to anchor the polypeptide in the membrane of the endoplasmic reticulum and/or the membrane of the Golgi apparatus in cells; the percentage of identity is calculated over the shortest of the two sequences, i.e., over the shortest of SEQ ID NO: 4 and of said transmembrane domain variant. A variant having at least 81%, at least 86%, at least 90% or at least 95% identity with SEQ ID NO:4 is defined as a variant by one or more addition(s) and/or one or more deletion(s) and/or one or more substitution(s). In a particular embodiment, a variant having at least 90% or at least 95% identity with SEQ ID NO:4 is obtained by respectively 1 or 2 substitutions in SEQ ID NO:4, preferably by conservative substitution(s) as defined in the literature, or according to the list above.

Whatever the sequence of the anchoring domain (preferably the transmembrane domain) as defined herein:

- the N-terminal extremity of said anchoring domain is, directly or indirectly, linked to the C-terminal extremity of the signal peptide as defined herein; and
- the C-terminal extremity of said anchoring domain is, directly or indirectly, preferably directly, linked to the first N-terminal amino acid residue of the cytoplasmic domain as defined herein.

In a particular embodiment, and whatever the sequence of the cytoplasmic domain upstream of the MAST-2 binding domain, the sequence of the MAST-2 binding domain and the sequence of the anchoring domain, the signal peptide (which may be optional as such or together with the anchoring domain) of the polypeptide of the invention is either:

- a peptide, whose size is from 3 to 60 residues, which targets (or has been shown to target) a polypeptide into the endoplasmic reticulum and optionally through the secretory pathway (FIG. 1); in a particular embodiment, the size of the signal peptide is from 10 to 40, preferably from 15 to 30, more preferably from 15 to 25 amino acid residues. In a particular embodiment, the size of the signal peptide is 19 amino acid residues. Any signal peptide may be selected as long as it targets the polypeptide of the invention into the endoplasmic reticulum and optionally through the secretory pathway. In a particular embodiment, the signal peptide used in the polypeptide described herein is the signal peptide of a known protein, such as the CD4 and CD8 proteins, the hemagglutinin (HA) or a cytokine receptor (e.g., IL1R1, EGFR1, HER2, HER3 or HER4). The correct targeting of the polypeptide of the invention may be determined by checking the affinity of the polypeptide of the invention for the PDZ domain of the human MAST2 protein, by implementing the method detailed above for the $K_D$ calculation; or the signal peptide of a rabies virus G protein, in particular the signal peptide of a G protein from an attenuated rabies virus strain or the signal peptide of the cytoplasmic domain of a G protein from a virulent rabies virus strain; in a preferred embodiment, the signal peptide of a rabies virus G protein corresponds to the 19 first amino acid residues of the G protein. In a particular embodiment, said signal peptide comprises or consists of the sequence MVPQALLFVPLLVFPLCFG (SEQ ID NO:3) or a variant having at least 68%, at least 73%, at least 89% or at least 94% identity with said SEQ ID NO:3, said variant retaining the capacity to target the polypeptide into the endoplasmic reticulum and optionally through the secretory pathway; the percentage of identity is calculated over the shortest of the two sequences, i.e., over the shortest of SEQ ID NO: 3 and of said signal peptide variant. A variant having at least 68%, at least 73%, at least 89% or at least 94% identity with SEQ ID NO:3 is defined as a variant by one or more addition(s) and/or one or more deletion(s) and/or one or more substitution(s). In a particular embodiment, a variant having at least 89% or at least 94% identity with SEQ ID NO:3 is obtained by respectively 1 or 2 substitutions in SEQ ID NO:3, preferably by conservative substitution(s) as defined in the literature, or according to the list above.

Whatever the sequence of the signal peptide as defined herein, said signal peptide, when present, is the most N-terminal element of the polypeptide of the invention.

By “direct link”, it is meant that the last C-terminal residue of a domain is linked by a peptide bond to the first N-terminal residue of the following domain.

In contrast, by “indirect link”, it is meant that the last C-terminal residue of a domain is linked by a peptide bond to the first N-terminal residue of a peptide linker, the last C-terminal residue of which is linked to the first N-terminal residue of the following domain. In a particular embodiment, and whatever the sequence of the cytoplasmic domain upstream of the MAST-2 binding domain, the sequence of the MAST-2 binding domain, the sequence of the signal peptide and the sequence of the anchoring domain, the polypeptide of the invention optionally comprises, between the signal peptide and the anchoring domain, both defined herein, a peptide linker consisting of one to four amino acids, preferably one to four amino acids of the C-terminal end of the ectodomain of a rabies virus G protein, preferably the last two C-terminal residues of the ectodomain of a rabies virus G protein, for example amino acid residues GK.

Thus, a particular polypeptide of the invention comprises or consists of, from N-terminal to C-terminal ends:

(1) a signal peptide as defined in SEQ ID NO:3, or a variant having at least 68% identity with said SEQ ID NO:3, said variant retaining the capacity to target the polypeptide into the endoplasmic reticulum and optionally through the secretory pathway;

(2) optionally, the last two C-terminal residues of the ectodomain of a rabies virus G protein, preferably amino acid residues GK;

(3) an anchoring domain as defined in SEQ ID NO:4 or a variant having at least 81% identity with said SEQ ID NO:4, said variant retaining the capacity to anchor the polypeptide in the membrane of the endoplasmic reticulum and/or the membrane of the Golgi apparatus in cells; and (4) a cytoplasmic domain comprising or consisting of (a) a peptide as defined in SEQ ID NO:2 or a variant having at least 80% identity with SEQ ID NO:2, and (b) a MAST-2 binding domain as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209. In a particular embodiment, the peptide as defined in SEQ ID NO:2 or the variant having at least 90% identity with SEQ ID NO:2 is located upstream (i.e., N-terminal to), preferably directly linked to, the MAST-2 binding domain.

The size of the polypeptide of the invention is at most 350, at most 250, at most 200 or at most 150 amino acid residues. In a preferred embodiment, the size of the polypeptide of the invention is at most 100 amino acid residues, and is preferably from 85 to 87 amino acid residues, and more preferably is 85, 86 or 87 amino acid residues.

In a particular embodiment of the invention the polypeptide of the invention is deprived of the ectodomain of the G protein of a rabies virus, preferably with the exception of the last two amino acids of the C-terminal end of the ectodomain. More particularly, the polypeptide of the invention is not a wild type full-length G protein of a rabies virus strain, neither from a non-apoptotic strain (neurovirulent strain, such as CVS-NIV strain) nor from an apoptotic strain (attenuated strain). In another particular embodiment, the polypeptide of the invention has less than 75% identity, less than 60% identity or less than 50% identity with a wild type full-length G protein of a rabies virus strain, over the shortest of the two sequences (i.e., over the shortest of the polypeptide of the invention and of a wild type full-length G protein of a rabies virus strain).

In a particular embodiment, the polypeptide of the invention consists of the sequence MVPQALLFVPLLVFPLCFGGKYVLLSAGALTALMLIIFLMTCCRRVNRS EPTQHNLRGTGREVSVTPQSGKIIS (SEQ ID NO:17), directly linked to a MAST-2 binding domain as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209. In another embodiment, the polypeptide of the invention consists of the sequence MVPQALLFVPLLVFPLCFGGKYVLLSAGALTALMLIIFLMTCCRRVNRSEPTQLNL RGTGREVSVTPQSGKIIS (SEQ ID NO:18), directly linked to a MAST-2 binding domain as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209.

The polypeptide of the invention does not comprise or does not consist of the sequence as defined in SEQ ID NO:9 (Neurovita 1).

Moreover, the Accession Number NCBI CAI43218 refers to the G glycoprotein consisting of the following sequence:

```
                                    (SEQ ID NO: 14)
MVPQALLFVPLLGFSLCFGKFPIYTIPDELGPWSPIDI

HHLSCPNNLVVEDEGCTNLSEFSYMELKVGYISAIKVN

GFTCTGVVTEAETYTNFVGYVTTTFKRKHFRPTPDACR

AAYNWKMAGDPRYEESLHNPYPDYHWLRTVRTTKESLI

IISPSVTDLDPYDKSLHSRVFPGGKCSGITVSSTYCST

NHDYTIWMPENPRPRTPCDIFTNSRGKRASKGNKTCGF
```

-continued

VDERGLYKSLKGACRLKLCGVLGLRLMDGTWVAMQTSD

ETKWCPDQLVNLHDFRSDEIEHLVVEELVKKREECLDA

LESIMTIKSVSFRRLSHLRKLVPGGKAYTIFNKTLMEA

DAHYKSVRTWNEIIPSKGCLKVGGRCHPHVNGVFFNGI

ILGPDGHVLIPEMQSSLLQQHMELLKSSVIPLMHPLAD

PSTVFKEGDEAEDFVEVHLPDVYKQISGVDLGLPNWGK

YVLMTAGAMIGLVLIFSLMTWCRRANRPESKQRSFGGT

GRNVSVTSQSGKVIPSWESYKSGGQTRL.

Thus, in a particular embodiment, the polypeptide of the invention does not comprise or consist of MVPQALLFVPLLGFSLCFGGKYVLMTAGAMIGLVLIFSLM TWCRRANRPESKQRSFGGTGRNVSVTSQSGKVIPSWESYKSGGQTRL (SEQ ID NO:15).

In another particular embodiment, the MAST-2 binding domain of a polypeptide of the invention is not SWESYKSGGQTRL (SEQ ID NO:16).

Particular examples of polypeptides of the invention are selected in the group consisting of (the MAST-2 binding domain is in bold):

(1) (SEQ ID NO: 210)
MVPQALLFVPLLVFPLCFGGKYVLLSAGALTALMLIIF
LMTCCRRVNRSEPTQHNLRGTGREVSVTPQSGKIISSW
EVHGGQTRL; (Neurovita 2)

(2) (SEQ ID NO: 211)
MVPQALLFVPLLVFPLCFGGKYVLLSAGALTALMLIIF
LMTCCRRVNRSEPTQHNLRGTGREVSVTPQSGKIISSW
EVHGQQTRL; (Neurovita 3)

(3) (SEQ ID NO: 212)
MVPQALLFVPLLVFPLCFGGKYVLLSAGALTALMLIIF
LMTCCRRVNRSEPTQHNLRGTGREVSVTPQSGKIISSW
EVATQQTRL;

(4) (SEQ ID NO: 213)
MVPQALLFVPLLVFPLCFGGKYVLLSAGALTALMLIIF
LMTCCRRVNRSEPTQHNLRGTGREVSVTPQSGKIISSW
EVYTGQTRL;

(5) (SEQ ID NO : 214)
MVPQALLFVPLLVFPLCFGGKYVLLSAGALTALMLIIF
LMTCCRRVNRSEPTQHNLRGTGREVSVTPQSGKIISSW
EVHTGQTRL;

(6) (SEQ ID NO: 215)
MVPQALLFVPLLVFPLCFGGKYVLLSAGALTALMLIIF
LMTCCRRVNRSEPTQHNLRGTGREVSVTPQSGKIISSW
EVHTQQTRL;

-continued (7) (SEQ ID NO: 216)
MVPQALLFVPLLVFPLCFGGKYVLLSAGALTALMLIIF
LMTCCRRVNRSEPTQHNLRGTGREVSVTPQSGKIISSW
EVAGGQTRL;

(8) (SEQ ID NO: 217)
MVPQALLFVPLLVFPLCFGGKYVLLSAGALTALMLIIF
LMTCCRRVNRSEPTQHNLRGTGREVSVTPQSGKIISSW
AEAQHTQQTRL;
and (9) (SEQ ID NO: 218)
MVPQALLFVPLLVFPLCFGGKYVLLSAGALTALMLIIF
LMTCCRRVNRSEPTQHNLRGTGREVSVTPQSGKIISSW
EVHASGGQTRL.

The term "polypeptide" as defined herein encompasses polypeptides, which have been modified by post-transcriptional modification and/or by synthetic chemistry, e.g., by adjunction of a non-proteinous chemical group and/or by modification of the tertiary structure of the polypeptide, e.g., by acetylation, acylation, hydroxylation, cyclisation, racemisation, phosphorylation, etc., as long as the resulting modified polypeptide keeps a high affinity, as defined above, for the PDZ domain of the human MAST2 protein.

The invention also relates to the MAST-2 binding domains as such, consisting from 11 to 13 amino acid residues as defined in the groups A to E above.

The invention is also directed to a polypeptide which comprises or consists of, from N-terminal to C-terminal:

(1) optionally, a signal peptide, preferably a signal peptide as defined in SEQ ID NO:3, or a variant having at least 68% identity with said SEQ ID NO:3, said variant retaining the capacity to target the polypeptide into the endoplasmic reticulum and optionally through the secretory pathway;

(2) optionally, the last two C-terminal residues of the ectodomain of a rabies virus G protein;

(3) a anchoring domain, preferably an anchoring domain as defined in SEQ ID NO:4 or a variant having at least 81% identity with said SEQ ID NO:4 retaining the capacity to anchor the polypeptide in the membrane of the endoplasmic reticulum and/or the membrane of the Golgi apparatus in cells; and (4) a cytoplasmic domain comprising or consisting of (a) a cytoplasmic part upstream of the MAST-2 binding domain, preferably a peptide as defined in SEQ ID NO:2 or a variant having at least 80% identity with SEQ ID NO:2, and (b) a MAST-2 binding domain as defined above in groups A to E. In a particular embodiment, said MAST-2 binding domain is as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209.

Thus, as a particular embodiment, the invention relates to a polypeptide, of at most 350 amino acids, comprising, from N-terminal to C-terminal, a domain for anchoring said polypeptide into the reticulum membrane and/or Golgi membrane (i.e., the anchoring domain), and a domain exposed cytoplasmically (i.e., the cytoplasmic domain)

when the polypeptide is anchored in the membrane, wherein said cytoplasmic domain ends with a MAST-2 binding domain as defined in the groups A to E above, whose size is from 11 to 13 amino acid residues. This polypeptide corresponds to the polypeptide as defined above but deprived of their signal peptide, following the cleavage of this signal peptide once the polypeptide as defined above anchors into the membrane. Thus, the invention also concerns a polypeptide which comprises or consists of, from N-terminal to C-terminal:

(1) optionally, the last two C-terminal residues of the ectodomain of a rabies virus G protein;

(2) a anchoring domain, preferably an anchoring domain as defined in SEQ ID NO:4 or a variant having at least 81% identity with said SEQ ID NO:4 retaining the capacity to anchor the polypeptide in the membrane of the endoplasmic reticulum and/or the membrane of the Golgi apparatus in cells; and (3) a cytoplasmic domain comprising or consisting of (a) a cytoplasmic part upstream of the MAST-2 binding domain, preferably a peptide as defined in SEQ ID NO:2 or a variant having at least 80% identity with SEQ ID NO:2, and (b) a MAST-2 binding domain as defined above in groups A to E. In a particular embodiment, said MAST-2 binding domain is as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209.

As a particular embodiment, this polypeptide consists of the following sequence:

residues 20 to 74 of SEQ ID NOs: 17 or 18, directly linked to a MAST-2 binding domain as defined above in groups A to E, such as the ones as defined in SEQ ID NO:19 to SEQ ID NO:209, preferably chosen from the group consisting of SEQ ID NO:19 to SEQ ID NO:101, SEQ ID NO:102 to SEQ ID NO:191 and SEQ ID NO:192 to SEQ ID NO:209, more preferably as defined in SEQ ID NOS: 64-68, 71, 74 and 208-209; or residues 20 to 85 of one of the sequences SEQ ID NOs:210 to 216 or residues 20 to 87 of SEQ ID NO:217 or 218.

The invention is also directed to any polynucleotide (or nucleic acid) encoding a polypeptide of the invention as defined herein, in accordance with the universal genetic code, taking due account of its degeneracy. In a particular embodiment, the polynucleotide of the invention is DNA, RNA either as a positive strand or negative strand (when for example found in a viral particle) or as cDNA (when for example expressed in a cell transfected by a viral particle). The size of the polynucleotide of the invention is at most 1050, at most 750, at most 600 or at most 450 base pairs (bp). In a preferred embodiment, the size of the polynucleotide of the invention is at most 300 by and is preferably from 255 to 261 bp, and more preferably is 255, 258 or 261 bp.

These are examples of polynucleotides encoding the different domains of the polypeptides of the invention described herein:

the signal peptide is for example encoded by a polynucleotide located from nucleotides 1 to 57 of SEQ ID NO:219 below;

the 2 last amino acid residues of the ectodomain are for example encoded by a polynucleotide located from nucleotides 58 to 63 of SEQ ID NO:219 below;

the transmembrane domain is for example encoded by a polynucleotide located from nucleotides 64 to 129 of SEQ ID NO:219 below; and the cytoplasmic part upstream of the MAST-2 binding domain is for example encoded by a polynucleotide located from nucleotides 130 to 222 of SEQ ID NO:219 below.

According to the size of the MAST-2 binding domain, the polynucleotide encoding the MAST-2 binding domain is located either from nucleotides 223 to 255 of a SEQ ID chosen from the group consisting of SEQ ID NOs:219 to 225, or from nucleotides 223 to 261 of SEQ ID NO: 226 or 227.

In a particular embodiment, the polynucleotides of the invention comprise, at their N-terminal part, a polynucleotide encoding a signal peptide.

Particular polynucleotides consist of the following sequences:

```
(1) polynucleotide encoding Neurovita2
(as defined in SEQ ID NO: 210):
                                        (SEQ ID NO: 219)
ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTACACGGGGGTCAGACCAGA

CTGTGA;

(2) polynucleotide encoding Neurovita3
(as defined in SEQ ID NO: 211):
                                        (SEQ ID NO: 220)
ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTACACGGGCAGCAGACCAGA

CTGTGA; (Neurovita3)

(3) polynucleotide encoding the polypeptide
as defined in SEQ ID NO: 212:
                                        (SEQ ID NO: 221)
ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTAGCCACGCAGCAGACCAGA

CTGTGA;

(4) polynucleotide encoding the polypeptide
as defined in SEQ ID NO: 213:
                                        (SEQ ID NO: 222)
ATGGTTCCTCAGGCTCTCCTGTTTGTACCCCTTCTGGTTTTT

CCATTGTGTTTTGGGGGGAAGTATGTATTACTGAGTGCAGGG
```

-continued

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTATACACGGGGCAGACCAGA

CTGTGA;

(5) polynucleotide encoding the polypeptide as defined in SEQ ID NO: 214:

(SEQ ID NO: 223)

ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTACACACGGGGCAGACCAGA

CTGTGA;

(6) polynucleotide encoding the polypeptide as defined in SEQ ID NO: 215:

(SEQ ID NO: 224)

ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTACACACGCAGCAGACCAGA

CTGTGA;

(7) polynucleotide encoding the polypeptide as defined in SEQ ID NO: 216:

(SEQ ID NO: 225)

ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTAGCCGGGGGGCAGACCAGA

CTGTGA;

(8) polynucleotide encoding the polypeptide as defined in SEQ ID NO: 217:

(SEQ ID NO: 226)

ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGCCGAAGCCCAGCACACGCAGCAG

ACCAGACTGTGA;

-continued (9) polynucleotide encoding the polypeptide as defined in SEQ ID NO: 218:

(SEQ ID NO: 227)

ATGGTTCCTCAGGCTCTCCTGTTTGTACCCCTTCTGGTTTTT

CCATTGTGTTTTGGGGGGAAGTATGTATTACTGAGTGCAGGG

GCCCTGACTGCCTTGATGTTGATAATTTTCCTGATGACATGT

TGTAGAAGAGTCAATCGATCAGAACCTACGCAACACAATCTC

AGAGGGACAGGGAGGGAGGTGTCAGTCACTCCCCAAAGCGGG

AAGATCATATCTTCATGGGAAGTACACGCCTCTGGGGGGCAG

ACCAGACTGTGA.

The polynucleotide encoding a polypeptide of the invention does not comprise or consist of the sequence as defined in SEQ ID NO:8 (Neurovita1).

The invention also relates to a nucleic acid vector (such as a plasmid) comprising a polynucleotide as defined herein, i.e., a polynucleotide encoding a polypeptide of the invention. In a particular embodiment, the vector is an expression vector, i.e., a vector which comprises, besides the elements explicitly mentioned, all the elements necessary to drive the expression of the polynucleotide of the invention (expression regulatory elements), and particularly transcription regulatory elements. “Transcription regulatory element” defines any DNA regions involved in the regulation of transcription of the polynucleotide and encompasses a promoter, such as CMV or EF1α, enhancer or cis-acting regulatory elements. These elements, and particularly the promoter, are chosen depending upon the nature of the cells to be transfected with the nucleic acid vector. The determination of the suitable promoter, according to the expression level sought or to the transfected cell, makes part of the knowledge of the person skilled in the art. It is noteworthy that, when the nucleic vector contains several polynucleotides (one of which is a polynucleotide of the invention), the transcription regulatory element(s) may be unique for all the polynucleotides or shared by some of them or in contrast each polynucleotide may be associated with one or more particular transcription regulatory element(s). In the latter case, the several transcription regulatory elements may be similar or different.

Within the present invention, the expression regulatory elements inserted into the nucleic acid vector of the invention are preferably adapted for an expression of the polynucleotide of the invention in neuronal cells, in particular in human neuronal cells, such as the human neuroblastoma cell line SH-SY5Y. These promoters include, but are not limited to, the following promoters: neuron specific enolase (NSE), synapsin-1 (SYN), platelet-derived growth factor (PDGF), tyrosine hydroxylase (TH) and dopamine β-hydroxylase (DBH) (Boulaire et al.; (2009).

The invention also concerns an expression lentivirus-derived vector, in particular a plasmid, comprising, in addition to the polynucleotide of the invention (i.e., a polynucleotide encoding a polypeptide of the invention), regulatory signals for transcription and expression of said polynucleotide (expression regulatory elements), a cis-acting central initiation region (cPPT) and a cis-acting termination region (CTS) both of lentiviral origin and regulatory signals of retroviral origin for reverse transcription, expression and packaging. This vector is the transfer vector when used in a transcomplementation system (vector/packaging system) (see below).

In a particular embodiment, the expression lentivirus-derived vector can be prepared from the genome of a lentivirus or retrovirus, and only contains, apart from the polynucleotide or the nucleic acid construct of the invention, the sequences of the lentiviral or retroviral genome which are non-coding regions of said genome, necessary to provide recognition signals for DNA or RNA synthesis and processing. Hence, an expression lentivirus-derived vector may be a replacement vector in which all the viral coding sequences, between the 2 long terminal repeats (LTRs) of a lentivirus or retrovirus genome, have been replaced by the polynucleotide of the invention, regulatory signals for transcription and expression of said polynucleotide (expression regulatory elements), a cis-acting central initiation region (cPPT) and a cis-acting termination region (CTS) both of lentiviral origin and regulatory signals of retroviral origin for reverse transcription, expression and packaging. In a particular embodiment, the expression lentivirus-derived vector is obtained from a HIV genome, in particular from a HIV-1 genome, in which all the viral coding sequences, between the 2 long terminal repeats (LTRs) have been replaced by the polynucleotide of the invention, regulatory signals for transcription and expression of said polynucleotide (expression regulatory elements), a cis-acting central initiation region (cPPT) and a cis-acting termination region (CTS) both of lentiviral origin and regulatory signals of retroviral origin for reverse transcription, expression and packaging, to give an expression HIV-derived vector, in particular an expression HIV-1-derived vector.

The invention also relates to the lentiviral vector genome i.e., the genetic material contained in the lentiviral vector particle, following the formation of the particles in the transcomplementation system, as well as any nucleic acid intermediates between the expression lentivirus-derived vector and the genetic material contained in the lentiviral vector particle, said lentiviral genome or nucleic acid intermediates comprising the polynucleotide of the invention, regulatory signals for transcription and expression of said polynucleotide (expression regulatory elements), a cis-acting central initiation region (cPPT) and a cis-acting termination region (CTS) both of lentiviral origin and regulatory signals of retroviral origin for reverse transcription, expression and packaging.

Thus, the invention also encompasses any appropriate nucleic acid, i.e., DNA or RNA, either double or single stranded, including in the form containing the DNA flap as a triplex sequence, depending upon the stage of cycle of the particles, including the expression lentivirus-derived—used for cotransfection of the host cells with the encapsidation plasmid and the envelope plasmid—for expression of the particles, or the RNA genome of the particles when formed, or including the various forms of the nucleic acid of this genome in the transduced cells of the host to whom particles are administered, including the vector pre-integration complex.

Thus, the expression lentivirus-derived vector, the lentiviral vector genome or any nucleic acid intermediates of the invention, comprise regulatory signals for transcription and expression of non lentiviral origin, such as a promoter and/or an enhancer, preferably promoter adapted for an expression of the polynucleotide of the invention in neuronal cells, in particular in human neuronal cells as described above. Examples of promoters are CMV also referred to as CMVie (CMV immediate early), EF1α promoter, PGK . . . . In a particular embodiment, the polynucleotide of the invention is under the control of regulatory signals for transcription and expression.

The expression lentivirus-derived vector, the lentiviral vector genome or any nucleic acid intermediates of the invention also comprises a cis-acting central initiation region (cPPT) and a cis-acting termination region (CTS) both of lentiviral origin. These two regions are known as DNA Flap or DNA triplex. The DNA flap suitable for the invention may be obtained from a lentivirus or from a retrovirus-like organism such as retrotransposon, or may be prepared synthetically (chemical synthesis) or by amplification of the DNA flap from any lentivirus genome such as by Polymerase chain reaction (PCR). The DNA flap may be obtained from a lentivirus and in particular a HIV retrovirus, or from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. In a more preferred embodiment, the DNA flap is obtained from an HIV retrovirus, for example HIV-1 or HIV-2 virus including any isolate of these two types. Preferred DNA flap comprises or consists in the sequences as defined in SEQ ID NOs: 228 to 234. It is noteworthy that the DNA flap is used as a DNA fragment isolated from its natural (lentiviral genome) nucleotide context i.e., out of the context of the pol gene in which it is naturally contained in the lentivirus genome. Therefore, the DNA flap is used, in the present invention, deleted from the unnecessary 5' and 3' parts of the pol gene and is recombined with sequences of different origin.

According to a particular embodiment, a DNA flap has a nucleotide sequence of about 90 to about 140 nucleotides. In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 178-base pair polymerase chain reaction (PCR) fragment encompassing the cPPT and CTS regions of the HIV-1 DNA.

In a particular embodiment, the cPTT and CTS regions are inserted, in a functional orientation, into the vector or lentiviral genome, in order to adopt a triplex conformation during reverse transcription.

In a particular embodiment, the DNA flap is inserted immediately upstream of the polynucleotide of the invention or immediately upstream from the promoter controlling the expression of the polynucleotide of the invention, advantageously to have a central or nearly central position in the vector genome.

The expression lentivirus-derived vector, the lentiviral vector genome or any nucleic acid intermediates of the invention also comprises regulatory signals of retroviral origin for reverse transcription, expression and packaging. Examples of such elements are at least one (preferably two) long terminal repeats (LTR), such as a LTR5' and a LTR3' and a psi sequence involved in the lentiviral genome encapsidation. In a particular embodiment of the invention, the LTR, preferably the LTR3', is deleted for the promoter and the enhancer of the U3 region; this modification has been shown to increase substantially the transcription of the transgene inserted in the lentiviral genome (WO01/27304).

The expression lentivirus-derived vector, the lentiviral vector genome or any nucleic acid intermediates of the invention may also optionally comprise at least one the following elements:

- elements selected among a splice donor site (SD), a splice acceptor site (SA) and/or a Rev-responsive element (RRE); and/or several unique restriction sites for cloning the polynucleotide of the invention; and/or a sequence of DNA at which replication is initiated, origin of replication (ori), whose sequence is dependent on the nature of cells where the lentiviral genome has to be expressed. Said ori may be from mammalian origin, most preferably of human origin, preferably adapted for replication in human neuronal cells. It is an advantageous embodiment of the invention to have an ori inserted into the lentiviral genome or the expression lentivirus-derived vector of the invention when the lentiviral genome does not integrate into the cell host genome; thus, the presence of an ori ensures that at least one lentiviral genome is present in each cell, even after cell division; and/or at least one scaffold attachment region (SAR) and/or a matrix attachment region (MAR). Indeed, these AT-rich sequences enable to anchor the lentiviral genome to the matrix of the cell chromosome, thus regulating the transcription of the polynucleotide of the invention.

In particular embodiments of the invention, either independently of or in combination with the embodiments discussed throughout the specification, the expression lentivirus-derived vector or the lentiviral vector genome is devoid of functional gag, pol and/or env lentiviral genes. By "functional" it is meant a gene that is correctly transcribed, and/or correctly expressed. Thus, the expression lentivirus-derived vector or the lentiviral vector genome of the invention in this embodiment contains at least one of, preferably all, the gag, pol and env genes that is either not transcribed or incompletely transcribed; the expression "incompletely transcribed" refers to the alteration in the transcripts gag, gag-pro or gag-pro-pol, one of these or several of these being not transcribed. In a particular embodiment the expression lentivirus-derived vector or the lentiviral vector genome is devoid of gag, pol and/or env lentiviral genes. In a particular embodiment, the expression lentivirus-derived vector or the lentiviral vector genome is also devoid of the coding sequences for Vif-, Vpr-, Vpu- and Nef-accessory genes (for HIV-1 lentiviral vectors), or of their complete or functional genes.

The lentiviral vector of the invention is non replicative i.e., the expression lentivirus-derived vector or the lentiviral vector genome are not able to form new particles budding from the infected host cell. This may be achieved by the absence in the expression lentivirus-derived vector or in the lentiviral vector genome of the gag, pol or env genes, as indicated in the above paragraph; this can also be achieved by deleting other viral coding sequence(s) and/or cis-acting genetic elements needed for particles formation. The absence of formation of particles should be distinguished from the replication of the expression lentivirus-derived vector or the lentiviral vector genome. Indeed, as described before, the expression lentivirus-derived vector or the lentiviral vector genome may contain an origin of replication ensuring the replication of the expression lentivirus-derived vector or the lentiviral vector genome without ensuring the formation of particles.

The invention also concerns a lentiviral vector pseudotyped particle comprising GAG structural proteins and a viral core made of (a) POL proteins and (b) a lentiviral vector genome comprising the polynucleotide of the invention, expression regulatory elements of said polynucleotide, a cis-acting central initiation region (cPPT) and a cis-acting termination region (CTS) both of lentiviral origin and regulatory signals of retroviral origin for reverse transcription, expression and packaging, wherein said particle is pseudotyped with the G protein of a VSV virus or the G protein of a rabies virus.

The expression "lentiviral vector pseudotyped particle" encompasses a lentiviral particle that comprises both proteins and genetic material, preferably encapsidated into these proteins. Particles are made of viral envelope proteins (encoded by an env gene) as well as structural proteins (encoded by a gag gene). Inside the particles, a viral core (or capsid) formed of three enzymes (encoded by a pol gene), i.e., the reverse transcriptase, the integrase and the protease, and genetic material (the lentiviral genome). The features of the expression regulatory elements of said polynucleotide, a cis-acting central initiation region (cPPT) and a cis-acting termination region (CTS) both of lentiviral origin and regulatory signals of retroviral origin for reverse transcription, expression and packaging contained in the lentiviral genome are as defined above for the expression lentivirus-derived vector. Indeed, the lentiviral genome contained in the lentiviral particle is a transcript of the nucleic acid contained in the expression lentivirus-derived vector.

The envelope protein of the lentiviral vector of the invention may be pseudotyped with the envelope protein of the lentivirus used to prepare the lentiviral vector, or alternatively with a heterogeneous envelope protein that is chosen with respect to the cells to be targeted into the host.

In a particular embodiment, said lentiviral particle is pseudotyped with a VSV-G protein. The VSV-G protein originates from the serotype Indiana, N.J., Piry, Chandipura, Isfahan, Cocal or the combination of at least two of these serotypes. In a particular embodiment, the VSV-G protein originating from a VSV is modified with respect to its native form, especially to improve pseudotyping.

In another embodiment, said lentiviral particle is pseudotyped with the G protein of a rabies virus. In a particular embodiment, the G protein originates from an attenuated strain such as the ERA-NIV (ERA) strain. In a particular embodiment, the G protein originates from a virulent strain such as the CVS-NIV (CVS) strain, the CVS-Gif-sur-Yvette strain (Prehaud et al. 1988), the CVS-11 strain, the N2C strain or the CVS-24 strain. In a particular embodiment, the G protein originates from the CVS24 B2c strain (Morimoto et al. 1998; Mentis et al. 2006). A lentiviral particle, comprising in its lentiviral genome a polynucleotide encoding for a polypeptide of the invention, pseudotyped with the G protein of a rabies virus, is a preferred product of the invention.

The original ERA and CVS strains of rabies virus (RABV) are available from the ATCC under deposit number vr332 and vr959, respectively (Prehaud C et al, 2003, and WO2010/116258).

The sequence of the G protein of the CVS-NIV strain is available under accession number AF406694 and is as defined in SEQ ID NO:12. The G protein of the CVS-NIV strain is available from the recombinant *E. coli* strain deposited, under number I-2758, on the 30$^{th}$ of November, 2001 at the CNCM (Institut Pasteur, 25 rue du Docteur Roux, 75724 PARIS Cedex 15—France) under the terms of the Budapest Treaty. This recombinant *E. coli* comprises a plasmid (plasmid pRev-TRE-G-CVS; WO 03/048198), which inducibly expresses the G protein of the CVS-NIV strain.

The sequence of the G protein of the ERA-NIV strain is available under accession number AF406693 and is as defined in SEQ ID NO:13. The G protein of the ERA strain is available from the recombinant *E. coli* strain deposited, under number I-2760, on the 30$^{th}$ of November, 2001 at the CNCM under the terms of the Budapest Treaty. This recombinant *E. coli* comprises a plasmid (plasmid pRev-TRE-G-ERA; WO 03/048198), which inducibly expresses the G protein of the ERA strain.

Appropriate conditions for the cultivation of the recombinant *E. coli* strain containing the plasmid CNCM I-2758 or the plasmid CNCM I-2760 comprise the incubation of said recombinant *E. coli* strain at 37° C. on a standard LB-TYM growth medium (in the presence of ampicillin).

The nucleotide and protein sequences of the G protein of the CVS24 B2c strain are as defined in SEQ ID NO:287 and SEQ ID NO:288, respectively.

In a particular embodiment, the integrase protein contained in the lentiviral vector pseudotyped particle is defective. The integrase protein is one of the proteins encoded by the pol gene. By "defective", it is meant that the integrase, of lentiviral origin, is devoid of the capacity of integration of the lentiviral genome into the genome of the host cells i.e., an integrase protein mutated to specifically alter its integrase activity. Accordingly the integrase capacity of the protein is altered whereas the correct expression of the GAG, PRO and POL proteins and/or the formation of the capsid and hence of the vector particles, as well as other steps of the viral cycle, preceding or subsequent to the integration step, such as the reverse transcription, the nucleus import, stay intact. An integrase is said defective when the integration that it should enable is altered in such a way that an integration step takes place less than 1 over 1000, preferably less than 1 over 10000, when compared to a lentiviral vector containing a corresponding wild-type integrase.

In a particular embodiment of the invention, the property of the integrase of being defective, results from a mutation of class 1, preferably amino acid substitutions (one-amino acid substitution) or short deletions giving rise to a protein fulfilling the requirements of the preceding paragraph. The mutation is carried out within the pol gene. Examples of mutations altering HIV-1 and enabling to obtain a non-functional integrase for integration (integration-incompetent integrase) are the following: H12N, H12C, H16C, H16V, S81 R, D41A, K42A, H51A, Q53C, D55V, D64E, D64V, E69A, K71A, E85A, E87A, D116N, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H. Another proposed substitution is the replacement of the amino acids residues RRK (positions 262 to 264) by the amino acids residues AAH. In a particular embodiment, the following substitutions are preferred: H12N, H12C, H16C, H16V, S81 R, D41A, K42A, H51A, Q53C, D55V, D64E, D64V, E69A, K71A, E85A, E87A, D116I, D116A, N120G, N120I, N120E, E152G, E152A, D35E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H. Other mutations are disclosed in Wanisch and Yáñez-Muñoz (2009). A particularly proper mutation is the D64V mutation.

Whatever the elements contained in the lentiviral vector genome, the nature of the envelope protein of the particle and the defective feature or not of the integrase protein, the lentiviral vector pseudotyped particle is preferably obtained by a transcomplementation system (vector/packaging system). Thus, a permissive cell (such as 293T cells) is in vitro transfected with a transfer vector which is a expression lentivirus-derived vector as defined herein and with at least one other plasmid providing, in trans, the gag, pol and env sequences encoding the polypeptides GAG, POL and the envelope protein(s), or for a portion of these polypeptides sufficient to enable formation of lentiviral particles. The transfer vector generates, as a transcript, the lentiviral genome, whereas the gag, pol and env provide respectively the GAG structural proteins, the POL protein for the viral core (preferably with a defective integrase) and the pseudotyped ENV proteins (preferably a G protein from VSV or a G protein from a rabies virus).

As an example, permissive cells are transfected with a first plasmid which is the expression lentivirus-derived vector of the invention (transfer vector), a second plasmid (envelope expression plasmid or pseudotyping env plasmid) comprising a gene encoding an envelope protein(s) (such as VSV-G or the protein G of a rabies virus), and a third plasmid (encapsidation plasmid or packaging construct) expressing the GAG and POL proteins.

The invention is also directed to a cell (preferably isolated) or a cell culture transfected with a vector of the invention or transduced by a lentiviral particle of the invention. Thus, the cell or cell culture of the invention comprises or expresses at least one polypeptide of the invention, and/or comprises at least one polynucleotide of the invention and/or at least one vector of the invention.

Said cell can be a eukaryotic cell [or a cell culture made of eukaryotic cells], preferably a mammal cell, for example a human cell or a non-human cell, most preferably a human cell. Preferably, said cell is not a human embryonic cell or a human germinal cell.

In a particular embodiment, said cell is a neuronal cell, preferably a human neuronal cell. In a particular embodiment, said cell are human pre-mitotic neurons, immature human neurons, such as neuroblastoma cells, Ntera 2D1 (ATCC CRL-1973), SK-N-SH (ATCC HTB11), SH-SY-5Y (ATCC CRL-2266), U373MG (human astrocytoma cell line; Babault N et al, 2011) (Prehaud C. et al, 2010, 2005 and 2003; Lafon M. et al, 2008 and 2006; Megret F. et al. 2007).

These are particular cells or cell culture that may be transfected or transduced according to the present specification:

- the SH-SY5Y cell culture, a human neuroblastoma cell line, which is available from the American Type Culture Collection (ATCC; 10801 University Blvd.; Manassas, Va. 20110-2209; U.S.A.) under deposit number CRL-2266. These cells, which are a sub clone of the human neuroblastoma cell line SK-N-SH (ATCC, HTB11), may differentiate when they are treated with the cell permeable db-cAMP. These differentiated cells have shown high plasticity, outgrowth and retraction (Loh S H Y et al. 2008);
- pure post-mitotic human neurons (NT2-N), which are obtained from the embryonic carcinoma cell line NTera 2cl.-D1 (ATCC CRL-1973), as described in the art, e.g., in Prehaud et al. 2005. Tera cells N2D1 can differentiate into pure cultures of human post-mitotic neurons (NT2-N) after induction of differentiation by all-trans retinoic acid (ATRA), then treatment with inhibitors of mitosis and purification arranged by trypsinization (Andrews P W, 1998). NT2-N cells have all the specific markers of differentiated human neurons (Guillemain I. 2000). They can establish in vitro synaptic contacts between them and the functional contacts with astrocytes in co-culture, as well as functional synapses.

rat pheochromocytoma cells (NS cells, Cellomics USA), which are a subclone of PC12 cells, differentiated with NGF. These differentiated cells present a strong and organized neurite network and have been validated for high throughput screening. NS cells extend neurites, become electrically excitable, become more responsive to exogenously applied acetylcholine, have increased numbers of calcium channels, and increase the synthesis of several neurotransmitters. NS cells grown in the presence of NGF resemble sympathetic neurons and are a model of noradrenergic neurons.

the SK-N-SH human neuroblastoma cell line (ATCC HTB11), which is a prototype of adrenergic immature neurons (Von Reitzentstein, 2001). These cells can be differentiated further by treatment with ATRA (Gaitonde et al. 2001; Wainwright et al. 2001).

Alternatively, said cell can be a prokaryotic cell [or a cell culture made of prokaryotic cells], preferably a bacterium, for example *E. coli.*

In a particular embodiment, the cell contains, integrated in its genome, the polynucleotide of the invention (expressing the polypeptide of the invention), especially when the cell or cell culture has been previously transduced by a lentiviral particle of the invention. Alternatively, the polynucleotide of the invention is not integrated in the genome of the cells, even when it has been previously transduced by a lentiviral particle of the invention, as a result of a defective integrase. In this latter case, the polynucleotide of the invention advantageously comprises an origin of replication.

The invention also concerns a composition comprising a polypeptide of the invention, a polynucleotide of the invention, a vector of the invention, an expression lentivirus-derived vector of the invention, a lentiviral vector pseudotyped particle of the invention or a cell of the invention, and optionally a pharmaceutically acceptable vehicle, excipient or carrier. The composition comprises the polypeptide, the polynucleotide, the vector, the expression lentivirus-derived vector, the lentiviral vector pseudotyped particle or the cell of the invention, as active principle, said composition being suitable for administration into a host, preferably a human host.

A preferred composition comprises a lentiviral vector particle pseudotyped with a rabies G protein of the invention. Indeed, the lentiviral vector particle pseudotyped with a rabies G protein of the invention combines at least the two advantageous features:

(1) the polypeptide of the invention, via the features of the MAST-2 binding domain of the cytoplasmic domain as defined above, has a high affinity for the PDZ domain of the human MAST2 protein. Thus, the use of the polypeptide of the invention improves the effects observed on the induction and/or the stimulation of the neurite outgrowth and/or on the neurosurvival, as compared to the polypeptides of the prior art; and (2) the pseudotyping of the particle with the G protein of a rabies virus enables to specifically target the neuronal cells, by retrograde transport from the muscle (site of injection of the composition), and thus to avoid the unnecessary transduction of other cell types.

A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation; suitable carriers include, but are not limited to, phosphate buffered saline solutions, distilled water, emulsions such as an oil/water emulsions, various types of wetting agents sterile solutions and the like, dextrose, glycerol, saline, ethanol, and combinations thereof. Such carriers enable the pharmaceutical compositions to be formulated as tablets, pills, dragees, capsules, liquids, gels, syrups, slurries, suspensions, and the like. Carriers for parenteral administration include aqueous solutions of dextrose, mannitol, mannose, sorbitol, saline, pure water, ethanol, glycerol, propyleneglycol, peanut oil, sesame oil, polyoxyethylene-polyoxypropylene block polymers, and the like.

A "pharmaceutically acceptable excipient" refers to a substance that is used as a carrier or for the manufacturing of the administrable form of polypeptide(s) of the invention. Suitable excipients include fillers such as sugars, including lactose, sucrose, mannitol, or sorbitol; cellulose preparations such as, for example, maize, wheat, rice, or potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate. Thus, for oral use of the polypeptide(s) of the invention, a solid excipient can be used, optionally grinding the resulting mixture, and processing the mixture of granules, after adding suitable auxiliaries if desired, to obtain tablets or dragee cores. Examples of excipients for coating of dragee or tablet are concentrated sugar solutions which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

The invention also relates to a polypeptide of the invention, a polynucleotide of the invention, a vector of the invention, an expression lentivirus-derived vector of the invention, a lentiviral vector pseudotyped particle of the invention, a cell of the invention or a composition of the invention (disclosed hereinafter as the products of the invention), for use as a medicament or a drug.

Regarding the use as a medicament, as well as the uses and treatments detailed below, a lentiviral vector particle pseudotyped with a rabies virus G protein of the invention or a composition comprising lentiviral vector particle(s) pseudotyped with a rabies virus G proteins of the invention, are preferred.

Thus, the products of the invention are used for inducing and/or stimulating neurite outgrowth, more particularly in the treatment and/or palliation and/or prevention of a disease, disorder or condition involving an insufficient or impaired neuritogenesis, more particularly an insufficient or impaired neurite outgrowth.

In accordance with the invention, the products of the invention, is intended as an effector of neurite outgrowth (and/or of axon and/or dendrite development), e.g., for neuron differentiation from neuron progenitors or neoplastic neurons, and/or for neuron regeneration of impaired neurons (both effects being obtained through stimulation of neurite outgrowth). In a particular embodiment, the products of the invention are for use to induce and/or to stimulate neuritogenesis, more particularly neurite outgrowth, still more particularly human neurite outgrowth. In another particular embodiment, the products of the invention are for use to induce and/or to stimulate neuritogenesis, more particularly neurite outgrowth from pre-mitotic neurons, neoplastic neurons, neuron progenitors, as well as from impaired neurons.

The products of the invention are for use as a neuroregenerative (generation of new functional neurons, glia, axons, myelin, and/or synapses) and/or neuroprotective agent (protection of neurons from apoptosis or degeneration).

The products of the invention are for use to stimulate and/or to induce neurite sprouting and/or axon growth and/or dendritic tree extension.

The products of the invention are for use to stimulate and/or to induce synaptogenesis and/or neurotransmission. Indeed, the polypeptide of the invention stimulates the activity of the growth cone. Furthermore, it prevents growth cone from collapsing upon contact with a growth collapsing agent, such as LPA or oxidative stress.

The products of the invention are for use to stimulate neuronal development and/or neuronal regeneration and/or axon growth and/or dendrite development and/or dendritic tree extension and/or neuronal plasticity and/or synaptogenesis and/or neurotransmission.

The products of the invention are for use to prevent and/or to inhibit and/or to block any kind of neurotoxicity which would lead to neurite retraction and/or growth cone collapse.

The products of the invention are for use to stimulate and/or to induce neurite outgrowth and/or growth cone activity after said neurite and/or cone has been in contact with a neurotoxic agent.

The products of the invention are for use to prevent and/or to inhibit and/or to block growth cone collapse and/or neurite retraction and/or axodendritic damage or lesion and/or disruption of synaptic integrity and/or loss of neuron connectivity and/or damage to nerve endings and/or neurotransmission impairment.

The products of the invention are for use to induce and/or stimulate neurite outgrowth, which is notably useful

- in inducing neuron differentiation, for example in the treatment and/or palliation and/or prevention of a neoplasm of the nervous system, as well as
- in regenerating impaired neurons, more particularly impaired neurites, for example
- in the treatment and/or palliation and/or prevention of a neurodegenerative disease, disorder or condition, in the treatment and/or palliation and/or prevention of microbial infections of the neurons, or in protecting neurons from neurotoxic agents or oxidative stress.

Therefore, the invention relates to products of the invention, for use in the treatment and/or palliation and/or prevention of any disease, disorder or condition which involves an insufficient or impaired neuritogenesis, more particularly an insufficient or impaired neurite outgrowth or an insufficient dendrites arborisation.

Said disease, disorder or condition is alternatively or complementarily defined as any disease, disorder or condition involving an unbalanced neuron cell cycle, wherein said neuron cell cycle is unbalanced:

- either by excessive or undesired presence of pre-mitotic neurons (more particularly, by insufficient neuron differentiation and/or by excessive or undesired re-entry of post-mitotic neurons into the neuron cell cycle, as is the case when a neoplasm develops in the nervous system), or
- by excessive or undesired neuron degeneration, more particularly excessive or undesired neurite degeneration (as is the case for a neurodegenerative disease, disorder or condition, and for certain microbial infection of the neurons).

The products of the invention are for use in the treatment and/or palliation and/or prevention of a disease, disorder or condition, which alters the Central Nervous System (CNS) and/or the Peripheral Nervous System (PNS), for example as a neurorestorative therapy and/or prevention and/or palliation. The expression "Central Nervous System" or "CNS" is herein intended as meaning the brain and (in case of a vertebrate animal) the spinal cord. The peripheral nervous system (PNS) is the vast network of spinal and cranial nerves linking the body to the brain and spinal cord. The PNS is subdivided into the autonomic nervous system (sympathetic NS and parasympathetic NS) and the somatic nervous system. The PNS consists of sensory neurons running from stimulus receptors to the CNS and motor neurons running from the CNS to the muscle and glands.

According to an embodiment of the invention, said disease, disorder or condition is or involves a microbial infection of the nervous system, such as a bacterial and/or viral infection, more particularly a viral infection. Preferably, said microbial infection is a microbial infection that induces neuron apoptosis, such as poliomyelitis (Blondel et al., 2005). As an example of viral infection is poliovirus infection or West Nile virus infection.

According to another embodiment of the invention, said disease, disorder or condition is or involves a non-viral disease, disorder or condition, more preferably a non-bacterial and non-viral disease, disorder or condition, still more preferably a non-microbial disease, disorder or condition.

According to an embodiment of the invention, said disease or disorder is or involves a neurodegenerative disease or disorder (for example, a chronic neurodegenerative disease or disorder), such as non-viral encephalopathy, Alzheimer's disease, Parkinson's disease, ALS, Huntington disease, multiple sclerosis (MS) or rare genetic disease. Preferably, said neurodegenerative disease or disorder is a non-viral disease or disorder, more preferably a non-bacterial and non-viral disease or disorder, still more preferably a non-microbial disorder.

According to an embodiment of the invention, said condition is or involves a neurodegenerative condition, such as aging. Preferably, said neurodegenerative condition is a non-viral condition, more preferably a non-bacterial and non-viral condition, still more preferably a non-microbial condition.

According to an embodiment of the invention, said disease, disorder or condition is or involves a physical or ischemic injury of the nervous system, such as seizure, stroke, trauma, epilepsy. Preferably, said physical or ischemic injury is a non-viral disease, disorder or condition, more preferably a non-bacterial and non-viral disease, disorder or condition, still more preferably a non-microbial disease, disorder or condition.

According to an embodiment of the invention, said disease, disorder or condition involves the presence of a chemical neurotoxic agent and/or of an oxidative stress. Preferably, said disease, disorder or condition is a non-viral disease, disorder or condition, more preferably a non-bacterial and non-viral disease, disorder or condition, still more preferably a non-microbial disease, disorder or condition.

According to an embodiment of the invention, said disease is a neoplasm, more particularly a neoplasm which comprises neoplastic neurons. The term "neoplasm" is herein more particularly intended as a malignant neoplasm, more particularly a cancer, still more particularly a tumor or a leukaemia, even still more particularly a tumor.

Any administration mode that the skilled person may find appropriate is encompassed by the present invention. Depending on how the product of the invention is formulated, it can be administered by parenteral or enteral (e.g., oral) administration, preferably by parenteral administration, more preferably by parenteral injection.

The invention also concerns the use of a polynucleotide of the invention, a vector of the invention, an expression lentivirus-derived vector of the invention, a lentiviral vector pseudotyped particle of the invention, a cell or a composition of the invention, for the manufacture of a medicament or a drug for the treatment and/or palliation and/or prevention of any disease, disorder or condition as defined above.

The invention also relates to a method of treatment of a subject, more particularly of a human being, in need thereof, which comprises administering to said subject or human being at least a polynucleotide of the invention, a vector of the invention, an expression lentivirus-derived vector of the invention, a lentiviral vector pseudotyped particle of the invention, a cell of the invention or a composition of the invention. This method of treatment is intended for the treatment and/or palliation and/or prevention of any disease, disorder or condition as defined above.

The products of the invention are not immunogenic agents or adjuvants, or at the very least are not used as immunogenic agents or adjuvants and are not used under conditions which would enable the polypeptide of the invention to act as an immunogenic agent or adjuvant. The products of the invention do not raise a detectable humoral immune response after administration.

The invention also concerns a method to determine the neurosurvival and/or neuroprotection activity of a given molecule in a cell, comprising:

(a) adding a molecule to be assayed in contact with a cell or cell culture;
(b) measuring the expression of a set of genes consisting of or comprising the five cellular genes ROBO1, POU4F1, PTN, PARD6B and PAFAH1B1, in a cell or cell culture of step a); and
(c) normalizing the expression of each of the genes measured in step b) on the expression of the same genes measured in a cell of the same cell type, which has not been in contact with the said molecule, wherein a statistically significant modulation of the expression of the genes of said set reveals that said molecule may have a neurosurvival and/or neuroprotection activity.

In a particular embodiment, step b) further comprises the measurement of the expression of at least one additional gene selected from the group consisting of the twelve cellular genes PIK3CG, BMP2, DRD1, PAX5, S100A6, DRD2, HDAC7, HEY2, INHBA, SHH, BTK and FOS. In that case, each additional gene is normalized in step c) on the expression of the same additional gene measured in a cell of the same cell type, which has not been contacted with said molecule.

Thus, in a particular embodiment, the method to determine the neurosurvival and/or neuroprotection activity of a molecule in a cell, comprises:

(a) adding a molecule to be assayed in contact with a cell or cell culture;
(b) measuring the expression of a set of genes consisting of or comprising the five cellular genes ROBO1, POU4F1, PTN, PARD6B and PAFAH1B1, and optionally at least one additional gene selected from the group consisting of the twelve cellular genes PIK3CG, BMP2, DRD1, PAX5, S100A6, DRD2, HDAC7, HEY2, INHBA, SHH, BTK and FOS, in a cell or cell culture of step a); and
(c) normalizing the expression of each of the genes measured in step b) on the expression of the same genes measured in a cell of the same cell type, which has not been in contact with said molecule, wherein a statistically significant modulation of the expression of the genes of said set reveals that said molecule may have a neurosurvival and/or neuroprotection activity.

The nucleotide sequences of the ROBO1, POU4F1, PTN, PARD6B, PAFAH1B1, PIK3CG, BMP2, DRD1, PAX5, S100A6, DRD2, HDAC7, HEY2, INHBA, SHH, BTK and FOS genes are as defined in SEQ ID NO:236 to SEQ ID NO:252 respectively.

This method (or process) comprises, in a first step, adding a molecule to be assayed in contact with a cell or cell culture.

By "adding a molecule to be assayed in contact with a cell or cell culture", it is meant that the molecule must be able to interact with the PDZ domain of the human MAST2 protein, and therefore must be expressed in the cytoplasm of this cell or cell culture, in particular in a cell or cell culture expressing the human MAST-2 protein. Thus, the first step consists of expressing the molecule to be assayed in the cytoplasm of the cell.

Thus, any method known from the person skilled in the art may used to transfect or transform cells, or make cell permeable to the molecule in particular according to the nature of the molecule.

As an illustration of said expression into the cytoplasm, whatever the nature of the molecule to be assayed, the molecule may be transported into the cytoplasm of a cell, using liposomes, by contacting said cell with a liposome containing the molecule to be assayed, or by electroporation or by nanoparticles delivery.

As a particular embodiment, and when the molecule is a protein or a polypeptide, the expression can result from the transfection of this cell by a nucleic acid, a plasmid or a vector containing the nucleic acid sequence encoding this protein or polypeptide. In this embodiment, the first step of the method consists in transfecting said cell with a nucleic acid, any plasmid or a vector containing the nucleic acid sequence encoding this protein or polypeptide. In a particular embodiment, the molecule is a polypeptide of the invention as defined herein. In this embodiment, the first step of the method consists in transfecting said cell with a polynucleotide or a vector as defined in the specification. Known methods encompass chemical-based transfection, such as calcium phosphate, cationic liposomes (DOTMA and DOPE, Lipofectamine and UptiFectin), cationic polymers (DEAE-dextran, polyethylenimine, Fugene, LT-1, GeneJuice and JetPEI), and non chemical methods, such as electroporation, sono-poration, optical transfection, gene electrotransfer or impalefection.

Alternatively, a cell or cell culture may also be transduced by a viral particle, which comprises in its viral genome, the nucleic acid sequence encoding the protein or polypeptide to be assayed. As a particular embodiment, the particles as defined in the present specification may be used to transduce cells or cell culture.

To determine the neurosurvival and/or neuroprotection activity of a molecule, the method is implemented into neuronal cell, in particular expressing the MAST-2 protein, preferably a human neuronal cell. In a particular embodiment, said cell are human pre-mitotic neurons, immature human neurons, such as neuroblastoma cells. The method is preferably implemented on the SH-SY5Y cells, the NT2-N cells, the NS cells or the NS-SK-N-SH cells, as defined above.

The second step comprises measuring, in a cell or cell culture; which has been in contact with the molecule to be assayed, the expression of a set of genes consisting of or comprising the five cellular genes ROBO1, POU4F1, PTN, PARD6B and PAFAH1B1. This step may further comprise the measurement of the expression of at least one additional gene, in particular 1, 2, 3, 4, 5, 6, 7, 8, 9, 10, 11 or 12 genes, selected from the group consisting of the twelve cellular genes PIK3CG, BMP2, DRD1, PAX5, S100A6, DRD2, HDAC7, HEY2, INHBA, SHH, BTK and FOS.

By "measuring", it is meant assaying, in particular detecting, the product or several products resulting from the expression of a cellular gene, this product being in the form of a nucleic acid, especially RNA, mRNA, cDNA, polypeptide, protein or any other formats. In a particular embodiment, the measurement of the gene expression comprises detecting a set of nucleotide targets, each nucleotide target corresponding to the expression product of a gene encompassed in the set.

The expression "nucleotide target" means a nucleic acid molecule whose expression must be measured, preferably quantitatively measured. By "expression measured", it is meant that the expression product(s), in particular the transcription product(s) of a gene, are measured. By "quantitative" it is meant that the method is used to determine the quantity or the number of copies of the expression products, in particular the transcription products or nucleotide targets. This must be opposed to the qualitative measurement, whose aim is to determine the presence or absence of said expression product(s) only.

A nucleotide target is in particular a RNA, and most particularly a total RNA. In a preferred embodiment, the nucleotide target is mRNA or transcripts. According to the methods used to measure the gene expression level, the mRNA may be used to obtain cDNA or cRNA, which is then detected and possibly measured.

The expression products or the nucleotide targets are preferably prepared from a cell culture, in particular after isolation or even purification. When the nucleotide targets are mRNA, a further step comprising or consisting in the retro-transcription of said mRNA into cDNA (complementary DNA) may also be performed prior to the step of detecting expression. Optionally, the cDNA may also be transcribed in vitro to provide cRNA.

During the step of preparation, and before assaying the expression, the expression product(s) or the nucleotide target(s) may be labelled, with isotopic (such as radioactive) or non isotopic (such as fluorescent, coloured, luminescent, affinity, enzymatic, magnetic, thermal or electrical) markers or labels.

It is noteworthy that steps carried out for assaying the gene expression must not alter the qualitative or the quantitative expression (number of copies) of the expression product(s) or of the nucleotide target(s), or must not interfere with the subsequent step comprising assaying the qualitative or the quantitative expression of said expression product(s) or nucleotide target(s).

The step of profiling gene expression comprises determining the expression of a set of genes. Such a set is defined as a group of genes that must be assayed for one test, and especially performed at the same time, on the same cell culture.

A set of gene consists of or comprises the five cellular genes ROBO1, POU4F1, PTN, PARD6B and PAFAH1B1. The set of genes may further comprise at least one additional gene selected from the group consisting of the twelve cellular genes PIK3CG, BMP2, DRD1, PAX5, S100A6, DRD2, HDAC7, HEY2, INHBA, SHH, BTK and FOS.

Moreover, in addition to these genes, step b) may encompass the measurement of the expression of other cellular genes, and in particular the measurement of the expression of at least one cellular gene(s) selected from the group consisting of genes involved in the PI3K/Akt signalling pathway or genes involved in cell proliferation, cell adhesion, cell differentiation, growth factors and synaptic functions.

In a particular embodiment, the set of genes used in step b) includes from 5 to 17 genes, in particular (1) exactly the five cellular genes ROBO1, POU4F1, PTN, PARD6B and PAFAH1B1, or (2) at least the five cellular genes ROBO1, POU4F1, PTN, PARD6B and PAFAH1B1, and from 1 to 12 genes, in particular 1 to 10 or 1 to 5 genes, selected from the group consisting of the twelve cellular genes PIK3CG, BMP2, DRD1, PAX5, S100A6, DRD2, HDAC7, HEY2, INHBA, SHH, BTK and FOS. Thus, in a particular embodiment, the set of genes consists of 5, 6, 7, 8, 9, 10, 11, 12, 13, 14, 15, 16 or 17 genes.

In step c) of the method, the expression of each gene of the set, as measured in step b) is normalized, i.e., that for each gene, the expression measured in step b) is compared to the expression of the same gene as measured in a cell of the same cell type, in particular of the same cell culture or cell line, which has not been in contact with the molecule to be assayed. Thus, the following ratio is calculated:

$$\frac{\text{expression of a gene, measured in a cell in contact with the molecule to be assayed}}{\text{expression of the same gene as measured in a cell not in contact with said molecule.}}$$

This ratio enables to determine the relative expression of each gene, i.e., whether the expression of each gene is increased or decreased as a result of the contact with the molecule to be assayed. By "increase" or "decrease", it is meant that the expression of a gene is statistically higher or statistically lower in a cell contacted with the molecule to be assayed as compared to a cell of the same cell type not contacted with this molecule. An expression is considered statistically different when the p-value (p) as calculated by the Student t test is $<0.05$.

Carrying out the method as described herein, a molecule, and in particular a polypeptide of the invention is considered as having a neurosurvival phenotype (i.e., neuroprotection, and/or neurogenesis and/or neuroregeneration and/or arborisation and/or neurorestoration), when the expression of the genes contained in the set as defined herein is modified in a statistically significant manner.

As an example, a molecule, and in particular a polypeptide of the invention is considered as having a neurosurvival phenotype (i.e., neuroprotection, and/or neurogenesis and/or neuroregeneration and/or arborisation and/or neurorestoration), when the respective ROBO1, POU4F1, PTN, PARD6B and PAFAH1B1genes are statistically under-expressed, in particular by a fold of at least 1.5, when compared to the expression of the same genes in a cell (culture) which has not been in contact with said molecule (negative control); the under-expression may be calculated by implementing the experiment described below in point A.5 (results in point B.10), in which the negative control is a mock-infected cell culture.

The invention is also directed to a kit, suitable to carry out the method as defined herein, comprising a. a plurality of pairs of primers specific for a set of genes as defined herein, in particular a set of genes consisting of or comprising the five cellular genes ROBO1, POU4F1, PTN, PARD6B and PAFAH1B1, and optionally at least one additional gene selected from the group consisting of the twelve cellular genes PIK3CG, BMP2, DRD1, PAX5, S100A6, DRD2, HDAC7, HEY2, INHBA, SHH, BTK and FOS; and b. optionally reagents necessary for the amplification of the nucleotide targets of these cellular genes by said primers, and optionally reagents for detecting the amplification products.

As defined herein, a pair of primers consists of a forward polynucleotide and a backward polynucleotide, each primer having the capacity to match its nucleotide target and to amplify, when appropriate conditions and reagents are brought, a nucleotide sequence framed by their complementary sequence, in the sequence of their nucleotide target.

The pairs of primers present in the kits of the invention are specific for a gene i.e., each pair of primers amplifies the nucleotide targets of one and only one gene among the set. Therefore, it is excluded that a pair of primers specific for a gene amplifies, in a exponential or even in a linear way, the nucleotide targets of another gene and/or other nucleic acids contained in sample. In this way, the sequence of a primer (whose pair is specific for a gene) is selected to be not found in a sequence found in another gene, is not complementary to a sequence found in this another gene and/or is not able to hybridize in amplification conditions as defined in the present application with the sequence of the nucleotide targets of this another gene.

In a particular embodiment, the forward and/or backward primer(s) may be labelled, either by isotopic (such as radioactive) or non isotopic (such as fluorescent, biotin, fluorochrome) methods. The label of the primer(s) leads to the labelling of the amplicon (product of amplification), since the primers are incorporated in the final product.

The design of a pair of primers is well known in the art and in particular may be carried out by reference to Sambrook et al. (Molecular Cloning, A laboratory Manual, Third Edition; chapter 8 and in particular pages 8.13 to 8.16). Various softwares are available to design pairs of primers, such as Oligo™ or Primer3.

Therefore, each primer of the pair (forward and backward) has, independently from each other, the following features:

their size is from 10 and 50 bp, preferably 15 to 30 bp; and they have the capacity to hybridize with the sequence of the nucleotide targets of a gene.

In a particular embodiment, when the pairs of primers are used in a simultaneous amplification reaction carried out on the sample, the various primers have the capacity to hybridize with their respective nucleotide targets at the same temperature and in the same conditions.

Conventional conditions for PCR amplification are well known in the art and in particular in Sambrook et al. An example of common conditions for amplification by PCR is dNTP (200 mM), $MgCl_2$ (0.5-3 mM) and primers (100-200 nM).

In a particular embodiment, the sequence of the primer is 100% identical to one of the strands of the sequence of the nucleotide target to which it must hybridize with, i.e. is 100% complementary to the sequence of the nucleotide target to which it must hybridize. In another embodiment, the identity or complementarity is not 100%, but the similarity is at least 80%, at least 85%, at least 90% or at least 95% with its complementary sequence in the nucleotide target. In a particular embodiment, the primer differs from its counterpart in the sequence of the sequence of the nucleotide target by 1, 2, 3, 4 or 5 mutation(s) (deletion, insertion and/or substitution), preferably by 1, 2, 3, 4 or 5 nucleotide substitutions. In a particular embodiment, the mutations are not located in the last 5 nucleotides of the 3' end of the primer.

In a particular embodiment, the primer, which is not 100% identical or complementary, keeps the capacity to hybridize with the sequence of the nucleotide target, similarly to the primer that is 100% identical or 100% complementary with the sequence of the nucleotide target (in the hybridization conditions defined herein). In order to be specific, at least one of the primers (having at least 80% similarity as defined above) of the pair specific for a gene can not hybridize with the sequence found in the nucleotide targets of another gene of the set and of another gene of the sample.

Examples of primers that may be used to measure the expression of the cellular genes listed herein are disclosed in Table 2.

TABLE 2

| Gene | Forward primer (SEQ ID) | Backward primer (SEQ ID) |
|---|---|---|
| ROBO1 | GTGTGGTGTGTGGCTTCA (253) | GTATACAGTCTCATGCC (254) |
| POU4F1 | CCCTCCCTGAGCACAAG (255) | GTGGGCAGGCAGGCCC (256) |
| PTN | GGCAAGAAACAGGAGAAGA (257) | GTTTGCTGATGTCCTTT (258) |
| PARD6B | CATATAGTCATTAGTATG (259) | CTGGGAGAATATCCACG (260) |
| PAFAH1B1 | CGGCAAGCTTCTGGCTTC (261) | GCATTCAAAGCCCTG (262) |
| PIK3CG | CGAGATCTACGACAAGTACC (263) | CCGGTGCGTGGCCTTCCAGT (264) |
| BMP2 | CCACCATGAAGAATCTTTG (265) | ATTAAAGAAGAATCTCCGG (266) |
| DRD1 | GTGTCAGAGCCCCTGATGTG (267) | GTCCCGTCCATGGCAGAG (268) |
| PAX5 | CGTCAGTTCCATCAACAGG (269) | GGAAGCTGGGACTGGTTG (270) |
| S100A6 | CACCGACCGCTATAAGG (271) | GCCAAATGCGACGCGAGCG (272) |
| DRD2 | CATTGTCACCCTGCTGGTC (273) | GGTGTTGACTCGCTTGC (274) |
| HDAC7 | GTAGTAGCAGCACGCCCG (275) | AGGATGGGATTGGGGC (276) |
| HEY2 | GCAGCCCTGCTCCAGCCCA (277) | CTGAAGTTGTGGAGAGG (278) |

TABLE 2-continued

| Gene | Forward primer (SEQ ID) | Backward primer (SEQ ID) |
|---|---|---|
| INHBA | GGGGGAGAGGAGTGAACTG (279) | GAAGACATGCCAGGTGC (280) |
| SHH | GCTGGCCCGCCTGGCGGTGG (281) | GCAGTGGATATGTGCCTTGG (282) |
| BTK | GAATATTTTATCTTGGAGGA (283) | AGCCTTCCTGCCCATTTTT (284) |
| FOS | GAGGAGGCCTTCACCCTGCC (285) | TGCTCTTGACAGGTTCCACT (286) |

In the application, the term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element(s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the present application, meant as more particularly encompassing the term "consisting of" ("consist(s) of"), and the term "essentially consisting of" ("essentially consist(s) of").

Each of the relevant disclosures of all references cited herein is specifically incorporated by reference. The following examples are offered by way of illustration, and not by way of limitation.

EXAMPLES

A. Material and Methods

A.1. Isothermal Titration Calorimetry (ITC) Calculation

ITC measurements were made using VP-ITC VP-ITC200 calorimeters (MicroCal). MAST2-PDZ was titrated at 298 K by injections of the polypeptides (25-45 consecutive aliquots of 5-7 μL at 6-min intervals). Raw data were normalized and corrected for heats of dilution of polypeptides. Equilibrium dissociation constants ($K_D$) were determined performing nonlinear curve fitting of the corrected data to a model with one set of sites using the Origin7.0 software (OriginLab). All samples were prepared in a buffer containing 50 mM Tris-HCl, 150 mM NaCl, pH7.5. Data were recorded with MAST2-PDZ at an initial concentration of 30 μM and with peptide at initial concentrations ranging from 250 μM to 350 μM.

A.2. Cell Culture

Human neuroblastoma cells, SH-SY-5Y and human NT2-N cell culture, were described respectively in Prehaud C. et al (2010) and Prehaud C. et al (2005), and are detailed in the above-specification. The NS cells are grown in RPMI medium as described by manufacturer's instructions (www.cellomics.com/content/menu/Neuroscreen-1_Cells/).

A.3. Lentivirus Production

The nucleotide sequences of Neurovita 1 and Neurovita1 delta PDZ-BS were cloned from the plasmid G-[SP-(2aa)-TM-Cyto] described in WO2010/116258 application. The nucleotide sequences of Neurovita1 and Neurovita1 delta PDZ-BS (disclosed in WO2010/116258) and of Neurovita2 were obtained by PCR and cloned in the pLenti6.3/V5-TOPO® by using the TA cloning kit (K5315-20, Invitrogen, France). Lentiviruses were obtained in 293T cells, transfected with vectors encoding the Neurovita1, Neurovita1 delta PDZ-BS or the Neurovita2 polypeptides, by the standard procedures as described in Vitry S. et al (2009). HIV particles quantity was assayed by using the HIV p24 ELISA kit (Perkin Elmer, NEK050). Infectivity of recombinant lentivectors on NS, SH-SY-5Y and NT2-N cells were systematically monitored by qRT-PCR.

A.4. Kinome Profiling

Kinome profiling was undertaken by Pepscan presto (Netherlands) on PepChip Kinase arrays according to the manufacturer instructions (http://www.pepscan.com/presto/products-services/pepchip/#kinase-profiling). Briefly, NT2-N cells were either mock-infected (control) or infected with the neurosurvival rRABV CVS HQ (Prehaud C. et al, 2010) for 45 h before harvesting. The rRABV CVS HQ (CVS-NIV strain) has been deposited at the CNCM on the 1$^{st}$ of April, 2009 under deposit number 1-4140. 10000 mm$^2$ of NT2-N cells were treated in duplicates for each condition. Cell lysates were prepared in anti-proteases-containing MPER buffer (Pierce, Thermofisher, France) and supernatants were deep frozen in liquid nitrogen before using. The PepChip kinase arrays covered the entire human kinome (Manning G. Et al, 2002). Data were subjected to Kolmogorov-Smirnov statistical analysis with a cut-off of p=0.001 before validation. A threshold means ratio >1.96SE was chosen (high stringency). Dots represent the organized kinase cluster as defined by Gene Network Central pro (Qiagen, Germany)

A.5. Pathway-focused Profiling

Gene expression was monitored by using the following pathway-focused profiling PCR arrays from QIAGEN (Germany) according to the manufacturer's instructions (www.sabiosciences.com/RTPCR.php): the Human PI3K-AKT Signaling PCR Array (ref.: PAHS-058) and the Human Neurogenesis and Neural Stem Cell PCR Array (ref.: PAHS-404). Briefly 15.7 mm$^2$ of NT2-N cells were infected with 900 ng of p24 lentivectors. Total RNA was isolated by using the RNEasy purification kit (QIAGEN, including the DNAse 1 treatment) and subjected to cDNA synthesis (SABioscience, USA) and qPCR (ABI Fast 7500 real time PCR apparatus). Experiments were realized in duplicates and quality control was assayed for each PCR plate. Data were analyzed with the QIAGEN web interface (www.sabiosciences.com/perarraydataanalysis.php).

Fold regulations were calculated accordingly to the comparative method. In the comparative or ΔΔCt method of qPCR data analysis, the Ct values obtained from two different experimental RNA samples were directly normalized to a housekeeping gene and then compared. This method assumes that the amplification efficiencies of the gene of interest and the housekeeping genes are close to 100% (meaning a standard or calibration curve slope of −3.32).

First, the difference between the Ct values (ΔCt) of the gene of interest and the housekeeping gene was calculated for each experimental sample. Then, the difference in the ΔCt values (MCt), between the experimental and control samples (mock-infected cells) was calculated. The fold-change in expression of the gene of interest between the two samples is then equal to 2^(−ΔΔCt). The fold difference (fold change) is calculated by the equation 2(−ΔΔC(t). For the fold regulation, any fold regulation (or fold change) less than 1 (meaning that the gene is down regulated) was negatively inversed, changing the fractional number into a whole number [for example, for a gene having a fold change value of 0.31, the fold regulation given is −3.2 fold, meaning that this particular gene is down regulated by 3.2 fold].

Genes clustering was realized by using Gene Network Central pro (Qiagen, Germany).

A.6. Neurite Outgrowth

Neurite outgrowth assays have been extensively described in Prehaud C. et al, 2010. SH-SY5Y human neuroblastoma cells are seeded on 24-well plates (Cell Bind plastic ware, Corning, USA) at a density of 40,000 cells per well in non differentiating medium [DMEMFI2 (Invitrogen, U.K.) with 20% Fetal Bovine Serum plus 1% Pen:Strep and 1% Glutamine], and cultured overnight at 37° C. 24 h post seeding non differentiation medium is replaced with differentiating medium [Neurobasal medium (Invitrogen, U.K.) supplemented with B27 supplement (Invitrogen, U.K.), 1% P/S, 1% Glutamine and 1 mM db-cAMP (dibutyril c-AMP is membrane permeable, Sigma)], and the cells are incubated for 6 h. Then, cells are infected with 30 ng of p24 lentivector in differentiating medium. After 1 h of incubation, cells are washed once with differentiating medium, and after adding differentiating medium they are incubated for 24 h at 37° C. Thirty hours post differentiation, the cells are fixed with 3% paraformaldehyde in phosphate buffered saline (PBS) for 20 min at room temperature (RT) followed by treatment for 5 mn with 0.1% Triton-X-100 and 50% normal goat serum (NGS) in PBS for 1 h at RT. Neuronal specific anti βIII tubulin Ab (Promega, France) and anti-RABV nucleocapsid Ab are used to stain the neurite processes and to reveal RABV infection respectively. Alternatively, cells are also stained with crystal violet which preserves the neurites processes.

NS cells were monitored for 72 h and treated with 200 ng/ml of NGF at time=0 (one hit only). Neurite outgrowth (NO) was basically undertaken as described above for SH-SY5Y with the exception that the NO was monitored 72 h post infection and NS cells were always grown in their feeding medium (Cellomics, USA).

In both cases, SH-SY5Y human neuroblastoma cells and NS cells are imaged using a Leica DM 5000B UV microscope equipped with a DC 300FX camera (×40 or ×20 objectives) and analyzed using ImageJ 1.38× Software (Wayne Rasband, NIH, USA, http://rsb.info.nih.gov/ij/) and its plug-in NeuronJ (Meijering et al. 2004; http://www.imagescience.org/meijering/software/neuronj/). The average neurite length per neuron is determined from triplicate experiments.

A.7. Scratch Assay (Axon Regeneration)

For scratch-induced assays, 200 mm$^2$ of NT2-N cells (n=8), infected with 30 ng of p24 lentivectors, were seeded on poly-D-Lysin-laminin coated cell+(Sarstedt, Germany) 12 wells plastic ware, and were grown for two days in order to recover completely after trypsinisation. The medium was changed 2 h before scratching. Individual wounds were made with an injection needle (26GX1/2", 12-4.5). At least 10 scratching were made on each individual well. Cells were fixed with PFA (4%) 6 days post wounding and stained with crystal violet solution. Cells are imaged using a Leica DM 5000B microscope equipped with a DC 300FX camera (×20 objective) and analysed using ImageJ 1.38× Software (Wayne Rasband, NIH, USA, rsb.info.nih.gov/ij/) and its plug-in NeuronJ. The average percentage of neuron in regeneration is determined from 8 experiments.

A.8. Arborisation

Sholl analysis which is a mean of measuring dendritic arborisation was assayed according to Sahay A. et al and Lioy D T. et al Nature 2011. Neurite complexity was analysed from 8-bit images by using the ImageJ Sholl Analysis plug-in (http://www-biology.ucsd.edu/labs/ghosh/software/). Images were taken 72 h post infection (p.i.) with lentivectors.

A.9. Silencing of MAST2

MAST2 gene expression was silenced with the specific set of shRNA based lentiviruses developed by the RNAI Consortium (TRC, MIT and Harvard, sold by Thermoscientific-ABgene, RHS4533-NM_015112). Recombinant lentiviruses were produced as described above. 15.7 mm$^2$ of NT2-N cells were infected with 900 ng of p24 of each lentivector. The efficiency of silencing was assessed by qRT-PCR, 2 days post infection with the specific primer set QT00042574 (Qiagen, Germany). Then, cells were used immediately after for experiments A.10. Neuritogenesis in Mouse Fœtal Cortical Neurons E16 swiss mouse cortical neurons were prepared according to Vitry et al (2009). $10^4$ cortical neurons were plated on 96 well dark sided cell bind plates (#3340, Corning, USA) and infected with 10 ng p24/well of lentivectors (NV1 eGFP or NV1Δ eGFP) 2 hours after seeding. Medium was changed 12 hours after infection. Three days post infection medium was removed carefully and neurons were fixed with 4% PFA for 20 mn at room temperature. Plates were washed three times with PBS and then cells were permeabilized with 0.3% Triton X100 for 10 mn at room temperature. βIII neuronal tubulin immunofluorescence was carried out according to Loh Shy et al. (2008). Neurite outgrowth was monitored by high throughput screening on a cellomics (USA) CellInsight reader by using the neuronal profiling bioapplication (n=10 wells, 20 fields/well, 250 neurons per well). Student t test was carried out on GraphPad Prism 6 (USA).

A.11. Mice Experiments with Lentivectors NV1 eGFP and NV1Δ eGFP

Groups of 10 swiss mice (3 days old) were injected directly into brain with 100 ng p24 of each lentivector (vehicle was 1% BSA containing PBS) or vehicle alone (1 mouse) as described in Vitry et al (2003). Mice development and phenotype were recorded over a four-month period. Weight was monitored for 20 days post injection. 4 months after injection, animals were euthanized and brains were isolated for immunochemistry and real time PCR as described by Vitry et al (2003). Neurovita expression was monitored with e-GFP expression. Immunostaining for Map2 antigen was used to detect the dendrites. Immunostaining for GFAP (Glial fibrillary acidic protein) was used to monitor astrogliosis. The anti-map2 antibody was from SIGMA, US (M1406); the anti-GFAP antibody was from Dako (Z0334); the anti-GFP antibody was from Rockland (600-106-215).

B. Results

B.1. Kinome Profiling in NT2-N Cells During RABV-mediated Neuroprotection

Figure 3:
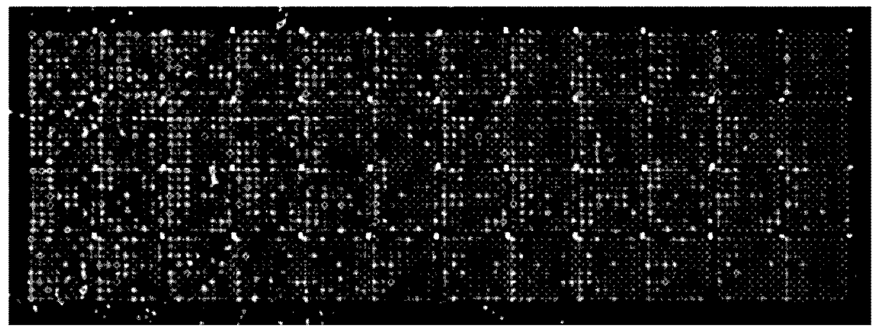
FIG. 3. Identification of kinases stimulated during RABV mediated neuroprotection: Kinome profiling in human post mitotic neurons NT2-N. (A) Slide of peptide microarrays covering the entire human kinome. (B) Schematic representation of the kinome profiling obtained for NT2-N cells infected with the recombinant rRABV (RABV-CVSHQ) for 45 h. The dots represent the kinases which are activated upon rRABV neurosurvival infection in NT2-N cells.
Figure 3:
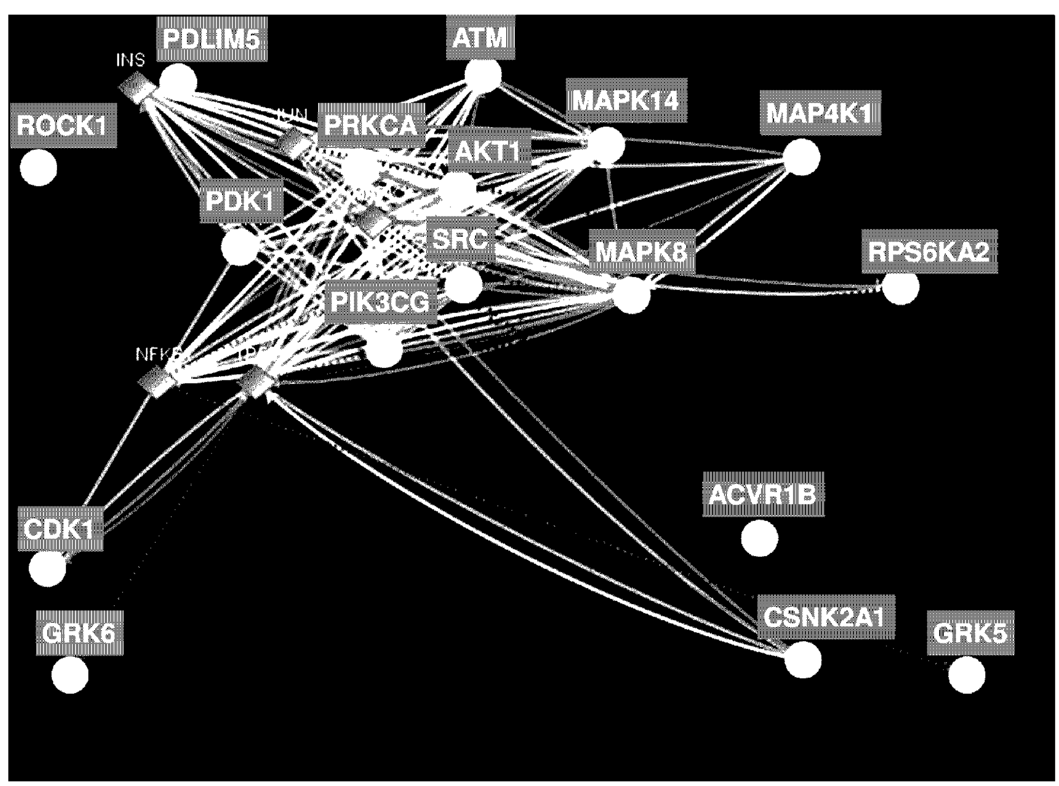

Incubation of the PepChip Kinomics array (covering the entire human kinome, i.e., more than 518 kinases) with cell lysates derived from NT2-N cells infected (45 h) with the neurosurvival rRABV CVS HQ reveals that only 17 kinases are stimulated, in high stringency conditions (Table 3). All these kinases are linked together, as shown in FIG. 3B.

TABLE 3

| Kinase | Name | Fold regulation of activation | Kinase Group |
|---|---|---|---|
| AKT1* | protein kinase B | 6.69693 | AGC |
| PIK3CG* | phosphoinositide-3-kinase, catalytic, gamma polypeptide | 3.81055 | Other |
| CSNK2A1* | casein kinase 2, alpha 1 | 3.30198 | Other |
| SRC | proto-oncogene tyrosine-protein kinase | 2.52567 | TKL |
| PDLIM5 | PDZ and LIM domain 5 | 2.47084 | TKL |
| MAP4K1 = MEKKK1 | mitogen-activated protein kinase kinase kinase kinase 1 | 2.26839 | STE |
| ROCK1 | Rho-associated, coiled-coil containing protein kinase 1 | 2.14479 | AGC |
| GRK6 | G protein-coupled receptor kinase 6 | 2.10186 | AGC |
| GRK5 | G protein-coupled receptor kinase 5 | 2.05385 | AGC |
| PDK1* | pyruvate dehydrogenase kinase, isozyme 1 | 1.82555 | AGC |
| CDK1 | cyclin-dependent kinase 1 | 1.82134 | GMC |
| ACVR1B | activin A receptor, type IB | 1.65481 | TKL |
| RPS6KA2 | ribosomal protein S6 kinase, 90 kDa | 1.65099 | AGC |
| MAPK14* = p38 alpha | mitogen-activated protein kinase 14 | 1.61328 | CMGC |
| ATM* | ataxia telangiectasia mutate | 0.61628 | Atypical |
| PRKCA* | protein kinase C, alpha | 0.35932 | PKC |
| MAPK8* JNK, JNK1, JNK1A2, JNK21B1/2, PRKM8, SAPK1 | mitogen-activated protein kinase 8 | 0.06722 | CMGC |

Kolmogorov-Smirnov statistical analysis; Cut-off p = 0.001

Threshold means ratios >1.96 SE

*involved in the Pi3K-AKT signalling pathway

Figure 4:
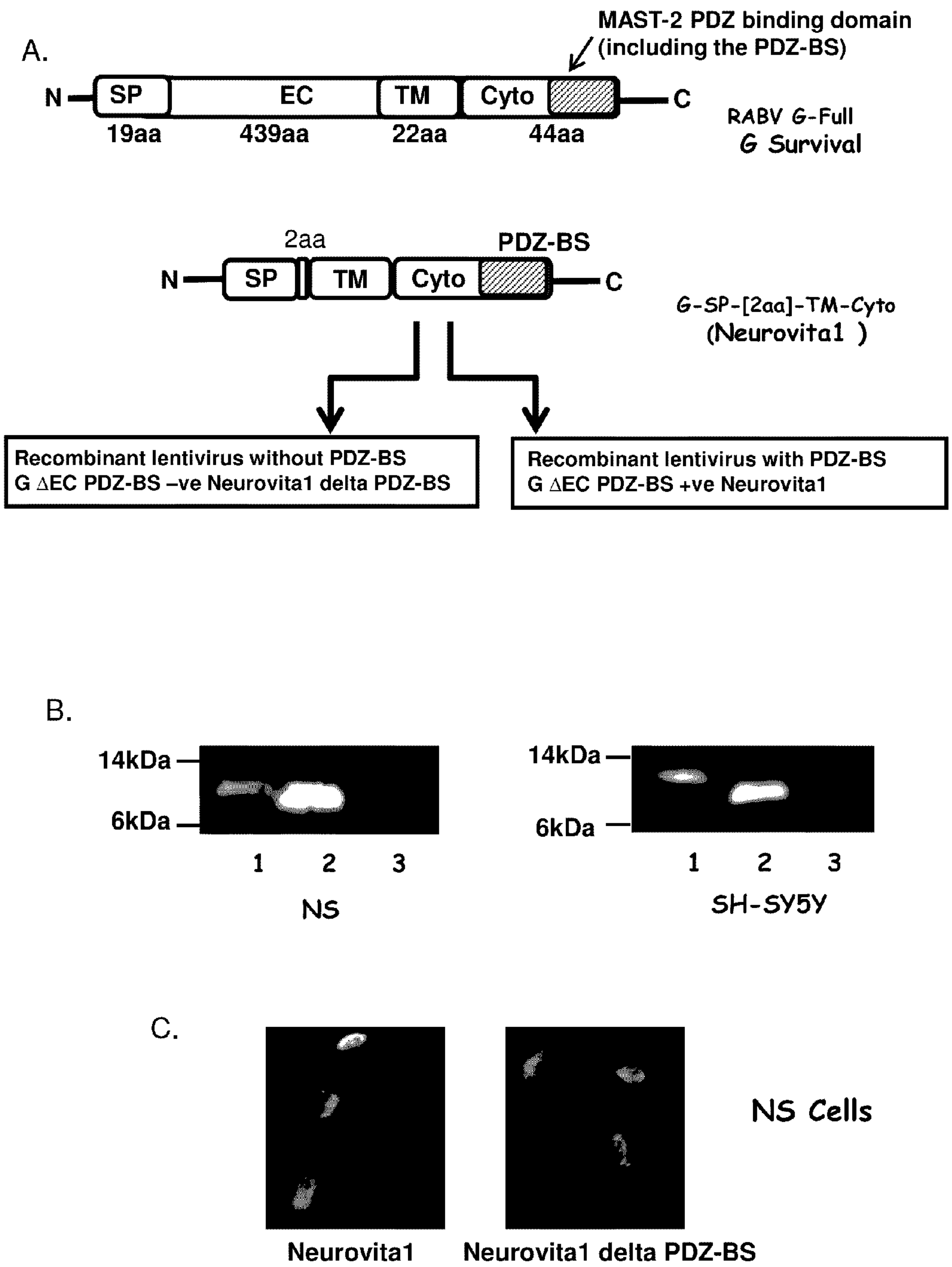
FIG. 4. (A) Schematic representation of G protein (first line) and Neurovita 1 polypeptide (second line); SP: Signal peptide, EC: extracellular domain, TM: transmembrane domain, Cyto: Cytoplasmic domain, PDZ-BS: PDZ binding site. The number of amino acid residues (aa) for each domain is also indicated (B) Expression of Neurovita1 and Neurovita 1 delta PDZ-BS by lentivectors in NS cells or human neuroblastoma cells (SH-SY5Y) by Western Blot 48 h post infection (p.i.) (1. Neurovita1; 2. Neurovita1 delta PDZ-BS; 3. Negative control) (C) Expression of Neurovita1 and Neurovita1 delta PDZ-BS by lentiviral vectors in NS cells by immunofluorescence 48 h p.i. In (B) and (C), detection was carried out with antibodies specific for RABV Cyto-G.

B.2. Neurite Outgrowth in SH-SY5Y Cells and in NS Cells Transduced with Neurovita1-expressing Lentivectors The following constructs were designed: Neurovita1 polypeptide and Neurovita1 delta PDZ-BS polypeptide (FIG. 4A). Their nucleotide and protein sequences are as follows:

Neurovita 1

-polynucleotide:

(SEQ ID NO: 8)

```
ATGGTTCCTCAGGCTCTCCTGTTTGTACCCCTTCTGGTTTTT
CCATTGTGTTTTGGGGGGAAGTATGTATTACTGAGTGCAGGG
GCCCTGACTGCCTTGATGTTGATAATTTTCCTGATGACATGT
TGTAGAAGAGTCAATCGATCAGAACCTACGCAACACAATCTC
AGAGGGACAGGGAGGGAGGTGTCAGTCACTCCCCAAAGCGGG
AAGATCATATCTTCATGGGAATCACACAAGAGTGGGGGTCAG
ACCAGACTGTGA.
```

-continued

-polypeptide:

(SEQ ID NO: 9)

```
MVPQALLFVPLLVFPLCFGGKYVLLSAGALTALMLIIFLMTC
CRRVNRSEPTQHNLRGTGREVSVTPQSGKIISSWESHKSGGQ
TRL.
```

Neurovita1 delta PDZ-BS (without the PDZ-BS domain)

-polynucleotide:

(SEQ ID NO: 10)

```
ATGGTTCCTCAGGCTCTCCTGTTTGTACCCCTTCTGGTTTTT
CCATTGTGTTTTGGGGGGAAGTATGTATTACTGAGTGCAGGG
GCCCTGACTGCCTTGATGTTGATAATTTTCCTGATGACATGT
TGTAGAAGAGTCAATCGATCAGAACCTACGCAACACAATCTC
AGAGGGACAGGGAGGGAGGTGTCAGTCACTCCCCAAAGCGGG
AAGATCATATCTTCATGGGAATCACACAAGAGTGGGGGTTGA.
```

-polypeptide:

(SEQ ID NO: 11)

```
MVPQALLFVPLLVFPLCFGGKYVLLSAGALTALMLIIFLMTC
CRRVNRSEPTQHNLRGTGREVSVTPQSGKIISSWESHKSGG.
```

The Western Blot experiments show that Neurovita1 and Neurovita 1 delta PDZ-BS are expressed in both cell lines (FIG. 4B). Moreover, FIG. 4C confirms that Neurovita1 and Neurovita 1 delta PDZ-BS exhibit a typical immunofluorescence pattern expected for Rhabdovirus glycoprotein.

Neurite outgrowth assay in SH-SY5Y cells shows that the Neurovita1 polypeptide exhibits a strong neurite outgrowth phenotype, which is PDZ-BS mediated (compare the polypeptide with and without the PDZ-BS domain, in FIG. 5A). Similarly, neurite outgrowth assay in NS cells shows that the Neurovita1 polypeptide not only exhibits a strong neurite outgrowth phenotype, which is PDZ-BS mediated but also increases the neurites network in the infected culture (FIG. 5B).

B.3. Molecular Signature of Neurovita1-mediated Protection

Pathway-focused gene expression profiling (Human Neurogenesis and Neural Stem Cell Array and PI3K/Akt signalling pathway) of NT2-N cells transfected with Neurovita1-expressing lentivector reveals a genetic molecular signature as represented in FIGS. 6A and 6B. This signature is characterized by the following fold regulation: SHH gene (−1.82), ROBO1 gene (−1.69), PTN gene (−1.83), POU4F1 gene (−1.50), PARD6B gene (−1.62), PAFAH1B1 gene (−1.57), INHBA gene (−1.92), HEY2 gene (−3.49), HDAC7 gene (−1.60), DRD2 gene (−1.64), S100A6 gene (+3.38), PAX5 gene (+1.97), DRD1 gene (+1.59), BMP2 gene (+1.52) and PIK3CG gene (+1.79).

This gene expression profiling was compared with the one obtained in NT2-N cells knocked out for the human MAST2 protein (76% of MAST-2 silencing), and also transfected with Neurovita1-expressing lentivector. Thus, the cluster of genes identified in FIG. 7B represents the genes regulated in Neurovita1 infection but differently regulated in NT2-N cells wherein the MAST2 expression was knocked down. The genetic molecular signature is characterized by the following fold regulation: SHH gene (−2.52), ROBO1 gene (+1.00), PTN gene (+1.01), POU4F1 gene (+1.21), PARD6B gene (+1.46), PAFAH1B1 gene (+1.03), INHBA gene (−1.31), HEY2 gene (−2.27), HDAC7 gene (−1.17), DRD2 gene (−1.15), S100A6 gene (−1.44), PAX5 gene (−1.01), DRD1 gene (+2.31), BMP2 gene (+1.23) and PIK3CG gene (−2.24). Of note is the inverted regulation of the genes ROBO1, PTN, POU4F1, PARD6B, PAFAH1B1, S100A6, PAX5 and PIK3CG when MAST2 expression is silenced, leading to the conclusion that MAST-2 controls the gene survival pattern mediated by Neurovita.

B.4. Axon Regeneration

Scratch assay performed on NT2-N cells shows that only Neurovita1-infected NT2-N cells can regenerate their axons post-scratching. Neither non infected nor Neurovita1 delta PDZ-BS-infected cells can do it (p<0.0001) (FIG. 8).

B.5. Molecular Signature of Neurovita1-mediated Axon Regeneration

FIG. 9 represents the pathway-focused gene expression profiling (on Human Neurogenesis and Neural Stem Cell and Human PI3K-AKT Signaling PCR Arrays) implementing Neurovita1-infected NT2-N cells tested after scratching (point B.4. above) as compared to non-infected cells after scratching. The genetic molecular signature is characterized by the following fold regulation:

FIG. 9A: Human PI3K-AKT Signaling PCR Array

EIF2AK2 (+1.57), FASLG (+2.13), FOXO3 (+1.5), GSK3B (+1.53), HRAS (+1.54), IRAK1 (+1.51), MAPK8 (+1.53), MTCP1 (+1.76), PDK1 (+2.71), PIK3CG (+3.78), RHEB (+1.84), RPS6KA1 (+1.99), TCLIA (+2.10), APC (−1.82), BTK (−1.61), GRB10 (−1.78), RPS6KB1 (−1.68) and TLR4 (−1.63); and FIG. 9B: Human Neurogenesis and Neural Stem Cell Array ALK (+2.49), GDNF (+1.5), NPTX1 (+1.56), NRG1 (+1.52), PAX5 (+1.65), S100A6 (+1.99), ASCL1 (−1.56), BDNF (−1.78), BMP15 (−2.27), BMP4 (−1.58), EGF (−2.10), INHBA (−1.89), NDP (−1.68), NEURODI (−3.92), NOTCH2 (−1.57), POU3F3 (−1.55) and ROBO1 (−1.98).

These molecular signatures show a strong regulation of genes involved in PI3K/Akt signalling pathway (FIG. 9A) and of genes involved in cell proliferation, adhesion and differentiation, growth factors and synaptic functions (FIG. 9B), and demonstrate that these genes are highly connected (FIG. 9C).

B.6. Design of Polypeptides with Optimized Sequences (Dissociation Constant and Thermodynamic Parameters)

From our high resolution NMR structures of MAST2-PDZ in complex with endogenous and viral ligands (Protein Data Bank codes 2KQF & 2KYL), an unexpected large surface of interaction between the domain and the polypeptides was characterized. It was demonstrated that the polypeptides interact similarly with the PDZ target not only through the very last four amino acids of canonical C-terminal regions, but also with another anchoring region at the N-terminal end of the assayed peptides. Even if the C-terminal residues of the peptides contribute mainly to the binding strength with MAST2-PDZ, the presence of an additional N-terminal interaction implying a specific position of the peptide and an original feature of the PDZ domain clearly reinforces the specificity and affinity of the interaction. This large and original surface of interaction is an opportunity to optimize peptide affinity and specificity for MAST2-PDZ.

Our detailed thermodynamical and structural (at an atomic level) descriptions of MAST2-PDZ/peptide complexes (FIG. 10) were used to design optimized sequences. We proposed a model of relationship between the affinity of polypeptides for MAST2-PDZ (Neurovita) and their neurosurvival properties, in which the highest the affinity of polypeptides for the MAST2-PDZ domain (i.e., the lowest the $K_D$), the highest the neurosurvival properties of these polypeptides (FIG. 10B).

In order to retain the high specificity driven by the N-terminal and C-terminal binding sites of the peptide and selected by the endogenous and viral ligands for the interaction with MAST2-PDZ, the terminal sequences were left unchanged. The central region of the peptide was modified in order to increase the affinity of sequences for MAST2-PDZ, by designing polypeptides whose MAST2-binding domain is from 11 to 13 amino acid residues. The general structure of these polypeptides is represented in FIG. 11A.

The polypeptides as described in the list below have been designed, and a complete thermodynamical description for each MAST2-PDZ/polypeptide complex (with the estimation of enthalpic and entropic parameters taking into account the flexibility and the polar contacts contributions to the binding strength) has been carried out (Table 4):

- a polypeptide ending with the MAST-2 binding domain as defined in SEQ ID NO:235;
- a polypeptide as defined in SEQ ID NO:9, ending with the MAST-2 binding domain as defined in SEQ ID NO:1;
- a polypeptide as defined in SEQ ID NO:215, ending with the MAST-2 binding domain as defined in SEQ ID NO:67;
- a polypeptide as defined in SEQ ID NO:210, ending with the MAST-2 binding domain as defined in SEQ ID NO:64;
- a polypeptide as defined in SEQ ID NO:218, ending with the MAST-2 binding domain as defined in SEQ ID NO:209;
- a polypeptide as defined in SEQ ID NO:217, ending with the MAST-2 binding domain as defined in SEQ ID NO:208;
- a polypeptide as defined in SEQ ID NO:213, ending with the MAST-2 binding domain as defined in SEQ ID NO:74;
- a polypeptide as defined in SEQ ID NO:211, ending with the MAST-2 binding domain as defined in SEQ ID NO:65;
- a polypeptide as defined in SEQ ID NO:214, ending with the MAST-2 binding domain as defined in SEQ ID NO:66;
- a polypeptide as defined in SEQ ID NO:216, ending with the MAST-2 binding domain as defined in SEQ ID NO:68; and
- a polypeptide as defined in SEQ ID NO:212, ending with the MAST-2 binding domain as defined in SEQ ID NO:71.

TABLE 4

| Polypeptide | Sequence of the MAST-2 binding domain | SEQ ID | MAST2-PDZ Kd (μM) (dissociation constant) | MAST2-PDZ erreur |
|---|---|---|---|---|
| ATT13 | **SWESHKSGGETRL** | 235 | 0.57 | +/-0.052 |
| VIR13 (Neurovita 1) | **SWESHKSGGQTRL** | 1 | 1.26 | +/-0.11 |
| 439 | **SWEVHTQQTRL** | 67 | 0.21 | +/-0.002 |
| 441 (Neurovita 2) | **SWEVHGGQTRL** | 64 | 0.12 | +/-0.001 |
| 442 | **SWEVHASGGQTRL** | 209 | 0.49 | +/-0.001 |
| 443 | **SWAEAQHTQQTRL** | 208 | 0.4 | +/-0.003 |
| 453 | **SWEVYTGQTRL** | 74 | 0.238 | — |
| 454 (Neurovita 3) | **SWEVHGQQTRL** | 65 | 0.0629 | — |
| 455 | **SWEVHTGQTRL** | 66 | 0.13 | — |
| 460 | **SWEVAGGQTRL** | 68 | 0.188 | — |
| 461 | **SWEVATQQTRL** | 71 | 0.126 | — |

| Polypeptide | MAST2-PDZ ΔH (enthalpy) | MAST2-PDZ TΔS (entropy) | n (stoechiometry) | PTPN4-PDZ Kd (μM) |
|---|---|---|---|---|
| ATT13 | — | — | — | 160 |
| VIR13 (Neurovita 1) | -9929 | -1878.39 | 0.9996 | 560 |
| 439 | -8454 | 646.66 | 1.022 | |
| 441 (Neurovita 2) | -10230 | -808.176 | 1.069 | 554 |
| 442 | -10340 | -1737.34 | 1.037 | — |
| 443 | -9088 | -360.878 | 1.007 | — |
| 453 | -6511 | 2521.08 | 0.846 | — |
| 454 (Neurovita 3) | -8715 | 1108.56 | 1.01 | — |
| 455 | -9434 | -42.316 | 0.906 | — |
| 460 | -7484 | 1686.68 | 0.916 | — |
| 461 | 7688 | 1722.44 | 0.806 | — |

Measure of the dissociation constant ($K_D$) and thermodynamics parameters (ΔH and TΔS) by ITC of MAST2-PDZ shows a significant gain of affinity of the optimized polypeptides of the invention for the MAST2-PDZ domain (Table 4). Thus, all the assayed polypeptides have a $K_D$ lower than 0.5 μM, i.e., a gain of affinity of at least 2.5 as compared to Neurovita1. The $K_D$ of the assayed polypeptides varies from 0.0629 to 0.49 μM, i.e. a gain of affinity as compared to Neurovita1 ranging from 2.5 to 20. A particularly interesting polypeptide is the polypeptide 454 (Neurovita3), whose MAST2-binding domain consists of SWEVHGQQTRL SEQ ID NO:65), which has a $K_D$ of 0.0629 μM.

Consequently, by modifying the sequence of the central flexible linker of the Neurovita sequence, taking into account the entropy/enthalpy compensation of the complexes, the affinity of the polypeptides of the invention for MAST2-PDZ was drastically enhanced.

As an example, the Neurovita2 polypeptide (whose MAST2-binding domain consists of SWEVHGGQTRL) (SEQ ID NO:64) shows a 10 fold gain in affinity for the MAST2-PDZ domain as compared to Neurovita1 (0.12 μM versus 1.26 μM). The comparison of the sequence of the cytoplasmic domain of Neurovita2 with the one of Neurovita1 and Neurovita1 delta PDZ-BS is described in FIG. 11B.

Expression of the Neurovita2 polypeptide in NS cells infected by a lentivector (in which the Neurovita2 sequence was cloned) was similar to the one obtained with infection by lentiviral vectors expressing Neurovita1 and Neurovita1 delta PDZ-BS polypeptides (FIG. 11C).

B.7. Neurite Outgrowth in NS Cells Infected with Neurovita2-expressing Lentivectors Neurite outgrowth assay in NS cells infected with Neurovita2-expressing lentivectors shows that Neurovita2, like Neurovita1, exhibits a strong neurite outgrowth phenotype which is PDZ-BS mediated ($p<0.0001$) (FIG. 12).

B.8. Arborisation in NS Cells Transduced with Neurovita2-Expressing Lentivectors Arborisation in NS cells transduced with Neurovita2-expressing lentivectors demonstrates that the Neurovita2-mediated neurite outgrowth in NS cells is characterized by a stronger complexity of the neurite tree which is specific of sympathetic neurons fully functional, as compared to neurovita1. Thus, Neurovita 2 increases the strength and complexity of the neurite tree which is a trait of functionality and survival (FIG. 13).

B.9. Molecular Signature of Neurovita2-Mediated Neuroprotection

The expression of four cellular genes, previously identified, have been assayed in NT2-N cells, 24 h p.i. FIG. 14 shows the following fold down-regulation: BTK (−1.64), FOS (−1.82), DRD2 (−2.35) and POU4F1 (−1.53).

B.10. Genetic Molecular Signatures of Neurovita 1 and Neurovita2 Molecules

Table 5 presents a summary of the fold regulation obtained with the Neurovita 1 or Neurovita2 infection of NT2-N cells.

A Black square indicates a gene which is regulated in the scratch assay; a white square indicates a gene for which regulation is inverted when MAST2 is silenced; a hatched square indicates a gene regulated in Neurovita2 infection (threshold x<−1.5, or x>+1.5).

The core of neurosurvival gene signature is then ROBO1, POU4F1, PTN, PARD6B and PAFAH1B1 which are genes regulated in the same way in both Neurovita1 and Neurovita2 infections and which regulation is inverted when MAST2 is silenced. Of note ROBO1 is also downregulated in the scratch assay.

The other genes are used to characterize more specifically either Neurovita1 (i.e., PIK3CG, BMP2, DRD1, PAX5, S100A6, HDAC7, HEY2, INHBA, SHH) or Neurovita2 (i.e., DRD2, BTK, FOS).

These genes and their function are listed in Table 7 below.

TABLE 5

| Genes | Neurovita 1 | Neurovita 2 |
|---|---|---|
| PIK3CG | 1.79 | -1.14 |
| BMP2 | 1.52 | -1.09 |
| DRD1 | 1.59 | -1.19 |
| PAX5 | 1.97 | -1.37 |
| S100A6 | 3.38 | -1.05 |
| DRD2 | -1.64 | -2.35 |
| HDAC7 | -1.6 | -1.05 |
| HEY2 | -3.49 | -1.03 |
| INHBA | -1.92 | 1.3 |
| PAFAH1B1 | -1.57 | -1.04 |
| PARD6B | -1.62 | -1.34 |
| POU4F1 | -1.5 | -1.53 |
| PTN | -1.83 | -1.29 |
| ROBO1 | -1.69 | -1.07 |
| SHH | -1.82 | -1.10 |
| BTK | -1.02 | -1.64 |
| FOS | -1.41 | -1.82 |

Genes regulated for Neurovita 1 axon regeneration

Genes disregulated when MAST2 is silenced

Genes regulated in Neurovita 2

>-1.5

<-1.5

-1.5<x<1.5

Table 6 is a heat map representation of the Neurovita1 genetic molecular signature (a) and Neurovita 2 genetic molecular signature (b).

TABLE 6 a)

| | | | |
|---|---|---|---|
| PIK3CG | S100A6 | INHBA | PTN |
| BMP2 | DRD2 | PAFAH1B1 | ROBO1 |
| DRD1 | HDAC7 | PARD6B | SHH |
| PAX5 | HEY2 | POU4F1 | BTK |
| FOS | | | |

b)

| | | | |
|---|---|---|---|
| PIK3CG | S100A6 | INHBA | PTN |
| BMP2 | DRD2 | PAFAH1B1 | ROBO1 |
| DRD1 | HDAC7 | PARD6B | SHH |
| PAX5 | HEY2 | POU4F1 | BTK |
| FOS | | | |

TABLE 7

| Genes | Known functions |
|---|---|
| | Neurovita 1 |
| PIK3CG | Familly member of the PI3/Akt signaling pathway (regulated by PTEN) |
| PAX5 | Regulator cell differentiation |
| S100A6 | Regulator cell cycle and cell proliferation |
| PAFAH1B1 | Regulator cell motility and cell migration |
| PARD6B | Regulator cell cycle and cell proliferation |
| POU4F1 | Transcription factor, repression early neurogenic genes, control terminal differentiation |
| PTN | Cytokine, regulator cell cycle |
| ROBO1 | Regulator cell adhesion |
| INHBA | Negative regulator of cell cycle |
| | Neurovita 2 |
| BTK | Regulator neurite outgrowth |
| FOS | Positive regulator of Apoptosis |
| DRD2 | Inhibitor of Wnt signaling pathway (Wnt is a major signaling pathway involved in neuronal growth, survival and branching) |
| POU4F1 | Transcription factor, repression early neurogenic genes, control terminal differentiation |

B.11. Transcription of rRABV and Lentivectors in NT2-N Cells

NT2-N cells were either infected with recombinant rabies viruses (rRABV CVS HQ, or rRABV CVS HΔ4) or the lentivectors as described above. rRABV CVS HQ virus expresses a full length G protein ending with a MAST-2 binding domain as defined in SEQ ID NO:1; rRABV CVS HΔ4 virus expresses a full length G protein ending with a MAST-2 binding domain consisting of SEQ ID NO:1 in which the Q, T, R and L residues have been deleted.

Total RNA were extracted 24 h p.i. for rRABV infections and 48 h for lentivectors infections. The specific transcription of the recombinant viruses (rRABV, lentiviruses) was assayed by RT-QPCR. The graph showed that NT2-N cells are efficiently infected with both types of viruses.

B.12. Transcription of a Representative Set of Immunity Genes in NT2-N Cells

The transcription was assayed by RT-qPCR in the cultures harvested above (FIG. 15).

The relative fold induction of a set of immunity genes were assayed in NT2-N cells infected with either the CVS-HQ strain or the CVS HΔ4 strain. Comparison of FIGS. 16A and 16B shows that the induction of immunity gene cluster and neurosurvival phenotype are dissociated.

Moreover, the relative fold induction of a set of immunity genes were assayed in NT2-N cells infected with lentiviral vectors expressing the Neurovita1, Neurovita1 delta PDZ-BS or Neurovita2. FIG. 16B shows that none of the Neurovita polypeptides alone is able to trigger immune gene response in human post mitotic neurons.

B.13. Axon Regeneration

FIG. 8 has shown that Neurovita1-infected NT2-N cells can regenerate their axons post-scratching. The inventors have assayed the involvement of MAST-2 in the regeneration mechanism.

As demonstrated in FIG. 17C, the silencing of the MAST2 expression (NV1/siMAST2) dramatically decreases the axon regeneration post-scratching, meaning that the promotion of axon regeneration by lentivector NV1 in human post mitotic dopaminergic Neurons (NT2-N) is dependent upon the expression of MAST2.

FIG. 17D shows that, like Lentivector Neurovita1 (NV1), Lentivector Neurovita2 (NV2) promotes axon regeneration in human post mitotic dopaminergic Neurons (NT2-N).

B.14. Protection Against Excessive Arborisation by Neurovita2

As shown in FIG. 18A, addition of KCl in non-infected NS cells (black squares) stimulates excessive outgrowth and arborisation. This observation is explained by the fact that KCl mimicks the depolarizing effects of persistent neuronal activity (neuron firing).

Infection with Neurovita2 lentivector in KCl-treated NS cells reduces the outgrowth and arborisation of NS cells as compared to the same treated, but non-infected, cells (stars, FIG. 18B). These results demonstrate that Neurovita2, not only stimulates the pathways involved in neuritogenesis, but also protects against excessive arborisation by controlling these pathways and by avoiding their runaway. Interestingly, this modulating effect of Neurovita 2 is also a sign for its non toxicity.

B.15. Protection Against LiCl Toxicity by Neurovita 1 and Neurovita2

As shown in FIG. 19A, addition of LiCl in non-infected NS cells inhibits neuritogenesis.

Neurovita 1 or Neurovita2 lentivector, but not Neurovita 1 Δ PDZ-BS lentivector, exhibits a neurite outgrowth phenotype which is PDZ-BS mediated in LiCl-treated NS cells (FIG. 19B). These results demonstrate that Neurovita 1 and Neurovita2 protects against the toxic effect of LiCl.

B.16. Neurite Outgrowth in NS Cells Infected with RABV G and Neurovita1-derived Polypeptides, Delivered by Lentivectors 6 types of polypeptides have been assayed (FIG. 20A): the RABV G full protein, the RABV G protein deleted for the PDZ-BS domain, the neurovita1 polypeptide, the neurovita1 polypeptide deleted for the PDZ-BS domain, the cytosolic form of the neurovita1 polypeptide and the cytosolic form of the neurovita1 polypeptide deleted for the PDZ-BS domain. FIG. 20 shows that, in neurite outgrowth assay, the neurovita1 polypeptide is the optimized form.

B.17. Expression of Neurovita Polypeptides from a Bicistronic Lentivector

Various Neurovita polypeptides (NV1, NV1Δ, NV2 and NV3) have been expressed via a bicistronic lentivector in NS cells. All these Neurovita polypeptides have been correctly expressed (Western Blot). NV1 and NV2 mRNAs are found at approximately the same level, whereas NV3 mRNAs are found at a higher level (FIG. 21).

The experiments also show that the GFP protein is correctly and sufficiently expressed in cells from this bicistronic lentivector B.18. Neurite Outgrowth and Arborisation in NS Cells Transduced with Neurovita3-expressing Lentivectors Arborisation experiments in NS cells transduced with Neurovita3-expressing lentivectors demonstrates that Neurovita3 promotes a strong complexity of the neurite tree as compared to a negative control (FIG. 22A). As reported previously in Table 4, Neurovita 3 has an affinity for MAST2 that is 20 times higher than the one of NV1.

Moreover, neurite outgrowth assay in NS cells infected with Neurovita3-expressing lentivectors shows that Neurovita3 exhibits a strong neurite outgrowth phenotype, more importantly than Neurovita1 ($p<0.00001$) and Neurovita 2 ($p<0.0003$) (FIGS. 22 B and C).

A comparison of the number of crossings (arborisation) between NV1, NV2 and NV3 has demonstrated that NV3 promotes neurite tree arborisation in NS cells more efficiently than NV1 ($p<0.0001$) and than NV2 ($p<0.0007$) (FIG. 23).

B.19. Experiments with a Cytosolic Form of Neurovita3

The Neurovita3 (NV3) polypeptide and its cytosolic form (NV3 cyto) (FIG. 24A) has been assayed for expression, for neurite outgrowth and for arborisation in NS cells. NV3 polypeptide has a high affinity for MAST2 (20× higher than the one of NV1), is processed by the ER and Golgi, and possesses a transmembrane domain (TM) domain allowing its anchorage into the cytoplasmic membrane. The NV3cyto polypeptide has the same affinity for MAST-2 than NV3, but is a cytosolic molecule.

Transcription analysis, via the bicistronic lentivector (FIG. 24B) shows that NV3cyto is correctly expressed, but at a lower level than NV3 (FIG. 24C). The expression of GFP from this biscistronic lentivector is also correct (FIG. 24D).

Arborisation experiments in NS cells transduced with NV3- and NV3 cyto-expressing lentivectors demonstrates that NV3cyto does not promote a neurite tree as complex as NV3 does (FIG. 25A).

Moreover, neurite outgrowth assay in NS cells infected with NV3- and NV3 cyto-expressing lentivectors confirms that NV3cyto promotes neurite outgrowth in NS, but not as efficiently as NV3 does. However, NV3-cyto is as good as NV1 (anchored form) to promote neurite outgrowth in NS cells (FIGS. 25B and 25C).

Interestingly, the absence of SP and TM domains in NV3cyto (absence which is known to reduce the neurite outgrowth promotion of Neurovita polypeptides; see NV1cyto in FIG. 20B) is counterbalanced by the high affinity of NV3 cyto (and NV3) for MAST2.

This conclusion is confirmed in neurite tree arborisation experiments, wherein NV3-Cyto is as good as NV1 to promote neuritic tree arborisation in NS cells (FIG. 26A, top panel).

Altogether, these experiments demonstrate that the neurite outgrowth promotion and neurite tree arborisation promotion of Neurovita polypeptides, such as the polypeptides of the invention, are dependent upon two factors: (1) the affinity of this polypeptide for MAST2, and (2) the anchoring of this polypeptide in the cytoplasmic membrane. Thus, a polypeptide, anchored into the cytoplasmic membrane and having a MAST-2 affinity comparable to the one of Neurovita1 (1.26 μM) or higher, is efficient to promote neurite outgrowth and neurite tree arborisation. Moreover, a cytosolic polypeptide having a MAST-2 affinity higher than the one of Neurovita1, and preferably comparable to the one of Neurovita3, is still efficient to promote neurite outgrowth and neurite tree arborisation, despite the absence of anchoring in the membrane.

B.20. Neuritogenesis in E16 Mouse Foetal Cortical Neurons

Neurite outgrowth experiments demonstrate that NV1 stimulates neuritogenesis in E16 mouse foetal cortical neurons (FIG. 27), in agreement with the results obtained in SH-SY-5Y and NS cells.

B.21. Absence of Toxicity of NV1 or NV1ΔLentivectors for Newborn Mice Infected with Lentivectors by Intracerebral Route As reported in FIG. 28A, there is no difference of weight between non-infected mice or mice infected with NV1 or NV1Δlentivectors. Moreover, no obvious phenotypic difference between those different mice could be detected, at day 4 or 20 post injection (FIG. 29).

Immunofluorescence histochemistry brains analysis indicated that NV1 (eGFP) and NV1Δ(eGFP) are expressed in the neurons of the striatum (FIGS. 30 and 31, panels marked with the neuronal marker Map2). Both for NV1 (eGFP) and NV1Δ(eGFP) infection, astrogliosis is very mild (FIGS. 30 and 31, panels marked with GFAP).

In addition, NV1 infected neurons exhibited neuritogenesis and extended differentiation of the dendritic-axonal tree (FIG. 30B), suggesting that NV lentivector allows neuritogenesis and neurite tree development not only in vitro but also in vivo. These in vivo results confirm, one the hand, the in vivo efficiency of the Neurovita polypeptides, such as NV1, and on the other hand, the safety of these Neurovita polypeptides on animal development, and in particular on brain development.

BIBLIOGRAPHY

Andrews, P W, 1998, APMIS, 106.158 to 167

Babault N et al 2011 Structure 19(10) 1518-24

Blondel et al., 2005, Poliovirus, pathogenesis of poliomyelitis, and apoptosis, CTMI, 289, 25-56.

Boulaire et al.; Advanced Drug Delivery Reviews 61, 2009, 589-602.

Gaitonde et al, Cell Growth and Differenciation, January 2001 Vol. 12, 19-27.

Guillemain, I., The Journal of Comparative Neurology, 2000.422, 380-395.

Jackson et al. 2008, J. Neurovirology, 14(5), 368-75.

Lafon M. et al, J Immunol. 2008 June 1; 180(11):7506-15.

Lafon M. et al, J Mol Neurosci. 2006; 29(3):185-94.

Lafon, M. Adv Virus Res. 2011; 79:33-53. Review

Loh S H Y et al, Cell Death and Differentiation. 2008 15, 283-298.

Megret F. et al. Hum Immunol. 2007 April; 68(4):294-302. (Epub 2006 Dec. 28)

Mentis et al. J Neurosci Methods. 2006 October 30; 157(2):208-17.

Morimoto K et al. Proc Natl Acad Sci USA. 1998 March 17; 95(6):3152-6

Owens R J et al Journal of Virology, January 1993, p. 360-365.

Prehaud C. et al, Sci Signal. 2010 January 19; 3(105):ra5.

Prehaud C. et al J. Virol. 2005 October; 79(20):12893-904.

Prehaud C. et al J Virol. 2003 October; 77(19):10537-47.

Préhaud et al. J Virol. 1988; 62(1): 1-7.

Sarmento et al. 2005; Journal of NeuroVirology 11: 571-581.

Schnell M J et al. 1998, The EMBO Journal Vol. 17 No. 5 pp. 1289-1296.

Schroth-Diez B et al. 2000 Bioscience Reports 20(6): 571-595.

Terrien et al., 2009 Biomol NMR Assign. June; 3(1):45-8.

Ugolini 2008; Dodet B, Fooks A R, Müller T, Tordo N, and the Scientific & Technical Department of the OIE (eds): Towards the Elimination of Rabies in Eurasia. Dev. Biol. Basel, Karger, vol. 131, pp. 493-506.

Ugolini 1995; The Journal of Comparative Neurology 356: 457-480.

Vitry et al. 2003 J Neurosci. November 19; 23(33):10724-31

Vitry S. et al. 2009, Mol. Cell Neurosci. 41(1) 8-18

Von Reitzentstein, 2001, Eur. J. Biochem. 268, 326-333.

Wainwright et al, 2001, PNAS vol. 98 no. 16. 9396-9400.

Wanisch and Yáñez-Muñoz 2009, Molecular Therapy vol. 17 no. 8, 1316-1332.

The invention claimed is:

1. Polypeptide, of at most 350 amino acids, comprising a cytoplasmic domain, wherein said cytoplasmic domain ends with a MAST-2 binding domain, wherein the size of said MAST-2 binding domain is from 11 to 13 amino acid residues, the first two residues of said MAST-2 binding domain are S and W, and the last four residues of said MAST-2 binding domain are Q, T, R and L, said MAST-2 binding domain being selected from the group consisting of:
   - (A) a sequence, whose size is 11 residues, consisting of $SWX_1X_2X_3X_4X_5QTRL$, wherein each of $X_1$, $X_2$, $X_3$, $X_4$ and $X_5$ is any amino acid residue (SEQ ID NO:19);
   - (B) a sequence, whose size is 11 residues, selected from the group consisting of: $SWX_1KSGGQTRL$ (SEQ ID NO:76), $SWX_1SSGGQTRL$ (SEQ ID NO:77), $SWX_1SHGGQTRL$ (SEQ ID NO:78), $SWX_1SHKGQTRL$ (SEQ ID NO:79), $SWX_1SHKSQTRL$ (SEQ ID NO:80), $SWX_1HSGGQTRL$ (SEQ ID NO:86), $SWX_1HKGGQTRL$ (SEQ ID NO:87), $SWX_1HKSGQTRL$ (SEQ ID NO:88), $SWX_1SKGGQTRL$ (SEQ ID NO:89), $SWX_1SKSGQTRL$ (SEQ ID NO:90), $SWX_1SHSGQTRL$ (SEQ ID NO:91), $SWX_1SHKGQTRL$ (SEQ ID NO:92) and $SWX_1SKGGQTRL$ (SEQ ID NO:93), wherein $X_1$ is any amino acid,
   - (C) a sequence, whose size is 12 residues, consisting of $SWX_1X_2X_3X_4X_5X_6QTRL$, wherein each of $X_1$, $X_2$, $X_3$, $X_4$, $X_5$ and $X_6$ is any amino acid residue (SEQ ID NO:112); and
   - (D) a sequence, whose size is 12 residues, selected from the group consisting of: $SWX_1HKSGGQTRL$ (SEQ ID NO:102), $SWX_1SKSGGQTRL$ (SEQ ID NO:103), $SWX_1SHSGGQTRL$ (SEQ ID NO:104), $SWX_1SHKGGQTRL$ (SEQ ID NO:105) and $SWX_1SHKSGQTRL$ (SEQ ID NO:106), wherein $X_1$ is any amino acid,
   - (E) a sequence, whose size is 13 residues, consisting of $SWX_1X_2X_3X_4X_5X_6X_7QTRL$, wherein each of $X_1$, $X_2$, $X_3$, $X_4$, $X_5$, $X_6$ and $X_7$, is any amino acid residue (SEQ ID NO:192), wherein said sequence does not consist of SWESHKSGGQTRL (SEQ ID NO:1), wherein said polypeptide presents a binding affinity for the PDZ domain of the human MAST2 protein which is higher than the binding affinity of rabies virus G protein comprising the SWESHKSGGQTRL (SEQ ID NO:1) sequence for the PDZ domain of the MAST2 protein.

2. Polypeptide according to claim 1, wherein said MAST-2 binding domain consists of the 11-residue sequence $SWX_1X_2X_3X_4X_5QTRL$, (SEQ ID NO:19), wherein $X_1$ is E or A and/or $X_2$ is S, E or V and/or $X_3$ is H, A or Y and/or $X_4$ is G or T and/or $X_5$ is G or Q.

3. Polypeptide according to claim 1, wherein said MAST-2binding domain consists of the 11-residue sequence S-W-E-V-H/A/Y-G/T-G/Q-Q-T-R-L as defined in SEQ ID NO:63.

4. Polypeptide according to claim 1, wherein said MAST-2binding domain consists of the 12-residue sequence $SWX_1X_2X_3X_4X_5X_6QTRL$ (SEQ ID NO:112), wherein $X_1$ is E, A, V or S, $X_2$ is S, V, H, A or Y, $X_3$ is H, A, Y, K or Q, $X_4$ is K, A, Q, S or H, $X_5$ is S, H, G or T and $X_6$ is G, T or Q, as defined in SEQ ID NO:191.

5. Polypeptide according to claim 1, wherein said MAST-2binding domain consists of the 13-residue sequence $SWX_1X_2X_3X_4X_5X_6X_7QTRL$ (SEQ ID NO:192), wherein $X_1$ is E or A and/or $X_2$ is S, V or E and/or $X_3$ is H, A or Y and/or $X_4$ is K, A or Q and/or $X_5$ is S or H and/or $X_6$ is G or T and/or $X_7$ is G or Q.

6. Polypeptide according claim 1, wherein the sequence of the cytoplasmic domain upstream of the MAST-2 binding domain is either:
   - a polypeptide containing 20 to 40 amino acid residues; or
   - a fragment of the cytoplasmic domain of a rabies virus G protein consisting of the sequence as defined in SEQ ID NO:2, or a variant having at least 80% identity with SEQ ID NO:2.

7. Polypeptide according to claim 1, further comprising a signal peptide and a domain for anchoring said polypeptide into the reticulum membrane and/or Golgi membrane, the anchoring domain, wherein said polypeptide, from N-terminal to C-terminal, (1) said signal peptide, (2) said anchoring domain, and (3) said cytoplasmic domain.

8. Polypeptide according to claim 7, wherein the anchoring domain is either:

a peptide, whose size is from 18 to 26 residues, which anchors the polypeptide in the membrane of the endoplasmic reticulum and/or the membrane of the Golgi apparatus in cells; or the transmembrane domain of a rabies virus G protein consisting of the sequence as defined in SEQ ID NO:4 or a variant having at least 81% identity with said SEQ ID NO:4 retaining capacity to anchor the polypeptide in the membrane of the endoplasmic reticulum and/or the membrane of a Golgi apparatus in a cell.

9. Polypeptide according to claim 7, comprising a signal peptide which is either:

a peptide, whose size is from 3 to 60 residues, which targets the polypeptide into the endoplasmic reticulum; or a signal peptide of a rabies virus G protein consisting of the sequence as defined in SEQ ID NO:3 or a variant having at least 68% identity with said SEQ ID NO:3 retaining capacity to target the polypeptide into the endoplasmic reticulum.

10. Polypeptide according to claim 7, which comprises, between the signal peptide and the anchoring domain, a linker consisting of 1 to 4 amino acid residues.

11. Polypeptide according to claim 7 which comprises, from N-terminal to C-terminal:

(1) a signal peptide as defined in SEQ ID NO:3, or a variant having at least 68% identity with said SEQ ID NO:3 retaining capacity to target the polypeptide into the endoplasmic reticulum;

(2) an anchoring domain as defined in SEQ ID NO:4 or a variant having at least 81% identity with said SEQ ID NO:4 retaining the capacity to anchor the polypeptide in the membrane of the endoplasmic reticulum and/or the membrane of a Golgi apparatus in a cell; and (3) a cytoplasmic domain comprising (a) a peptide as defined in SEQ ID NO:2 or a variant having at least 80% identity with SEQ ID NO:2, and (b) a MAST-2 binding domain as defined in SEQ ID NO:19 to SEQ ID NO:209, optionally chosen from the group consisting of SEQ ID NO:19 to SEQ ID NO:101, SEQ ID NO:102 to SEQ ID NO:191 and SEQ ID NO:192 to SEQ ID NO:209.

12. Polypeptide according to claim 1, for which a constant of dissociation ($K_D$) of the complex formed between said polypeptide and a PDZ domain of the human MAST2 protein is less than 0.5 μM, measured by Isothermal Titration Calorimetry (ITC).

13. Polypeptide according claim 1, the sequence of which is selected from the group consisting of SEQ ID NO:210 to SEQ ID NO:218.

14. Polypeptide according to claim 3, wherein said MAST-2 binding domain is selected from the group consisting of SWEVHGGQTRL (SEQ ID NO:64), SWEVHGQQTRL (SEQ ID NO:65), SWEVHTGQTRL (SEQ ID NO:66), SWEVHTQQTRL (SEQ ID NO:67), SWEVAGGQTRL (SEQ ID NO:68), SWEVAGQQTRL (SEQ ID NO:69), SWEVATGQTRL (SEQ ID NO:70), SWEVATQQTRL (SEQ ID NO:71) SWEVYGGQTRL (SEQ ID NO:72), SWEVYGQQTRL (SEQ ID NO:73), SWEVYTGQTRL (SEQ ID NO:74) or SWEVYTQQTRL (SEQ ID NO:75).

15. Polypeptide according to claim 6, wherein the variant having at least 80% identity with SEQ ID NO:2 comprises RRVNRSEPTQLNLRGTGREVSVTPQSGKIIS (SEQ ID NO:5).

16. Polypeptide according to claim 8, wherein the anchoring domain is a transmembrane domain.

17. Polypeptide according to claim 9, wherein the signal peptide targets the polypeptide through the secretory pathway.

18. Polypeptide according to claim 10, wherein the linker consists of the last two C-terminal residues of the ectodomain of a rabies virus G protein.

19. Polypeptide according to claim 11 which comprises, between the signal peptide and the anchoring domain, the last two C-terminal residues of the ectodomain of a rabies virus G protein.

20. Polypeptide according to claim 12, wherein the constant of dissociation ($K_D$) of the complex formed between said polypeptide and a PDZ domain of the human MAST2 protein is less than 0.2 μM, measured by Isothermal Titration Calorimetry (ITC).

21. A composition comprising a polypeptide as defined in claim 1, wherein the composition further comprises a pharmaceutically acceptable vehicle, excipient or carrier.

* * * * *